(12) United States Patent
Lee et al.

(10) Patent No.: US 10,424,741 B2
(45) Date of Patent: Sep. 24, 2019

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Bum Sung Lee, Cheonan-si (KR); Yeon Hee Choi, Cheonan-si (KR); Jung Cheol Park, Suwon-si (KR); Yong Wook Park, Anseong-si (KR); Hee Sun Ji, Cheonan-si (KR); Moon Sung Kang, Cheonan-si (KR); Seungwon Yeo, Daejeon (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

(21) Appl. No.: 15/318,739

(22) PCT Filed: Jun. 11, 2015

(86) PCT No.: PCT/KR2015/005877
§ 371 (c)(1),
(2) Date: Dec. 14, 2016

(87) PCT Pub. No.: WO2015/194791
PCT Pub. Date: Dec. 23, 2015

(65) Prior Publication Data
US 2017/0125689 A1    May 4, 2017

(30) Foreign Application Priority Data
Jun. 18, 2014  (KR) .................. 10-2014-0074261

(51) Int. Cl.
| | | |
|---|---|---|
| *H01L 51/00* | (2006.01) | |
| *C07B 59/00* | (2006.01) | |
| *C07D 333/74* | (2006.01) | |
| *C07D 409/12* | (2006.01) | |
| *C07D 333/76* | (2006.01) | |
| *C07D 307/91* | (2006.01) | |
| *C09K 11/06* | (2006.01) | |
| *H01L 51/50* | (2006.01) | |

(52) U.S. Cl.
CPC ........ *H01L 51/0061* (2013.01); *C07B 59/002* (2013.01); *C07D 307/91* (2013.01); *C07D 333/74* (2013.01); *C07D 333/76* (2013.01); *C07D 409/12* (2013.01); *C09K 11/06* (2013.01); *H01L 51/006* (2013.01); *H01L 51/0059* (2013.01); *C07B 2200/05* (2013.01); *C09K 2211/1022* (2013.01); *C09K 2211/1088* (2013.01); *C09K 2211/1092* (2013.01); *H01L 51/0052* (2013.01); *H01L 51/0054* (2013.01); *H01L 51/0058* (2013.01); *H01L 51/0073* (2013.01); *H01L 51/0074* (2013.01); *H01L 51/0081* (2013.01); *H01L 51/0085* (2013.01); *H01L 51/5012* (2013.01); *H01L 51/5056* (2013.01); *H01L 51/5064* (2013.01); *H01L 51/5088* (2013.01); *Y02E 10/549* (2013.01)

(58) Field of Classification Search
None
See application file for complete search history.

(56) References Cited

U.S. PATENT DOCUMENTS

2013/0105771 A1 * 5/2013 Ryu .................. C09K 11/06
257/40

FOREIGN PATENT DOCUMENTS

| KR | 10-2011-0034103 A | 4/2011 |
|---|---|---|
| KR | 10-2012-0047706 A | 5/2012 |
| KR | 10-2013-0040133 A | 4/2013 |
| KR | 10-2014-0000611 A | 1/2014 |
| WO | 2014/181878 A1 | 11/2014 |
| WO | WO-2014/181878 A1 * | 11/2014 |

OTHER PUBLICATIONS

Machine English translation of Park et al. (KR 10-2013-0040133). Nov. 21, 2017.*
Machine English translation of Matsumoto et al. (WO-2014/181878 A1).*

* cited by examiner

*Primary Examiner* — Jay Yang
(74) *Attorney, Agent, or Firm* — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminescent efficiency, stability, and life span.

10 Claims, 1 Drawing Sheet

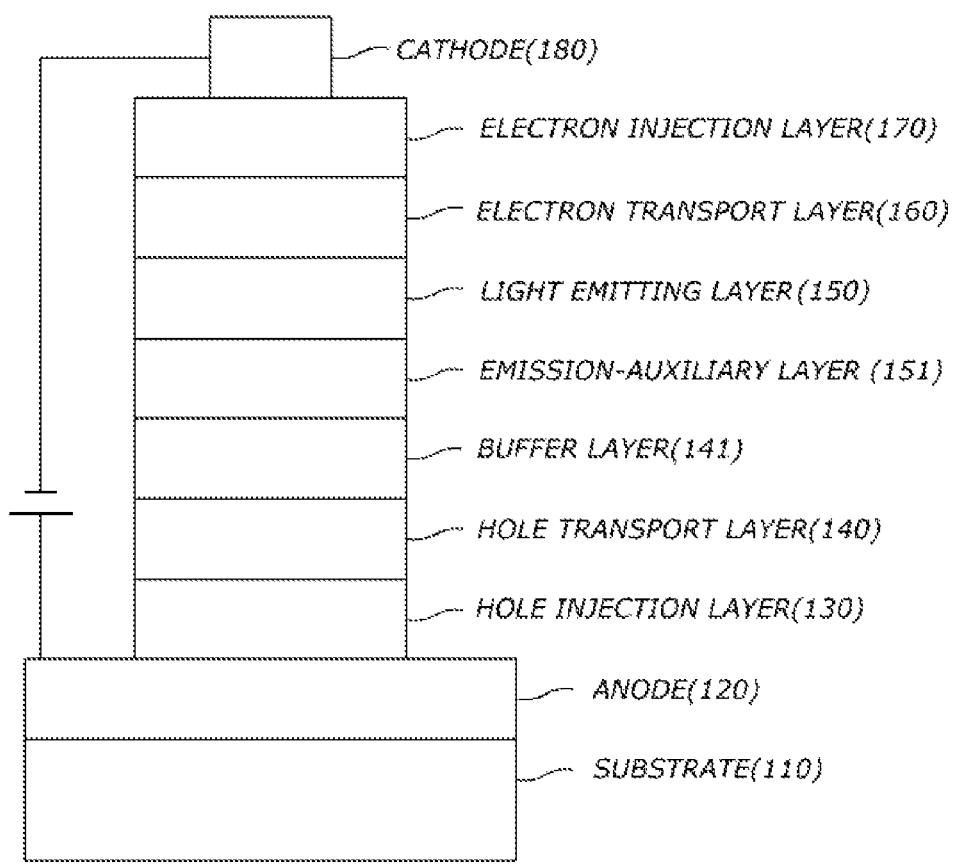

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims benefit under 35 U.S.C. 119, 120, 121, or 365, and is a National Stage entry from International Application No. PCT/KR2015/005877, filed Jun. 11, 2015, which claims priority to Korean Patent Application No. 10-2014-0074261 filed on Jun. 18, 2014, the contents of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is formed between the hole transport layer and a light emitting layer, and it is time to develop different material of emission-auxiliary layers according to respective pixel-domain(R, G, B) of light emitting layers.

In general, an exciton is formed by recombination of an electron which transfers from an electron transport layer to a light emitting layer and a hole which transfers from a hole transport layer to the light emitting layer.

However, it mainly has a low T1 value because a material used in a hole transporting layer should have a low HOMO value, thereby excitons generated from a light emitting layer are transported to the hole transporting layer, resulting in a charge unbalance in the light emitting layer. Thus, light emission occurs in the hole transporting layer or at an interface of the hole transporting layer so that color purity, efficiency and lifespan of the organic electroluminescent device are reduced.

Further, when a material with rapid hole mobility is used in order to reduce a driving voltage in the organic electroluminescent device, it shows tendency to lower the efficiency. The general organic electric element has a hole mobility higher than an electron mobility. This causes a charge unbalance in the light emitting layer resulting in low emitting efficiency and lifespan.

Therefore, in order to solve a problem of a hole transport layer, it needs to form the light emitting layer as material which has a hole transport ability to have a proper driving voltage, high T1(electron block) value and wide bandgap.

These requirements are not satisfied only by structural characteristics of a core of the emission-auxiliary layer material, and it is possible to satisfy these requirements when characteristics of core and sub substituents have an appropriate combination.

Therefore, it is necessary strongly to develop of the material for the emission-auxiliary layer having high T1 energy value and wide band gap, to improve efficiency and lifespan of the organic electric element.

In order to allow an organic electric element to fully exhibit the above-mentioned excellent features, it should be prerequisite to support a material forming an organic material layer of the element, for example, a hole injection material, a hole transport material, a light emitting material, an electron transport material, an electron injection material, an emission-auxiliary layer material or the like, by a stable and efficient material. However, such a stable and efficient organic material layer material for an organic electric element has not yet been fully developed. Accordingly, there is a continuous need to develop new materials for an organic material layer, specially, there are strong needs to develop materials for an emission-auxiliary layer and a hole transport layer.

SUMMARY

In order to solve one or more of the above-mentioned problems occurring in the prior art, an aspect of the present invention is to provide a compound which allows an organic electric element to improve in luminescence efficiency, stability and lifespan, an organic electric element containing the same, and an electronic device including the organic electric element.

In accordance with an aspect of the present invention, the compound represented by the following Formula is provided.

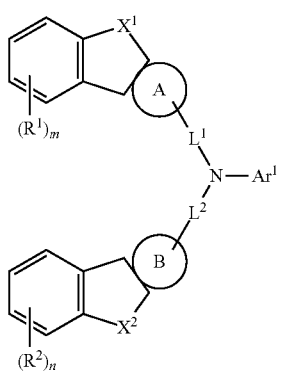

In another aspect of the present invention, organic electric elements containing the compound represented by the formula above and electronic devices including the organic electric element are provided.

By employing the compound of the present invention, the organic electric element according to one or more embodiments of the present invention can have improved luminescence efficiency, high heat-resistant, color purity and lifespan.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component. In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), iodine (I) and so on.

Unless otherwise stated, the term "alkyl" or "alkyl group" as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cyclo alkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

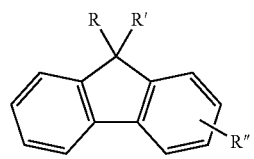

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

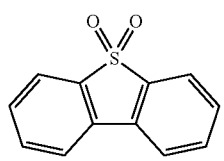 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

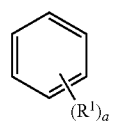

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different each other, and are linked to the benzene ring as follows. when a is an integer of 4 to 6, the substituents $R^1$s are linked to carbon atom of the benzene ring in a similar manner to that. Meanwhile, hydrogen atoms linked to carbon constituting the benzene ring may not be represented as usual.

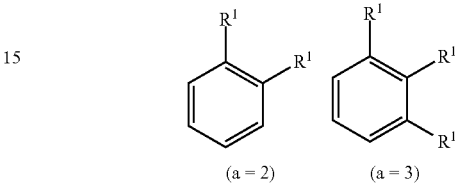

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer therebetween which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, at least one of the layers may not be formed. The organic material layer may further include a hole blocking layer, an electron blocking layer, an emission-auxiliary layer 151, a buffer layer 141 and so on, and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as materials of the hole injection layer 130, the hole transport layer 140, the electron transport layer 160, the electron injection layer 170, the light emitting layer 150, a capping layer, an emission-auxiliary layer and so on. For example, the inventive compound may be used as materials of a hole transport layer 140 and/or an emission-auxiliary layer(151).

Meanwhile, since depending on the type of a substituent and position to which a substituent is attached, a band gap, electrical properties, interfacial properties, and the like may vary even in the same core, it is very important what the types of core and a combination of core and substituent attached to the core. Specially, long life span and high efficiency can be simultaneously achieved when an optimal combination of energy levels and T1 values, inherent material properties (mobility, interfacial properties, etc.), and the like among the respective layers of the organic material layer is given.

As already described above, in order to solve the emission problem with a hole transport layer in a conventional organic electric element, an emission-auxiliary layer is preferably formed between the hole transport layer and a light emitting layer, and it is necessary to form different emission-auxiliary layers corresponding to respective light emitting layers (R, G, B). Meanwhile, even when a similar core is used, it is very difficult to infer the characteristics of an emission-auxiliary layer if a used organic material layer varies because the correlation between the emission-auxiliary layer and a hole transport layer and between the emission-auxiliary layer and a light emitting layer (host) must be figured out.

Accordingly, in the present invention, energy levels, T1 values and inherent material properties (mobility, interfacial properties, etc.) among the respective organic material layers are optimized by forming a hole transport layer or/and an emission-auxiliary layer employing the inventive compounds, and thus the life span and efficiency of the organic electric element can be improved at the same time.

The organic electric element according to an embodiment of the present invention may be manufactured using a deposition method, for example, each layer of the organic electric element may be formed using a deposition method such as a PVD (physical vapor deposition) or CVD (chemical vapor deposition). For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Further, the organic material layer may be manufactured in such a manner that a smaller number of layers are formed using various polymer materials by a soluble process or solvent process, for example, for example, spin coating, nozzle printing, inkjet printing, slot coating, dip coating, roll-to-roll, doctor blading, screen printing, or thermal transfer process. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

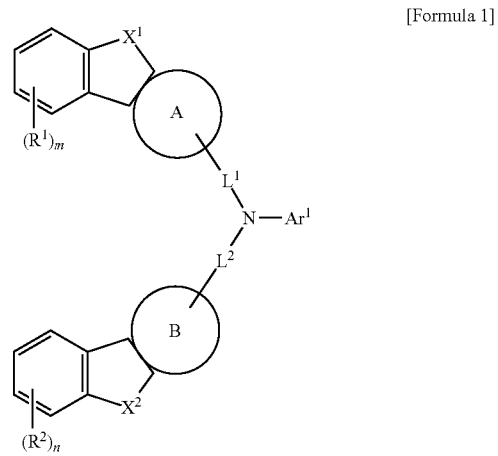

[Formula 1]

In formula 1, $X^1$ and $X^2$ may be each independently O or S, and except that both $X^1$ and $X^2$ are O.

A ring and B ring may be each independently a $C_6$-$C_{18}$ aryl group and may be substituted with at least one R, wherein i) R may be selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{50}$ alkyl group; a fused ring formed by a $C_6$-$C_{60}$ aromatic ring and a $C_3$-$C_{60}$ aliphatic ring; a $C_2$-$C_{20}$ alkenyl group; a $C_1$-$C_{00}$ alkoxy group; and a $C_6$-$C_{30}$ aryloxy group or ii) at least one couple of adjacent Rs may be linked to form at least one ring and R not forming a ring is the same as defined in i) above.

Preferably, A ring and B ring may be each independently a $C_6$-$C_{18}$ aryl group, also preferably $C_6$-$C_{14}$ aryl group, also preferably benzene, naphthalene, phenanthrene and the like.

Also, preferably, A ring and B ring in formula 1 may be each independently any one of the following structures of 1a to 1d:

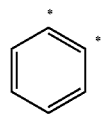

1a

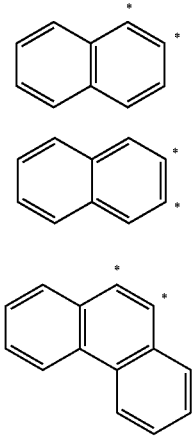

Wherein * indicates the position of bonding.

In formula 1, i) $R^1$ and $R^2$ may be each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{50}$ alkyl group; a fused ring formed by a $C_6$-$C_{60}$ aromatic ring and a $C_3$-$C_{60}$ aliphatic ring; a $C_2$-$C_{20}$ alkenyl group; a $C_1$-$C_{30}$ alkoxy group; and a $C_6$-$C_{30}$ aryloxy group or ii) at least one couple of adjacent $R^1$ s and adjacent $R^2$s may be linked to form at least one ring and $R^1$ and $R^2$ not forming a ring are the same as defined in i) above.

m and n may be each an integer of 0 to 4, and plural $R^1$ s and $R^2$s may be each same or different each other where m and n are each an integer of 2 or more.

With the proviso that, preferably, at least one couple of adjacent $R^1$ s and adjacent $R^2$s may be linked to form at least one ring where both A ring and B ring are a $C_6$ aryl group, wherein $R^1$ s and $R^2$s may be fused with benzene that they are bonded to, and thus a compound of polycyclic ring assemblies such as naphthalene, phenanthrene, perylene and the like may be formed.

Preferably, both m and n may be "0", or adjacent $R^1$ s and/or adjacent $R^2$s may be linked to form at least one ring, wherein $R^1$ s and $R^2$s may be fused with benzene that they are bonded to, and thus a compound of polycyclic ring assemblies such as naphthalene, phenanthrene, perylene and the like may be formed.

Also, in formula 1, $L^1$ and $L^2$ may be each independently a single bond or a $C_6$-$C_{60}$ arylene group, preferably, a single bond or a $C_6$-$C_{18}$ arylene group, also preferably, a phenyl, a naphthalene, a biphenyl, a phenanthrene, a terphenyl(including m-terphenyl and p-terphenyl and the like) and the like. And $L^1$ and $L^2$ may be each substituted with a phenyl, a naphthalene, a biphenyl, deuterium and the like.

In formula 1, $Ar^1$ may be a $C_6$-$C_{60}$ aryl group, preferably, a substituted or unsubstituted $C_6$-$C_{18}$ aryl group, also preferably, a substituted or unsubstituted $C_6$, $C_{10}$, $C_{12}$, $C_{14}$, $C_{16}$ or $C_{18}$ aryl group, also preferably a phenyl, a biphenyl, a naphthalene, a terphenyl, a phenanthrene or a pyrene and the like which may be each further substituted with one or more substituents such as a phenyl, naphthty, biphenyl, phenanthryl, pyrenyl, deuterium, methyl, prophenyl, fluorine and the like.

Meanwhile, each of the above aryl group, fluorenyl group, heterocyclic group, fused ring group, alkyl group, alkenyl group, alkoxy group, aryloxy group of R, $R^1$ and $R^2$, aryl group of $Ar^1$, and arylene group of $L^1$ and $L^2$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

In formula 1, at least one of adjacent $R^1$ s and adjacent $R^2$s may be linked to form at least one ring. Preferably, the above formula 1 may be any one of the following formulas 2 to 16.

In formula 2, it is excluded that both A ring and B ring are a $C_6$ aryl group, and thus both or one thereof may be a polycyclic ring, here, at least one of adjacent $R^1$ s and adjacent $R^2$s may be linked to form at least one ring, or both $R^1$ s and $R^2$s may not form a ring. Meanwhile, where adjacent $R^1$ s are linked each other and fused with benzene which $R^1$ s are bonded to, and thus form a naphthalene, Formula 1 may be represented by any one of the following formulas 3, 6 and 9. Further, where adjacent $R^1$ s are linked each other and fused with benzene which $R^1$ s are bonded to, and thus form a phenanthrene, Formula 1 may be represented by the following formula 12. Furthermore, where adjacent $R^1$ s and adjacent $R^2$s are linked each other and fused with benzene which $R^1$ s and $R^1$ s are bonded to, and thus form a naphthalene or phenanthrene, Formula 1 may be represented by any one of the following formulas 4, 5, 7, 8, 10, 11, 13, 14 and 16.

<Formula 2>

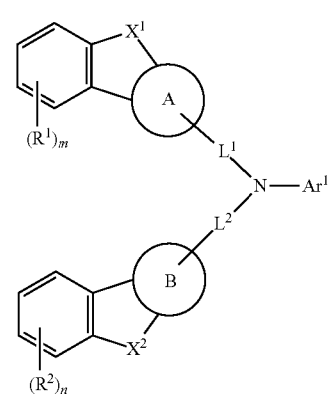

<Formula 3>

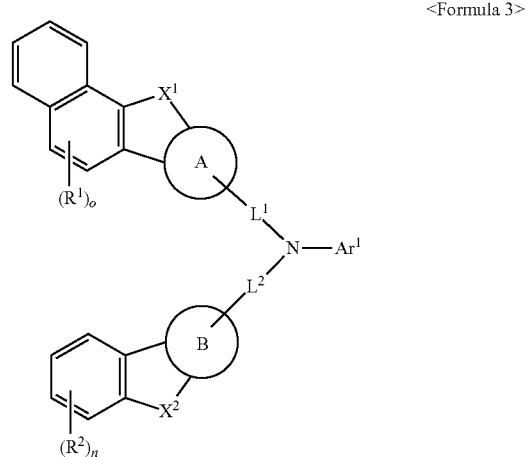

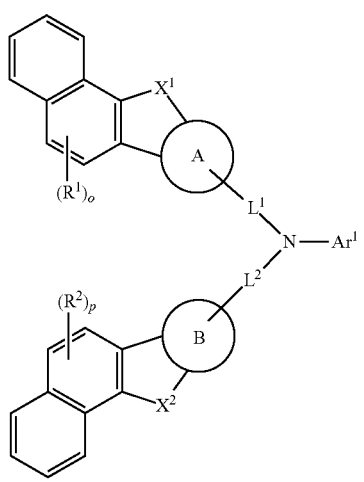
<Formula 4>
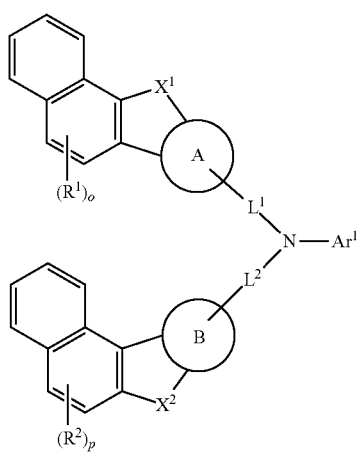
<Formula 5>
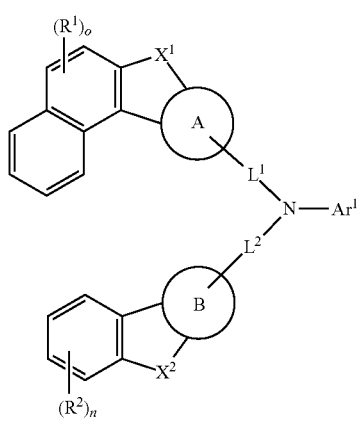
<Formula 6>
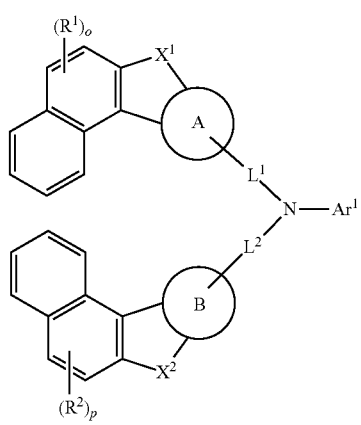
<Formula 7>
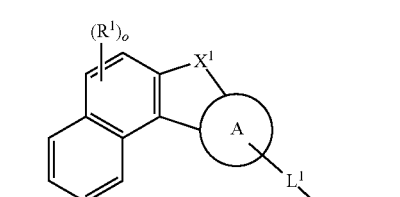
<Formula 8>
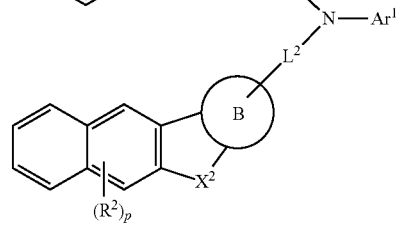
<Formula 8>
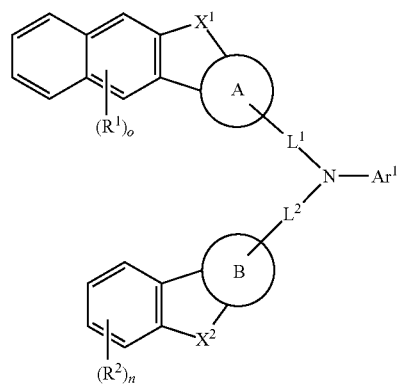
<Formula 9>
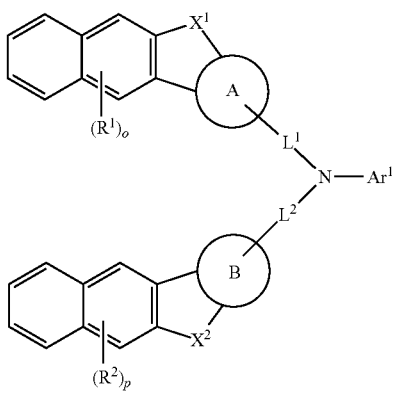
<Formula 10>

<Formula 11>
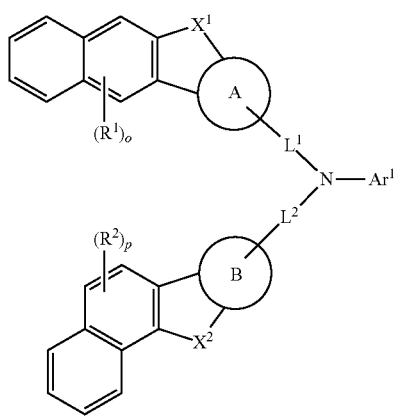
<Formula 12>
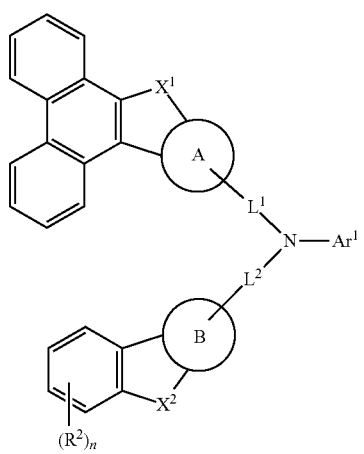
<Formula 13>
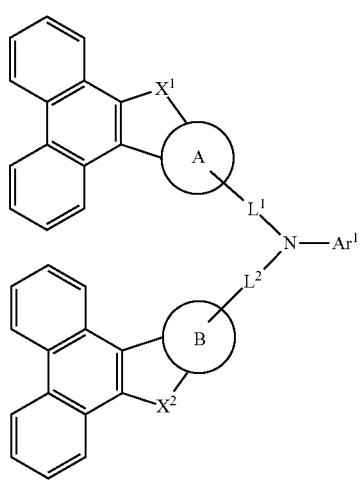
<Formula 14>
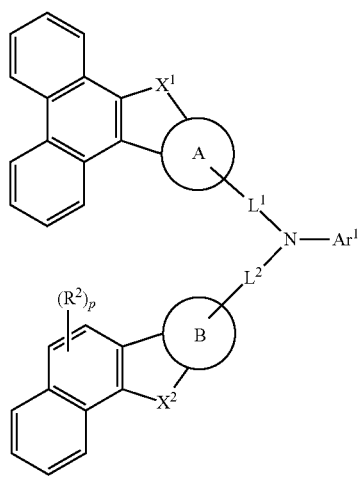
<Formula 15>
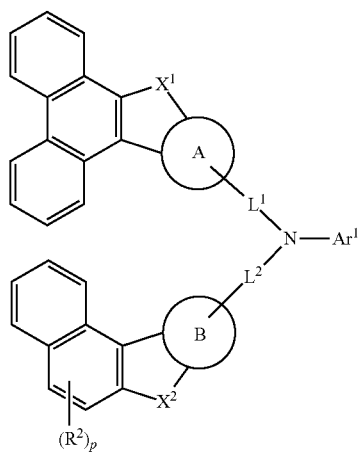
<Formula 16>
In formulas 2 to 16, o and p may be each an integer of 0 to 2, and $X^1$, $X^2$, A ring, B ring, $R^1$, $R^2$, $Ar^1$, $L^1$, $L^2$, m and n may be each the same as defined in Formula 1 above. With the proviso that, it is excluded that both A ring and B ring are a $C_6$ aryl group in formula 2.

Specifically, the compound represented by Formula 1 may be any one of the following compounds.
P-1
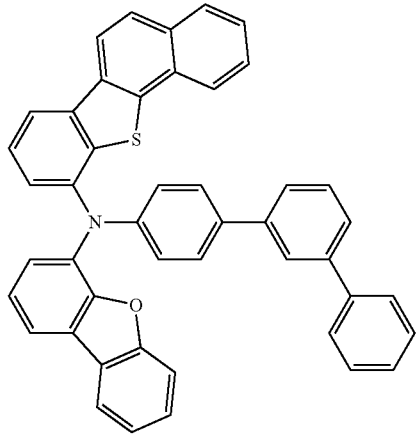
P-2
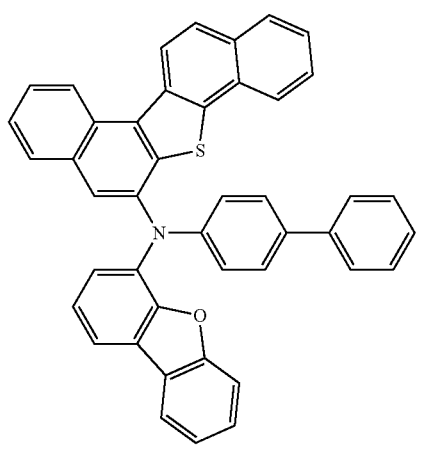
P-3
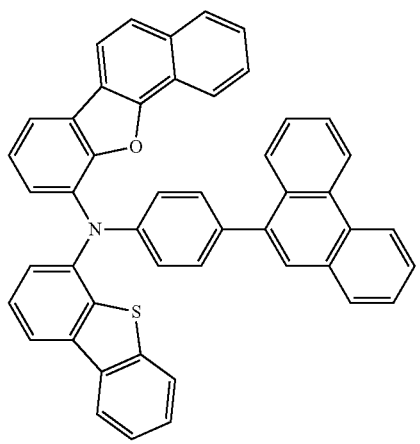
P-4
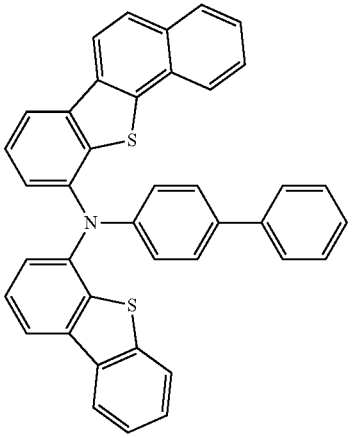
P-5
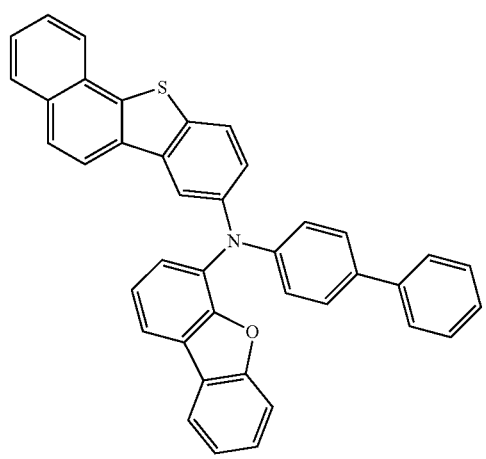
P-6
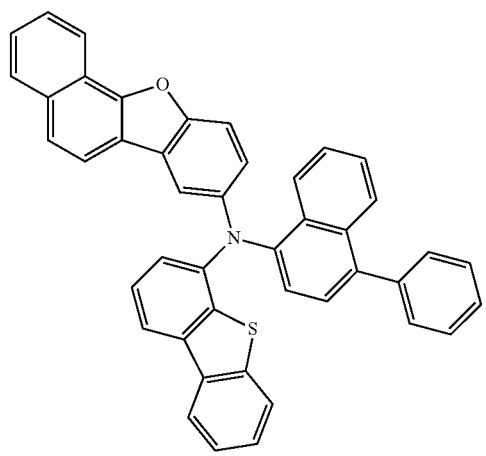

-continued
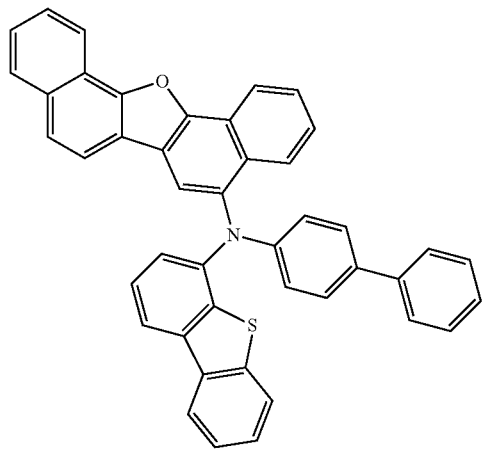
P-7
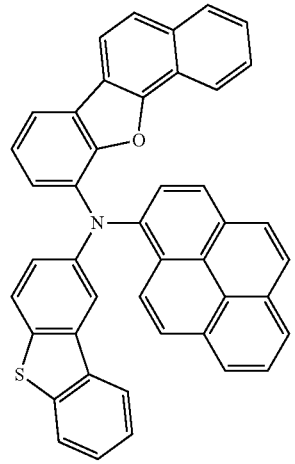
P-10
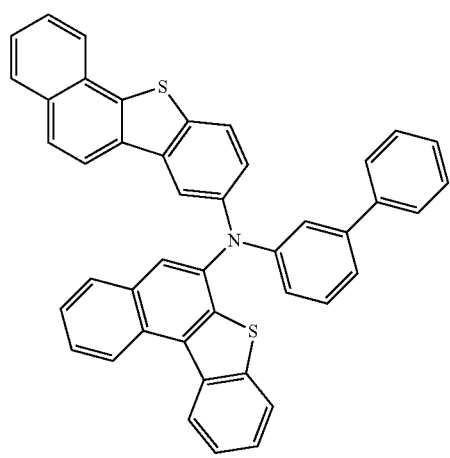
P-8
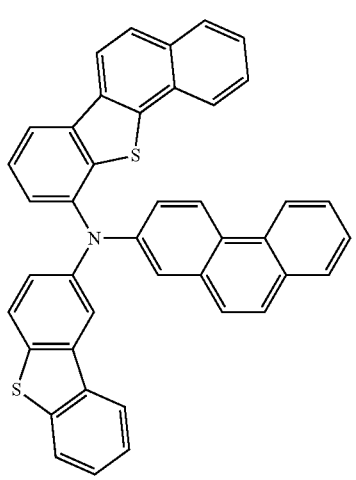
P-11
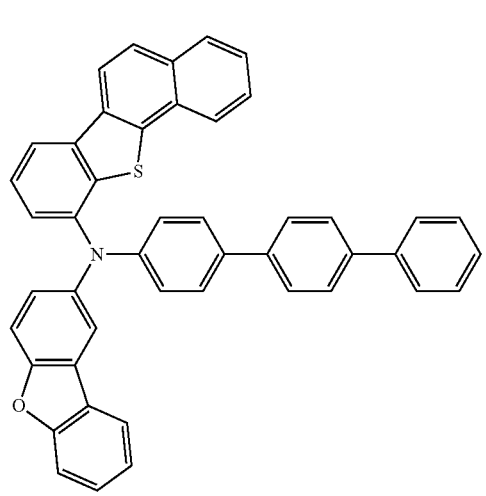
P-9
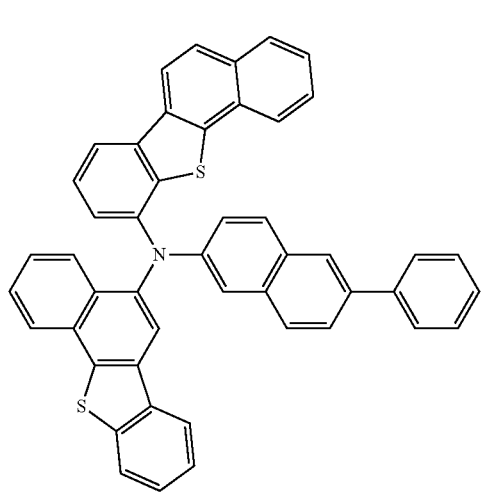
P-12

P-13
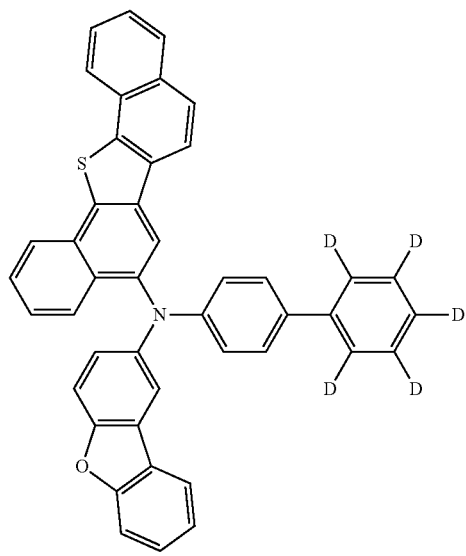
P-14
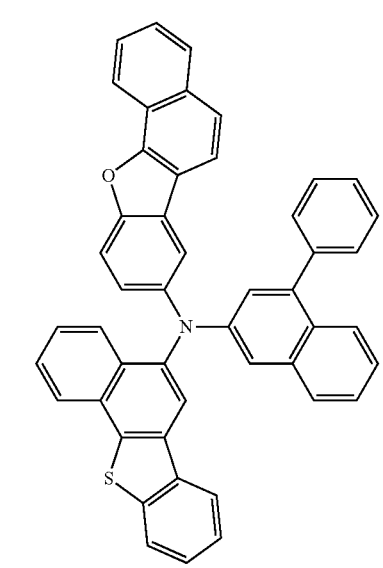
P-15
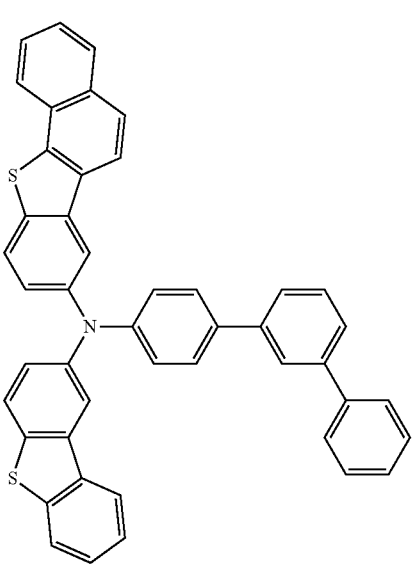
P-16
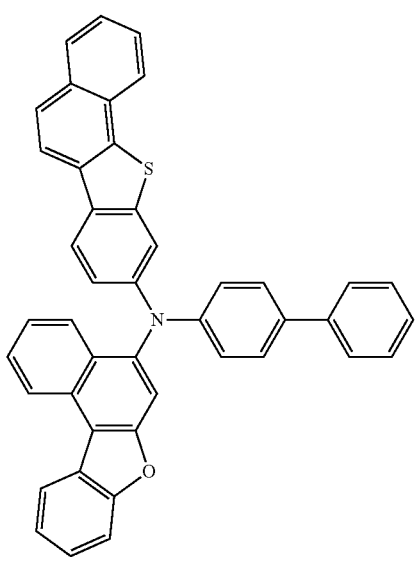
P-17
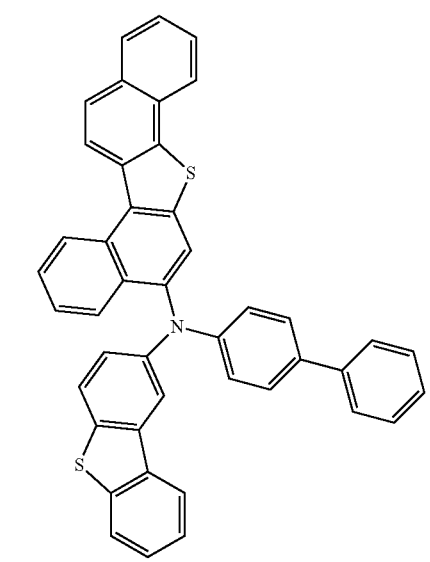
P-18
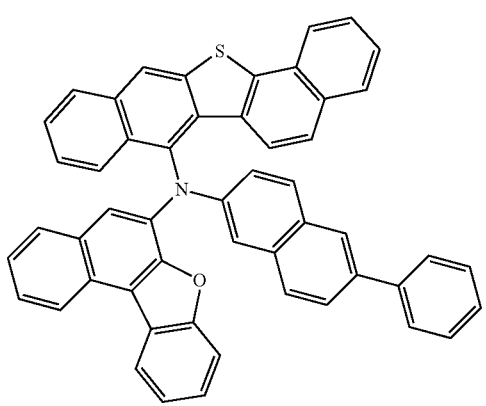

-continued
P-19
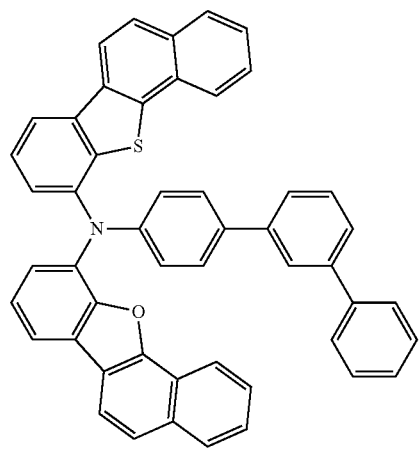
P-22
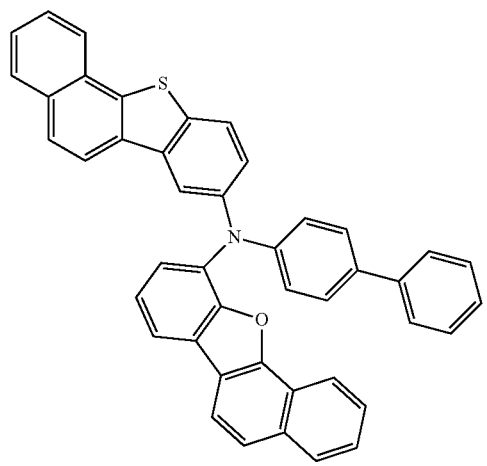
P-20
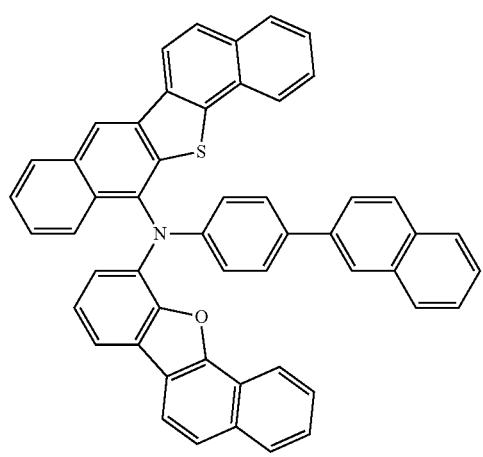
P-23
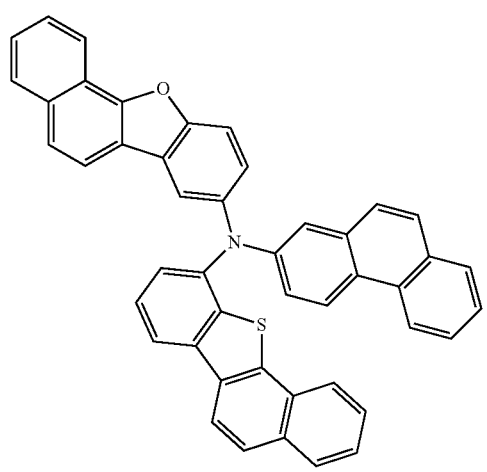
P-21
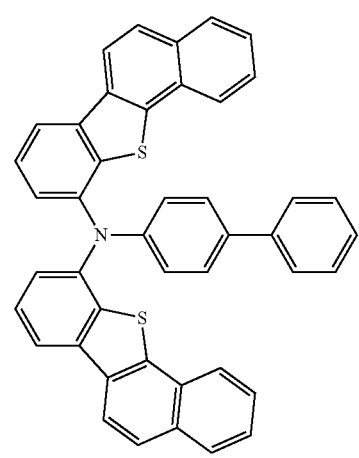
P-24
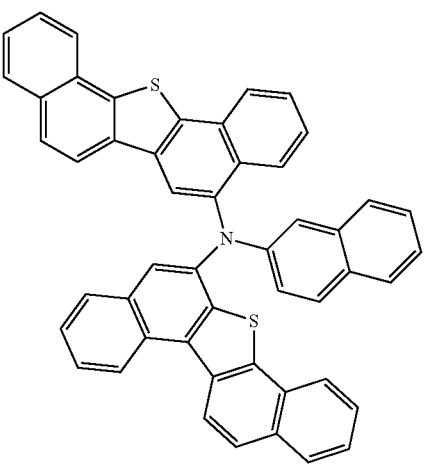

P-25
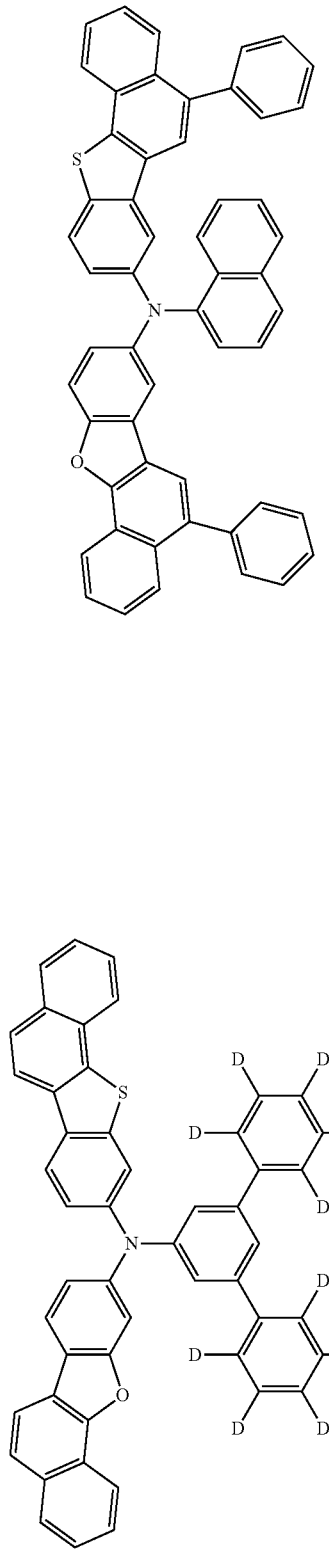
P-26
P-27
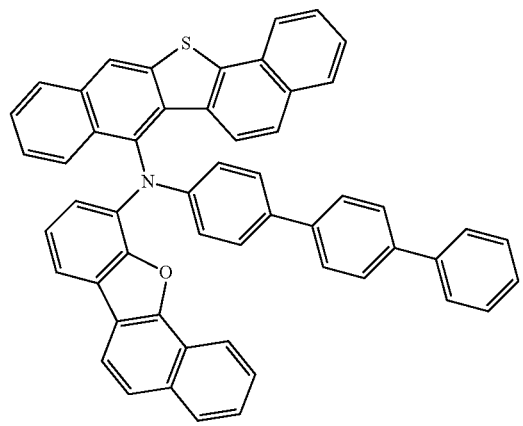
P-28
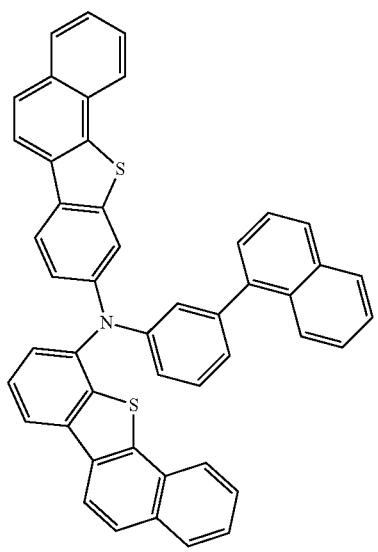
P-29
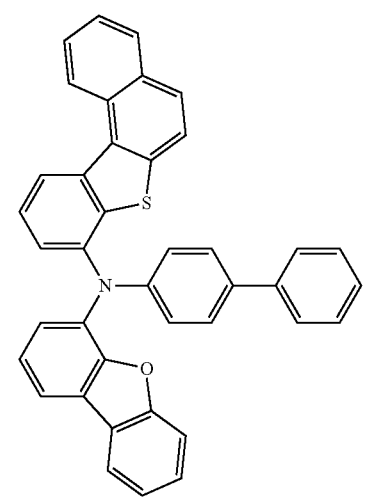

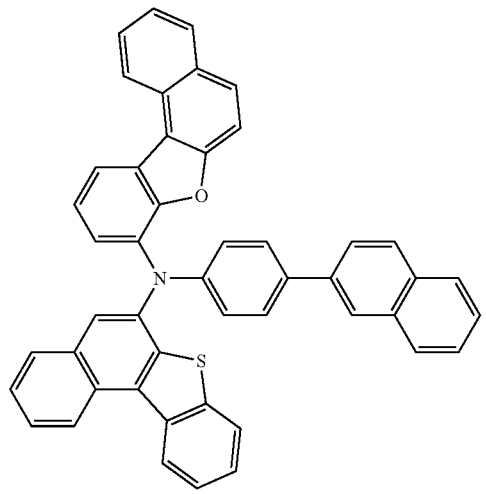
P-30
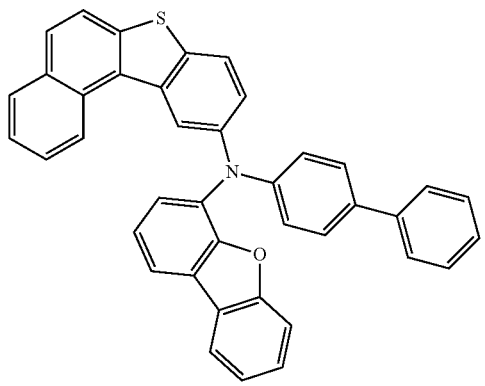
P-33
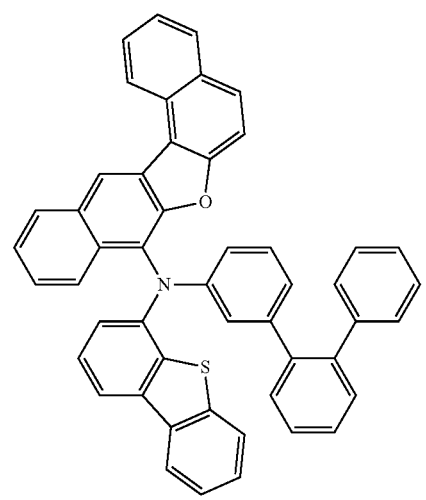
P-31
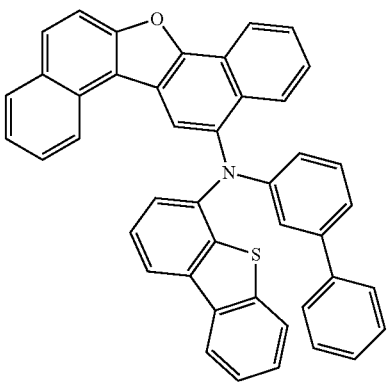
P-34
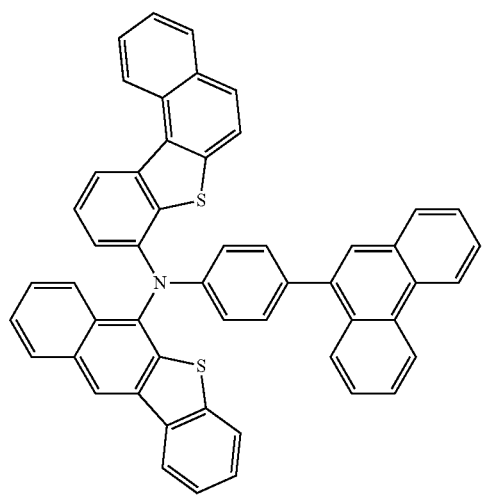
P-32
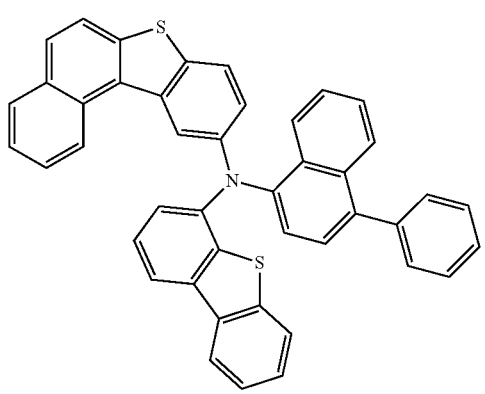
P-35

P-36
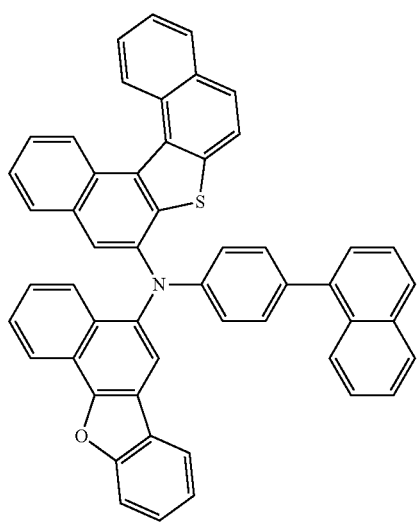
P-39
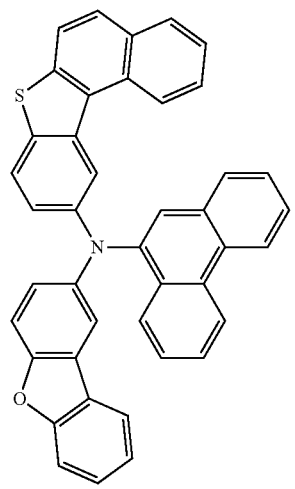
P-37
P-40
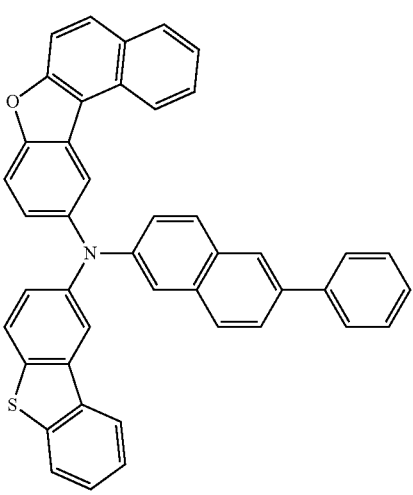
P-38
P-41
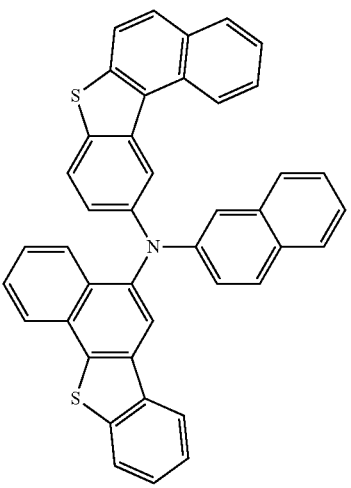

P-42
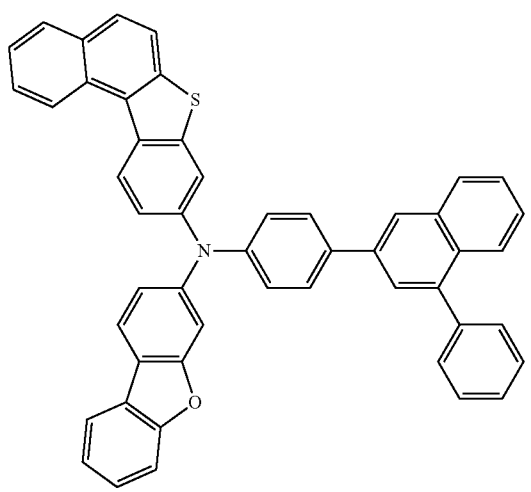
P-43
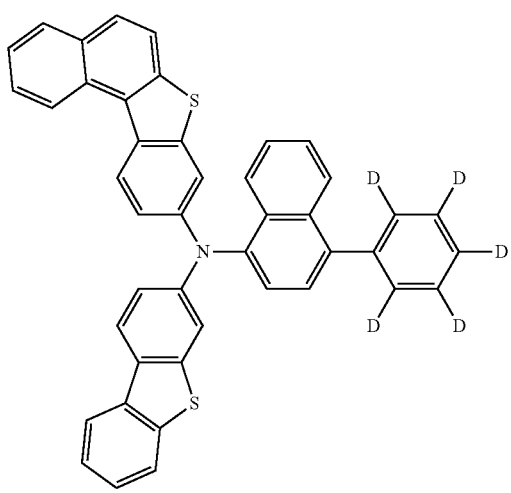
P-44
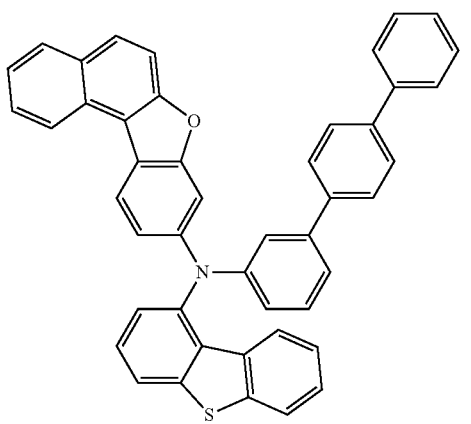
P-45
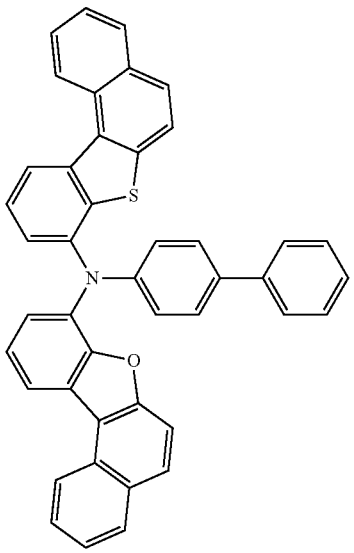
P-46
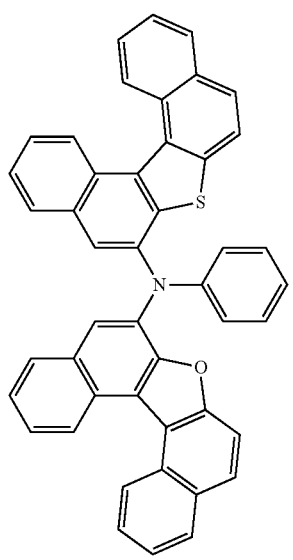
P-47
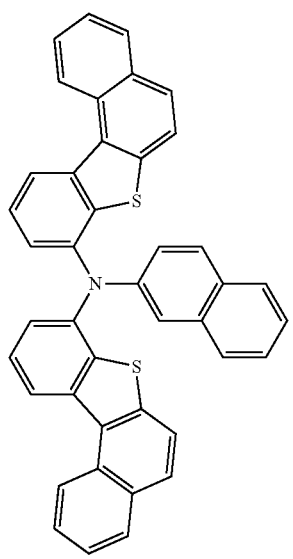

P-48
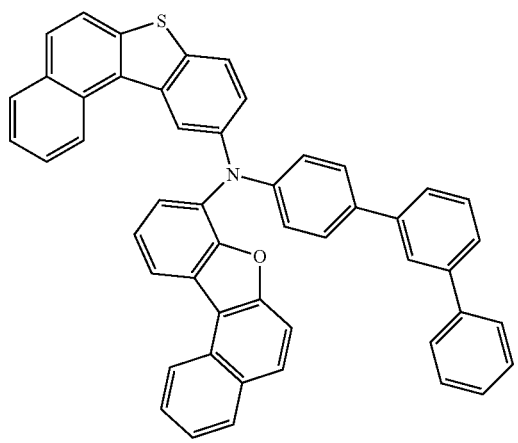
P-51
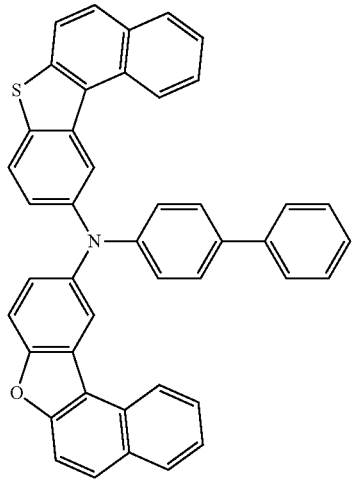
P-49
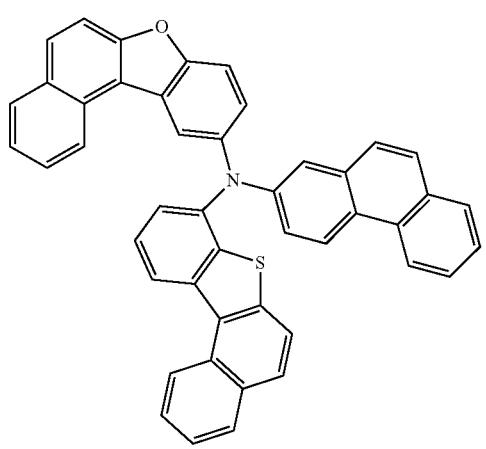
P-52
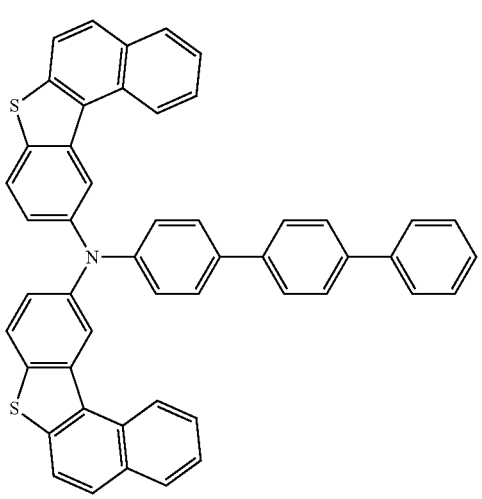
P-50
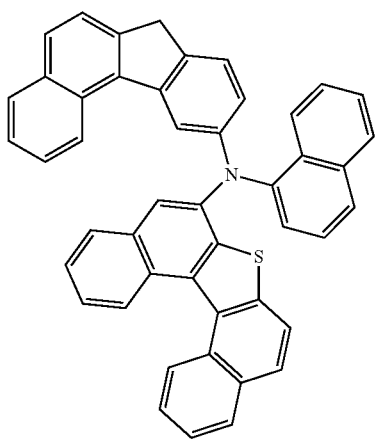
P-53
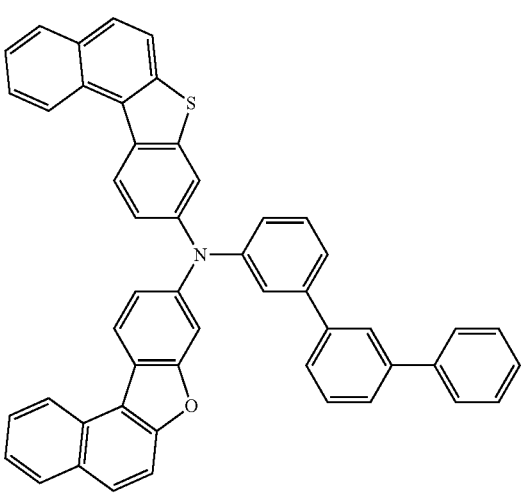

P-54
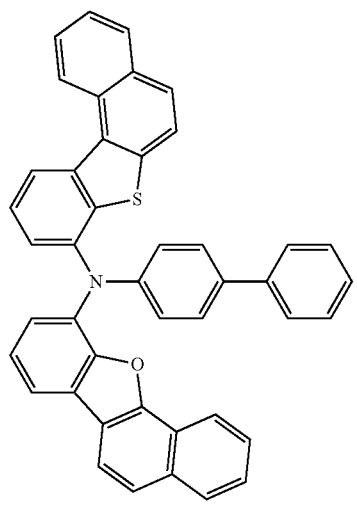
P-57
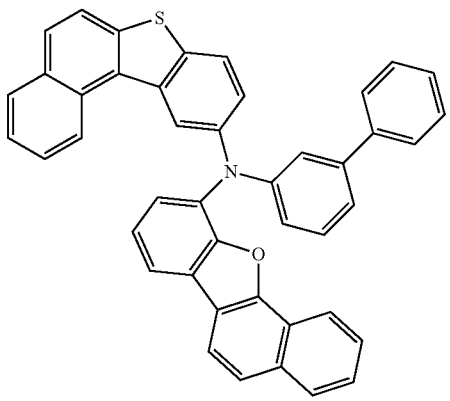
P-55
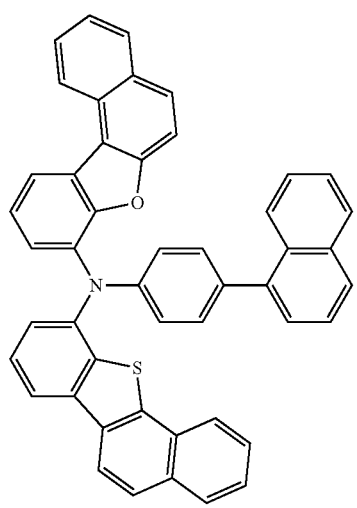
P-58
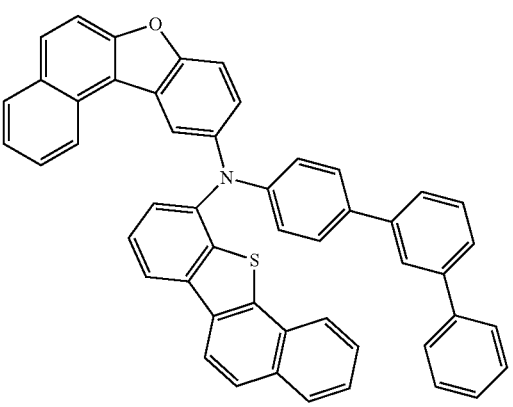
P-56
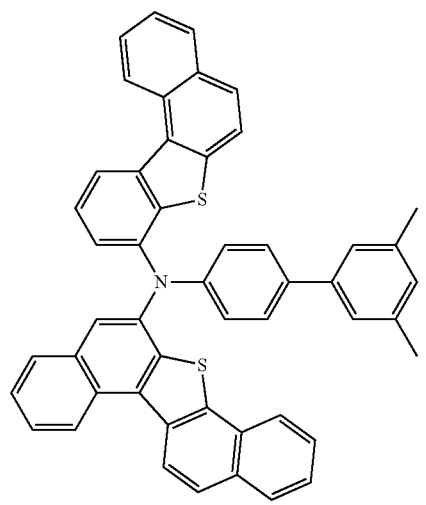
P-59
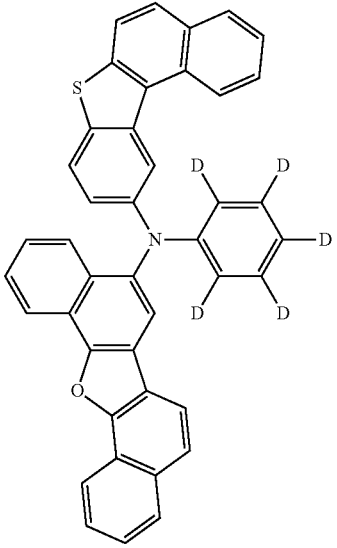

P-60
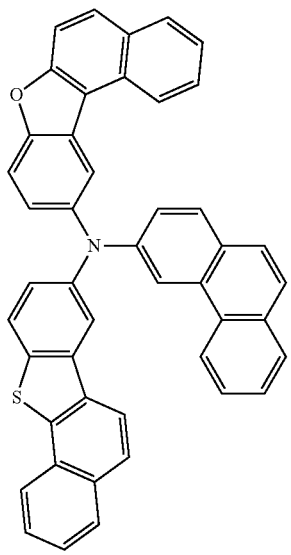
P-61
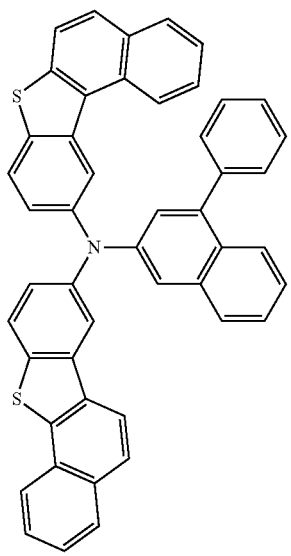
P-62
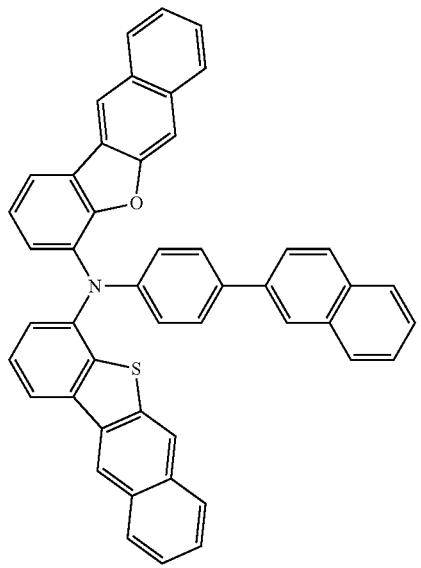
P-63
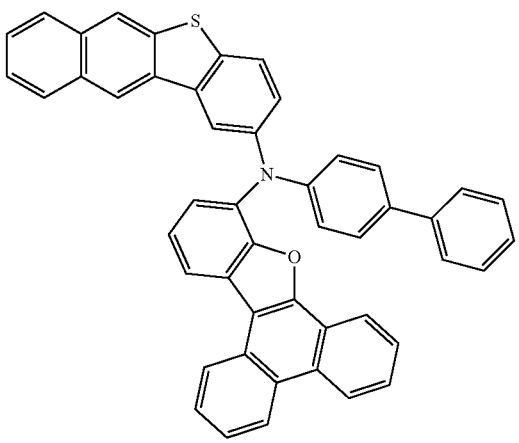
P-64
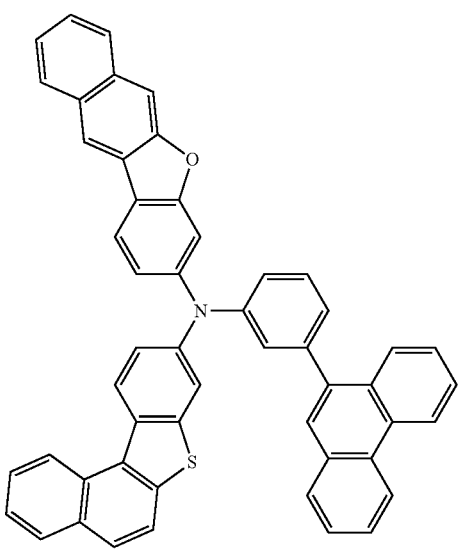
P-65
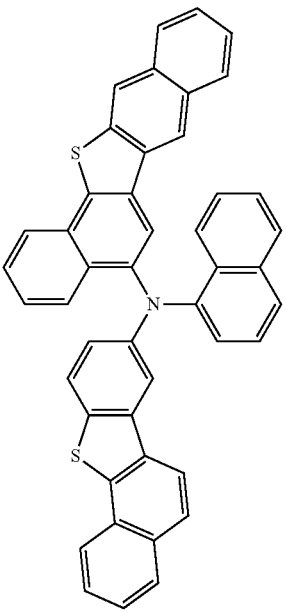

37
-continued
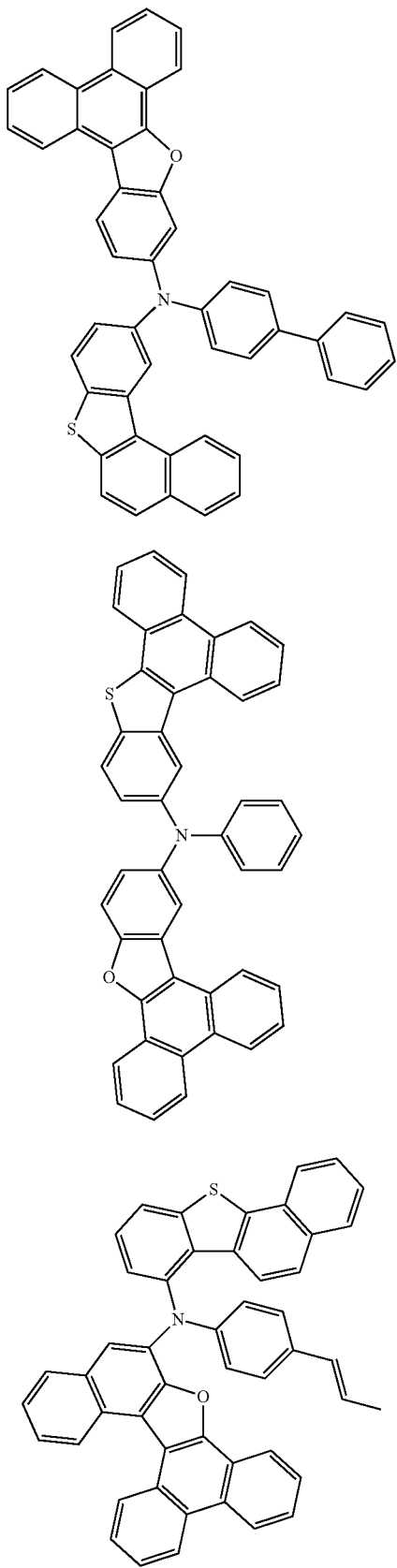
P-66
P-67
P-68
38
-continued
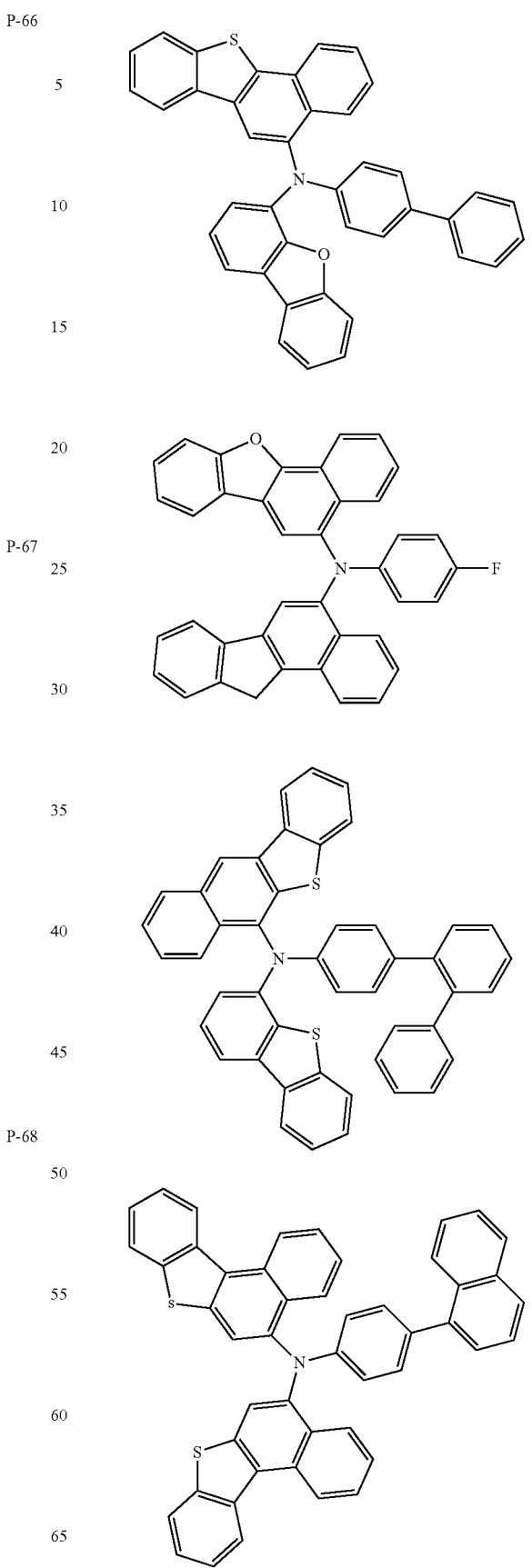
P-69
P-70
P-71
P-72

P-73
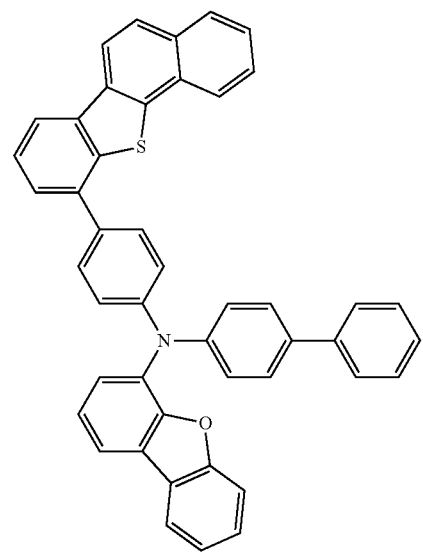
P-74
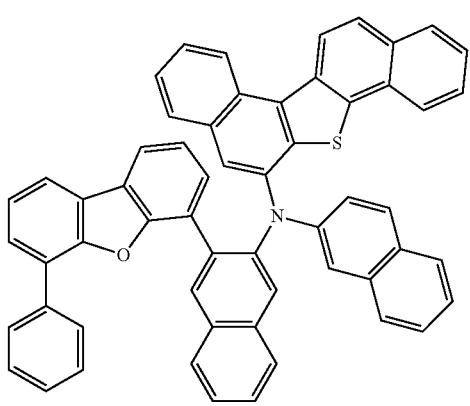
P-75
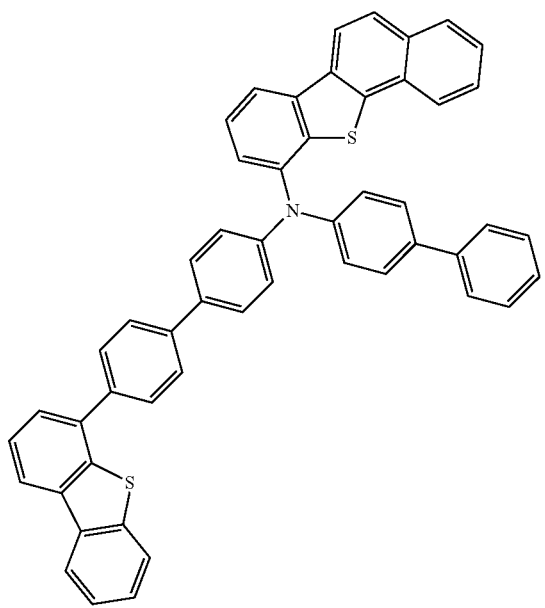
P-76
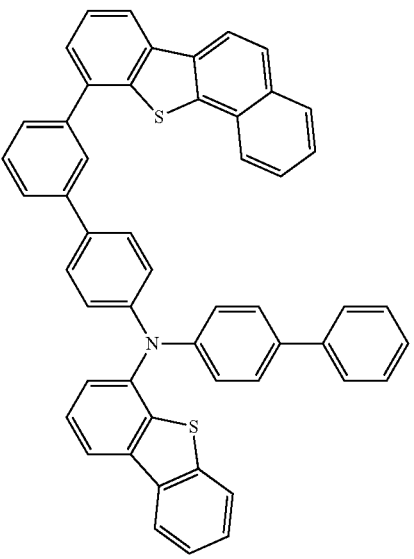
P-77
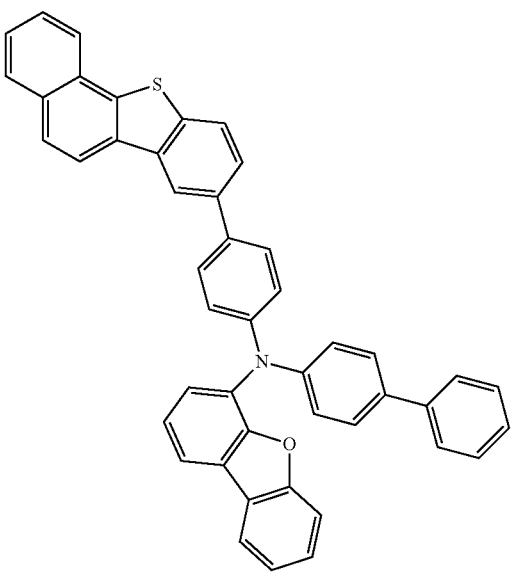

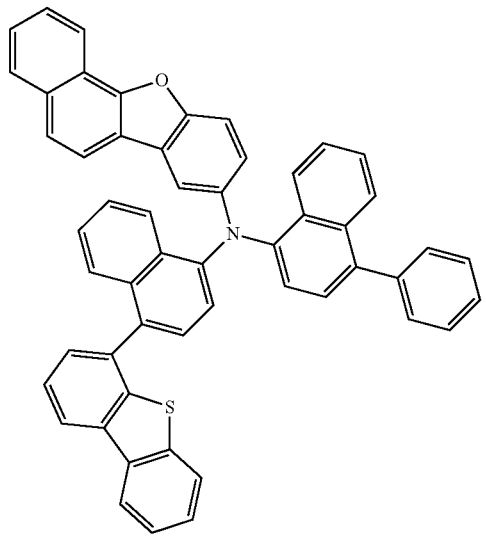
P-78
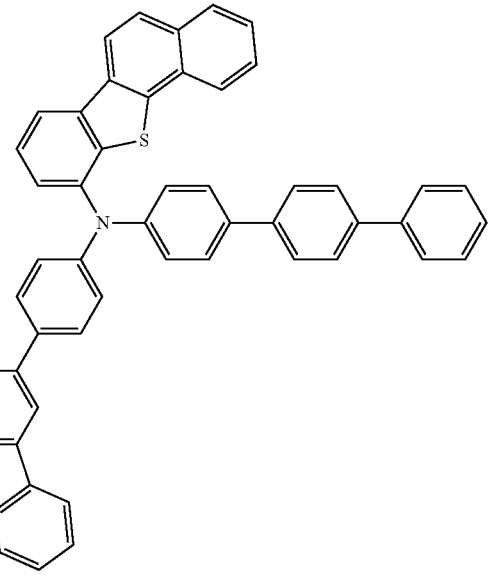
P-80
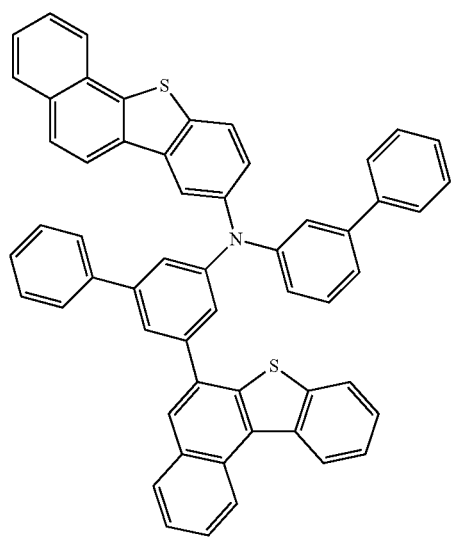
P-79
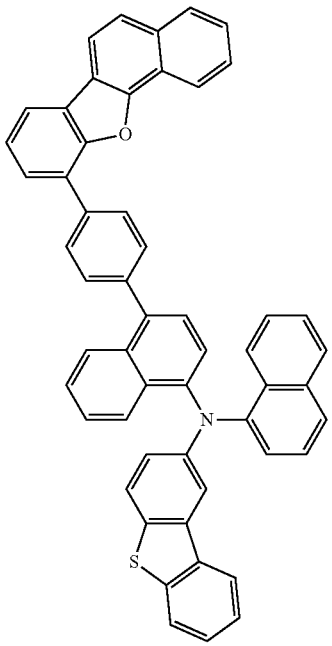
P-81

-continued
P-82
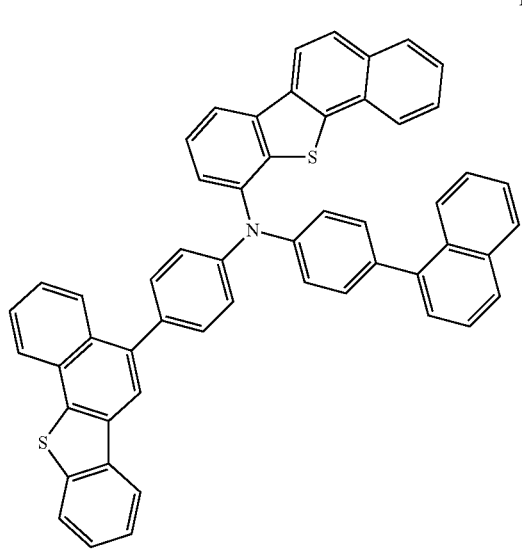
P-84
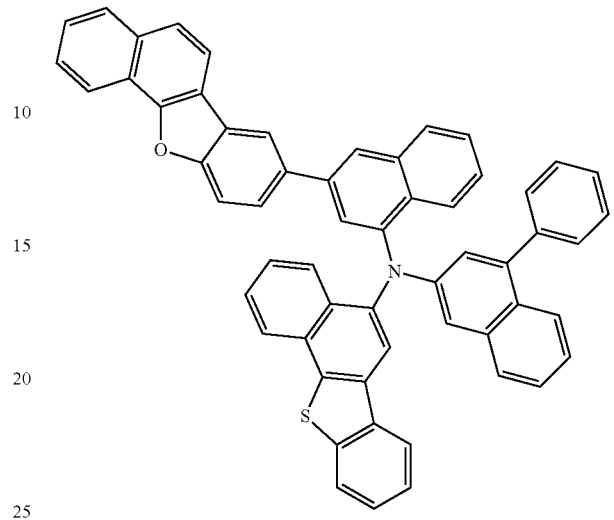
P-83
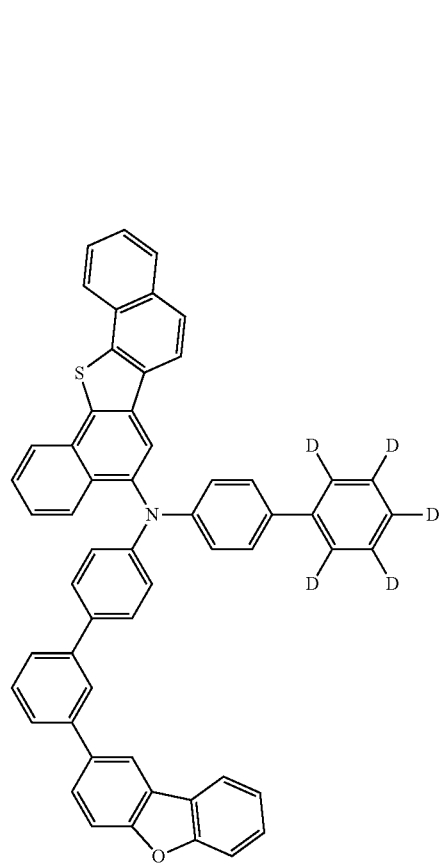
P-85
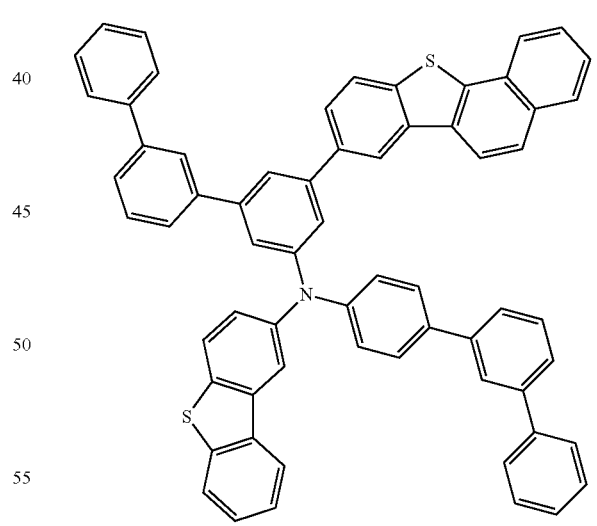

P-86
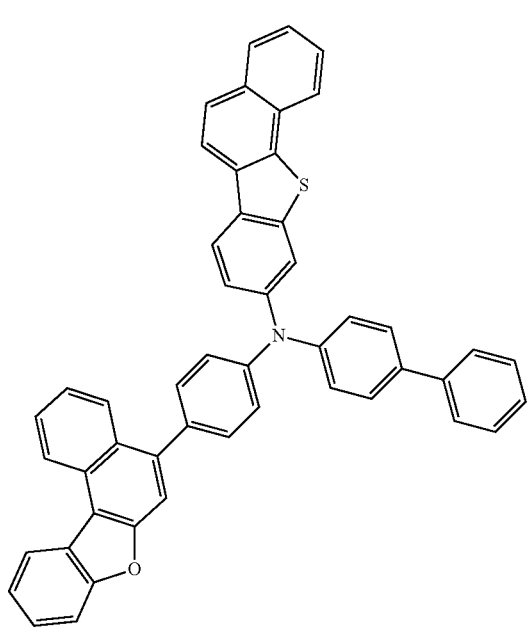
P-88
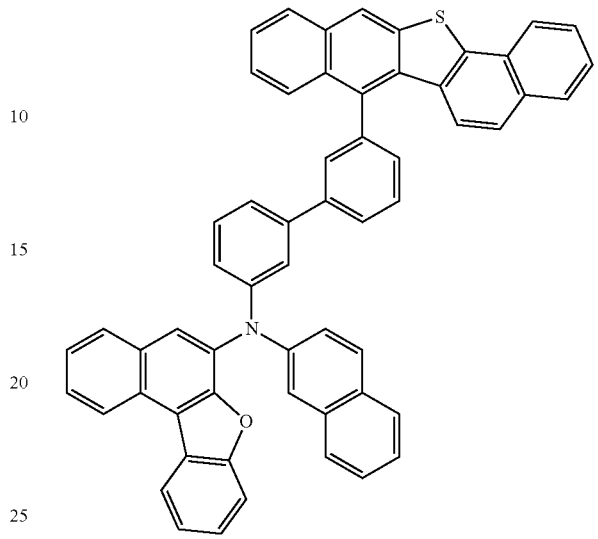
P-87
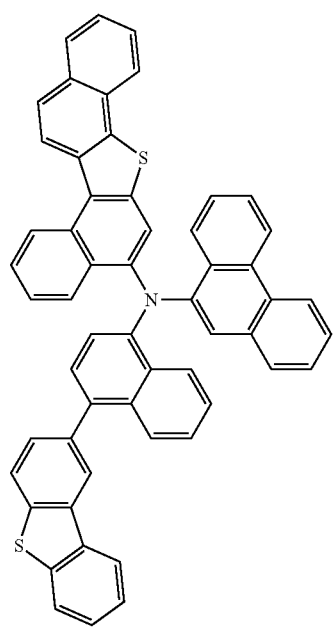
P-89
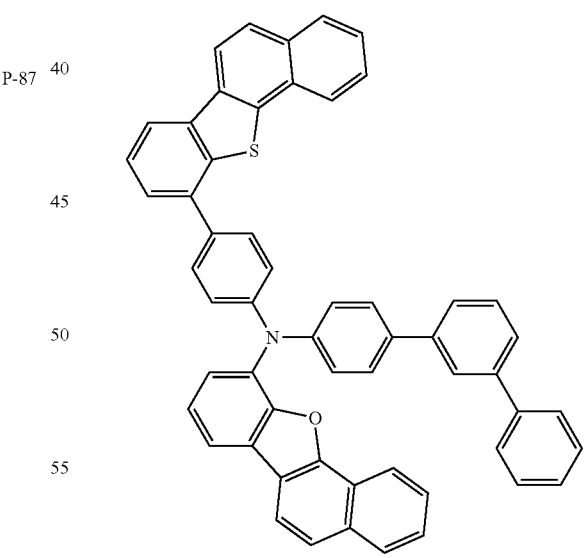

P-90
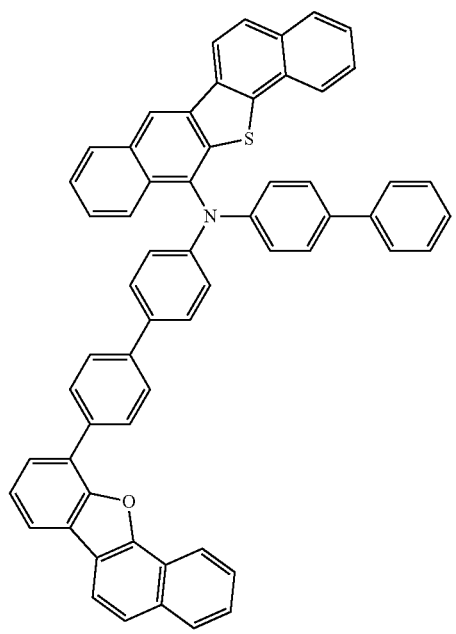
P-92
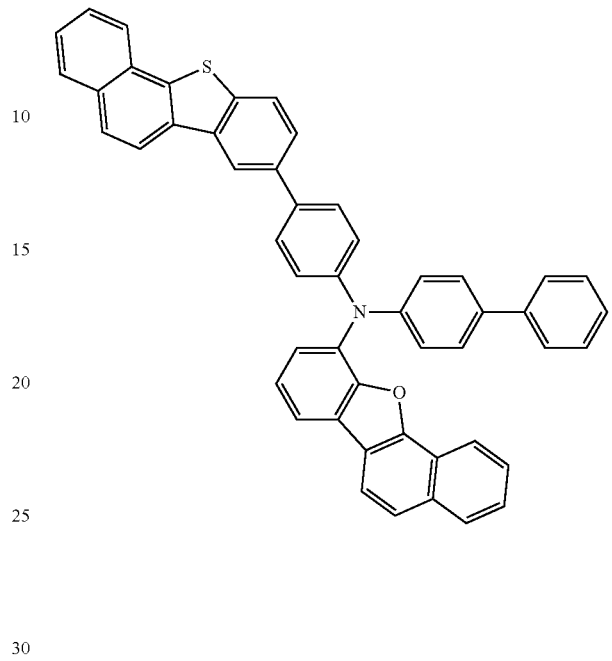
P-91
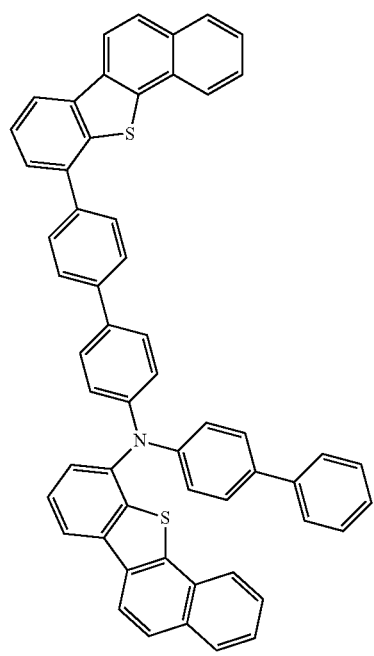
P-93

P-94
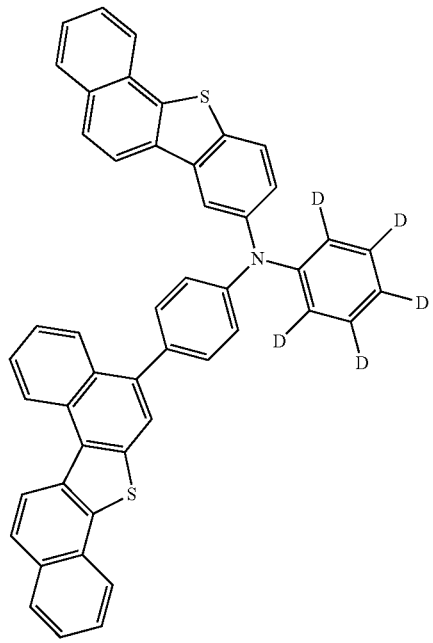
P-95
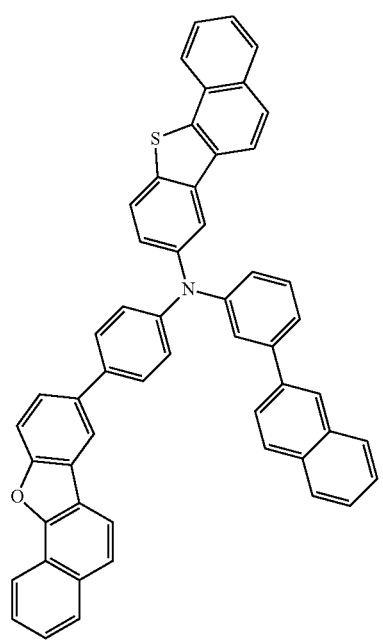
P-96
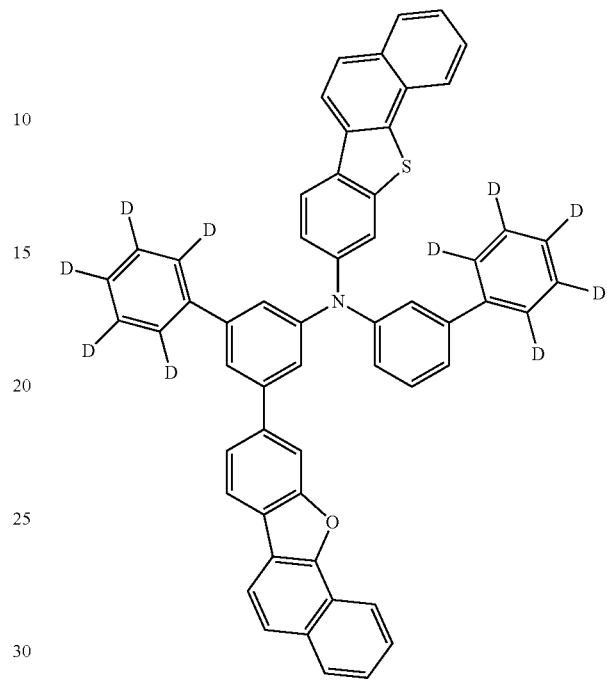
P-97
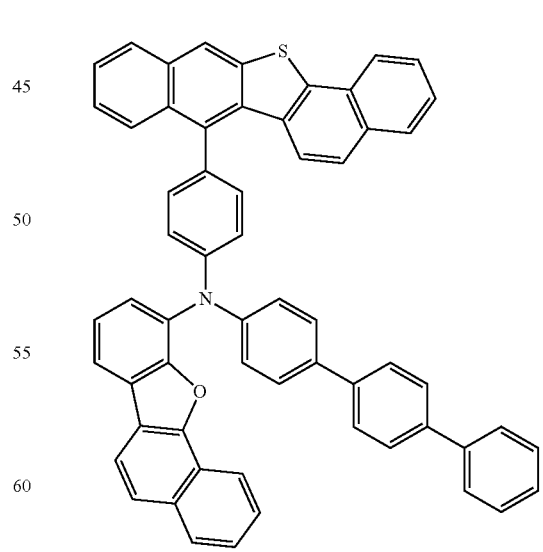

-continued
P-98
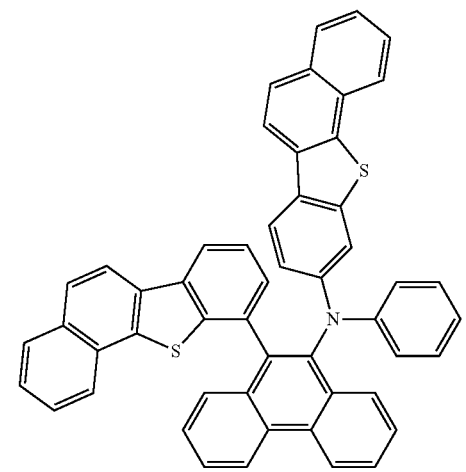
P-99
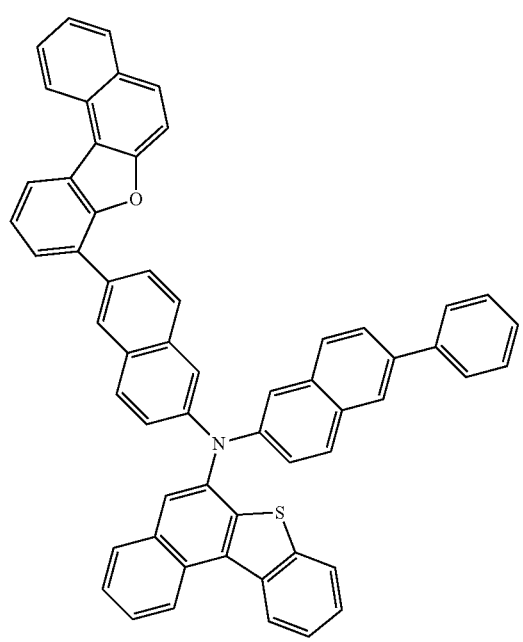
P-100
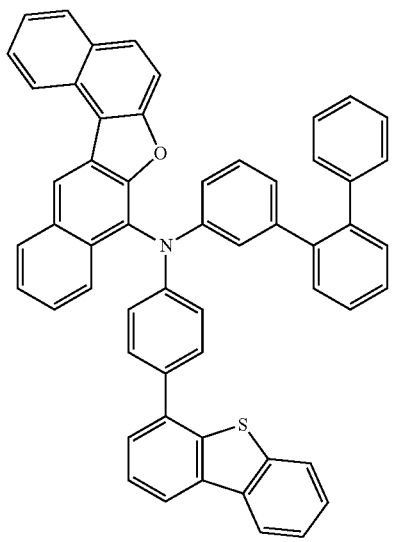
-continued
P-101
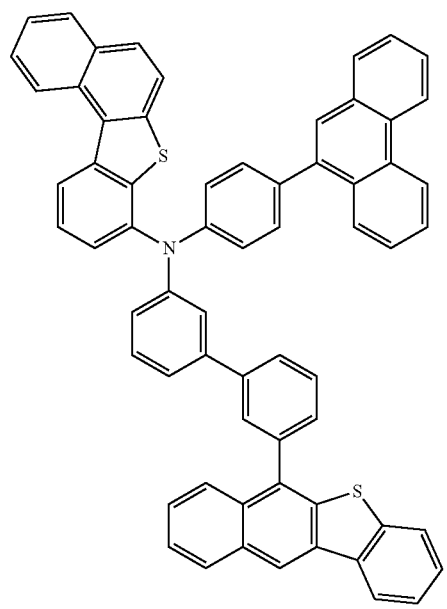
P-102
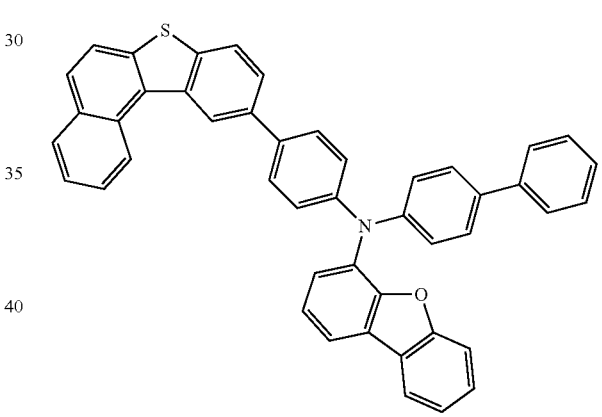
P-103
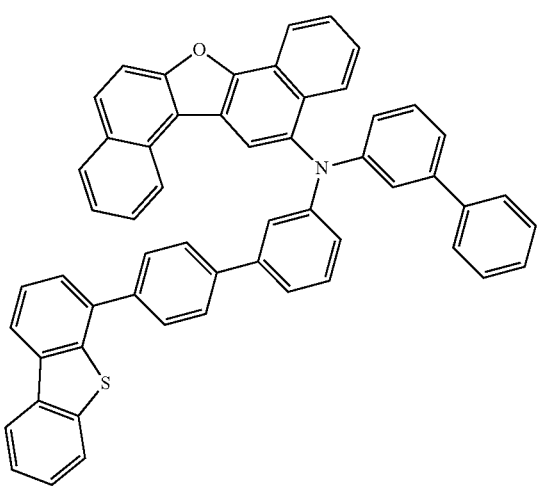

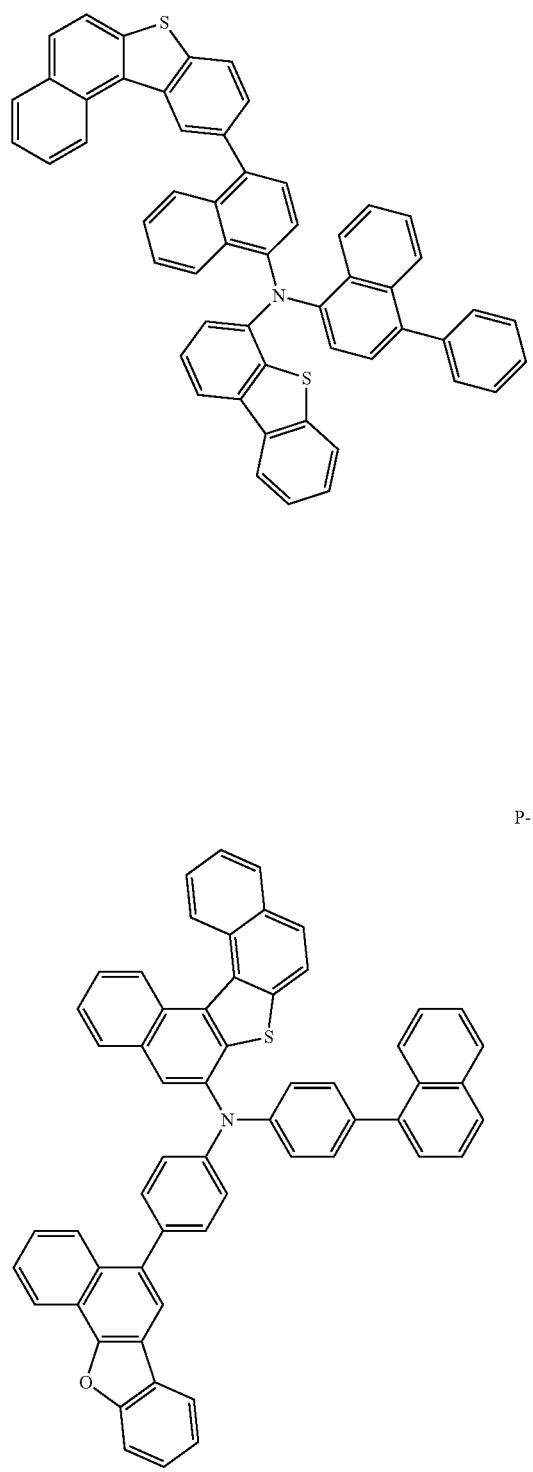
P-104
P-105
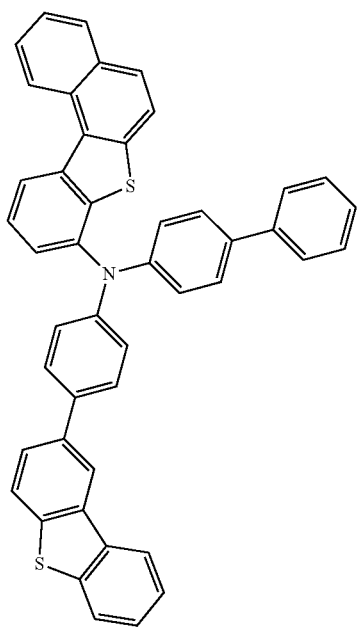
P-106
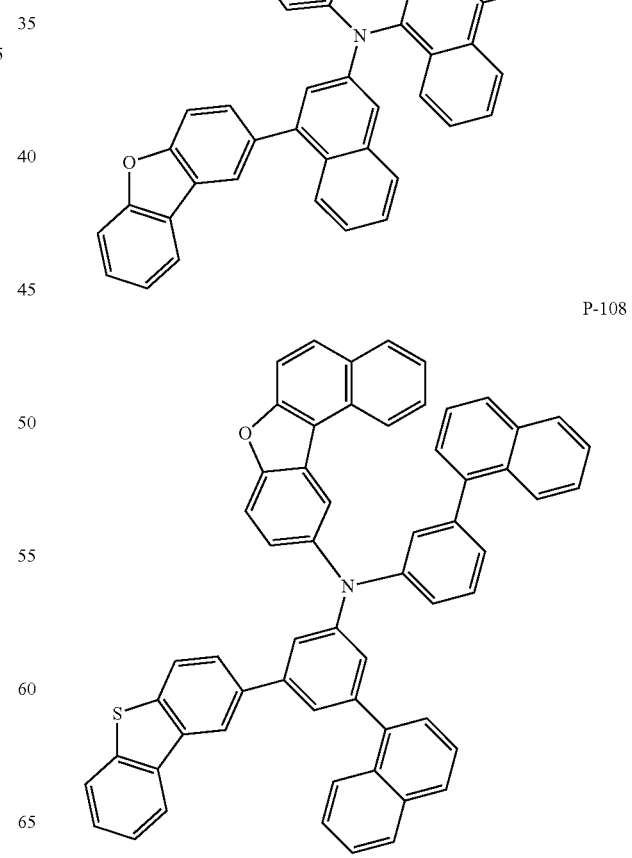
P-107
P-108

P-109
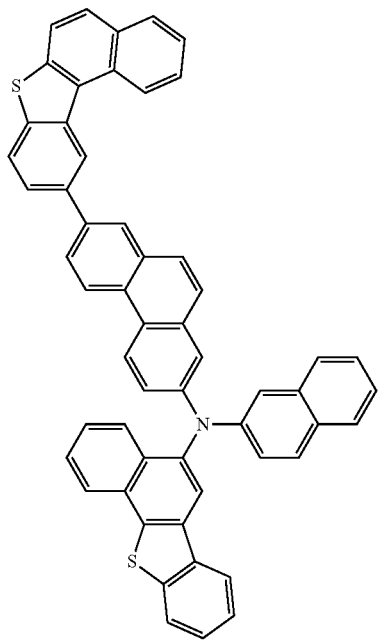
P-111
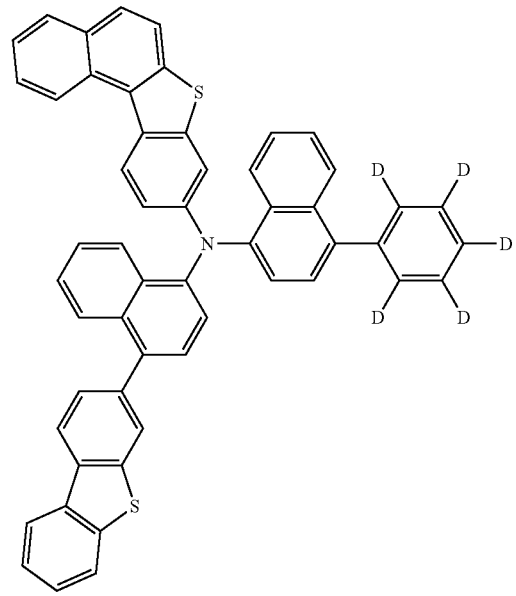
P-110
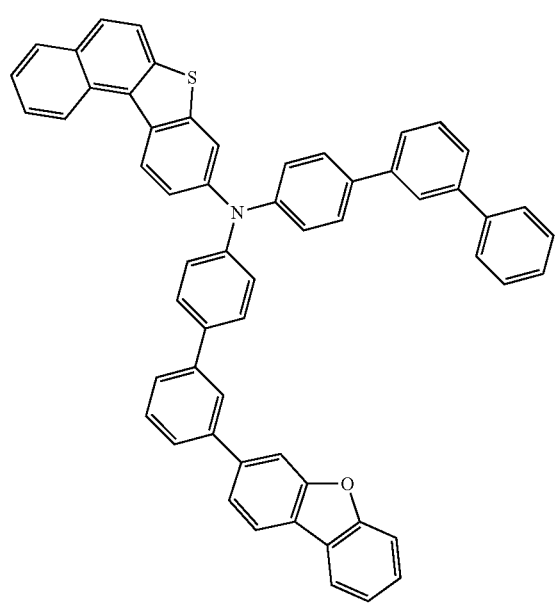
P-112
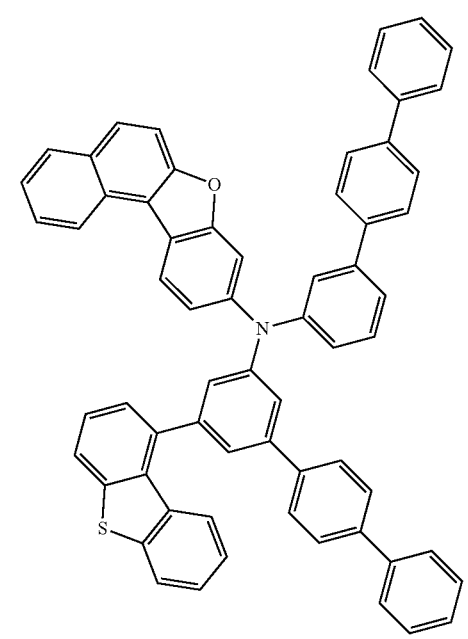

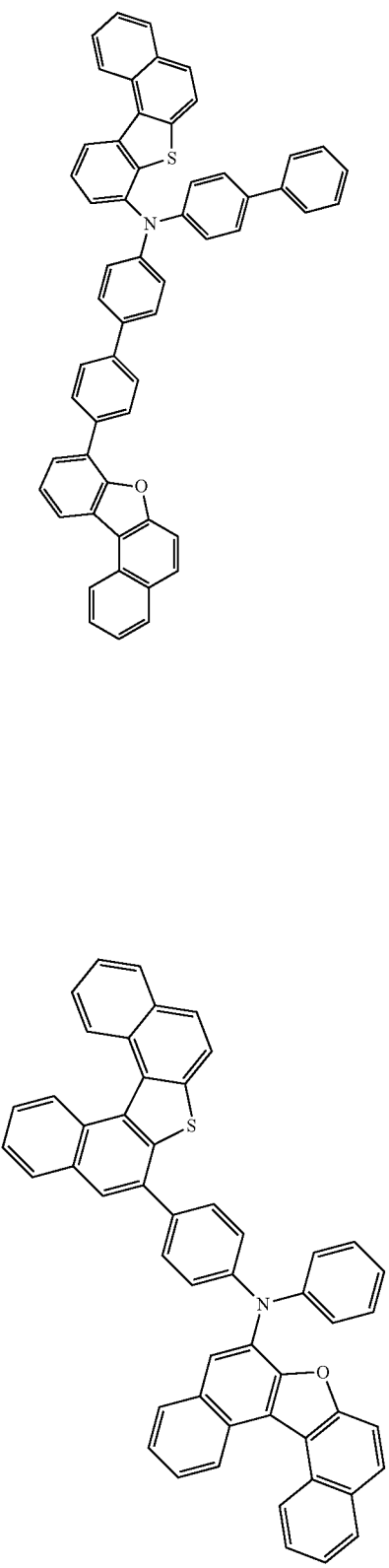
P-113
P-114
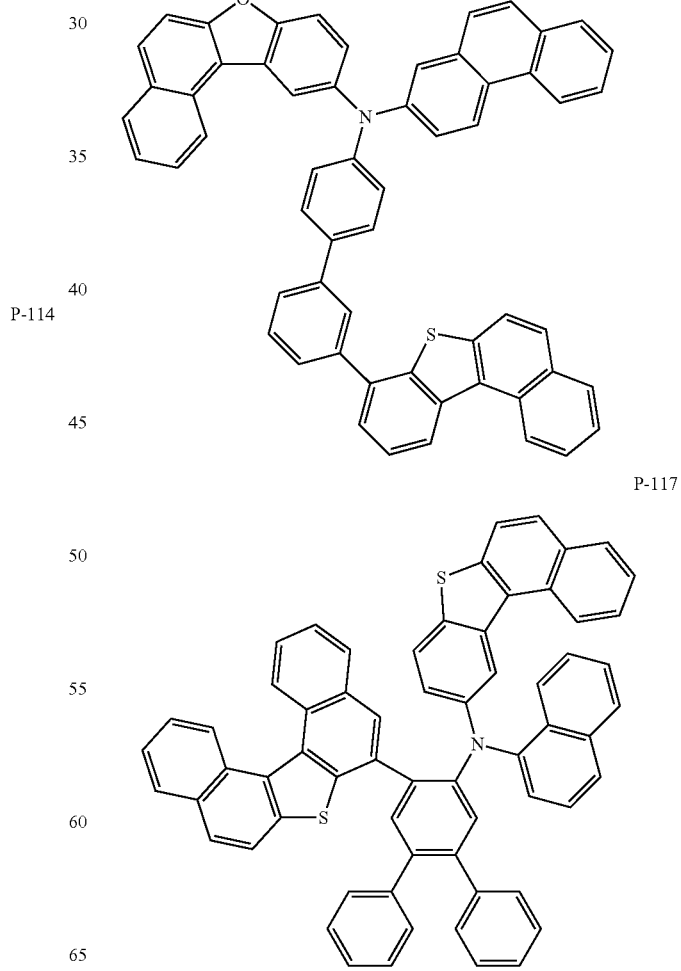
P-115
P-116
P-117

P-118
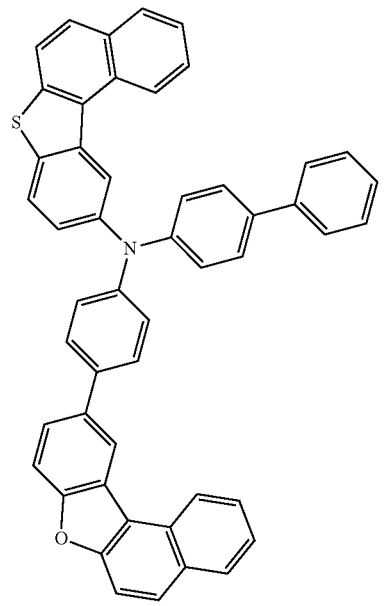
P-120
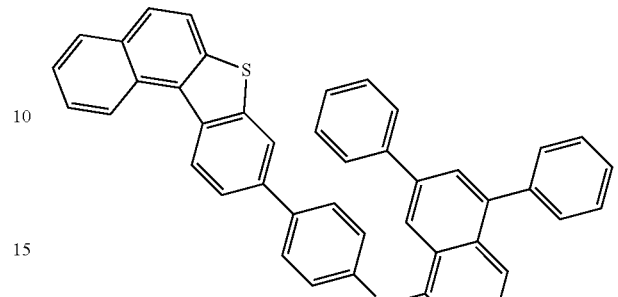
P-119
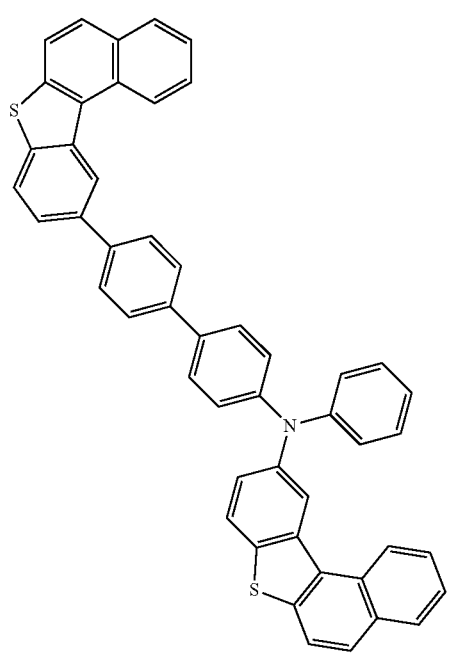
P-121
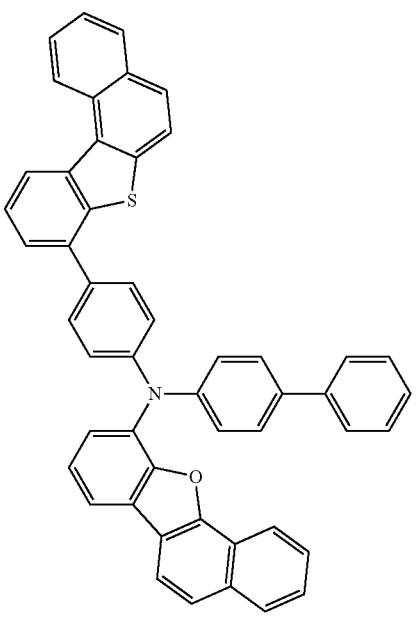

P-122
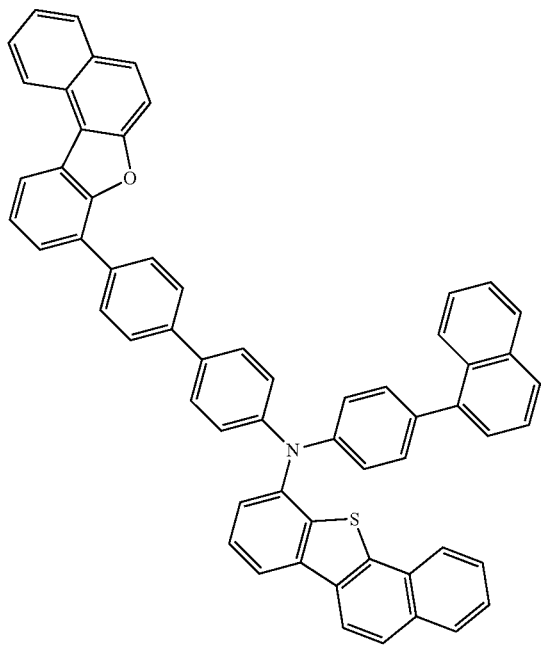
P-123
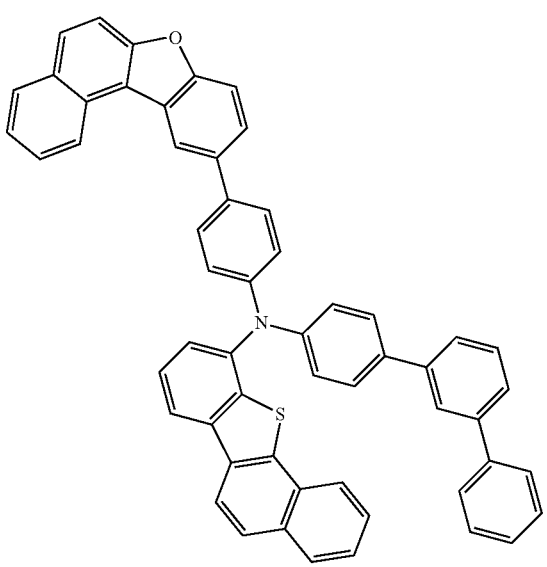
P-124
P-125
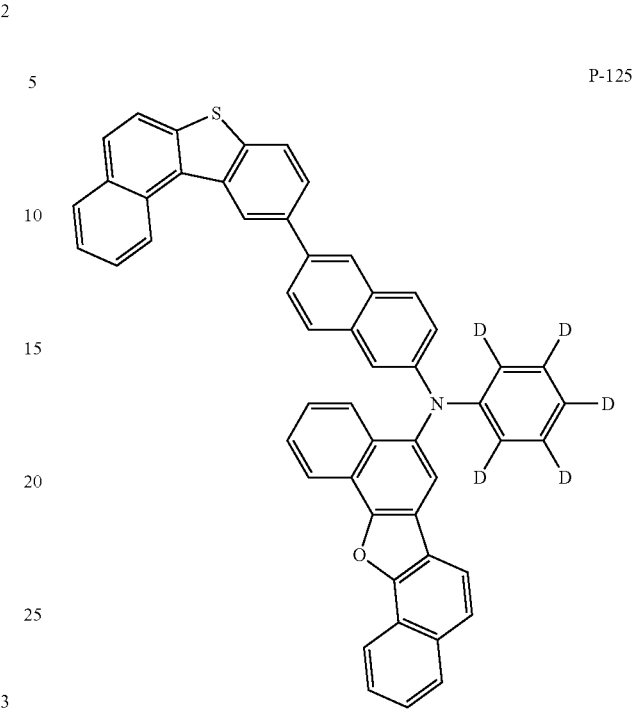
P-126
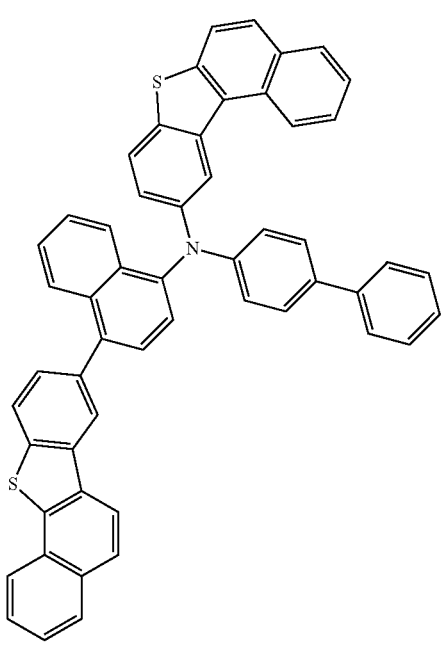

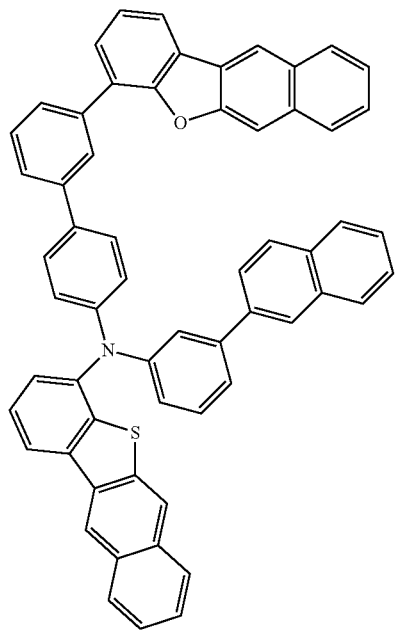
P-127
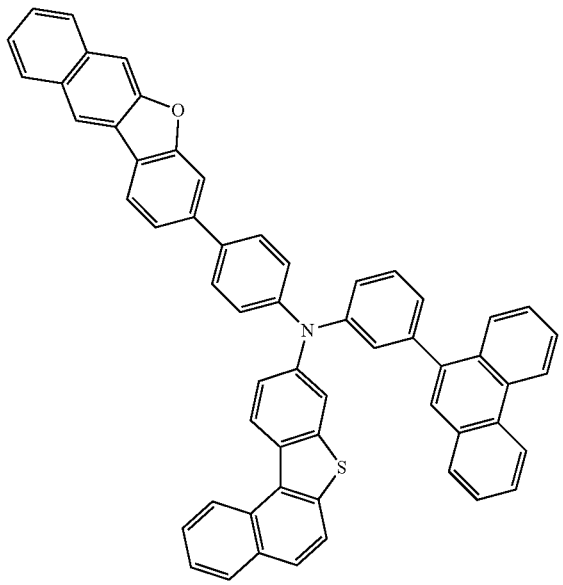
P-129
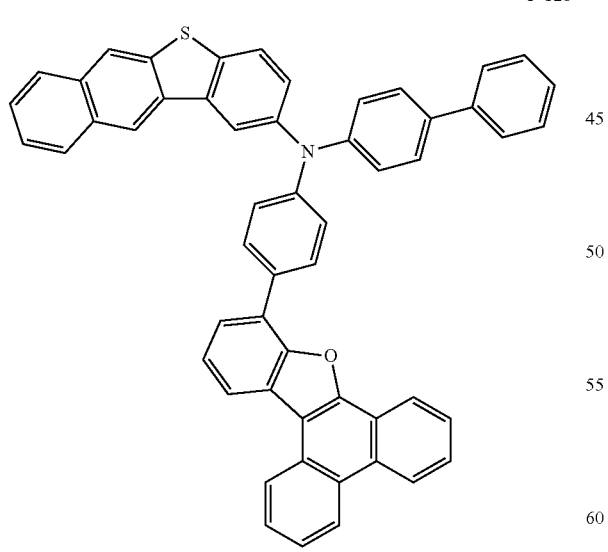
P-128
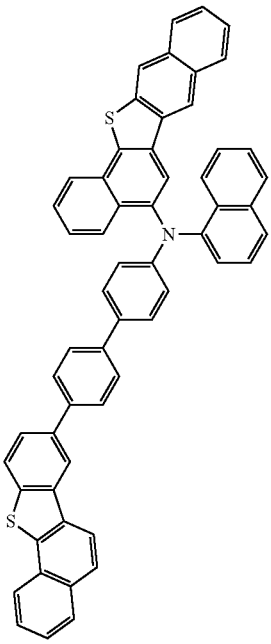
P-130

P-131
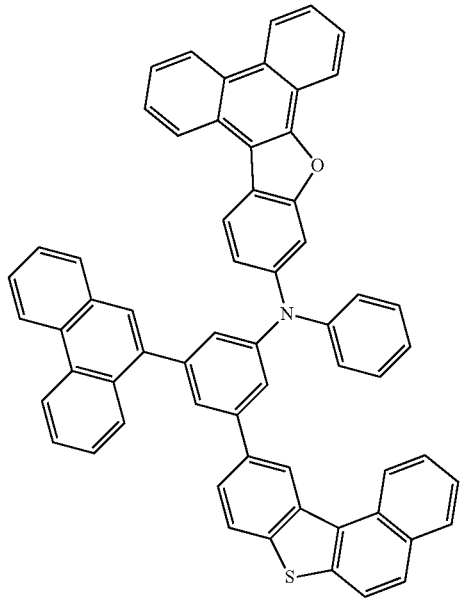
P-132
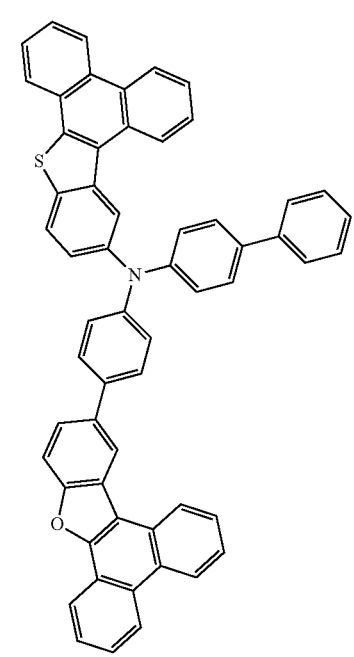
P-133
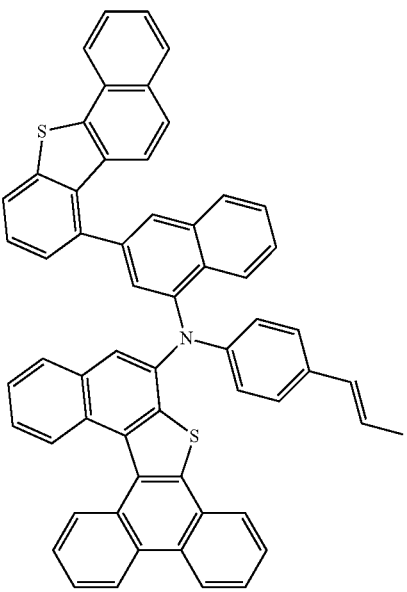
P-134
P-135
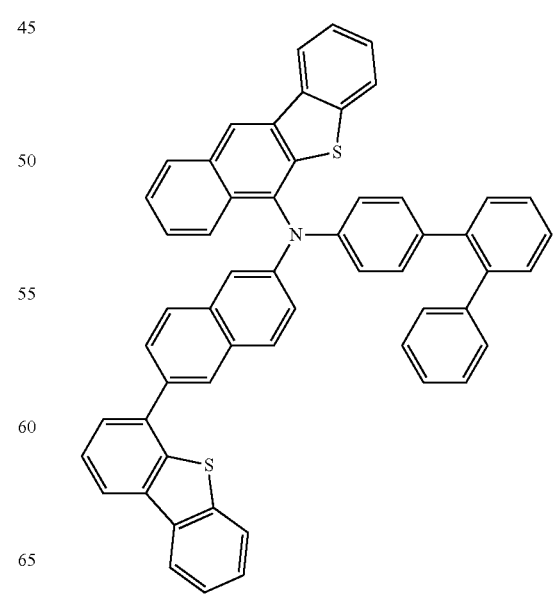

P-136
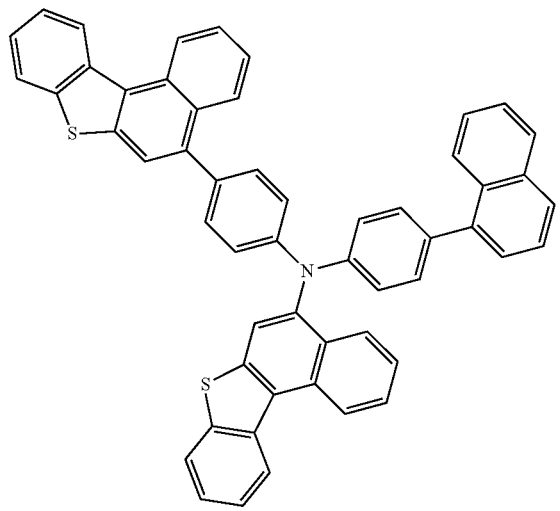
P-137
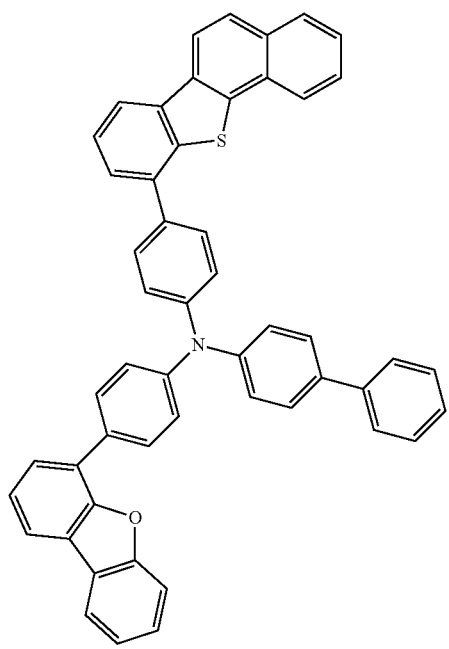
P-138
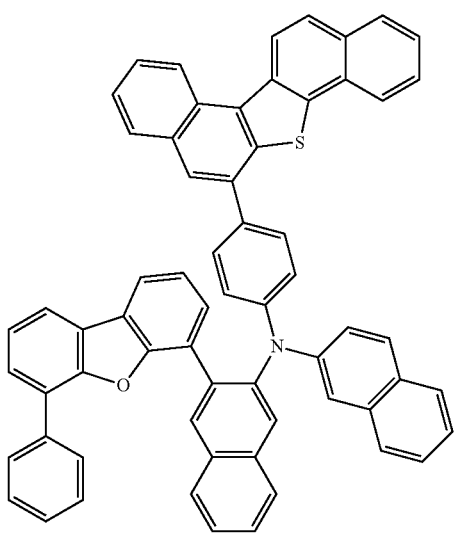
P-139
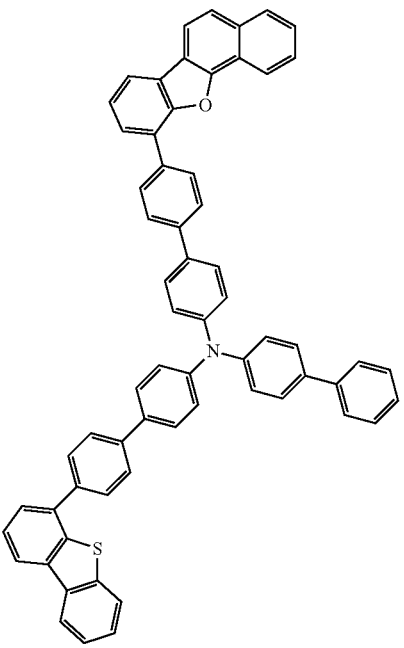

P-140
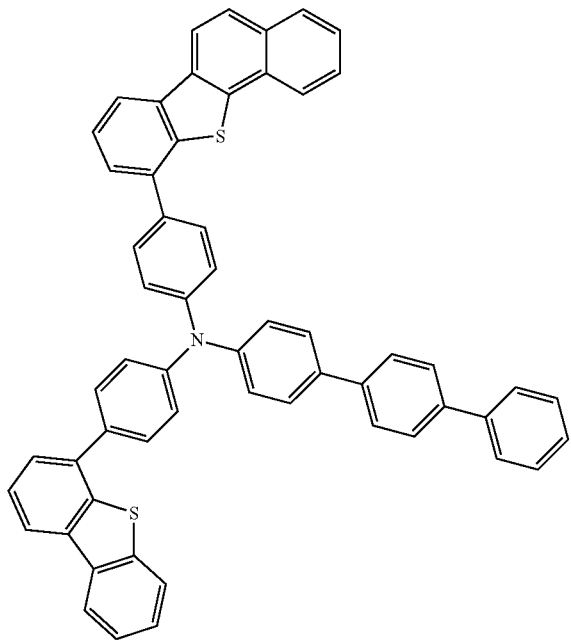
P-142
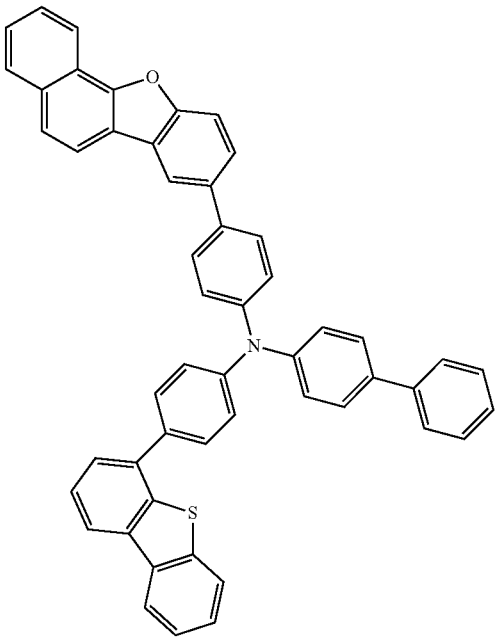
P-141
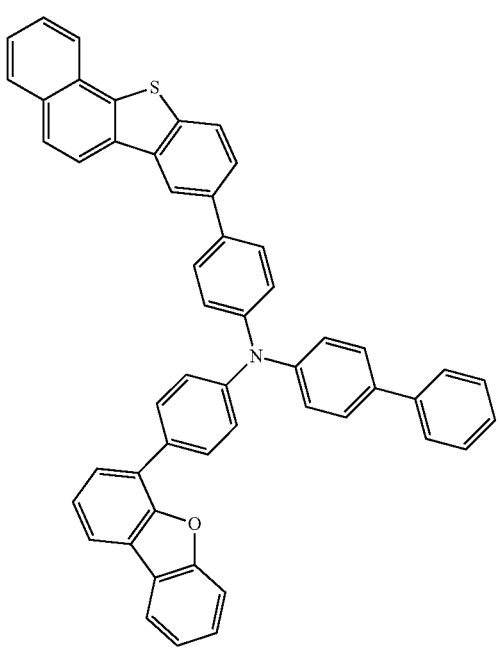
P-143
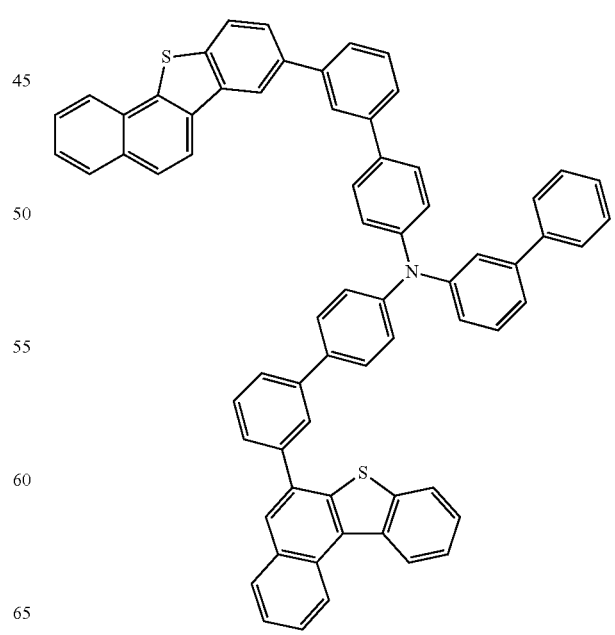

-continued
P-144
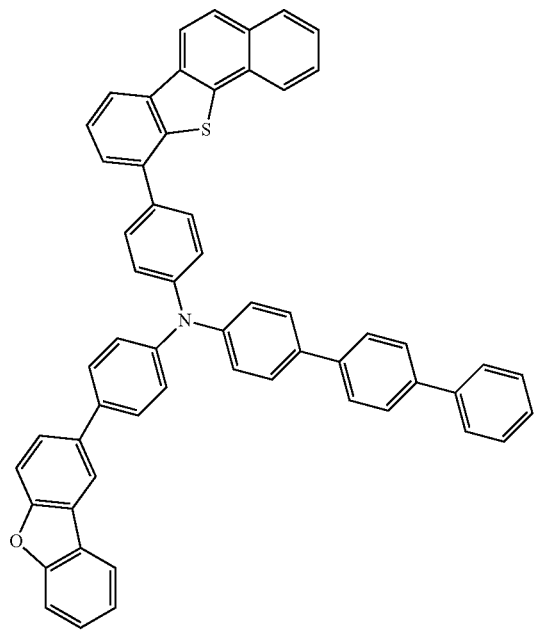
P-146
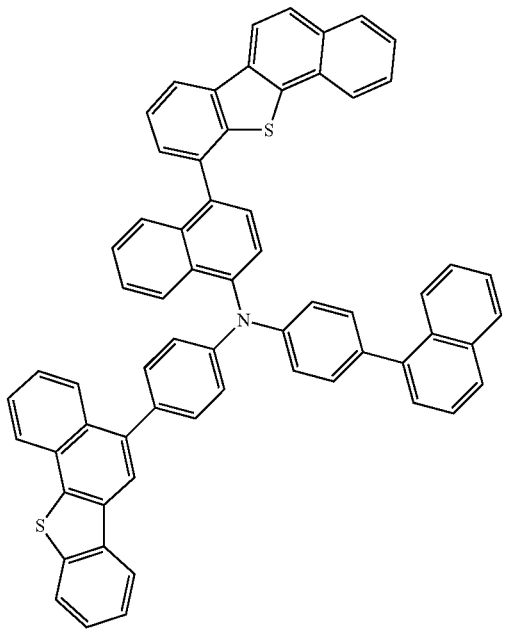
P-145
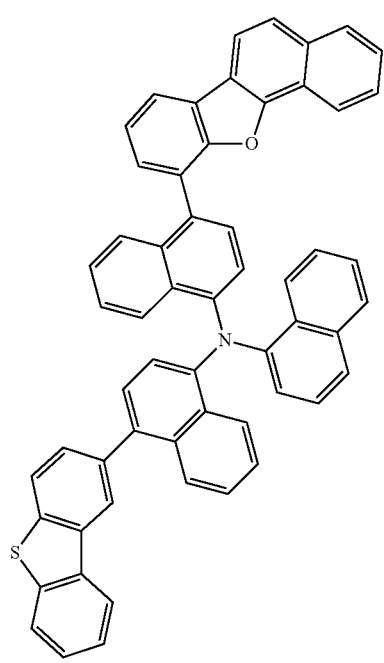
P-147
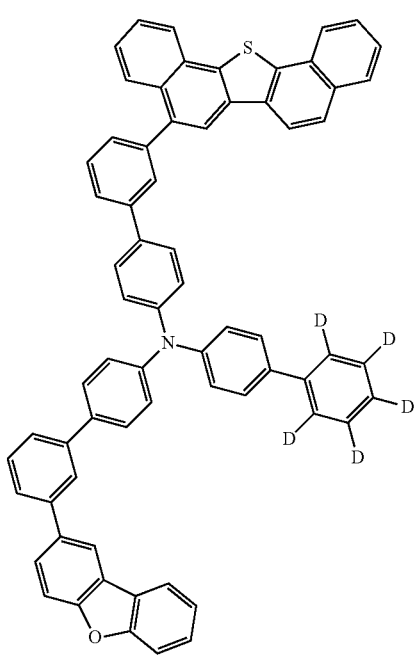

P-148
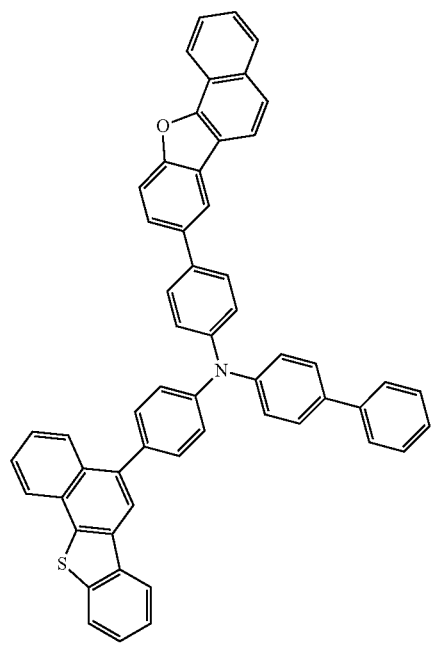
P-150
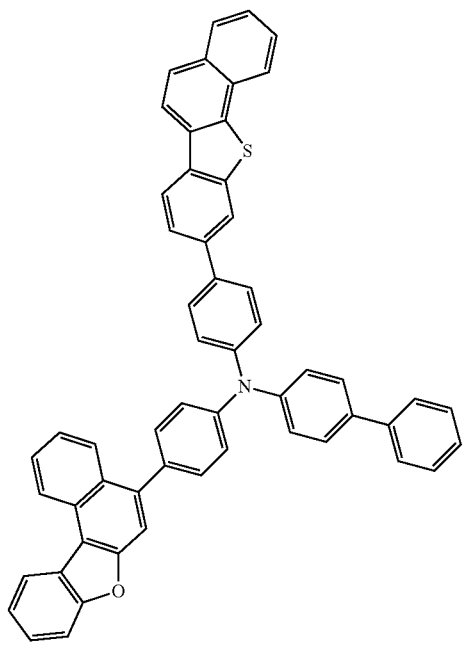
P-149
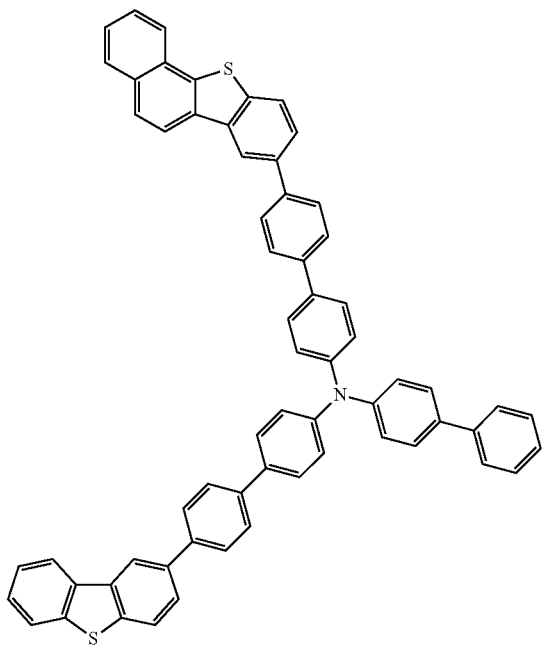
P-151
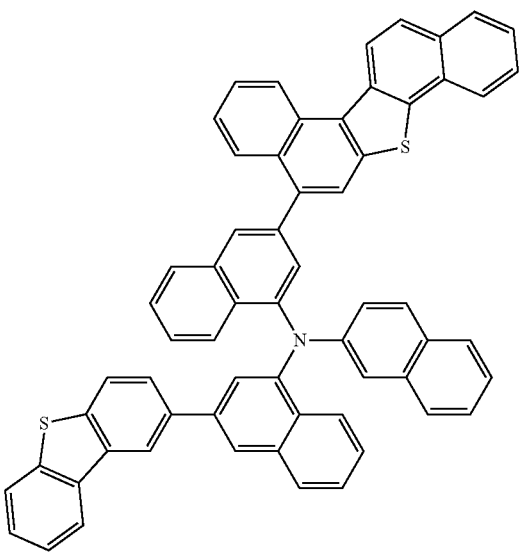

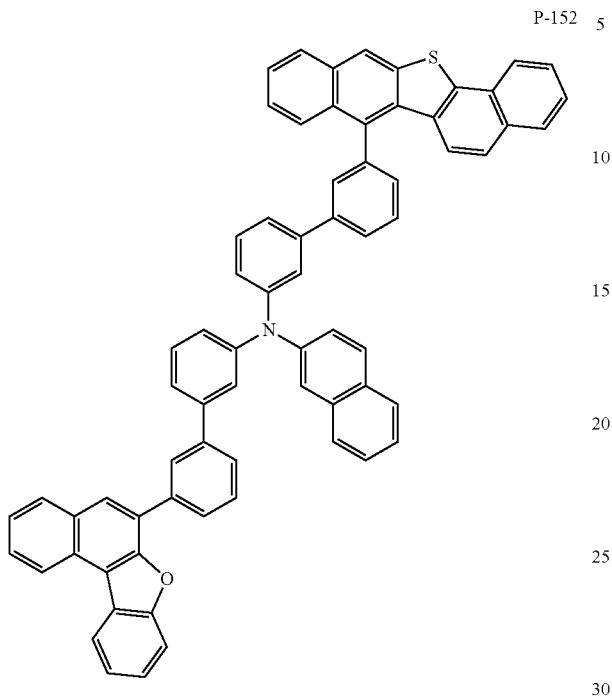
P-152
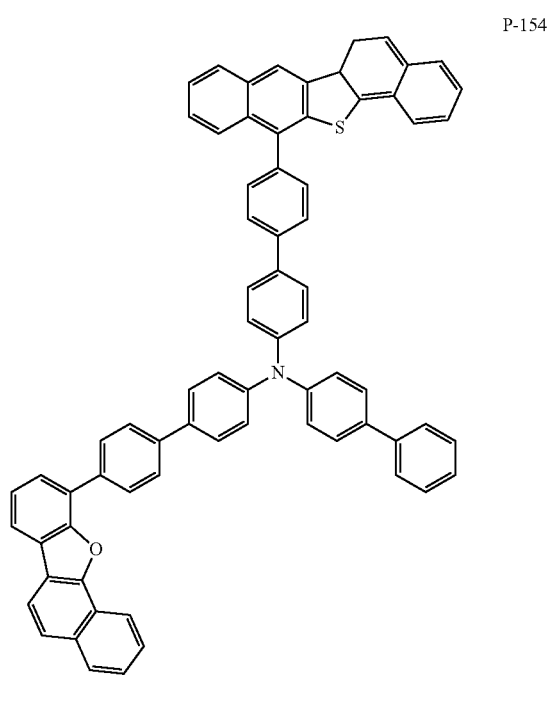
P-154
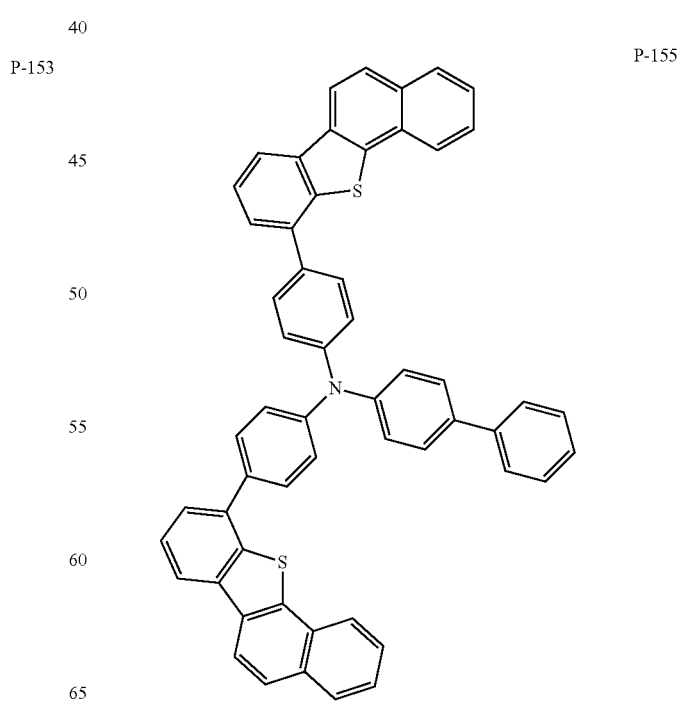
P-153
P-155

P-156 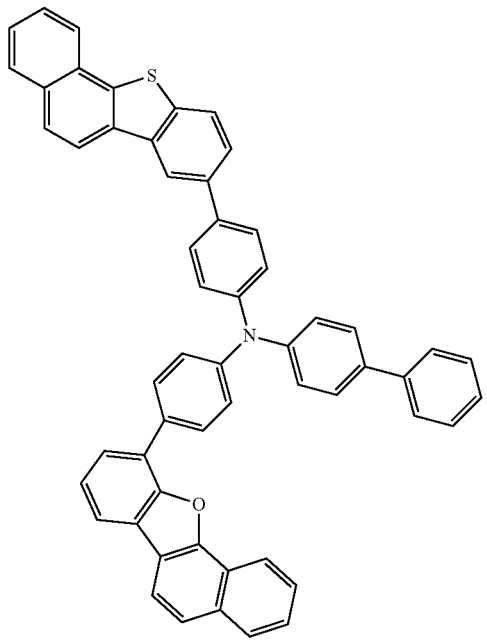
P-158 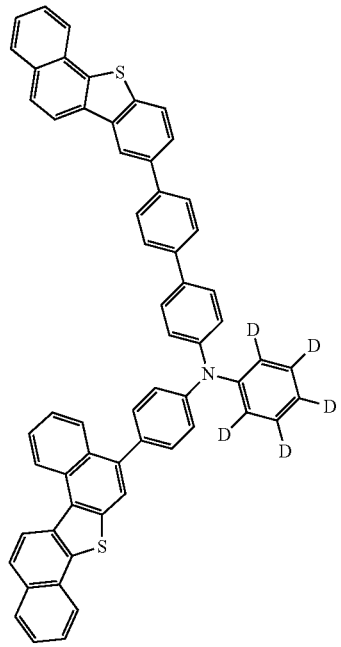
P-157 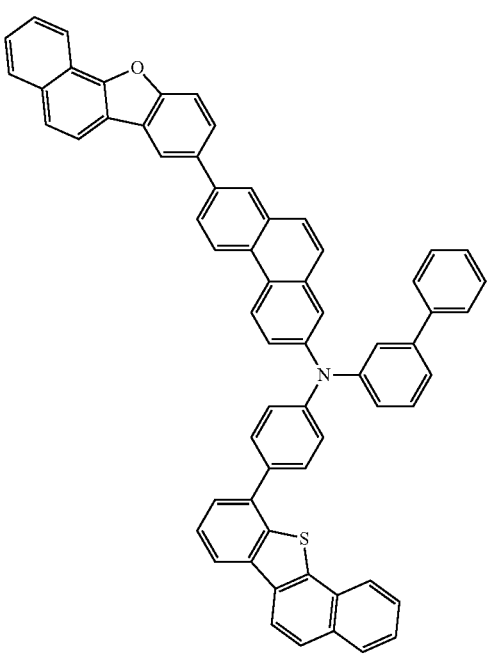
P-159 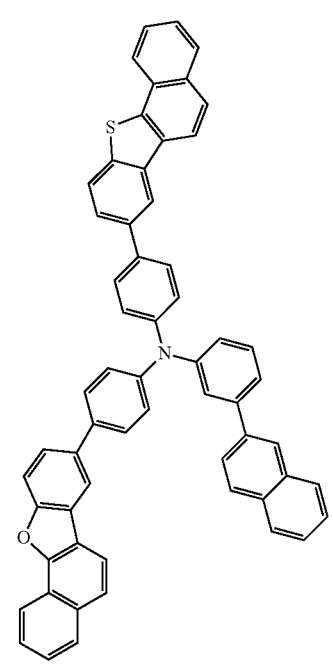

P-160
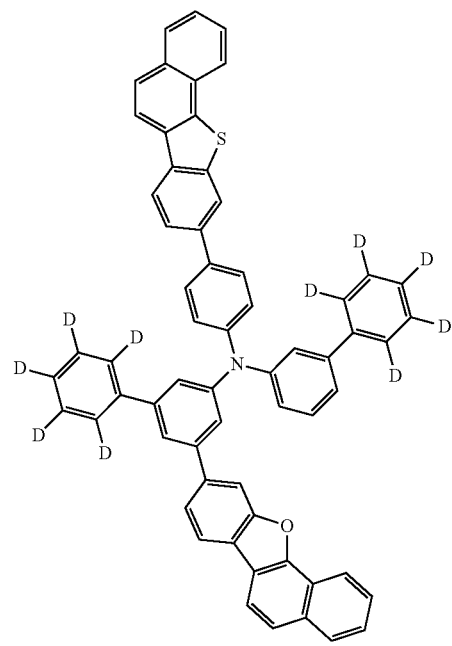
P-162
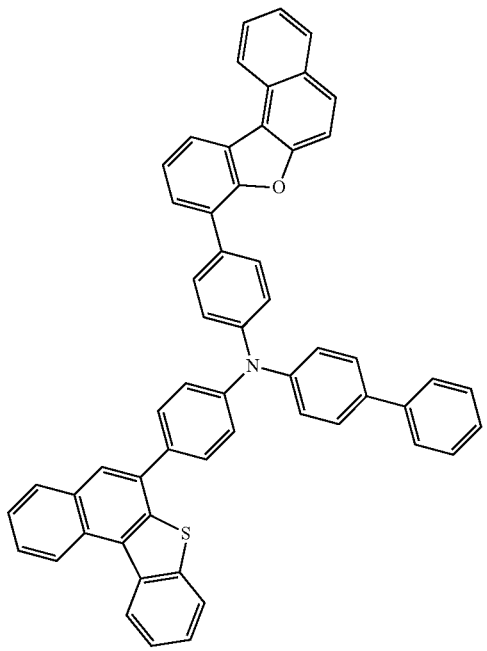
P-161
P-163
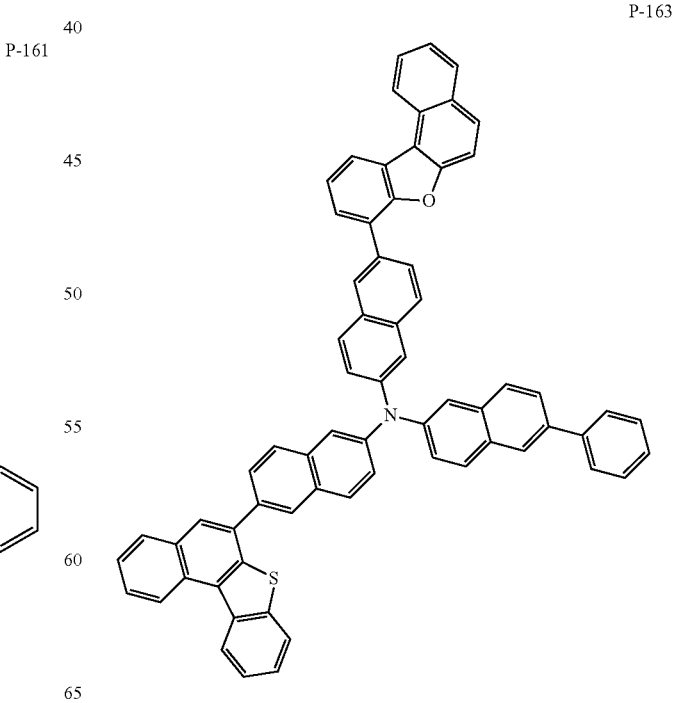

P-164
P-166
P-165
P-167
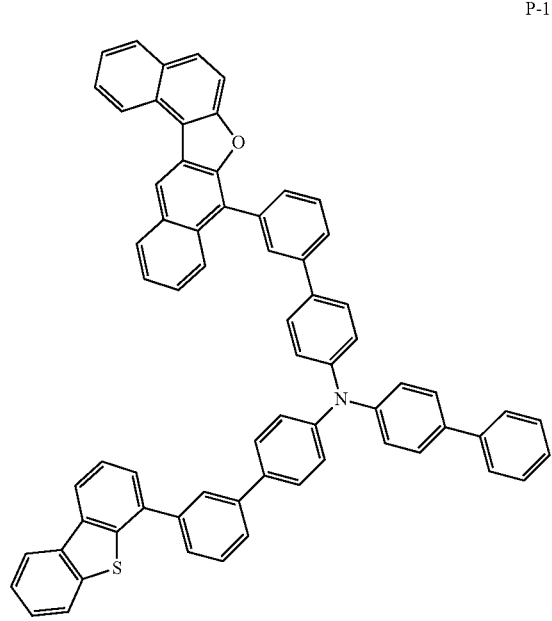
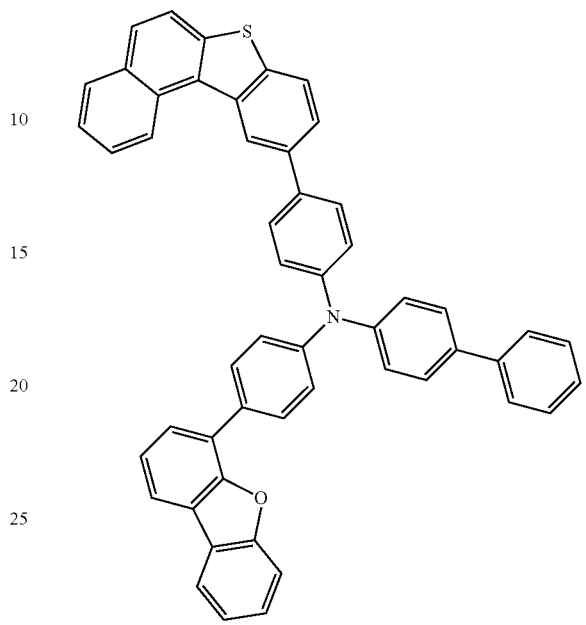
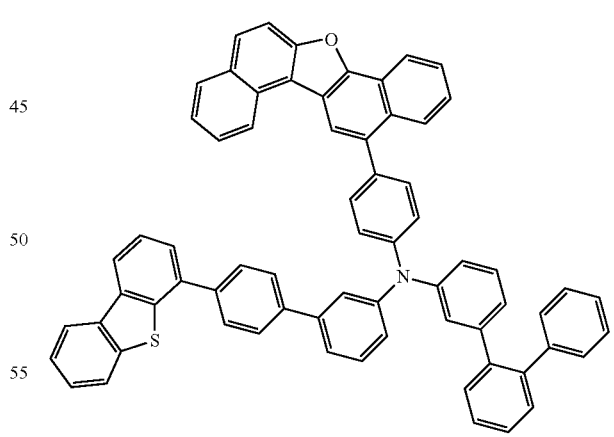

P-168
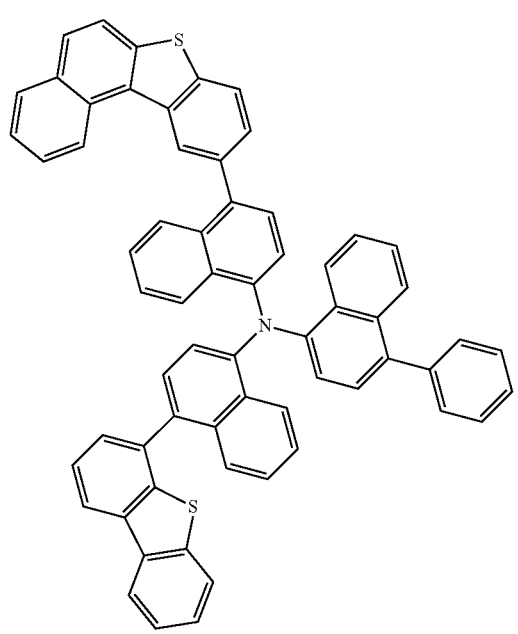
P-170
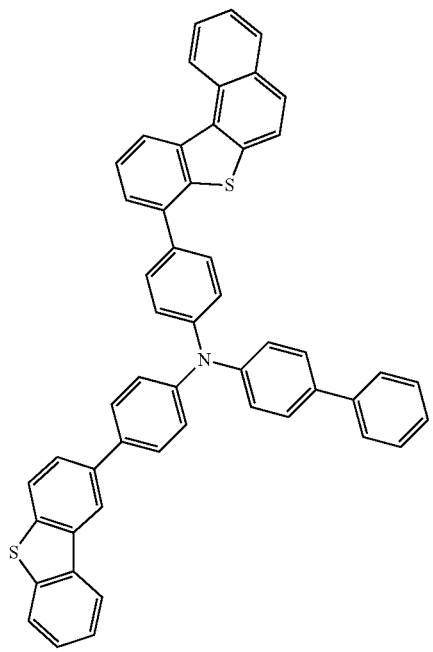
P-169
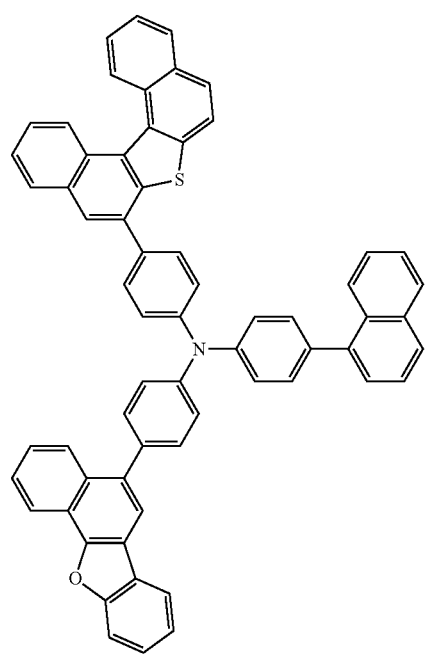
P-171
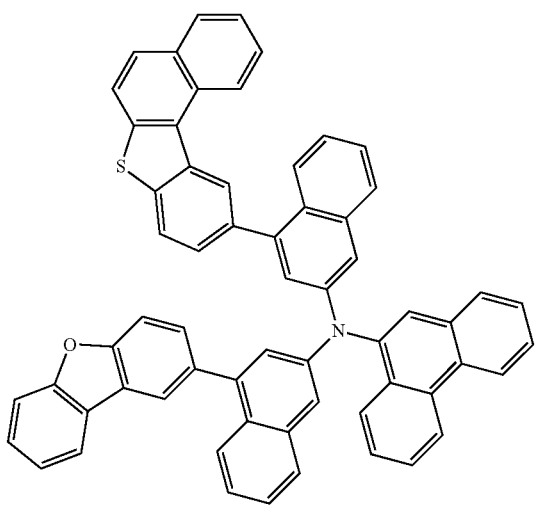

P-172
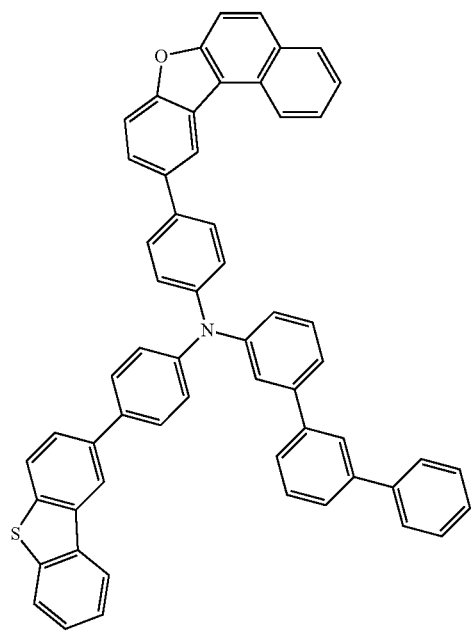
P-173
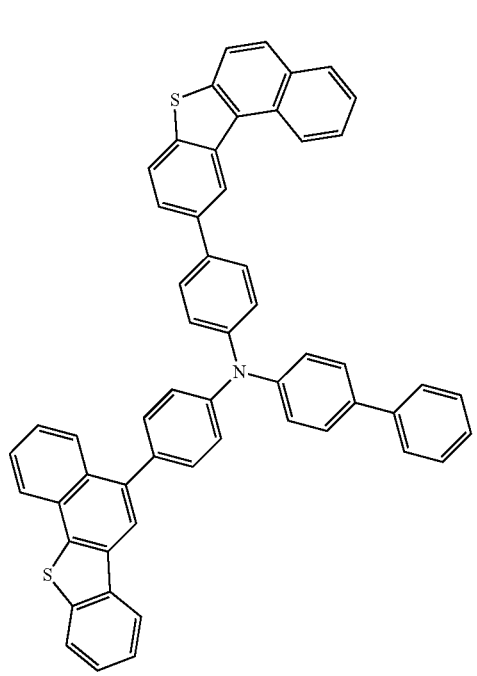
P-174
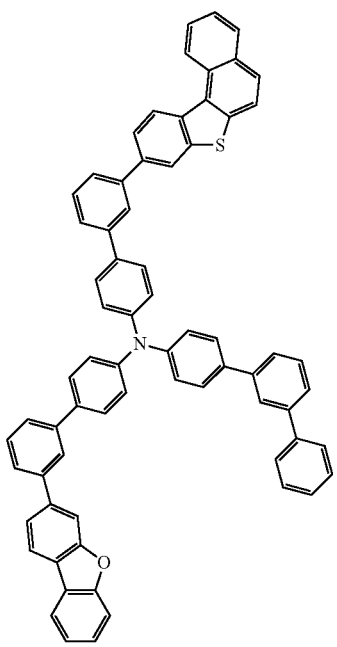
P-175
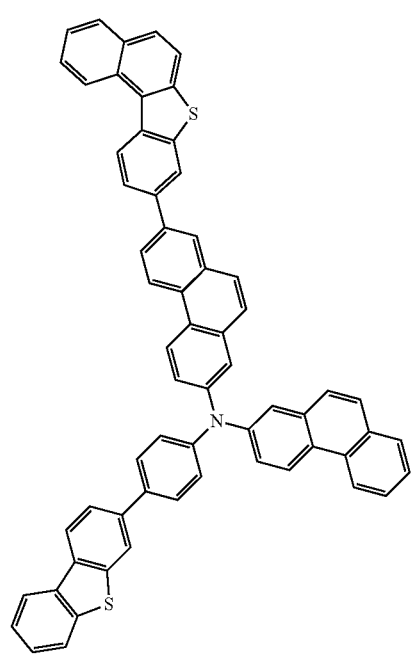

P-176
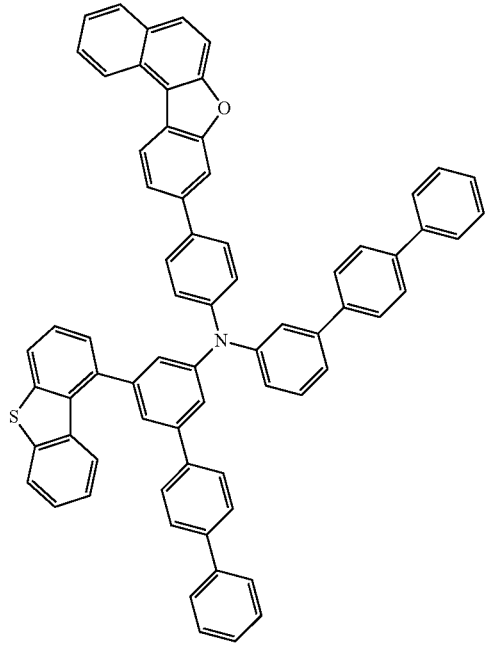
P-178
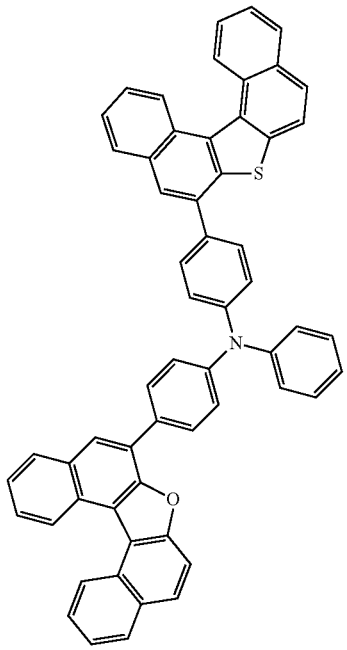
P-177
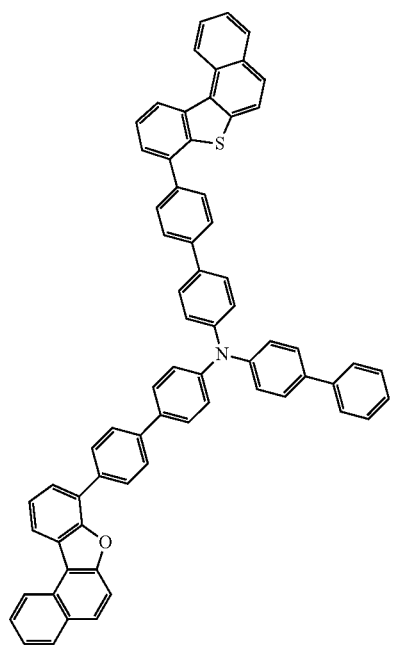
P-179
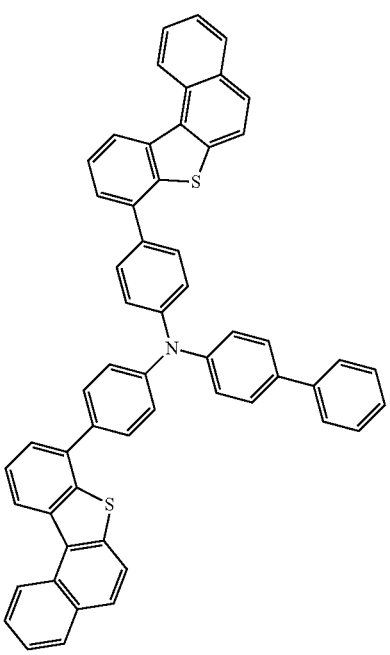

-continued
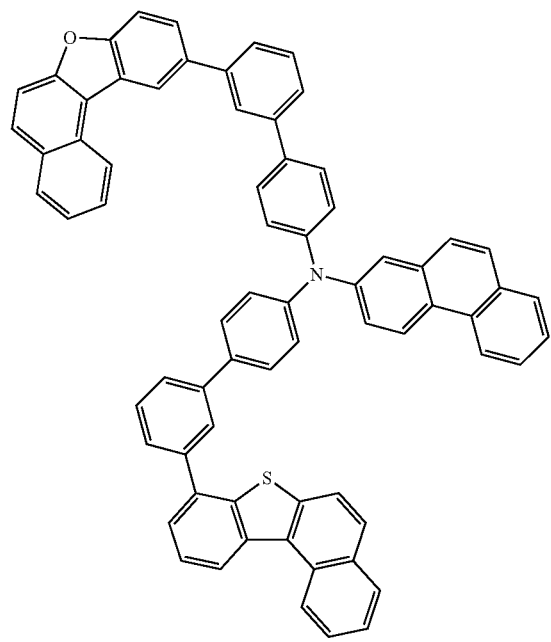
P-180
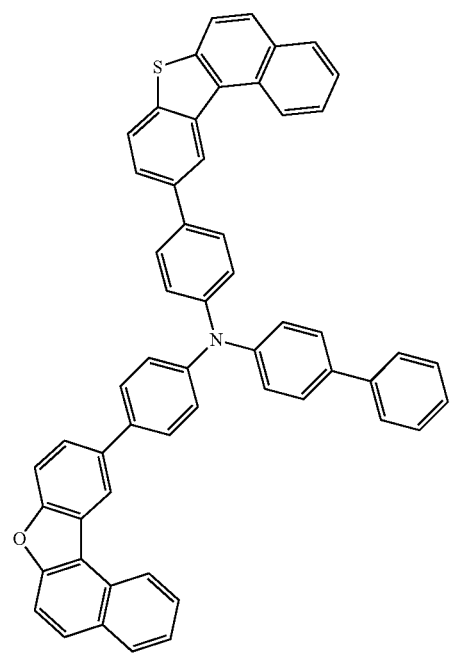
P-182
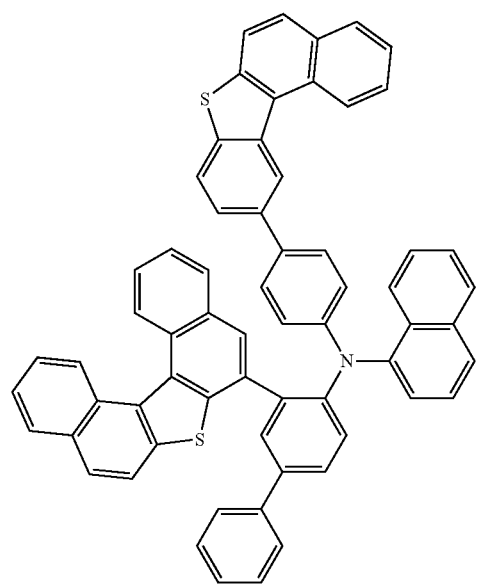
P-181
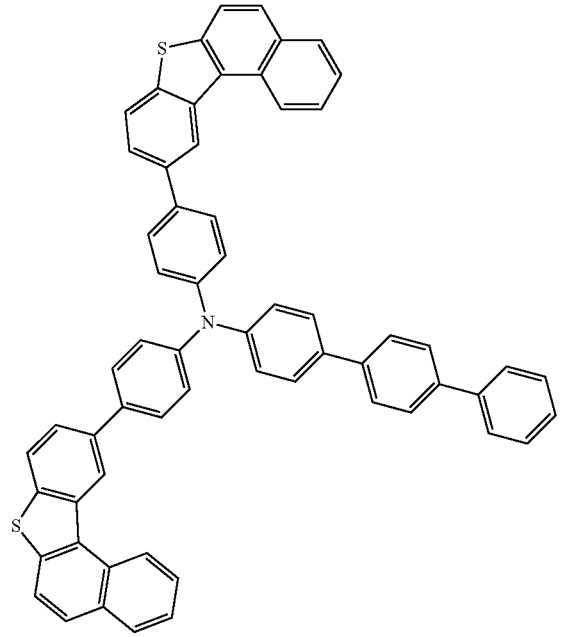
P-183

P-184
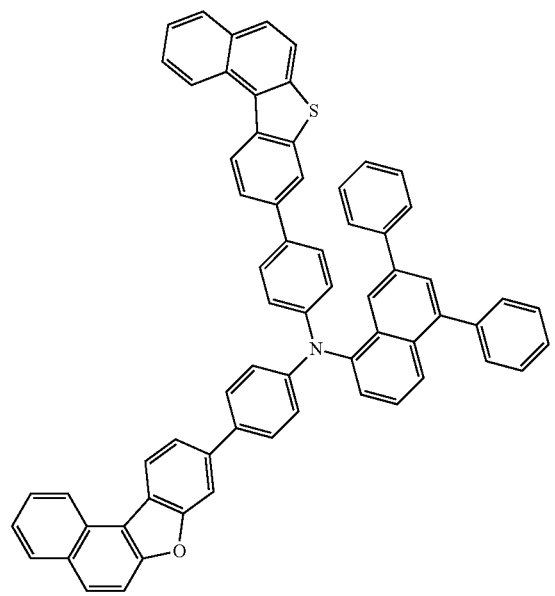
P-185
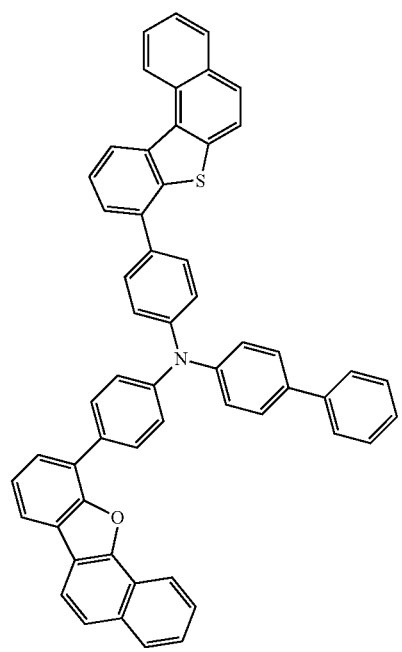
P-186
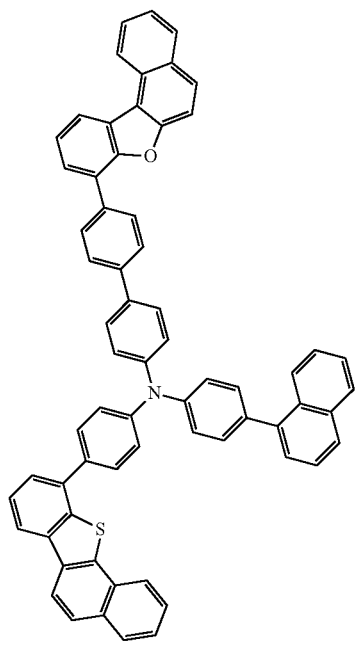
P-187
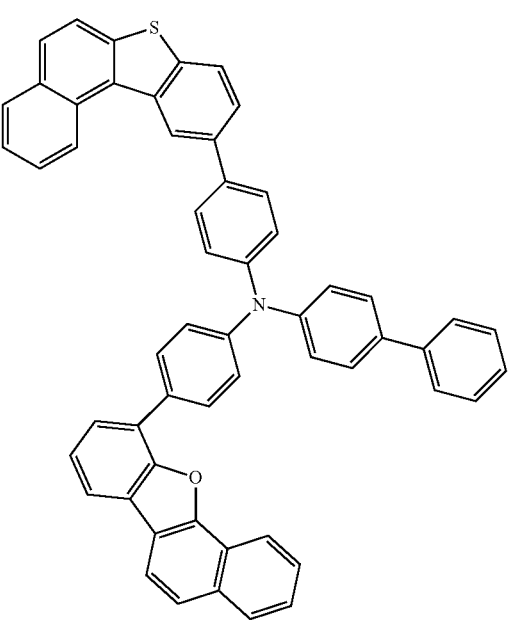

P-188
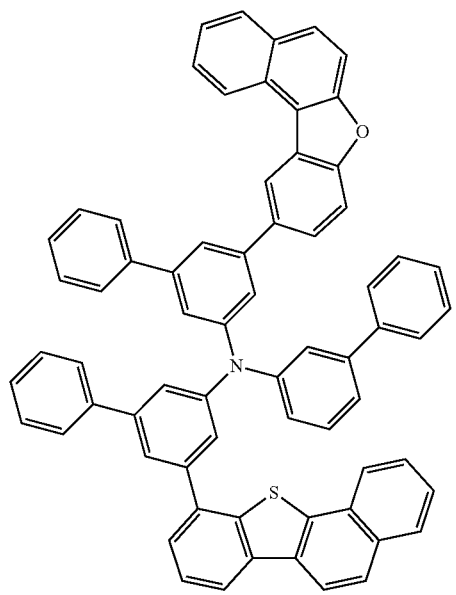
P-190
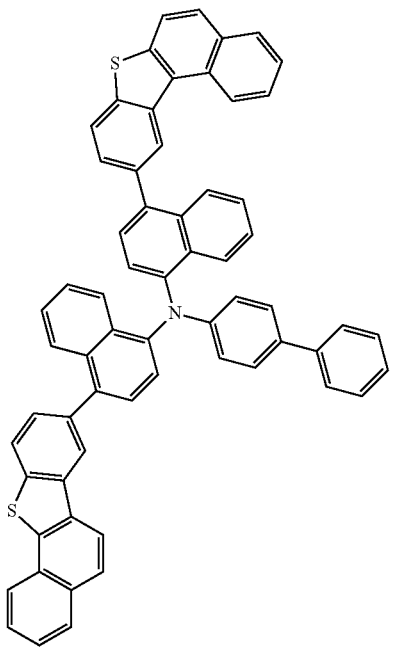
P-189
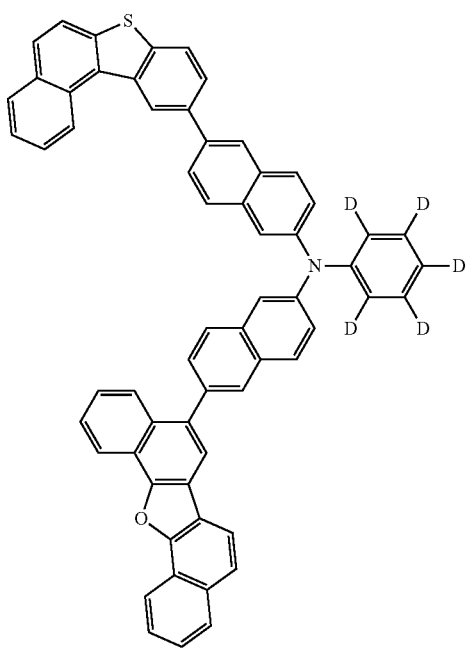
P-191
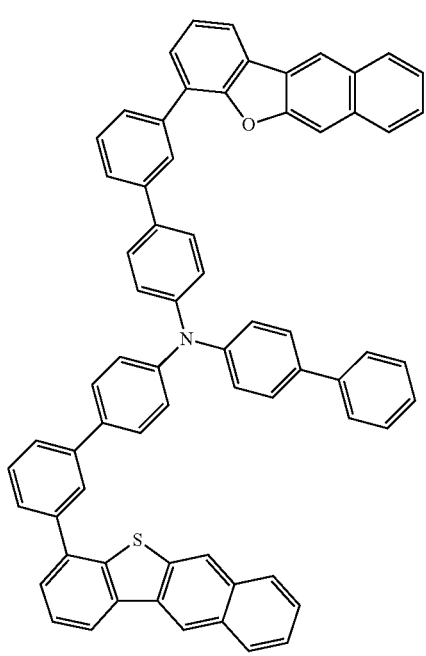

P-192
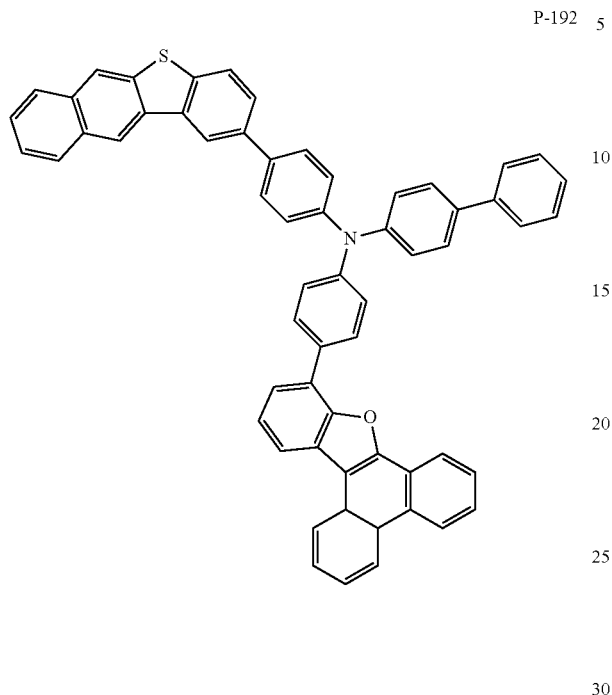
P-193
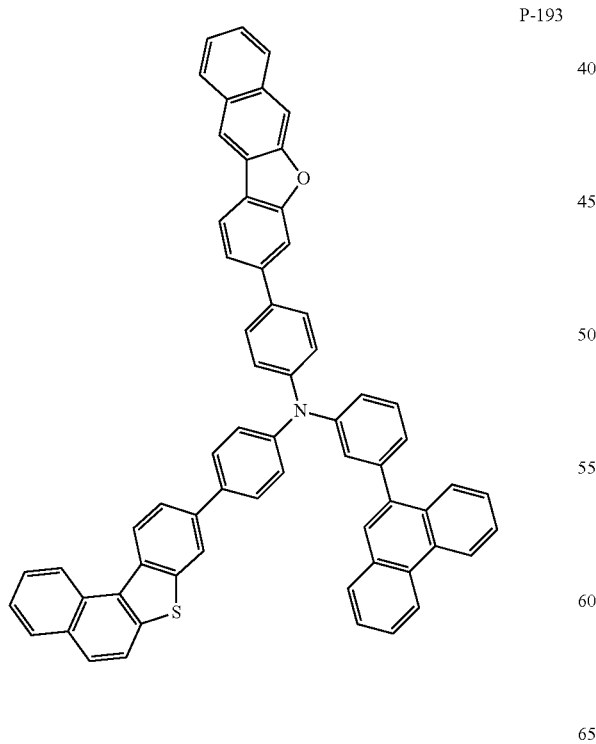
P-194
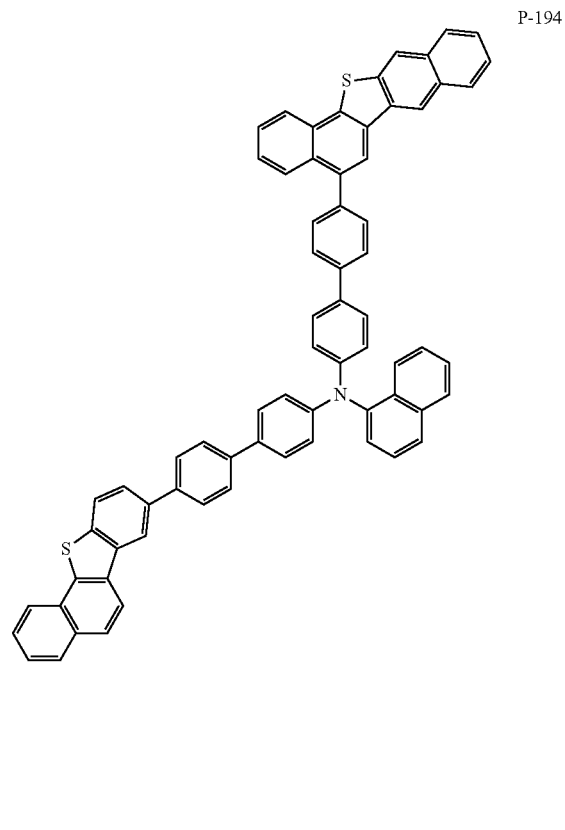
P-195
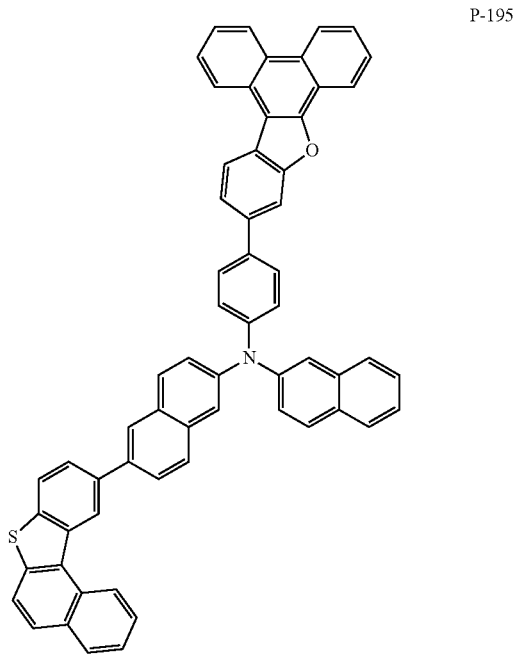

P-196
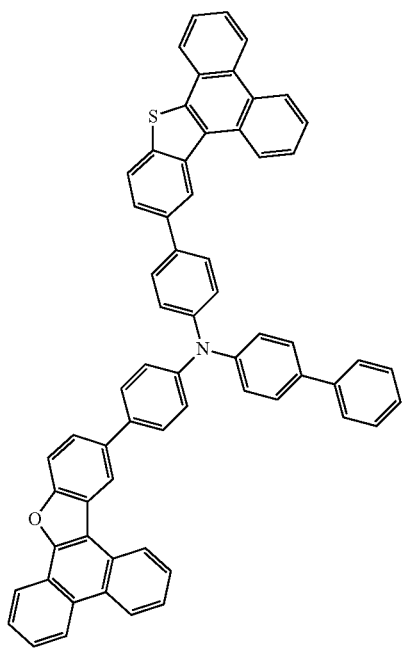
P-197
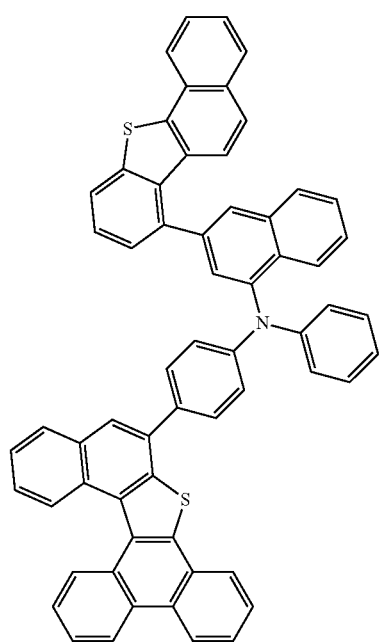
P-198
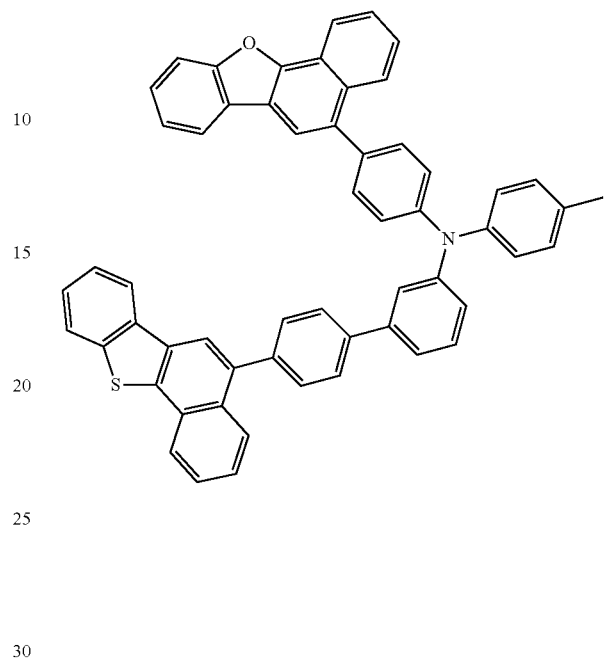
P-199

-continued

P-200

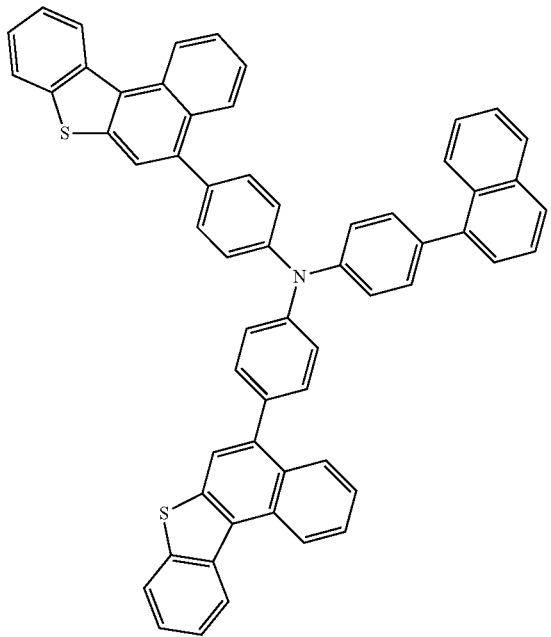

In another aspect of the present invention, there is provided a compound for an organic electric element represented by Formula 1 above.

In another aspect of the present invention, there is provided an organic electric element comprising the compound represented by Formula 1 above.

The organic electric element can comprise a first electrode, a second electrode, and an organic material layer disposed between the first electrode and the second electrode, wherein the organic material layer may comprise the compound represented by Formula 1. The compound by represented Formula 1 may be contained in at least one layer of a hole injection layer, a hole transport layer, an emission-auxiliary layer, and a light emitting layer of the organic material layer. In order words, the compound represented by Formula 1 may be used as materials of a hole injection layer, a hole transport layer, an emission-auxiliary layer, or a light emitting layer. Preferably, there is provided an organic electric element comprising at least one of the compounds represented by Formulas 2 to 16, and more preferably, comprising an organic layer that comprises at least one of the compounds P-1 to P-200.

Preferably, the compounds included in the organic layer may be the same kind or a mixture of two or more different kinds represented by Formula 1. For example, a hole transport layer or/and an emission-auxiliary layer of an organic material layer may be formed as single compound among compounds P-1 to P-200 or a mixture of compounds P-16 and P-36.

In another aspect of the present invention, the present invention provides an organic electric element further including a layer to improve luminescent efficiency which is formed on at least one of the sides the first or second electrodes, which is opposite to the organic material layer.

In another aspect of the present invention, the present invention provides an electronic device including a display device, which includes an organic electric element comprising a compound according to the present invention, and a control unit for controlling the display device. Here, the organic electric element may be any one of an organic light emitting diode, an organic solar cell, an organic photo conductor, an organic transistor, and an element for monochromatic or white illumination.

Hereinafter, Synthesis method of the inventive compound according to one embodiment of the present invention and Preparation method of an organic electric element will be described in detail by way of example. However, the following examples are only for illustrative purposes and are not intended to limit the scope of the present invention.

SYNTHESIS EXAMPLE

The compounds(final products) of the present invention represented by Formula 1 can be synthesized by reaction of Sub and Sub 2 as illustrated in, but not limited to, the following Reaction Scheme 1.

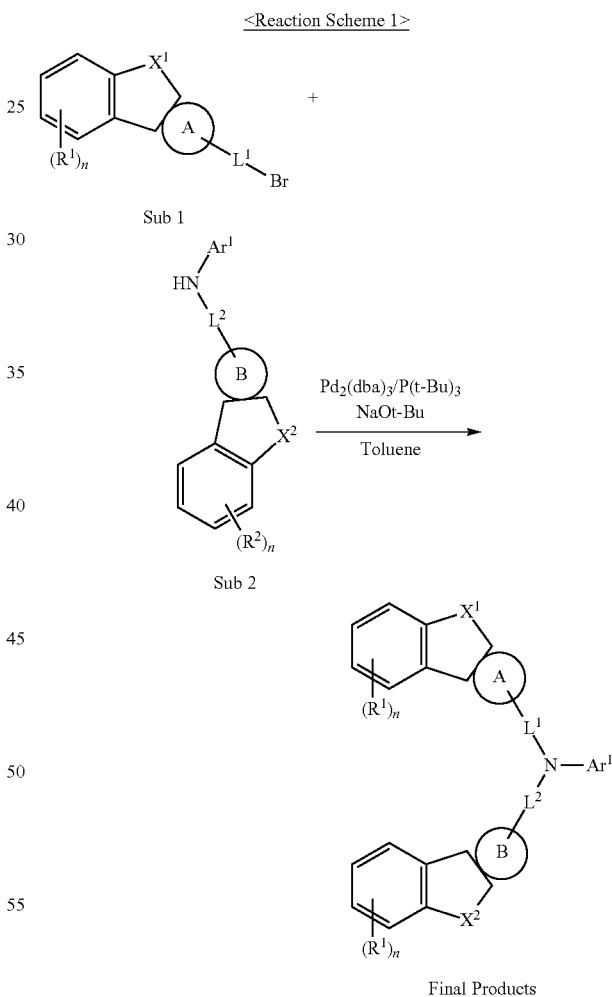

$(X^1, X^2, A \text{ ring}, B \text{ ring}, Ar^1, L^1, L^2, R^1, R^2, m \text{ and } n$ are each the same as defined in Formula 1 above.)

I. Synthesis of Sub 1

Compound Sub 1 of Reaction Scheme 1 can be synthesized, but not limited to, by any one reaction of the following Reaction Schemes 2 to 4.

<Reaction Scheme 2>

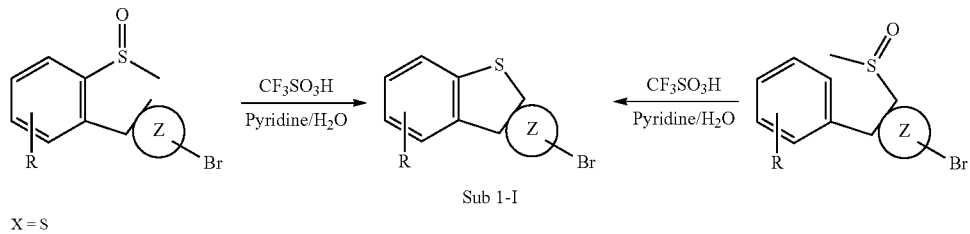

<Reaction Scheme 3>

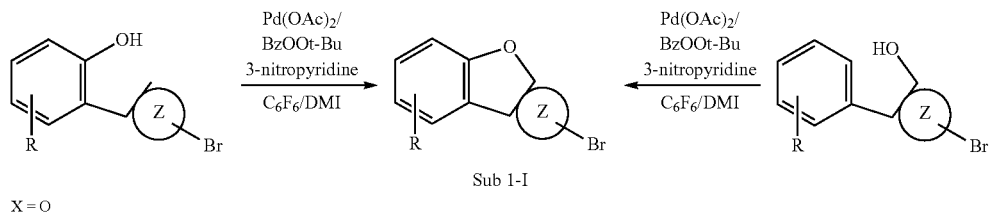

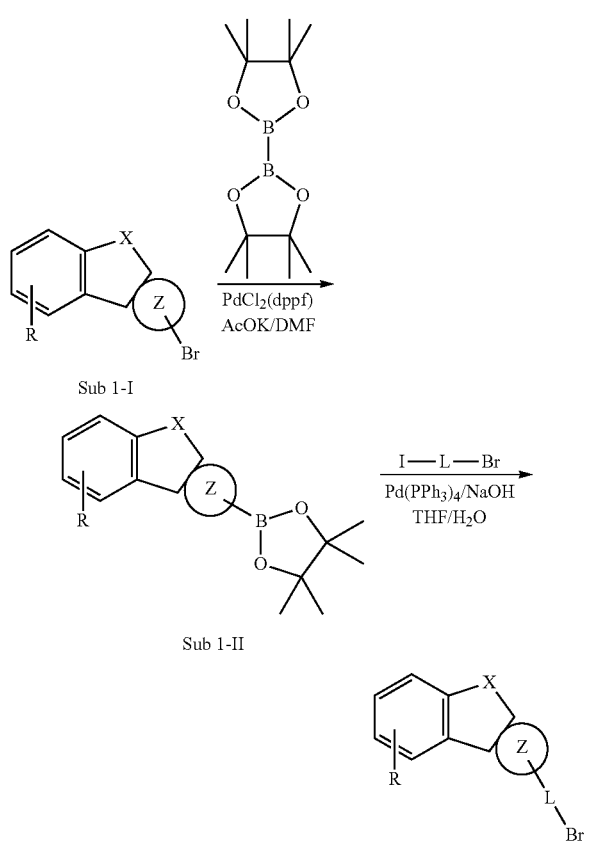

In Reaction Schemes 2 to 4, R corresponds to $(R^1)_m$ or $(R^2)_n$ of Formula 1, X corresponds to $X^1$ or $X^2$ of Formula 1, L corresponds to $L^1$ or $L^2$ of Formula 1, and Z ring corresponds to A ring or B ring of Formula 1.

Synthesis Examples of compounds comprised in Sub 1 are as followings.

1. Synthesis Example of Sub 1-10

<Reaction Scheme 5>

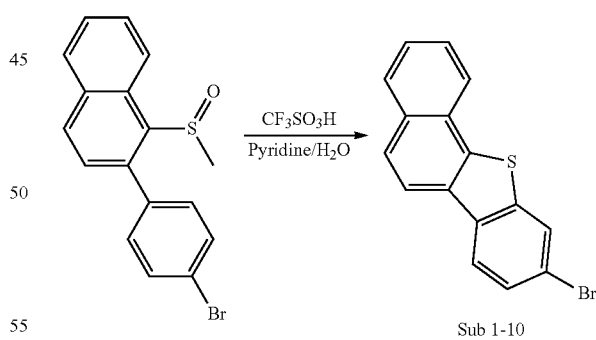

2-(4-bromophenyl)-1-(methylsulfinyl)naphthalene (35.08 g, 101.6 mmol) as a starting material and triflic acid (134.9 ml, 1524.1 mmol) were loaded into a round bottom flask and then stirred at room temperature for 24 hours, followed by adding dropwise pyridine(aq) (1780 ml, pyridine: H2O=1:5) slowly and refluxing and stirring for 30 minutes. Upon the completion of the reaction, the reaction product was extracted with $CH_2Cl_2$ and washed with water. After that, the extracted organic layer was dried with $MgSO_4$ and then concentrated. The concentrated resultant was separated by silica gel column chromatography, and was then recrystallized, whereby a final product was obtained in the amount of 27.05 g in 85% yield.

2. Synthesis Example of Sub 1-16

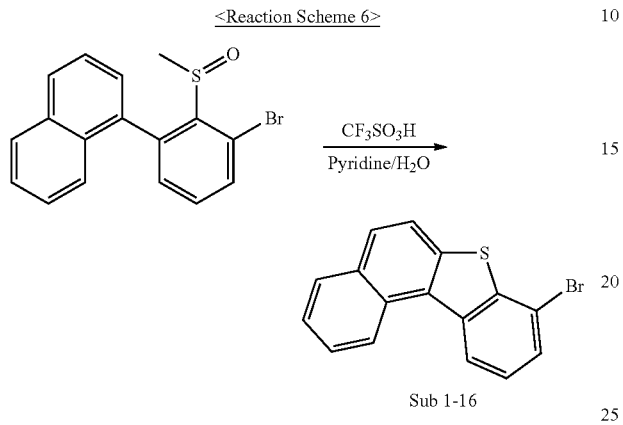

Sub 1-16

Product was obtained in the amount of 57.88 g (yield: 83%) where 1-(3-bromo-2-(methylsulfinyl)phenyl)naphthalene (76.87 g, 222.7 mmol) as a starting material, triflic acid (295.5 ml, 3339.8 mmol) and pyridine(aq) (3900 ml, pyridine:H$_2$O=1:5) were used in the same manner as described above for the synthesis of compound Sub 1-10.

3. Synthesis Example of Sub 1-25

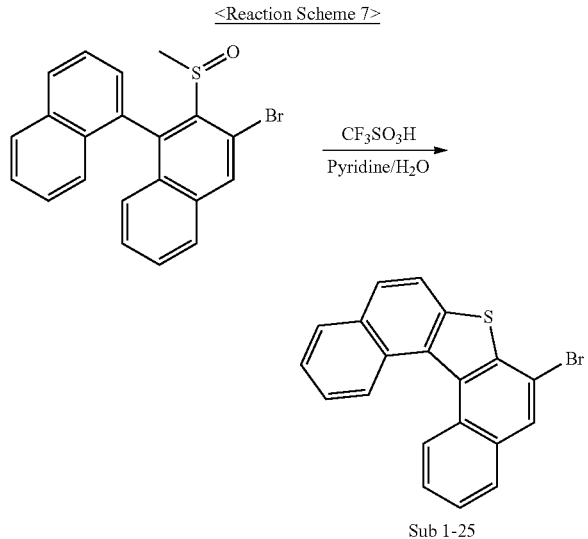

Sub 1-25

Product was obtained in the amount of 42.38 g (yield: 73%) where 3-bromo-2-(methylsulfinyl)-1,1'-binaphthalene (63.18 g, 159.8 mmol) as a starting material, triflic acid (212 ml, 2397.4 mmol) and pyridine(aq) (2800 ml, pyridine:H$_2$O=1:5) were used in the same manner as described above for the synthesis of compound Sub 1-10.

4. Synthesis Example of Sub 1-31

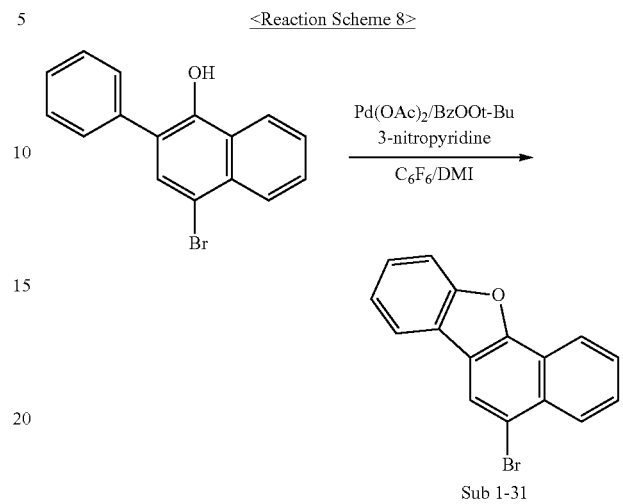

Sub 1-31

4-bromo-2-phenylnaphthalen-1-ol (68.13 g, 227.7 mmol) as a starting material, Pd(OAc)$_2$ (5.11 g, 22.8 mmol) and 3-nitropyridine (2.83 g, 22.8 mmol) were loaded into a round bottom flask and were dissolved in C$_6$F$_6$ (345 ml) and DMI (230 ml), followed by adding tert-butyl peroxybenzoate (88.47 g, 455.5 mmol) and then stirring at 90° C. Upon the completion of the reaction, the reaction product was extracted with CH$_2$Cl$_2$ and washed with water. After that, the extracted organic layer was dried with MgSO$_4$ and then concentrated. The concentrated resultant was separated by silica gel column chromatography, and was then recrystallized, whereby final product was obtained in the amount of 30.45 g (yield: 45%).

5. Synthesis Example of Sub 1-33

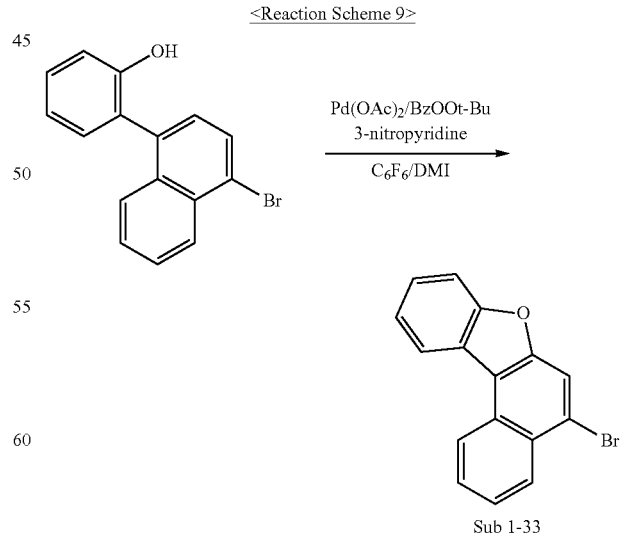

Sub 1-33

Product was obtained in the amount of 21.81 g (yield: 48%) where 2-(4-bromonaphthalen-1-yl)phenol (45.74 g, 152.9 mmol) as a starting material, Pd(OAc)$_2$ (3.43 g, 15.3 mmol), 3-nitropyridine (1.9 g, 15.3 mmol), tert-butyl peroxybenzoate (59.39 g, 305.8 mmol), C$_6$F$_6$ (225 ml) and DMI (150 ml) were used in the same manner as described above for the synthesis of compound Sub 1-31.

6. Synthesis Example of Sub 1-67

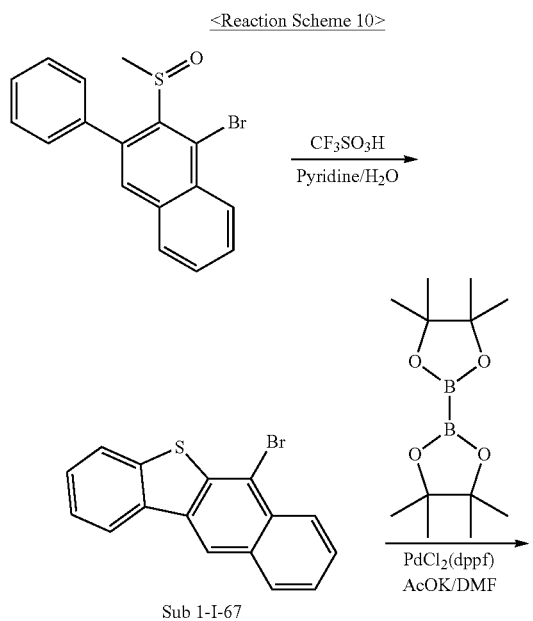

(1) Synthesis of Sub 1-I-67

Product was obtained in the amount of 8.92 g (yield: 78%) where 1-bromo-2-(methylsulfinyl)-3-phenylnaphthalene (12.61 g, 36.5 mmol) a starting material, triflic acid (48.5 ml, 547.9 mmol) and pyridine(aq) (640 ml, pyridine:H$_2$O=1:5) were used in the same manner as described above for the synthesis of compound Sub 1-10.

(2) Synthesis of Sub 1-II-67

Sub 1-I-67 (8.92 g, 28.5 mmol) in a round bottom flask was dissolved in DMF (140 ml), followed by adding Bis (pinacolato)diboron (7.96 g, 31.3 mmol), Pd(dppf)Cl$_2$ (0.7 g, 0.9 mmol) and KOAc (8.38 g, 85.4 mmol) and then stirring at 90° C. after. After the completion of the reaction, DMF was removed by distillation and the distillated product was extracted with CH$_2$Cl$_2$ and water. After that, the extracted organic layer was dried with MgSO$_4$ and then concentrated. The concentrated resultant was separated by silica gel column chromatography, and was then recrystallized, whereby final product was obtained in the amount of 7.18 g (yield: 70%).

(3) Synthesis of Sub 1-67

Sub 1-II-67 (7.18 g, 19.9 mmol) in a round bottom flask was dissolved in THF (70 ml), followed by stirring at 80° C. after adding 4-bromo-4'-iodo-1,1'-biphenyl (7.87 g, 21.9 mmol), Pd(PPh$_3$)$_4$ (0.69 g, 0.6 mmol), NaOH (2.39 g, 59.8 mmol) and water (35 ml). Upon the completion of the reaction, the product was extracted with CH$_2$Cl$_2$ and washed with water. After that, the extracted organic layer was dried with MgSO$_4$ and then concentrated. The concentrated resultant was separated by silica gel column chromatography, and was then recrystallized, whereby a final product was obtained in the amount of 6.68 g (yield: 72%).

7. Synthesis Example of Sub 1-80

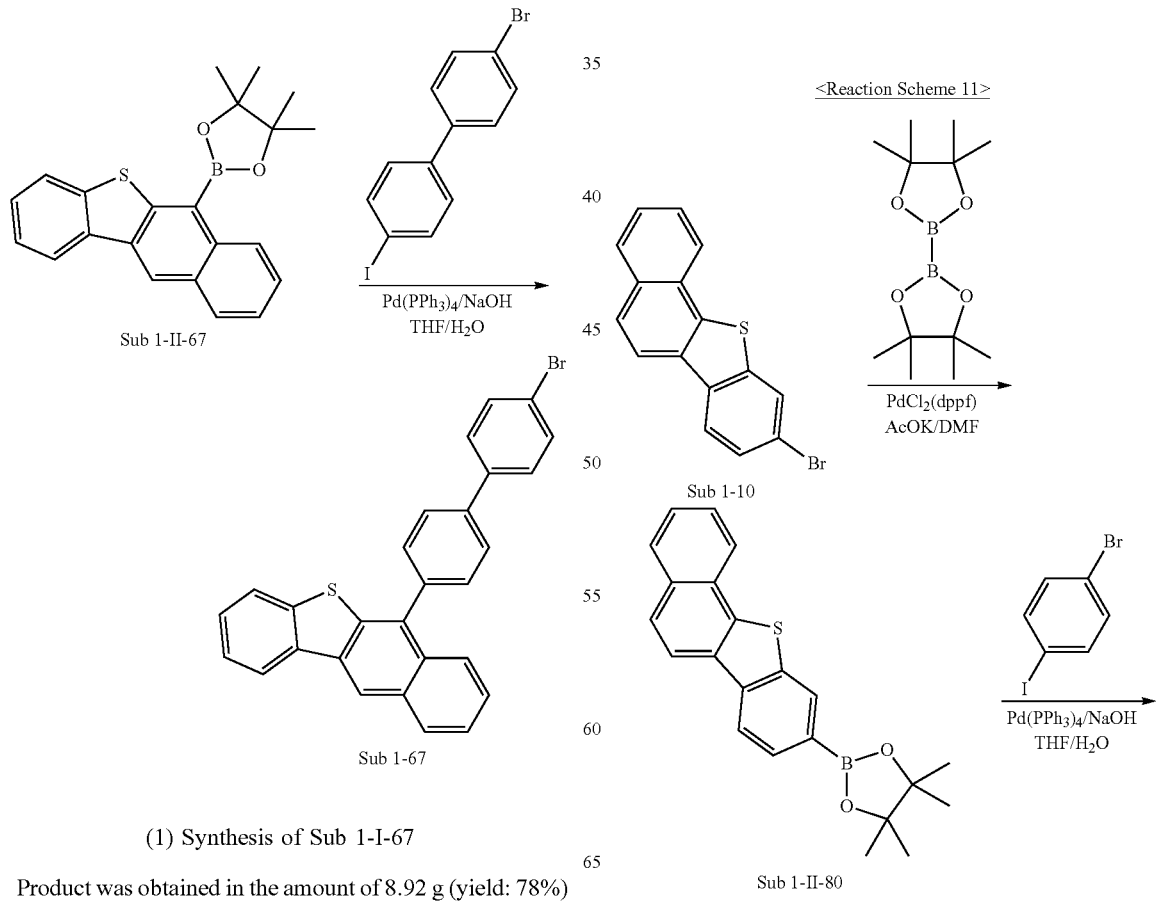

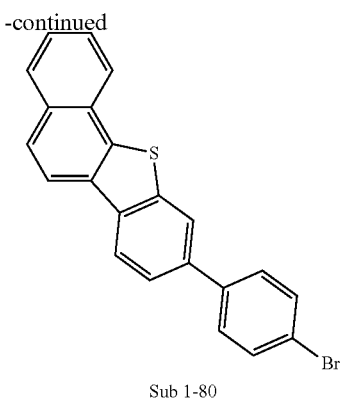

Sub 1-80

(1) Synthesis of Sub 1-II-80

Product was obtained in the amount of 15.29 g (yield: 87%) where Sub 1-10 (15.28 g, 48.8 mmol), Bis(pinacolato)diboron (13.63 g, 53.7 mmol), Pd(dppf)Cl$_2$ (1.2 g, 1.5 mmol), KOAc (14.36 g, 146.4 mmol) and DMF (245 ml) were used in the same manner as described above for the synthesis of compound Sub 1-II-67.

(2) Synthesis of Sub 1-80

Product was obtained in the amount of 13.88 g (yield: 84%) where Sub 1-II-80 (15.29 g, 42.4 mmol), 1-bromo-4-iodobenzene (13.21 g, 46.7 mmol), Pd(PPh$_3$)$_4$ (1.47 g, 1.3 mmol), NaOH (5.09 g, 127.3 mmol), THF (150 ml) and water (75 ml) were used in the same manner as described above for the synthesis of compound Sub 1-67.

8. Synthesis Example of Sub 1-89

<Reaction Scheme 12>

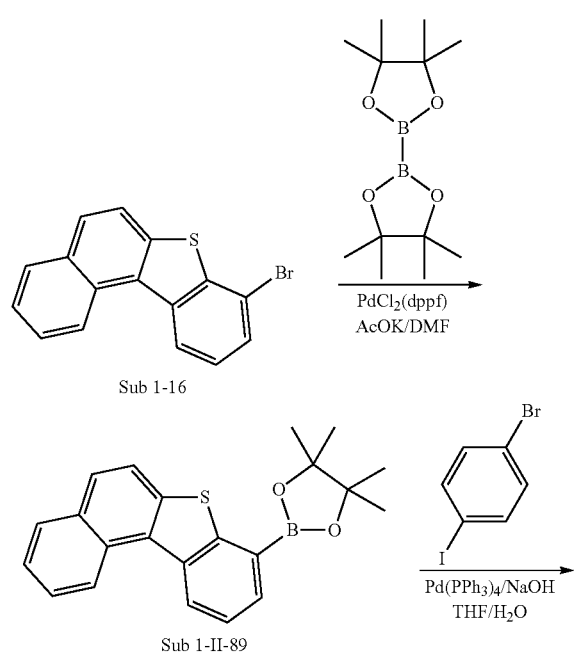

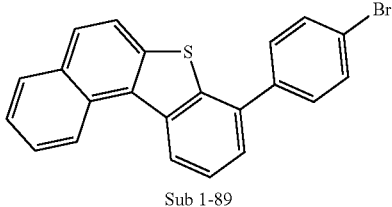

Sub 1-89

(1) Synthesis of Sub 1-II-89

Product was obtained in the amount of 35.21 g (yield: 73%) where Sub 1-16 (41.93 g, 133.9 mmol), Bis(pinacolato)diboron (37.39 g, 147.3 mmol), Pd(dppf)Cl$_2$ (3.28 g, 4 mmol), KOAc (39.41 g, 401.6 mmol) and DMF (670 ml) were used in the same manner as described above for the synthesis of compound Sub 1-II-67.

(2) Synthesis of Sub 1-89

Product was obtained in the amount of 16.69 g (yield: 80%) where Sub 1-II-89 (19.31 g, 53.6 mmol), 1-bromo-4-iodobenzene (16.68 g, 59 mmol), Pd(PPh$_3$)$_4$ (1.86 g, 1.6 mmol), NaOH (6.43 g, 160.8 mmol), THF (190 ml) and water (95 ml) were used in the same manner as described above for the synthesis of compound Sub 1-67.

9. Synthesis Example of Sub 1-91

<Reaction Scheme 13>

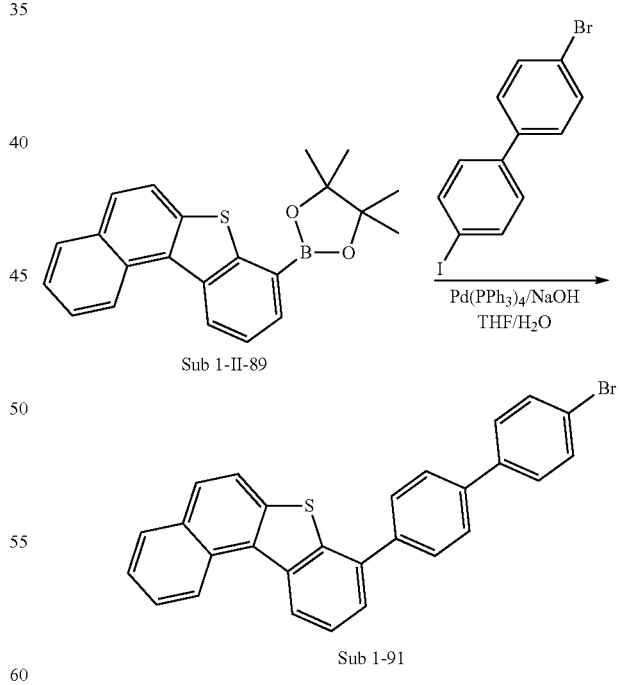

Product was obtained in the amount of 15.49 g (yield: 77%) where Sub 1-II-89 (15.57 g, 43.2 mmol), 4-bromo-4'-iodo-1,1'-biphenyl (17.07 g, 47.5 mmol), Pd(PPh$_3$)$_4$ (1.5 g, 1.3 mmol), NaOH (5.19 g, 129.6 mmol), THF (150 ml) and water (75 ml) were used in the same manner as described above for the synthesis of compound Sub 1-67.

10. Synthesis Example of Sub 1-96

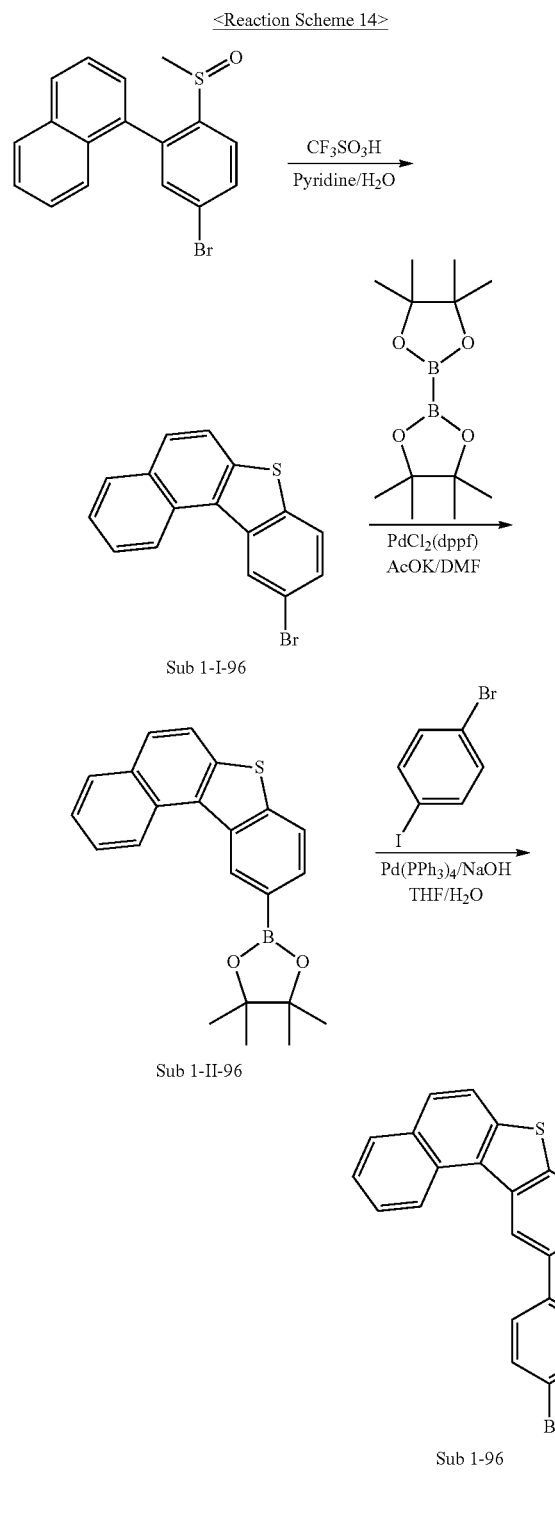

Sub 1-I-96

Sub 1-II-96

Sub 1-96

(1) Synthesis of Sub 1-I-96

Product was obtained in the amount of 29.41 g (yield: 82%) where 1-(5-bromo-2-(methylsulfinyl)phenyl)naphthalene (39.53 g, 114.5 mmol) as a starting material, triflic acid (152 ml, 1717.5 mmol) and pyridine(aq) (2000 ml, pyridine: $H_2O$=1:5) were used in the same manner as described above for the synthesis of compound Sub 1-10.

(2) Synthesis of Sub 1-II-96

Product was obtained in the amount of 26.39 g (yield: 78%) where Sub 1-I-96 (29.41 g, 93.9 mmol), Bis(pinacolato)diboron (26.23 g, 103.3 mmol), Pd(dppf)Cl$_2$ (2.3 g, 2.8 mmol), KOAc (27.65 g, 281.7 mmol) and DMF (470 ml) were used in the same manner as described above for the synthesis of compound Sub 1-11-67.

(3) Synthesis of Sub 1-96

Product was obtained in the amount of 13.88 g (yield: 81%) where Sub 1-II-96 (15.86 g, 44 mmol), 1-bromo-4-iodobenzene (13.7 g, 48.4 mmol), Pd(PPh$_3$)$_4$ (1.53 g, 1.3 mmol), NaOH (5.28 g, 132.1 mmol), THF (160 ml) and water (80 ml) were used in the same manner as described above for the synthesis of compound Sub 1-67.

11. Synthesis Example of Sub 1-100

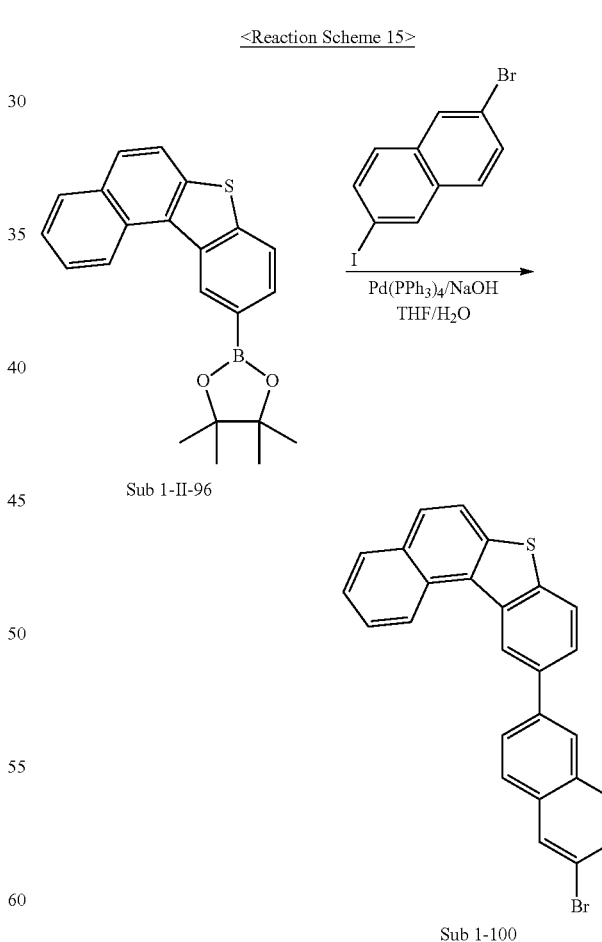

Sub 1-II-96

Sub 1-100

Product was obtained in the amount of 9.04 g (yield: 79%) where Sub 1-II-96 (9.38 g, 26 mmol), 2-bromo-6-iodonaphthalene (9.54 g, 28.6 mmol), Pd(PPh$_3$)$_4$ (0.9 g, 0.8 mmol), NaOH (3.12 g, 78.1 mmol), THF (90 ml) and water (45 ml)

were used in the same manner as described above for the synthesis of compound Sub 1-67.

12. Synthesis Example of Sub 1-111

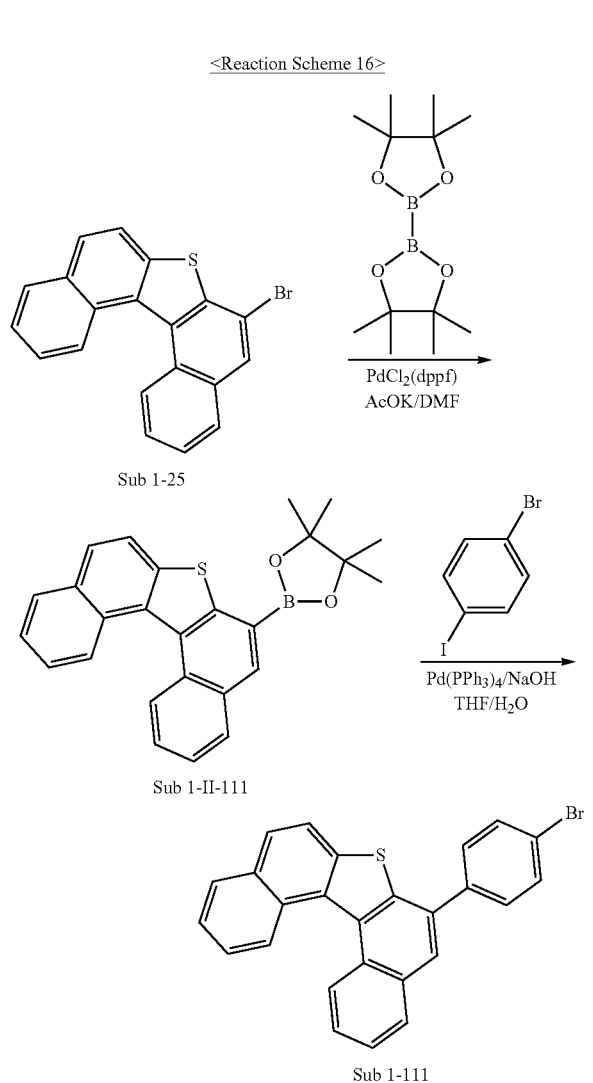

Reaction Scheme 16

Sub 1-25

Sub 1-II-111

Sub 1-111

(1) Synthesis of Sub 1-II-III

Product was obtained in the amount of 14.07 g (yield: 60%) where Sub 1-25 (20.76 g, 57.1 mmol), Bis(pinacolato)diboron (15.96 g, 62.9 mmol), Pd(dppf)Cl$_2$ (1.4 g, 1.7 mmol), KOAc (16.83 g, 171.4 mmol) and DMF (285 ml) were used in the same manner as described above for the synthesis of compound Sub 1-II-67.

(2) Synthesis of Sub 1-111

Product was obtained in the amount of 9.49 g (yield: 63%) where Sub 1-II-111 (14.07 g, 34.3 mmol), 1-bromo-4-iodobenzene (10.67 g, 37.7 mmol), Pd(PPh$_3$)$_4$ (1.19 g, 1 mmol), NaOH (4.11 g, 102.9 mmol), THF (120 ml) and water (60 ml) were used in the same manner as described above for the synthesis of compound Sub 1-67.

13. Synthesis Example of Sub 1-116

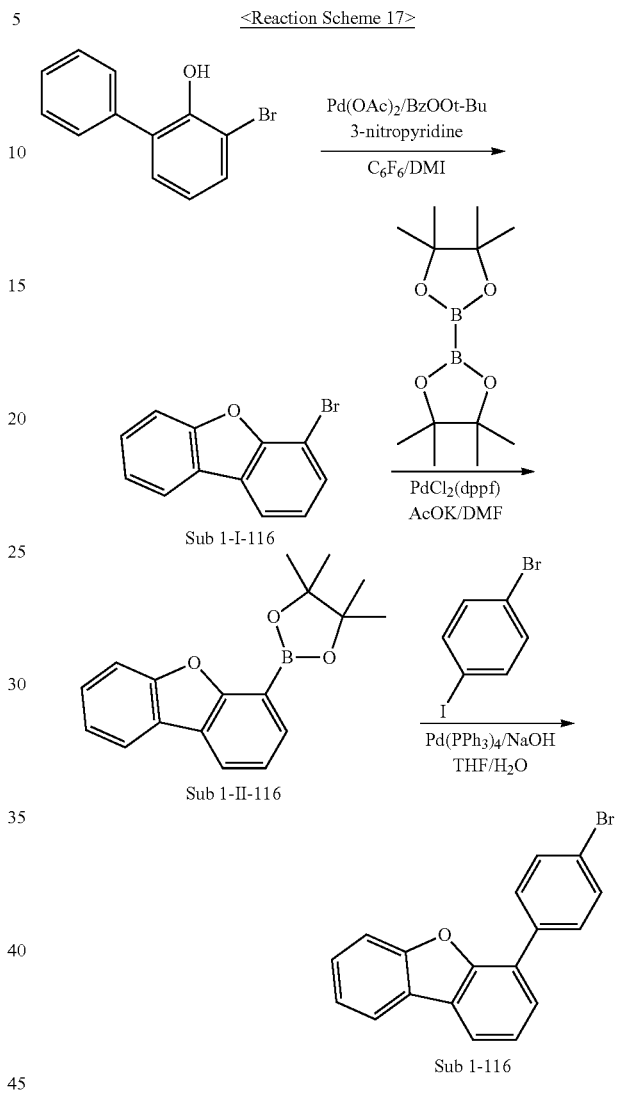

Reaction Scheme 17

Sub 1-I-116

Sub 1-II-116

Sub 1-116

(1) Synthesis of Sub 1-I-116

Product was obtained in the amount of 11.69 g (yield: 49%) where 3-bromo-[1,1'-biphenyl]-2-ol (24.05 g, 96.5 mmol), Pd(OAc)$_2$ (2.17 g, 9.7 mmol), 3-nitropyridine (1.2 g, 9.7 mmol), tert-butyl peroxybenzoate (37.5 g, 193.1 mmol), C$_6$F$_6$ (150 ml) and DMI (100 ml) were used in the same manner as described above for the synthesis of compound Sub 1-31.

(2) Synthesis of Sub 1-II-116

Product was obtained in the amount of 11.83 g (yield: 85%) where Sub 1-I-116 (11.69 g, 47.3 mmol), Bis(pinacolato)diboron (13.22 g, 52 mmol), Pd(dppf)Cl$_2$ (1.16 g, 1.4 mmol), KOAc (13.93 g, 141.9 mmol) and DMF (240 ml) were used in the same manner as described above for the synthesis of compound Sub 1-II-67.

(3) Synthesis of Sub 1-116

Product was obtained in the amount of 10.66 g (yield: 82%) where Sub 1-II-116 (11.83 g, 40.2 mmol), 1-bromo-4-iodobenzene (12.52 g, 44.2 mmol), Pd(PPh$_3$)$_4$ (1.39 g, 1.2 mmol), NaOH (4.83 g, 120.7 mmol), THF (140 ml) and water (70 ml) were used in the same manner as described above for the synthesis of compound Sub 1-67.

14. Synthesis Example of Sub 1-123

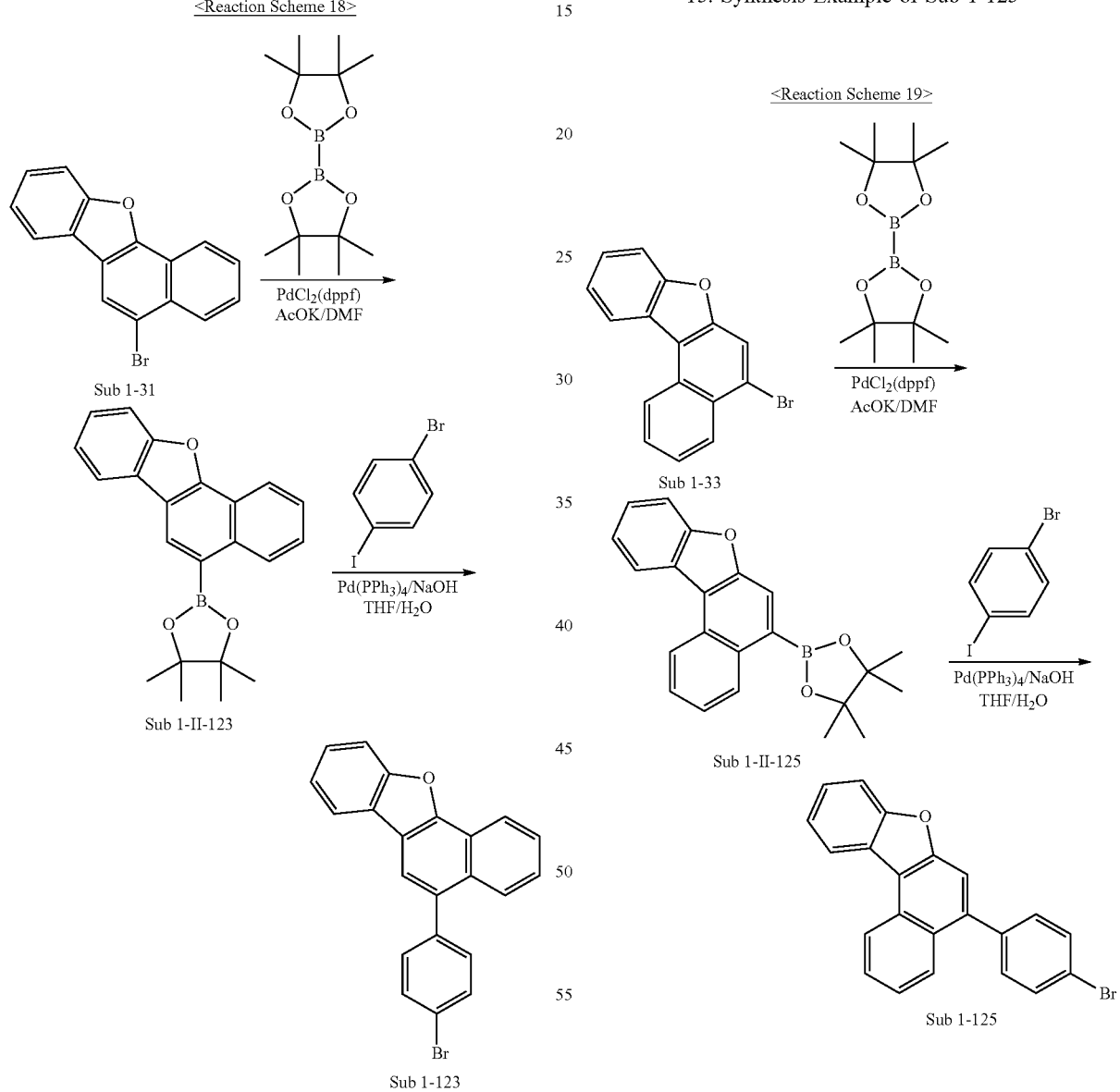

(1) Synthesis of Sub 1-II-123

Product was obtained in the amount of 18.51 g (yield: 65%) where Sub 1-31 (24.58 g, 82.7 mmol), Bis(pinacolato) diboron (23.11 g, 91 mmol), Pd(dppf)Cl$_2$ (2.03 g, 2.5 mmol), KOAc (24.35 g, 248.2 mmol) and DMF (415 ml) were used in the same manner as described above for the synthesis of compound Sub 1-II-67.

(2) Synthesis of Sub 1-123

Product was obtained in the amount of 15.45 g (yield: 77%) where Sub 1-II-123 (18.51 g, 53.8 mmol), 1-bromo-4-iodobenzene (16.73 g, 59.2 mmol), Pd(PPh$_3$)$_4$ (1.86 g, 1.6 mmol), NaOH (6.45 g, 161.3 mmol), THF (190 ml) and water (95 ml) were used in the same manner as described above for the synthesis of compound Sub 1-67.

15. Synthesis Example of Sub 1-125

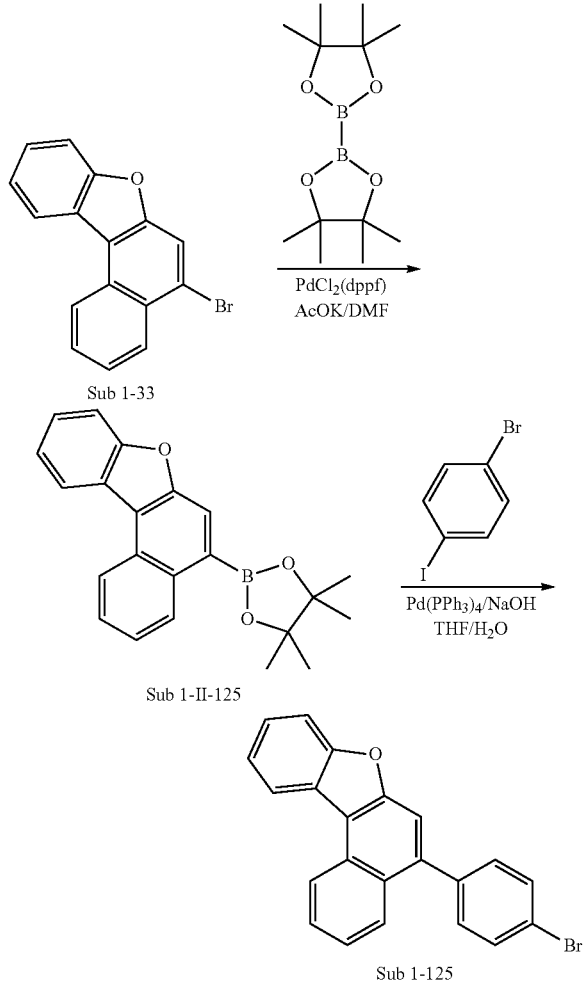

(1) Synthesis of Sub 1-II-125

Product was obtained in the amount of 11.28 g (yield: 64%) where Sub 1-33 (15.21 g, 51.2 mmol), Bis(pinacolato) diboron (14.3 g, 56.3 mmol), Pd(dppf)Cl$_2$ (1.25 g, 1.5 mmol), KOAc (15.07 g, 153.6 mmol) and DMF (255 ml) were used in the same manner as described above for the synthesis of compound Sub 1-II-67.

(2) Synthesis of Sub 1-125

Product was obtained in the amount of 9.17 g (yield: 75%) where Sub 1-II-125 (11.28 g, 32.8 mmol), 1-bromo-4-iodobenzene (10.2 g, 36 mmol), Pd(PPh$_3$)$_4$ (1.14 g, 1 mmol), NaOH (3.93 g, 98.3 mmol), THF (120 ml) and water (60 ml) were used in the same manner as described above for the synthesis of compound Sub 1-67.

16. Synthesis Example of Sub 1-148

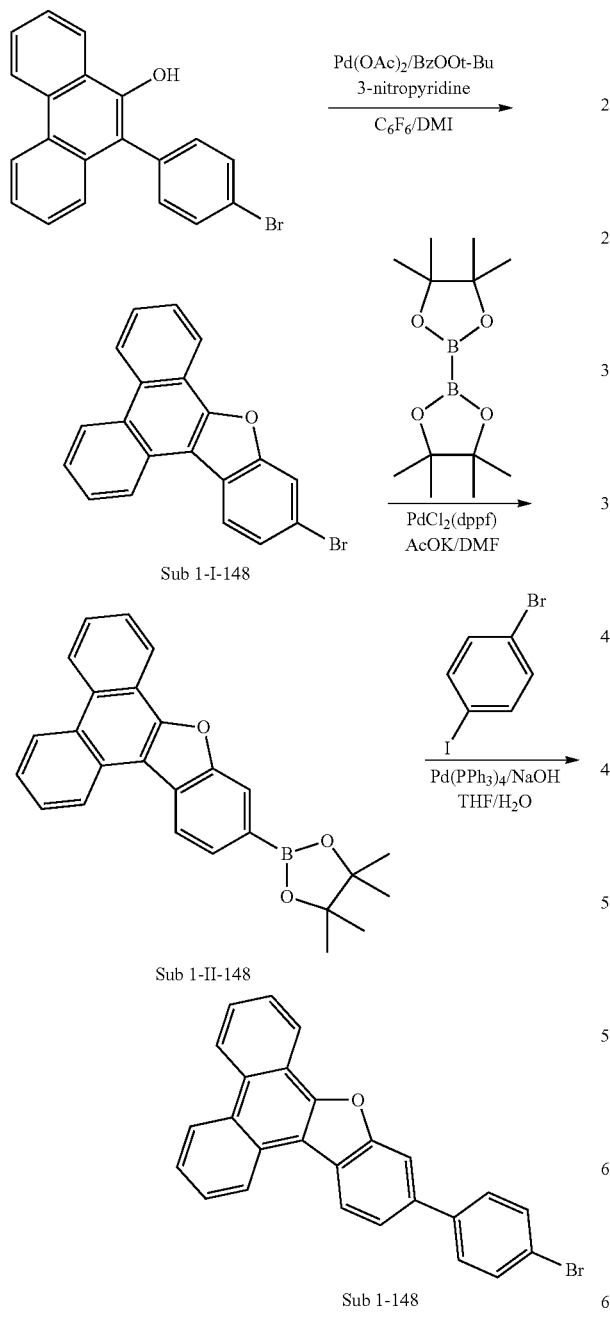

(1) Synthesis of Sub 1-I-148

Product was obtained in the amount of 26.62 g (yield: 42%) where 10-(4-bromophenyl)phenanthren-9-ol (63.74 g, 182.5 mmol) as a staring material, Pd(OAc)$_2$ (4.1 g, 18.3 mmol), 3-nitropyridine (2.27 g, 18.3 mmol), tert-butyl peroxybenzoate (70.9 g, 365 mmol), C$_6$F$_6$ (270 ml) and DMI (180 ml) were used in the same manner as described above for the synthesis of compound Sub 1-31.

(2) Synthesis of Sub 1-II-148

Product was obtained in the amount of 20.25 g (yield: 67%) where Sub 1-I-148 (26.62 g, 76.7 mmol), Bis(pinacolato)diboron (21.42 g, 84.3 mmol), Pd(dppf)Cl$_2$ (1.88 g, 2.3 mmol), KOAc (22.57 g, 230 mmol) and DMF (385 ml) were used in the same manner as described above for the synthesis of compound Sub 1-II-67.

(3) Synthesis of Sub 1-148

Product was obtained in the amount of 15.65 g (yield: 72%) where Sub 1-II-148 (20.25 g, 51.4 mmol), 1-bromo-4-iodobenzene (15.98 g, 56.5 mmol), Pd(PPh$_3$)$_4$ (1.78 g, 1.5 mmol), NaOH (6.16 g, 154.1 mmol), THF (180 ml) and water (90 ml) were used in the same manner as described above for the synthesis of compound Sub 1-67.

The compounds comprised in Sub 1 may be, but not limited to, the following compounds, and Table 1 below shows FD-MS (Field Desorption-Mass Spectrometry) data of the compounds.

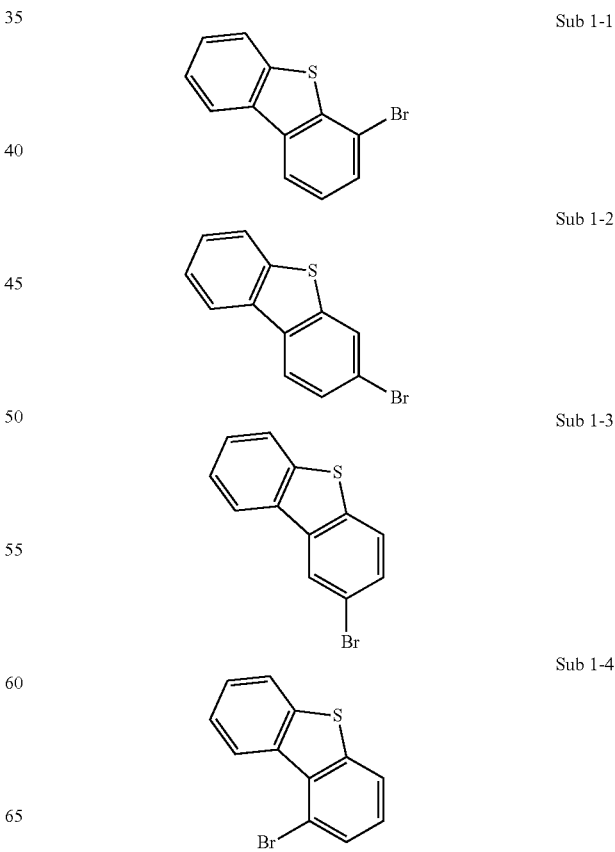

Sub 1-5
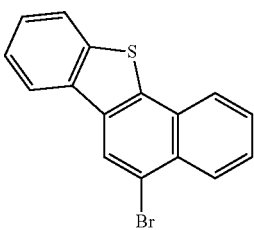
Sub 1-6
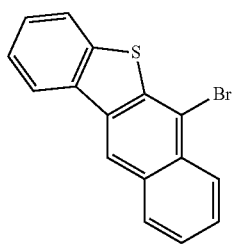
Sub 1-7
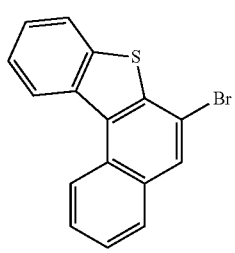
Sub 1-8
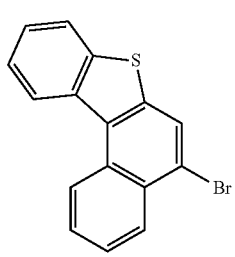
Sub 1-9
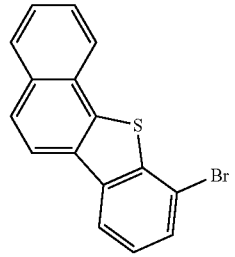
Sub 1-10
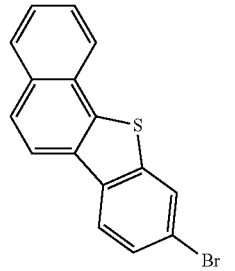
Sub 1-11
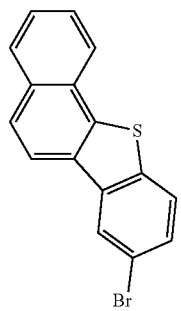
Sub 1-12
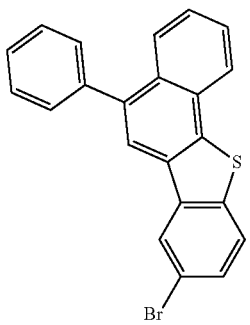
Sub 1-13
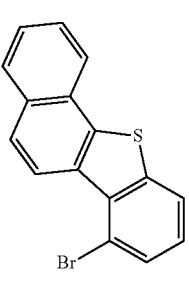
Sub 1-14
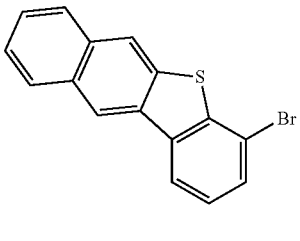
Sub 1-15
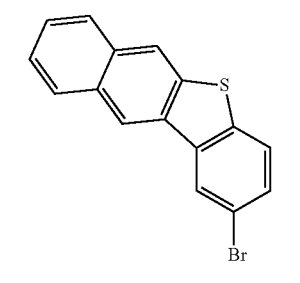
Sub 1-16
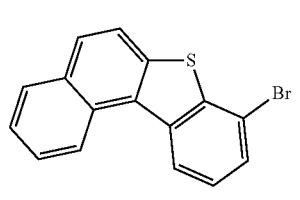

-continued
Sub 1-17
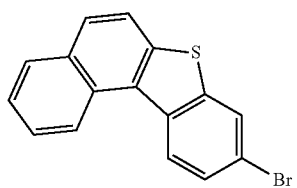
Sub 1-18
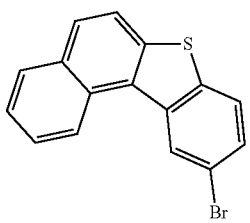
Sub 1-19
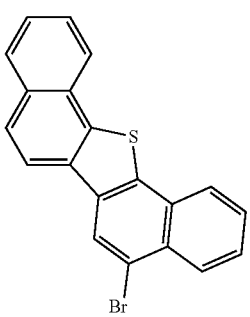
Sub 1-20
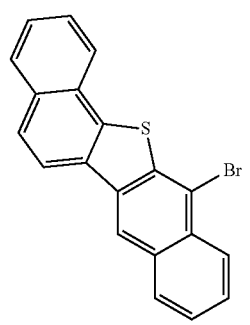
Sub 1-21
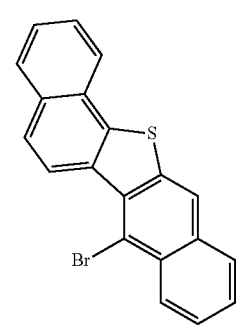
-continued
Sub 1-22
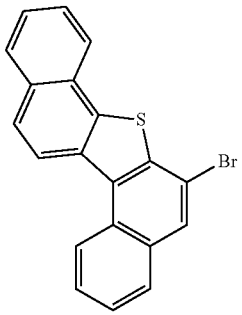
Sub 1-23
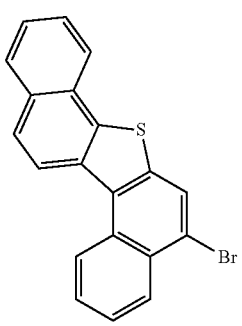
Sub 1-24
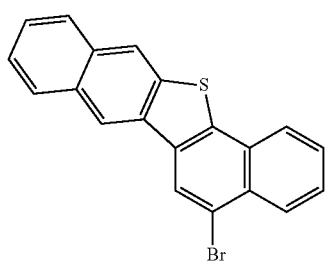
Sub 1-25
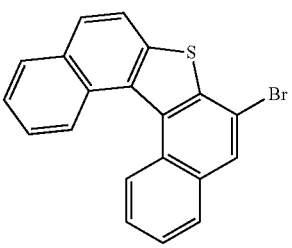
Sub 1-26
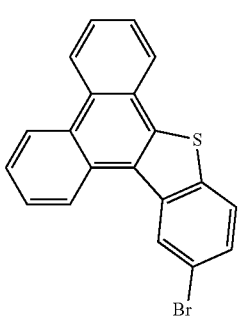

Sub 1-27
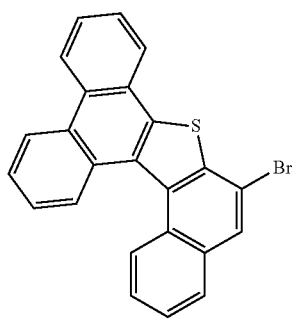
Sub 1-28
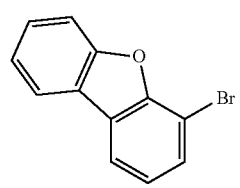
Sub 1-29
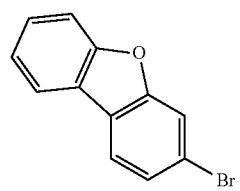
Sub 1-30
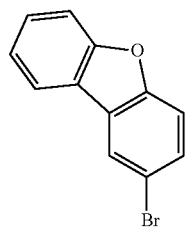
Sub 1-31
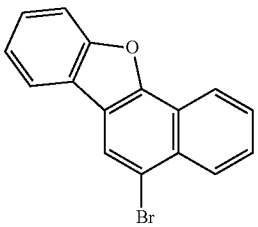
Sub 1-32
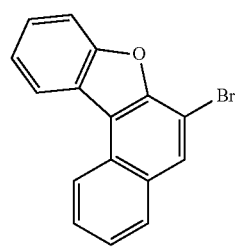
Sub 1-33
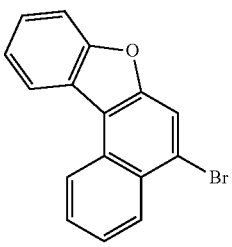
Sub 1-34
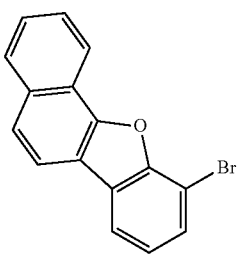
Sub 1-35
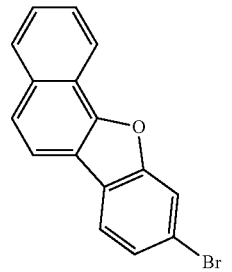
Sub 1-36
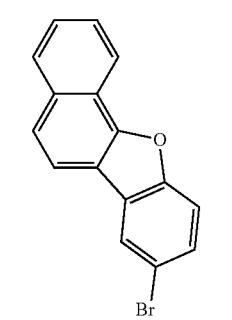
Sub 1-37
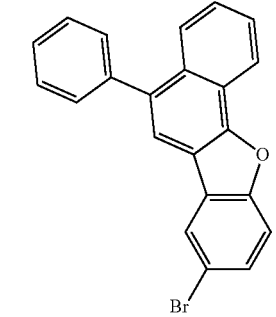
Sub 1-38
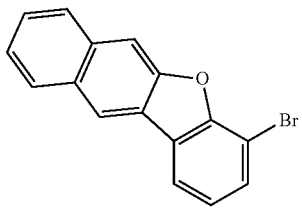

Sub 1-39
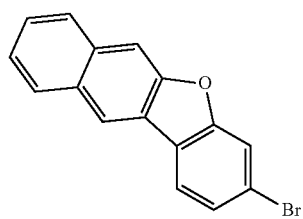
Sub 1-40
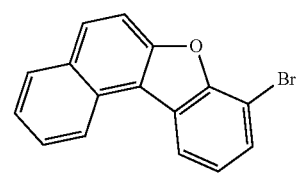
Sub 1-41
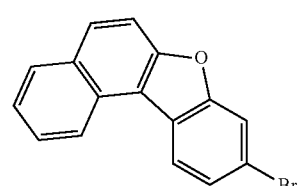
Sub 1-42
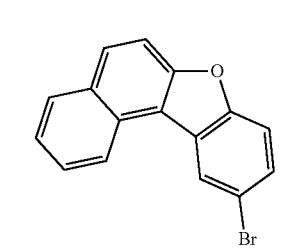
Sub 1-43
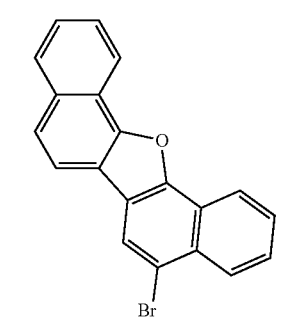
Sub 1-44
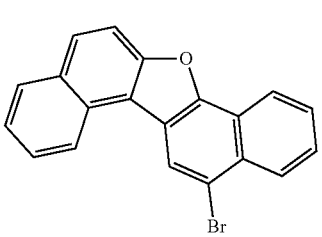
Sub 1-45
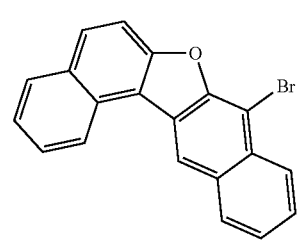
Sub 1-46
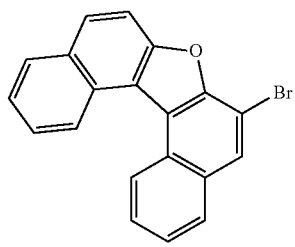
Sub 1-47
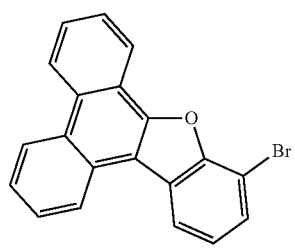
Sub 1-48
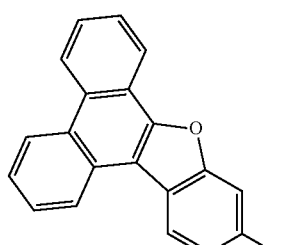
Sub 1-49
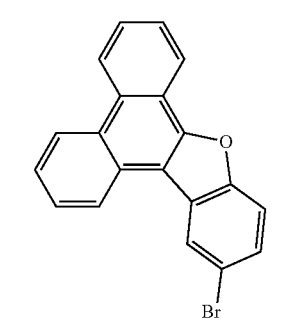
Sub 1-50
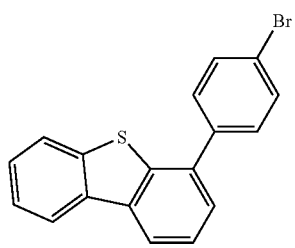
Sub 1-51
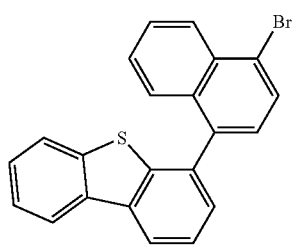

-continued
Sub 1-52
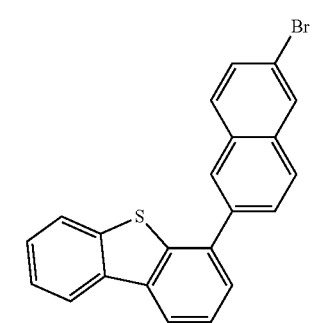
Sub 1-53
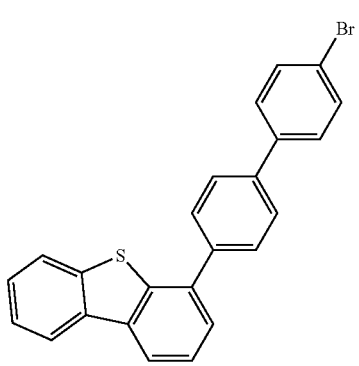
Sub 1-54
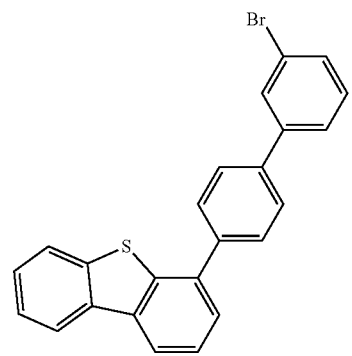
Sub 1-55
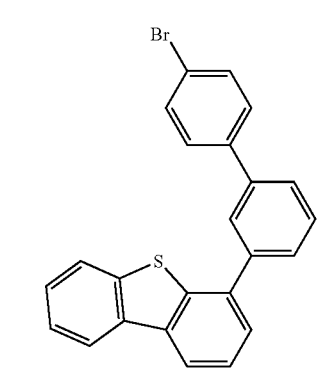
-continued
Sub 1-56
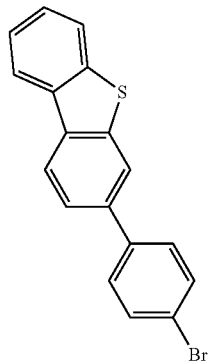
Sub 1-57
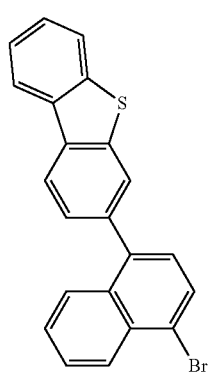
Sub 1-58
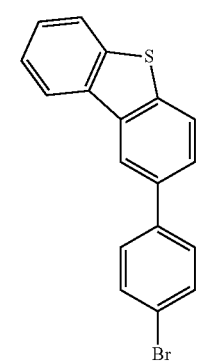
Sub 1-59
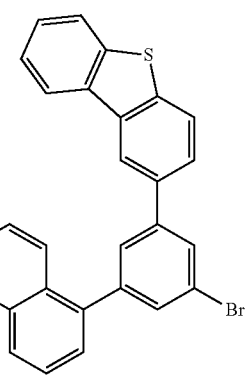

Sub 1-60
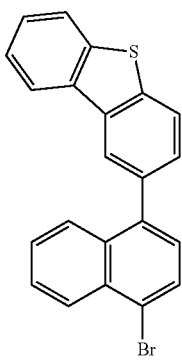
Sub 1-61
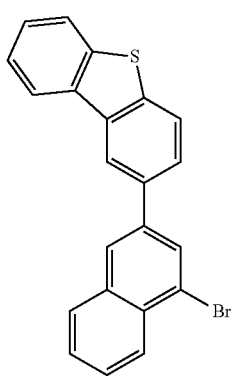
Sub 1-62
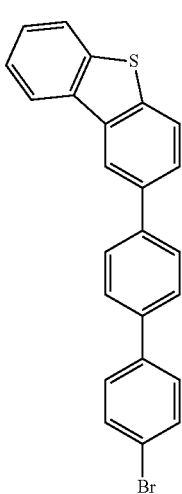
Sub 1-63
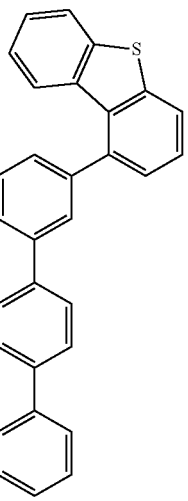
Sub 1-64
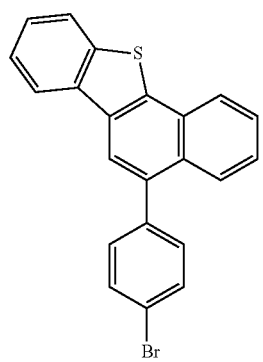
Sub 1-65
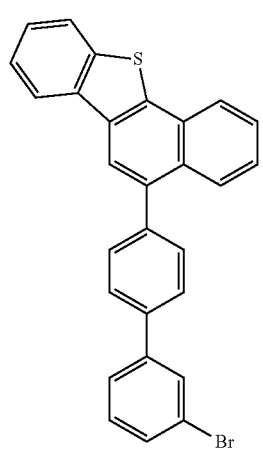
Sub 1-66
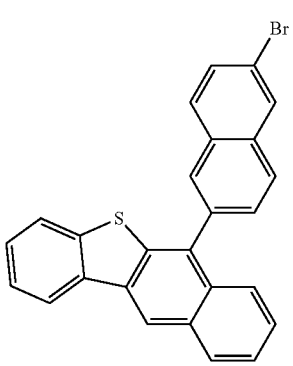

-continued
Sub 1-67
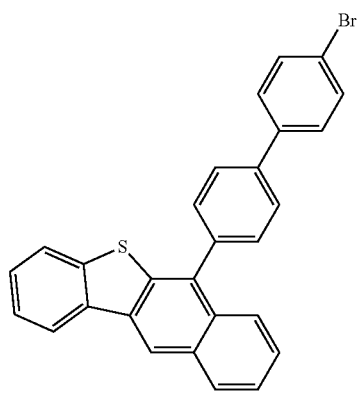
Sub 1-68
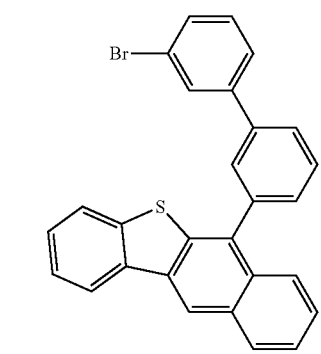
Sub 1-69
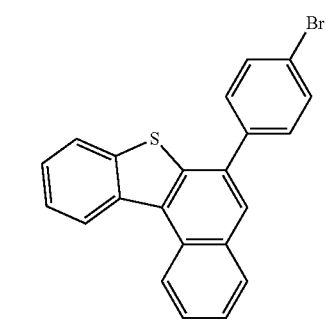
Sub 1-70
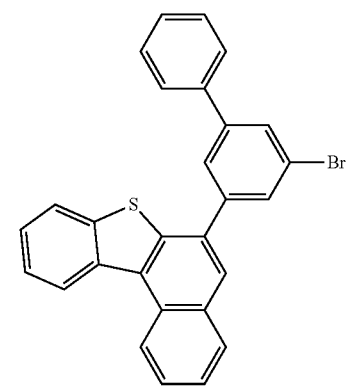
-continued
Sub 1-71
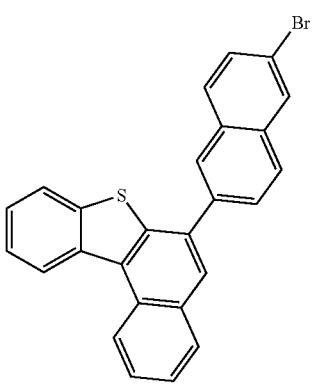
Sub 1-72
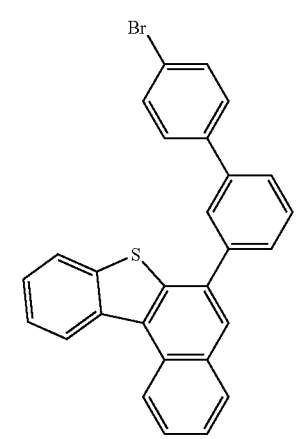
Sub 1-73
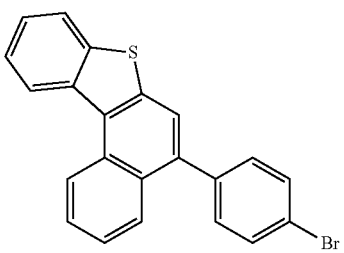
Sub 1-74
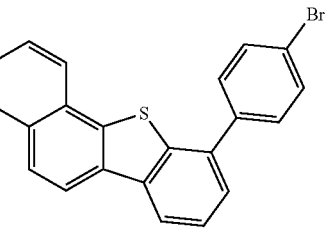
Sub 1-75
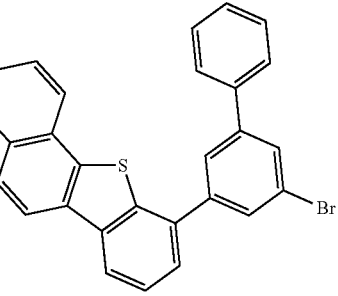

Sub 1-76
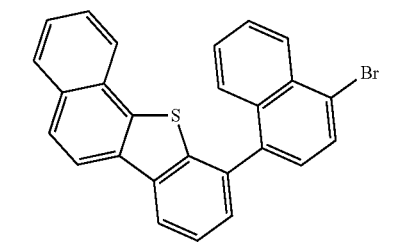
Sub 1-77
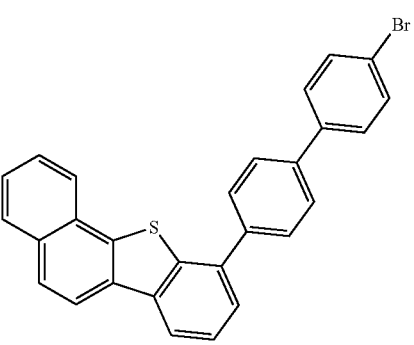
Sub 1-78
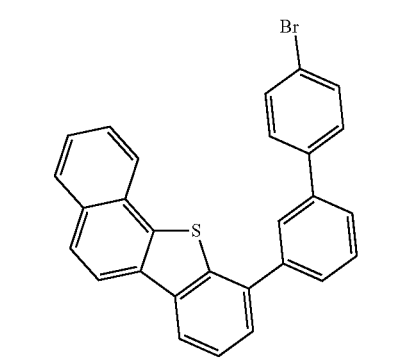
Sub 1-79
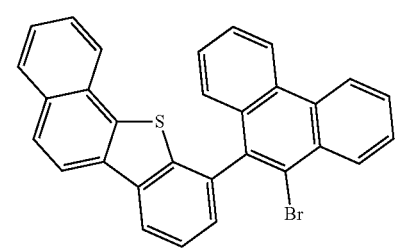
Sub 1-80
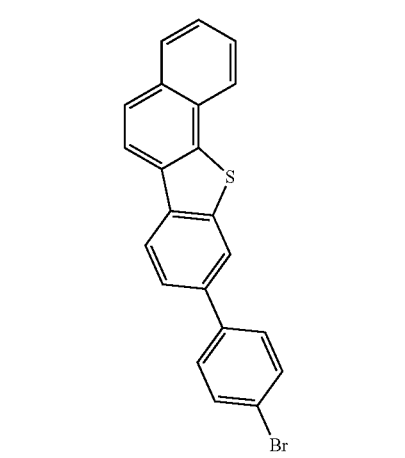
Sub 1-81
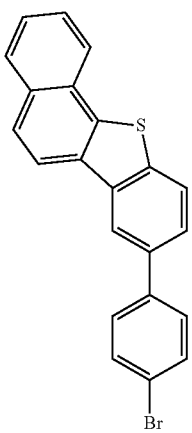
Sub 1-82
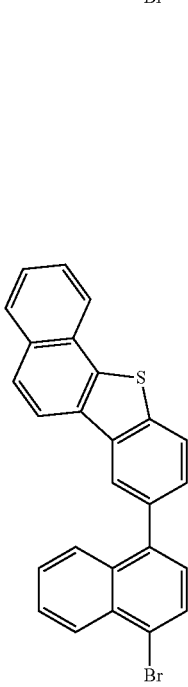
Sub 1-83
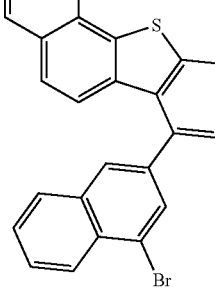

-continued
Sub 1-84
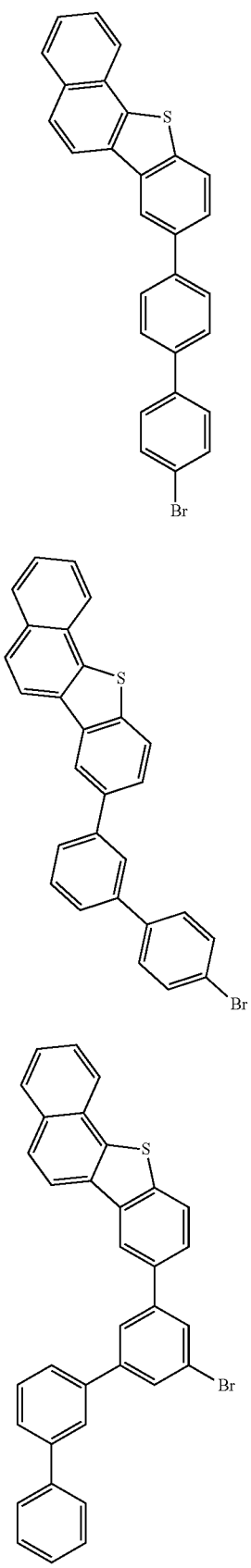
Sub 1-85
Sub 1-86
Sub 1-87
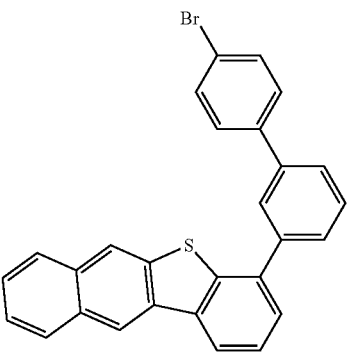
Sub 1-88
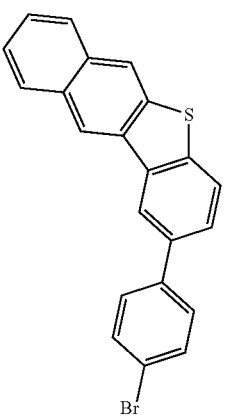
Sub 1-89
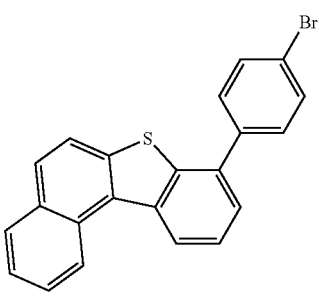
Sub 1-90
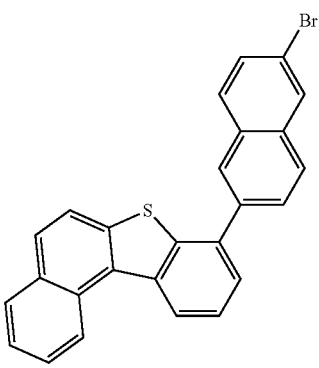

-continued
Sub 1-91
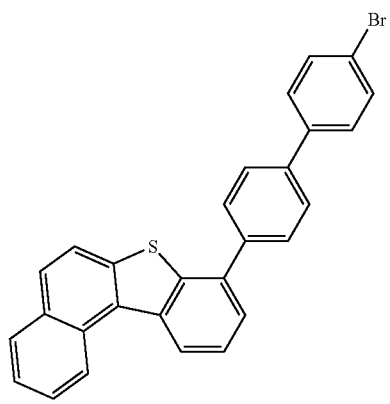
Sub 1-92
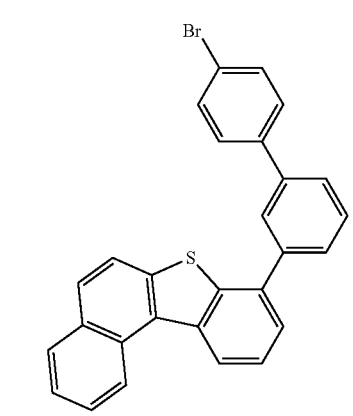
Sub 1-93
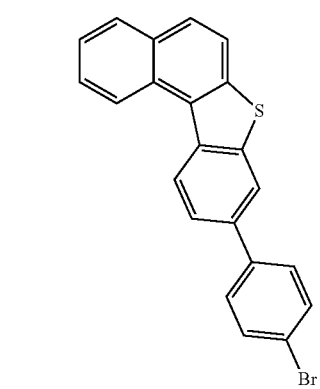
Sub 1-94
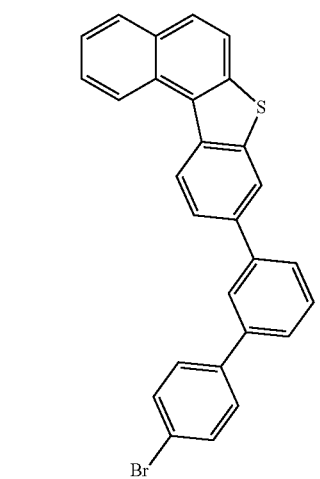
-continued
Sub 1-95
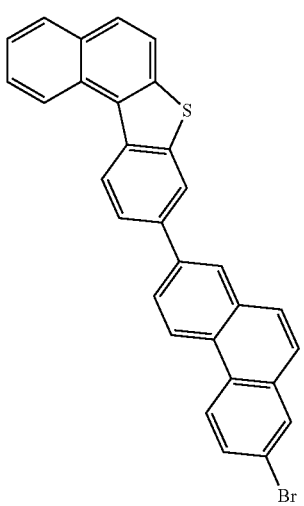
Sub 1-96
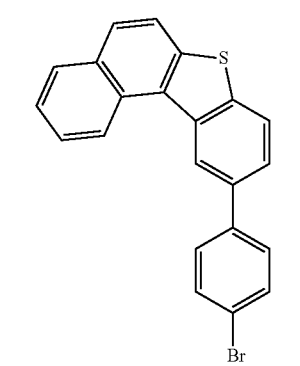
Sub 1-97
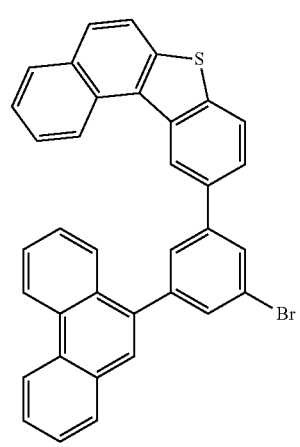
Sub 1-98
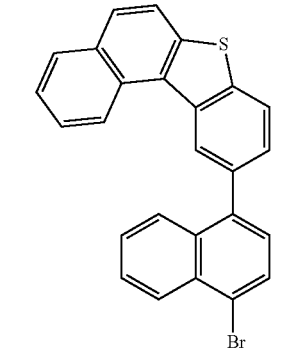

Sub 1-99
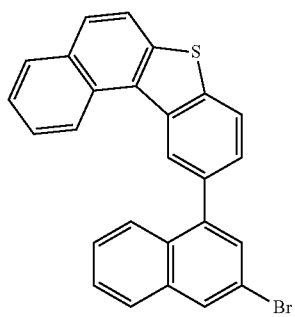
Sub 1-100
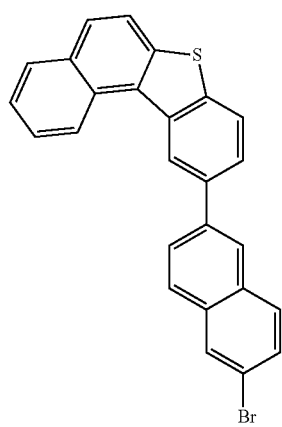
Sub 1-101
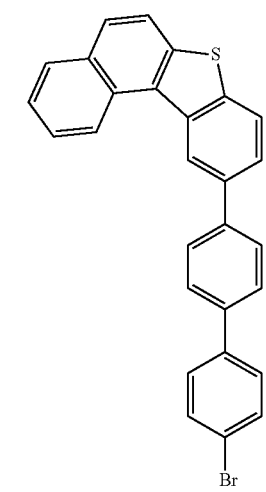
Sub 1-102
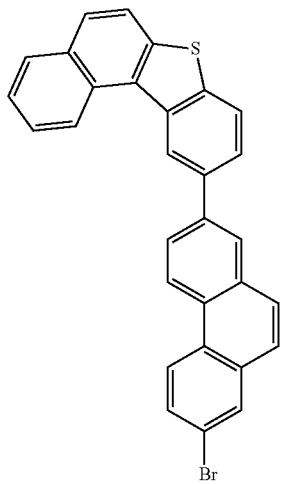
Sub 1-103
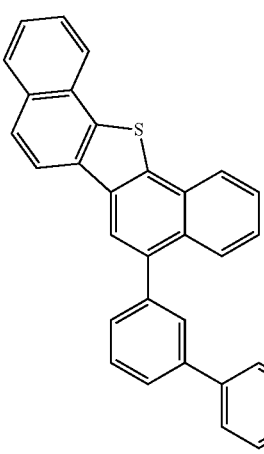
Sub 1-104
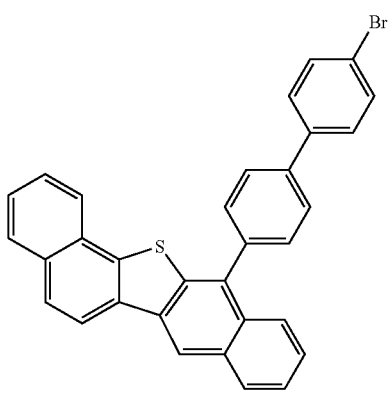
Sub 1-105
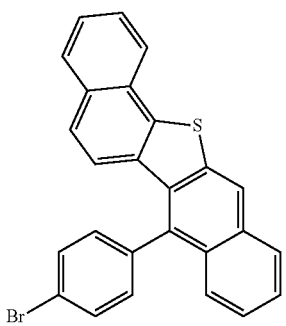

-continued
Sub 1-106
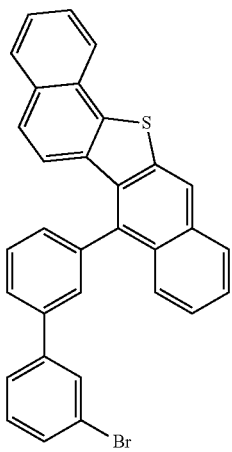
Sub 1-107
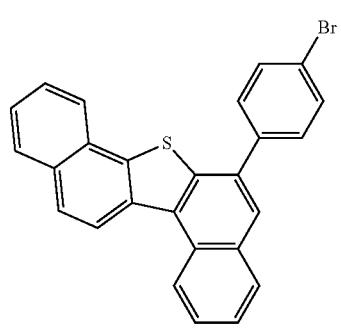
Sub 1-108
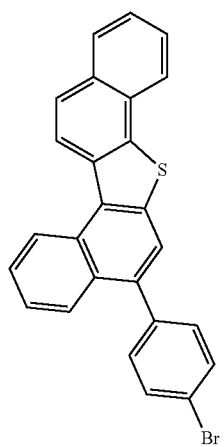
-continued
Sub 1-109
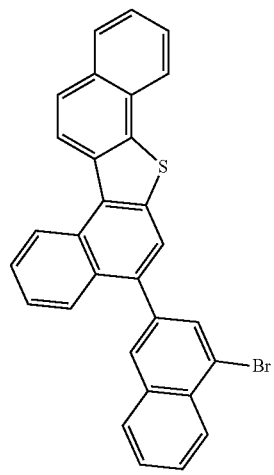
Sub 1-110
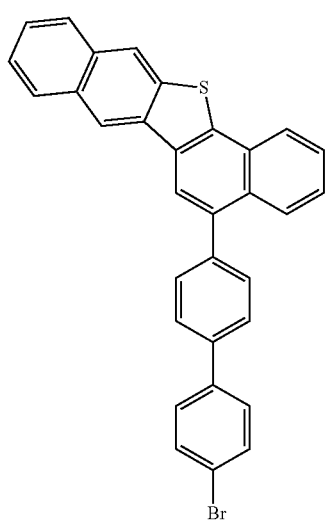
Sub 1-111
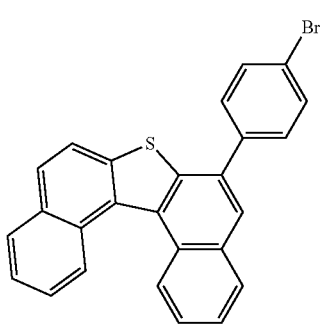
Sub 1-112
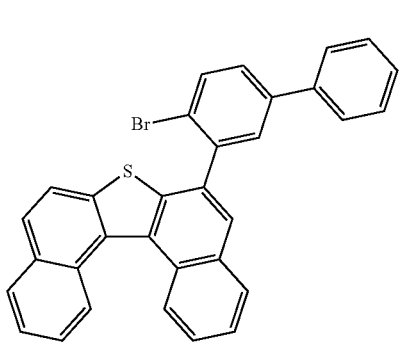

-continued
Sub 1-113
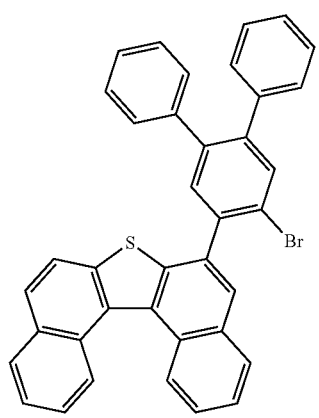
Sub 1-114
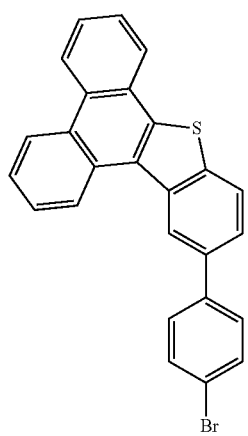
Sub 1-115
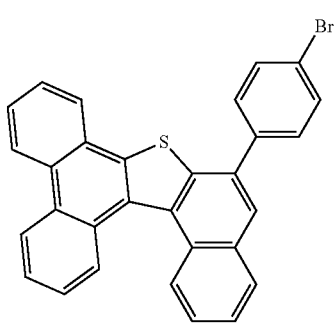
Sub 1-116
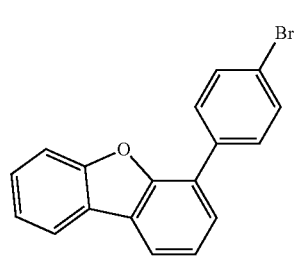
-continued
Sub 1-117
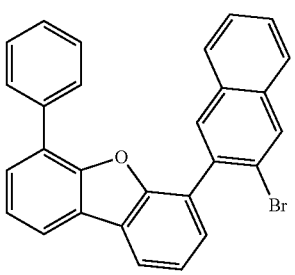
Sub 1-118
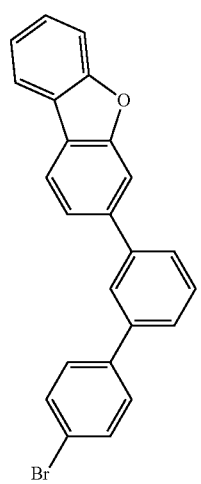
Sub 1-119
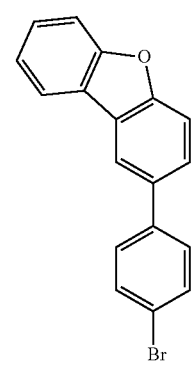
Sub 1-120
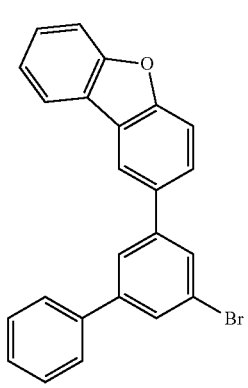

Sub 1-121
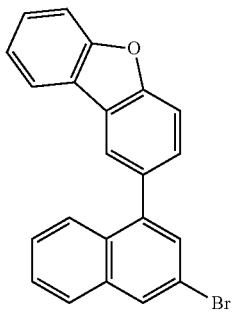
Sub 1-122
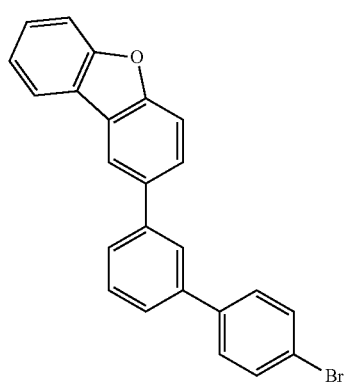
Sub 1-123
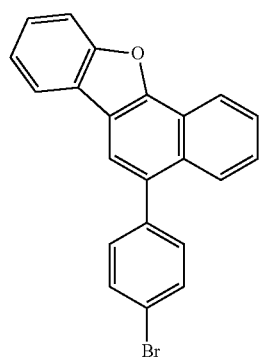
Sub 1-124
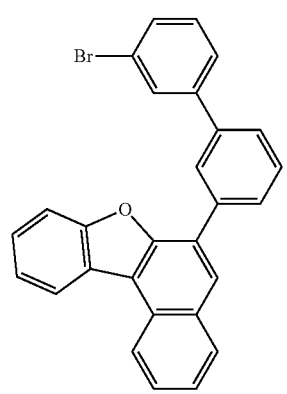
Sub 1-125
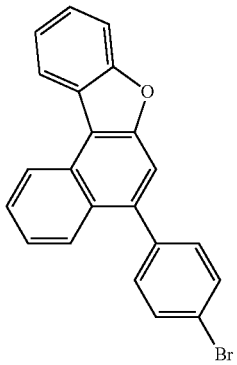
Sub 1-126
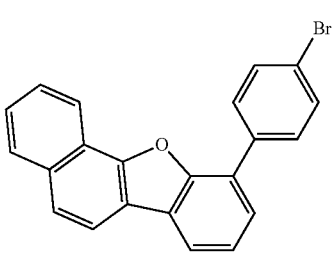
Sub 1-127
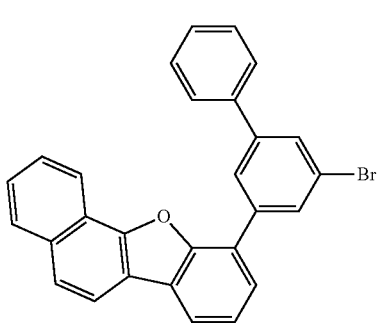
Sub 1-128
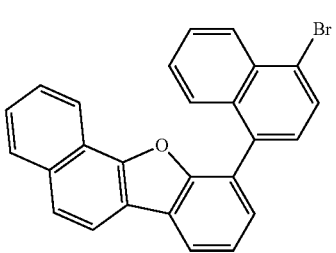
Sub 1-129
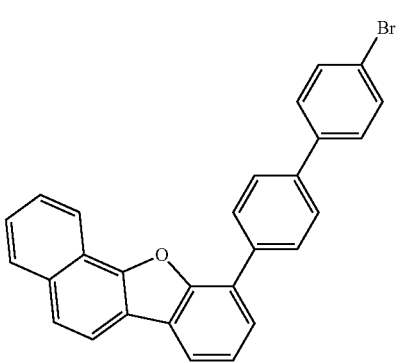

-continued
Sub 1-130
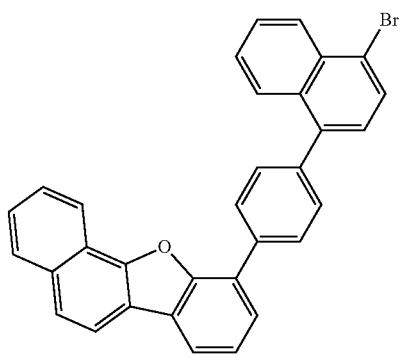
Sub 1-131
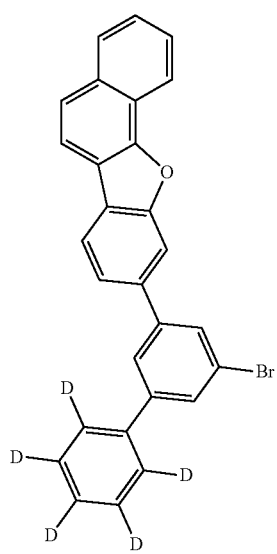
Sub 1-132
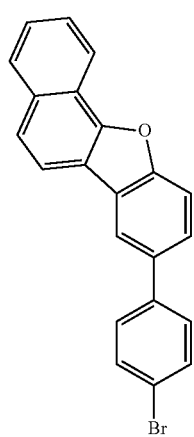
Sub 1-133
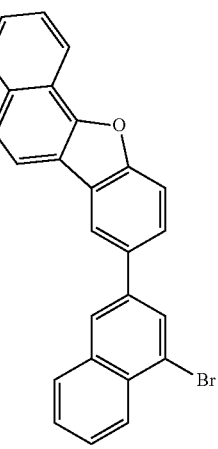
Sub 1-134
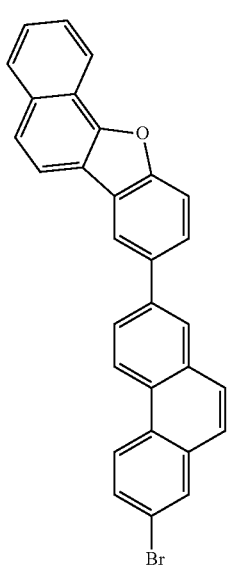
Sub 1-135
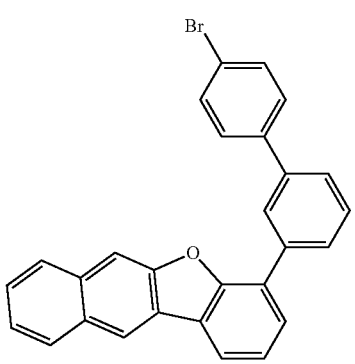

-continued
Sub 1-136
Sub 1-137
Sub 1-138
Sub 1-139
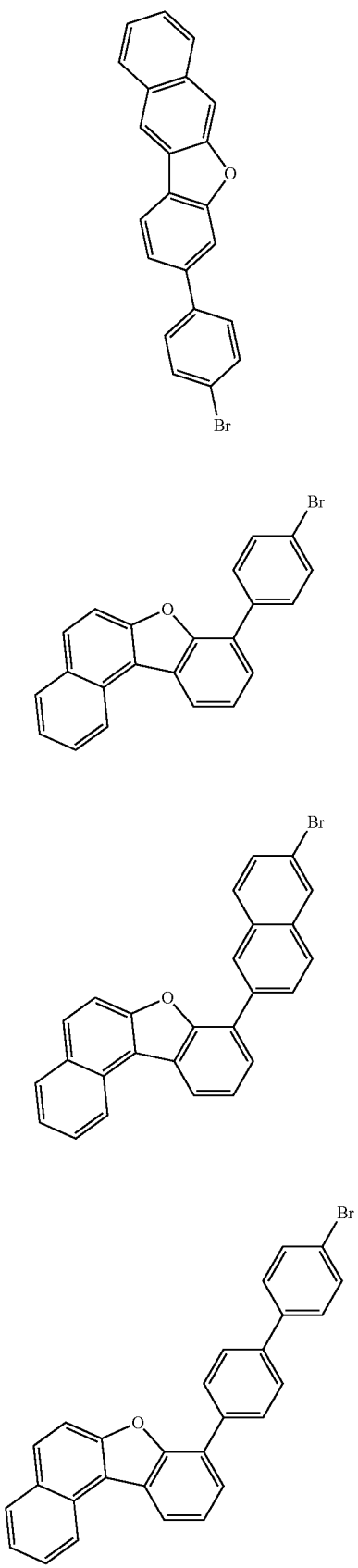
-continued
Sub 1-140
Sub 1-141
Sub 1-142
Sub 1-143
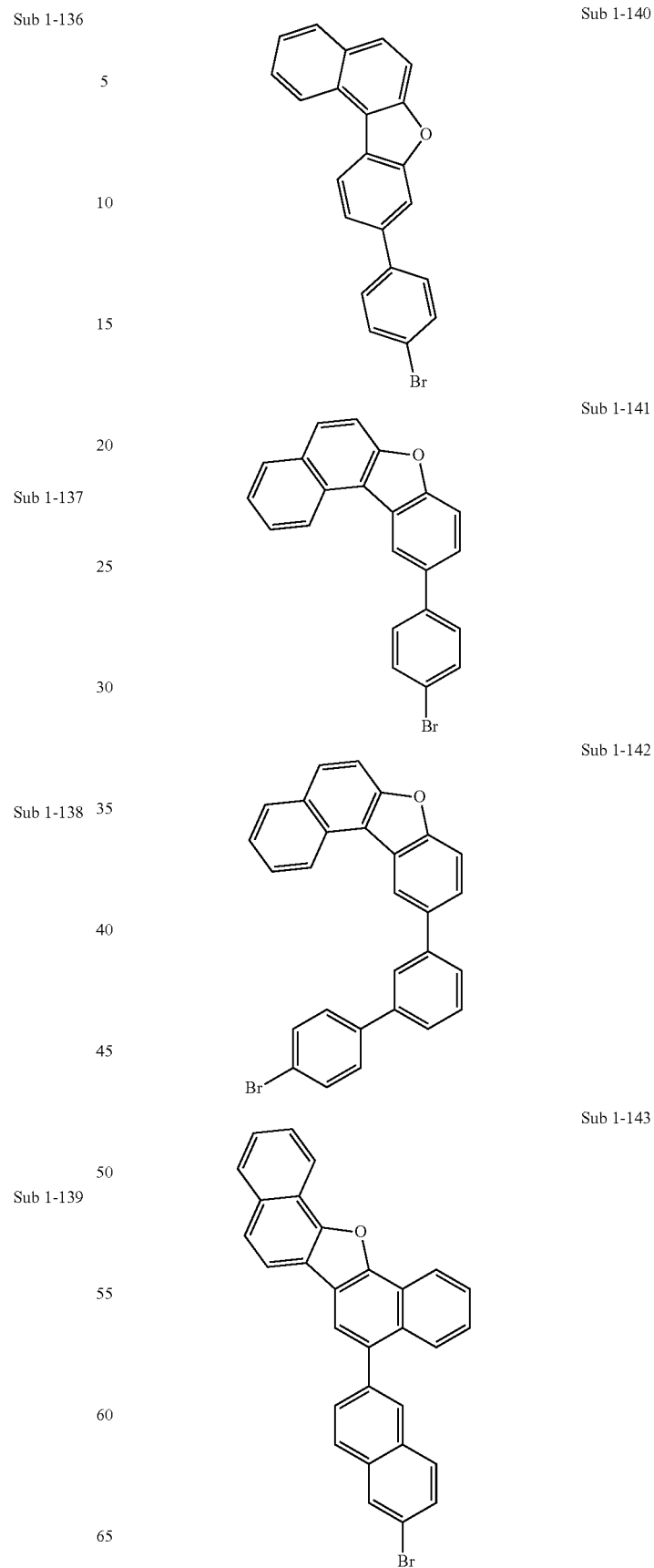

Sub 1-144
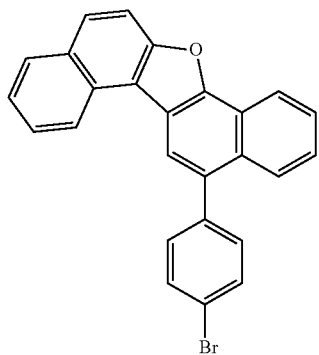

Sub 1-147
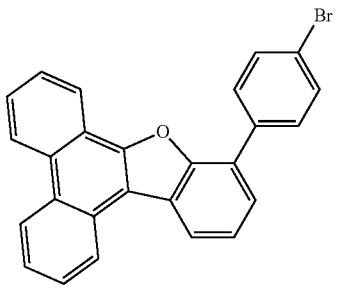

Sub 1-145
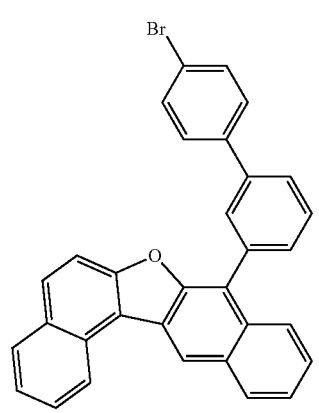

Sub 1-148
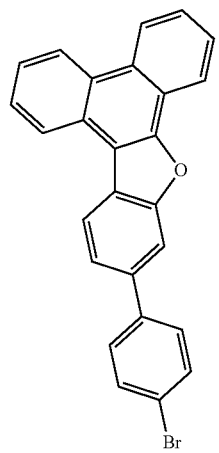

Sub 1-146
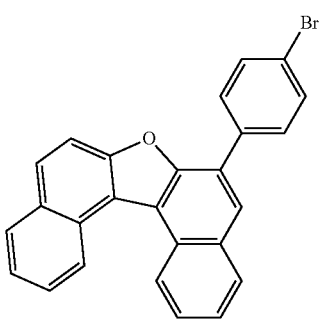

Sub 1-149
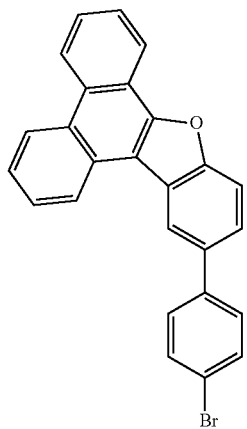

TABLE 1

| Compound | FD-MS | Compound | FD-MS |
| --- | --- | --- | --- |
| Sub 1-1 | m/z = 261.95($C_{12}H_7BrS$ = 263.15) | Sub 1-2 | m/z = 261.95($C_{12}H_7BrS$ = 263.15) |
| Sub 1-3 | m/z = 261.95($C_{12}H_7BrS$ = 263.15) | Sub 1-4 | m/z = 261.95($C_{12}H_7BrS$ = 263.15) |
| Sub 1-5 | m/z = 311.96($C_{16}H_9BrS$ = 313.21) | Sub 1-6 | m/z = 311.96($C_{16}H_9BrS$ = 313.21) |
| Sub 1-7 | m/z = 311.96($C_{16}H_9BrS$ = 313.21) | Sub 1-8 | m/z = 311.96($C_{16}H_9BrS$ = 313.21) |
| Sub 1-9 | m/z = 311.96($C_{16}H_9BrS$ = 313.21) | Sub 1-10 | m/z = 311.96($C_{16}H_9BrS$ = 313.21) |
| Sub 1-11 | m/z = 311.96($C_{16}H_9BrS$ = 313.21) | Sub 1-12 | m/z = 387.99($C_{22}H_{13}BrS$ = 389.31) |
| Sub 1-13 | m/z = 311.96($C_{16}H_9BrS$ = 313.21) | Sub 1-14 | m/z = 311.96($C_{16}H_9BrS$ = 313.21) |
| Sub 1-15 | m/z = 311.96($C_{16}H_9BrS$ = 313.21) | Sub 1-16 | m/z = 311.96($C_{16}H_9BrS$ = 313.21) |
| Sub 1-17 | m/z = 311.96($C_{16}H_9BrS$ = 313.21) | Sub 1-18 | m/z = 311.96($C_{16}H_9BrS$ = 313.21) |
| Sub 1-19 | m/z = 361.98($C_{20}H_{11}BrS$ = 363.27) | Sub 1-20 | m/z = 361.98($C_{20}H_{11}BrS$ = 363.27) |
| Sub 1-21 | m/z = 361.98($C_{20}H_{11}BrS$ = 363.27) | Sub 1-22 | m/z = 361.98($C_{20}H_{11}BrS$ = 363.27) |
| Sub 1-23 | m/z = 361.98($C_{20}H_{11}BrS$ = 363.27) | Sub 1-24 | m/z = 361.98($C_{20}H_{11}BrS$ = 363.27) |
| Sub 1-25 | m/z = 361.98($C_{20}H_{11}BrS$ = 363.27) | Sub 1-26 | m/z = 361.98($C_{20}H_{11}BrS$ = 363.27) |
| Sub 1-27 | m/z = 411.99($C_{24}H_{13}BrS$ = 413.33) | Sub 1-28 | m/z = 245.97($C_{12}H_7BrO$ = 247.09) |
| Sub 1-29 | m/z = 245.97($C_{12}H_7BrO$ = 247.09) | Sub 1-30 | m/z = 245.97($C_{12}H_7BrO$ = 247.09) |
| Sub 1-31 | m/z = 295.98($C_{16}H_9BrO$ = 297.15) | Sub 1-32 | m/z = 295.98($C_{16}H_9BrO$ = 297.15) |

TABLE 1-continued

| Compound | FD-MS | Compound | FD-MS |
|---|---|---|---|
| Sub 1-33 | m/z = 295.98($C_{16}H_9BrO$ = 297.15) | Sub 1-34 | m/z = 295.98($C_{16}H_9BrO$ = 297.15) |
| Sub 1-35 | m/z = 295.98($C_{16}H_9BrO$ = 297.15) | Sub 1-36 | m/z = 295.98($C_{16}H_9BrO$ = 297.15) |
| Sub 1-37 | m/z = 372.01($C_{22}H_{13}BrO$ = 373.24) | Sub 1-38 | m/z = 295.98($C_{16}H_9BrO$ = 297.15) |
| Sub 1-39 | m/z = 295.98($C_{16}H_9BrO$ = 297.15) | Sub 1-40 | m/z = 295.98($C_{16}H_9BrO$ = 297.15) |
| Sub 1-41 | m/z = 295.98($C_{16}H_9BrO$ = 297.15) | Sub 1-42 | m/z = 295.98($C_{16}H_9BrO$ = 297.15) |
| Sub 1-43 | m/z = 346.00($C_{20}H_{11}BrO$ = 347.20) | Sub 1-44 | m/z = 346.00($C_{20}H_{11}BrO$ = 347.20) |
| Sub 1-45 | m/z = 346.00($C_{20}H_{11}BrO$ = 347.20) | Sub 1-46 | m/z = 346.00($C_{20}H_{11}BrO$ = 347.20) |
| Sub 1-47 | m/z = 346.00($C_{20}H_{11}BrO$ = 347.20) | Sub 1-48 | m/z = 346.00($C_{20}H_{11}BrO$ = 347.20) |
| Sub 1-49 | m/z = 346.00($C_{20}H_{11}BrO$ = 347.20) | Sub 1-50 | m/z = 337.98($C_{18}H_{11}BrS$ = 339.25) |
| Sub 1-51 | m/z = 387.99($C_{22}H_{13}BrS$ = 389.31) | Sub 1-52 | m/z = 387.99($C_{22}H_{13}BrS$ = 389.31) |
| Sub 1-53 | m/z = 414.01($C_{24}H_{13}BrS$ = 415.34) | Sub 1-54 | m/z = 414.01($C_{24}H_{13}BrS$ = 415.34) |
| Sub 1-55 | m/z = 414.01($C_{24}H_{13}BrS$ = 415.34) | Sub 1-56 | m/z = 337.98($C_{18}H_{11}BrS$ = 339.25) |
| Sub 1-57 | m/z = 387.99($C_{22}H_{13}BrS$ = 389.31) | Sub 1-58 | m/z = 337.98($C_{18}H_{11}BrS$ = 339.25) |
| Sub 1-59 | m/z = 464.02($C_{28}H_{17}BrS$ = 465.40) | Sub 1-60 | m/z = 387.99($C_{22}H_{13}BrS$ = 389.31) |
| Sub 1-61 | m/z = 387.99($C_{22}H_{13}BrS$ = 389.31) | Sub 1-62 | m/z = 414.01($C_{24}H_{15}BrS$ = 415.34) |
| Sub 1-63 | m/z = 490.04($C_{30}H_{19}BrS$ = 491.44) | Sub 1-64 | m/z = 387.99($C_{22}H_{13}BrS$ = 389.31) |
| Sub 1-65 | m/z = 464.02($C_{28}H_{17}BrS$ = 465.40) | Sub 1-66 | m/z = 438.01($C_{26}H_{15}BrS$ = 439.37) |
| Sub 1-67 | m/z = 464.02($C_{28}H_{17}BrS$ = 465.40) | Sub 1-68 | m/z = 464.02($C_{28}H_{17}BrS$ = 465.40) |
| Sub 1-69 | m/z = 387.99($C_{22}H_{13}BrS$ = 389.31) | Sub 1-70 | m/z = 464.02($C_{28}H_{17}BrS$ = 465.40) |
| Sub 1-71 | m/z = 438.01($C_{26}H_{15}BrS$ = 439.37) | Sub 1-72 | m/z = 464.02($C_{28}H_{17}BrS$ = 465.40) |
| Sub 1-73 | m/z = 387.99($C_{22}H_{13}BrS$ = 389.31) | Sub 1-74 | m/z = 387.99($C_{22}H_{13}BrS$ = 389.31) |
| Sub 1-75 | m/z = 464.02($C_{28}H_{17}BrS$ = 465.40) | Sub 1-76 | m/z = 438.01($C_{26}H_{15}BrS$ = 439.37) |
| Sub 1-77 | m/z = 464.02($C_{28}H_{17}BrS$ = 465.40) | Sub 1-78 | m/z = 464.02($C_{28}H_{17}BrS$ = 465.40) |
| Sub 1-79 | m/z = 488.02($C_{30}H_{17}BrS$ = 489.42) | Sub 1-80 | m/z = 387.99($C_{22}H_{13}BrS$ = 389.31) |
| Sub 1-81 | m/z = 387.99($C_{22}H_{13}BrS$ = 389.31) | Sub 1-82 | m/z = 438.01($C_{26}H_{15}BrS$ = 439.37) |
| Sub 1-83 | m/z = 438.01($C_{26}H_{15}BrS$ = 439.37) | Sub 1-84 | m/z = 464.02($C_{28}H_{17}BrS$ = 465.40) |
| Sub 1-85 | m/z = 464.02($C_{28}H_{17}BrS$ = 465.40) | Sub 1-86 | m/z = 540.05($C_{34}H_{21}BrS$ = 541.50) |
| Sub 1-87 | m/z = 464.02($C_{28}H_{17}BrS$ = 465.40) | Sub 1-88 | m/z = 387.99($C_{22}H_{13}BrS$ = 389.31) |
| Sub 1-89 | m/z = 387.99($C_{22}H_{13}BrS$ = 389.31) | Sub 1-90 | m/z = 438.01($C_{26}H_{15}BrS$ = 439.37) |
| Sub 1-91 | m/z = 464.02($C_{28}H_{17}BrS$ = 465.40) | Sub 1-92 | m/z = 464.02($C_{28}H_{17}BrS$ = 465.40) |
| Sub 1-93 | m/z = 387.99($C_{22}H_{13}BrS$ = 389.31) | Sub 1-94 | m/z = 464.02($C_{28}H_{17}BrS$ = 465.40) |
| Sub 1-95 | m/z = 488.02($C_{30}H_{17}BrS$ = 489.42) | Sub 1-96 | m/z = 387.99($C_{22}H_{13}BrS$ = 389.31) |
| Sub 1-97 | m/z = 564.05($C_{36}H_{21}BrS$ = 565.52) | Sub 1-98 | m/z = 438.01($C_{26}H_{15}BrS$ = 439.37) |
| Sub 1-99 | m/z = 438.01($C_{26}H_{15}BrS$ = 439.37) | Sub 1-100 | m/z = 438.01($C_{26}H_{15}BrS$ = 439.37) |
| Sub 1-101 | m/z = 464.02($C_{28}H_{17}BrS$ = 465.40) | Sub 1-102 | m/z = 488.02($C_{30}H_{17}BrS$ = 489.42) |
| Sub 1-103 | m/z = 514.04($C_{32}H_{19}BrS$ = 515.46) | Sub 1-104 | m/z = 514.04($C_{32}H_{19}BrS$ = 515.46) |
| Sub 1-105 | m/z = 438.01($C_{26}H_{15}BrS$ = 439.37) | Sub 1-106 | m/z = 514.04($C_{32}H_{19}BrS$ = 515.46) |
| Sub 1-107 | m/z = 438.01($C_{26}H_{15}BrS$ = 439.37) | Sub 1-108 | m/z = 438.01($C_{26}H_{15}BrS$ = 439.37) |
| Sub 1-109 | m/z = 488.02($C_{30}H_{17}BrS$ = 489.42) | Sub 1-110 | m/z = 514.04($C_{32}H_{19}BrS$ = 515.46) |
| Sub 1-111 | m/z = 438.01($C_{26}H_{15}BrS$ = 439.37) | Sub 1-112 | m/z = 514.04($C_{32}H_{19}BrS$ = 515.46) |
| Sub 1-113 | m/z = 590.07($C_{38}H_{23}BrS$ = 591.56) | Sub 1-114 | m/z = 438.01($C_{26}H_{15}BrS$ = 439.37) |
| Sub 1-115 | m/z = 488.02($C_{30}H_{17}BrS$ = 489.42) | Sub 1-116 | m/z = 322.00($C_{18}H_{11}BrO$ = 323.18) |
| Sub 1-117 | m/z = 448.05($C_{28}H_{17}BrO$ = 449.34) | Sub 1-118 | m/z = 398.03($C_{24}H_{15}BrO$ = 399.28) |
| Sub 1-119 | m/z = 322.00($C_{18}H_{11}BrO$ = 323.18) | Sub 1-120 | m/z = 398.03($C_{24}H_{15}BrO$ = 399.28) |
| Sub 1-121 | m/z = 372.01($C_{22}H_{13}BrO$ = 373.24) | Sub 1-122 | m/z = 398.03($C_{24}H_{15}BrO$ = 399.28) |
| Sub 1-123 | m/z = 372.01($C_{22}H_{13}BrO$ = 373.24) | Sub 1-124 | m/z = 448.05($C_{28}H_{17}BrO$ = 449.34) |
| Sub 1-125 | m/z = 372.01($C_{22}H_{13}BrO$ = 373.24) | Sub 1-126 | m/z = 372.01($C_{22}H_{13}BrO$ = 373.24) |
| Sub 1-127 | m/z = 448.05($C_{28}H_{17}BrO$ = 449.34) | Sub 1-128 | m/z = 422.03($C_{26}H_{15}BrO$ = 423.30) |
| Sub 1-129 | m/z = 448.05($C_{28}H_{17}BrO$ = 449.34) | Sub 1-130 | m/z = 498.06($C_{32}H_{19}BrO$ = 499.40) |
| Sub 1-131 | m/z = 453.08($C_{28}H_{12}D_5BrO$ = 454.37) | Sub 1-132 | m/z = 372.01($C_{22}H_{13}BrO$ = 373.24) |
| Sub 1-133 | m/z = 422.03($C_{26}H_{15}BrO$ = 423.30) | Sub 1-134 | m/z = 472.05($C_{30}H_{17}BrO$ = 473.36) |
| Sub 1-135 | m/z = 448.05($C_{28}H_{17}BrO$ = 449.34) | Sub 1-136 | m/z = 372.01($C_{22}H_{13}BrO$ = 373.24) |
| Sub 1-137 | m/z = 372.01($C_{22}H_{13}BrO$ = 373.24) | Sub 1-138 | m/z = 422.03($C_{26}H_{15}BrO$ = 423.30) |
| Sub 1-139 | m/z = 448.05($C_{28}H_{17}BrO$ = 449.34) | Sub 1-140 | m/z = 372.01($C_{22}H_{13}BrO$ = 373.24) |
| Sub 1-141 | m/z = 372.01($C_{22}H_{13}BrO$ = 373.24) | Sub 1-142 | m/z = 448.05($C_{28}H_{17}BrO$ = 449.34) |
| Sub 1-143 | m/z = 472.05($C_{30}H_{17}BrO$ = 473.36) | Sub 1-144 | m/z = 422.03($C_{26}H_{15}BrO$ = 423.30) |
| Sub 1-145 | m/z = 498.06($C_{32}H_{19}BrO$ = 499.40) | Sub 1-146 | m/z = 422.03($C_{26}H_{15}BrO$ = 423.30) |
| Sub 1-147 | m/z = 422.03($C_{26}H_{15}BrO$ = 423.30) | Sub 1-148 | m/z = 422.03($C_{26}H_{15}BrO$ = 423.30) |
| Sub 1-149 | m/z = 422.03($C_{26}H_{15}BrO$ = 423.30) | | |

II. Synthesis of Sub 2

Sub 2 of Reaction Scheme 1 can be synthesized, but not limited to, by reaction of the following Reaction Scheme 21.

<Reaction Scheme 21>

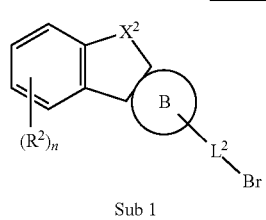

Sub 1

-continued

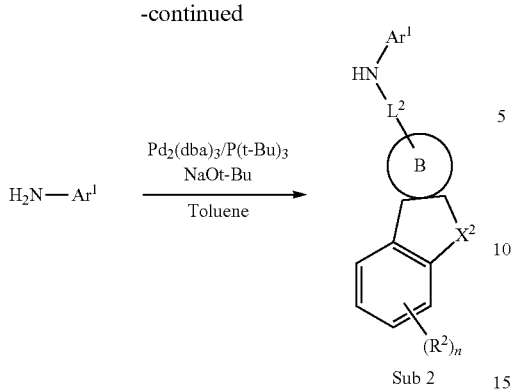

Sub 2

Synthesis Examples of compounds comprised in Sub 2 are as followings.

1. Synthesis Example of Sub 2-22

<Reaction Scheme 22>

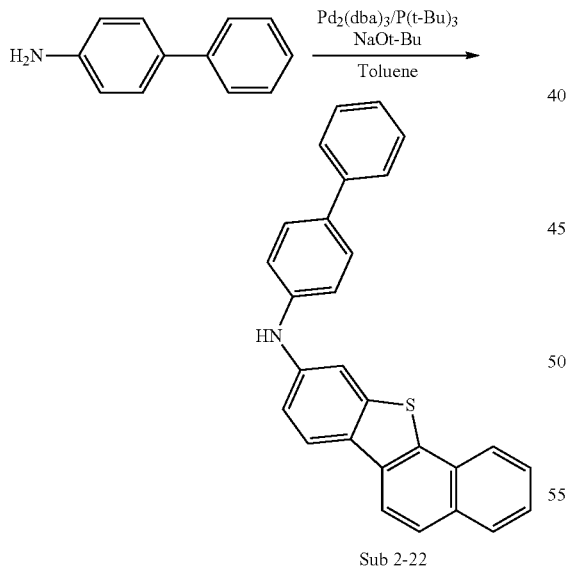

Sub 1-10 (11.46 g, 36.6 mmol) in a round bottom flask was dissolved in toluene (420 ml), followed by adding [1,1'-biphenyl]-4-amine (8.05 g, 47.6 mmol), $Pd_2(dba)_3$ (1.01 g, 1.1 mmol), 50% $P(t\text{-}Bu)_3$ (1.4 ml, 2.9 mmol) and NaOt-Bu (10.55 g, 109.8 mmol) and then stirring at 80° C. Upon the completion of the reaction, the reaction product was extracted with $CH_2Cl_2$ and water. After that, the extracted organic layer was dried with $MgSO_4$ and then concentrated. The concentrated resultant was separated by silica gel column chromatography, and was then recrystallized, whereby final product was obtained in the amount of 12.49 g (yield: 85%).

2. Synthesis Example of Sub 2-32

<Reaction Scheme 23>

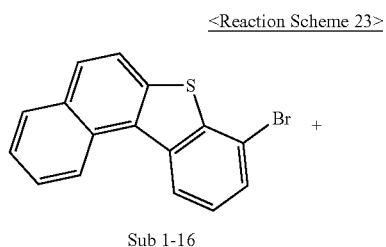

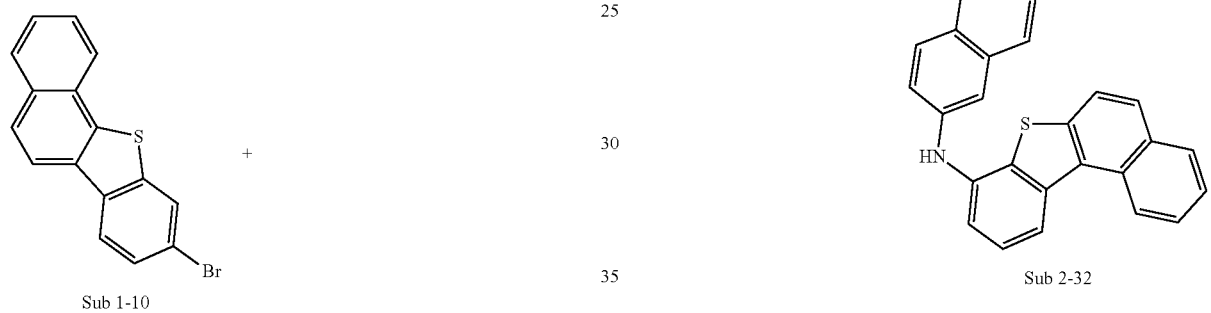

Sub 2-32

Product was obtained in the amount of 10.75 g (yield: 87%) where Sub 1-16 (10.31 g, 32.9 mmol), naphthalen-2-amine (6.13 g, 42.8 mmol), $Pd_2(dba)_3$ (0.9 g, 1 mmol), 50% $P(t\text{-}Bu)_3$ (1.3 ml, 2.6 mmol) and NaOt-Bu (9.49 g, 98.8 mmol) and toluene (380 ml) were used in the same manner as described above for the synthesis of compound Sub 2-22.

3. Synthesis Example of Sub 2-53

<Reaction Scheme 24>

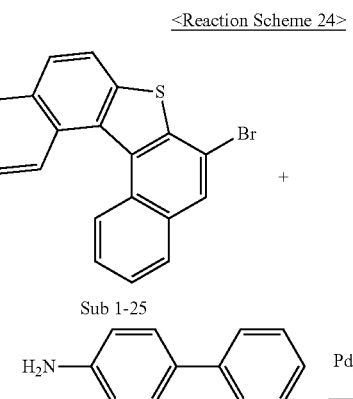

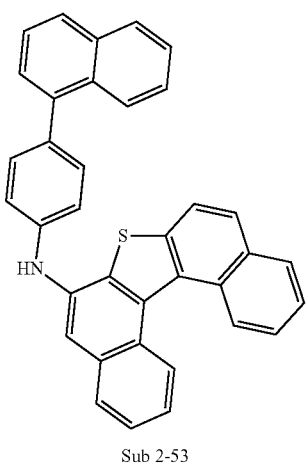

Sub 2-53

Product was obtained in the amount of 20.41 g (yield: 72%) where Sub 1-25 (20.53 g, 56.5 mmol), 4-(naphthalen-1-yl)aniline (16.11 g, 73.5 mmol), Pd$_2$(dba)$_3$ (1.55 g, 1.7 mmol), 50% P(t-Bu)$_3$ (2.2 ml, 4.5 mmol), NaOt-Bu (16.29 g, 169.5 mmol) and toluene (650 ml) were used in the same manner as described above for the synthesis of compound Sub 2-22.

4. Synthesis Example of Sub 2-96

<Reaction Scheme 25>

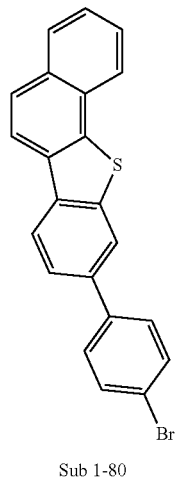

Sub 1-80

+

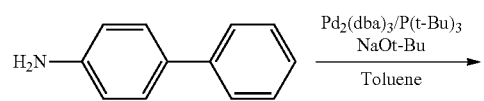

Pd$_2$(dba)$_3$/P(t-Bu)$_3$
NaOt-Bu
———————→
Toluene

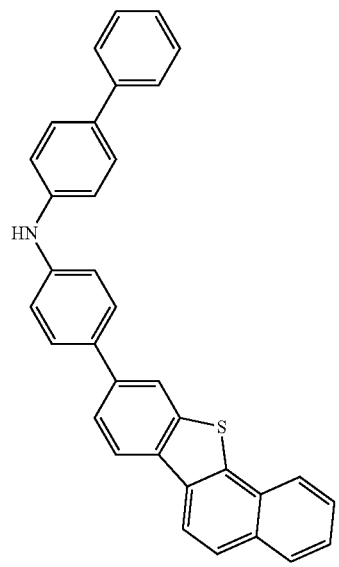

Sub 2-96

Product was obtained in the amount of 13.26 g (yield: 79%) where Sub 1-80 (13.68 g, 35.1 mmol), [1,1'-biphenyl]-4-amine (7.73 g, 45.7 mmol), Pd$_2$(dba)$_3$ (0.97 g, 1.1 mmol), 50% P(t-Bu)$_3$ (1.4 ml, 2.8 mmol), NaOt-Bu (10.13 g, 105.4 mmol) and toluene (405 ml) were used in the same manner as described above for the synthesis of compound Sub 2-22.

5. Synthesis Example of Sub 2-101

<Reaction Scheme 26>

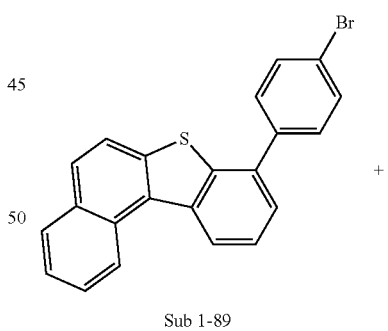

Sub 1-89

+

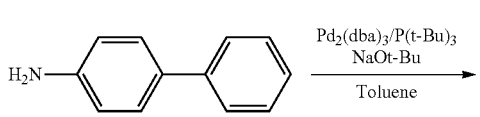

Pd$_2$(dba)$_3$/P(t-Bu)$_3$
NaOt-Bu
———————→
Toluene

-continued

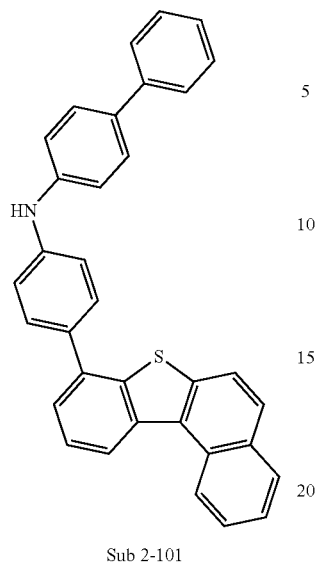

Sub 2-101

Product was obtained in the amount of 11.66 g (yield: 81%) where Sub 1-89 (11.73 g, 30.1 mmol), [1,1'-biphenyl]-4-amine (6.63 g, 39.2 mmol), $Pd_2(dba)_3$ (0.83 g, 0.9 mmol), 50% $P(t-Bu)_3$ (1.2 ml, 2.4 mmol), NaOt-Bu (8.69 g, 90.4 mmol) and toluene (345 ml) were used in the same manner as described above for the synthesis of compound Sub 2-22.

6. Synthesis Example of Sub 2-102

-continued

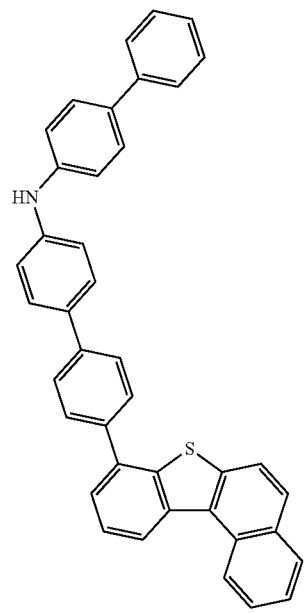

Sub 2-102

Product was obtained in the amount of 12.43 g (yield: 70%) where Sub 1-91 (14.93 g, 32.1 mmol), [1,1'-biphenyl]-4-amine (7.06 g, 41.7 mmol), $Pd_2(dba)_3$ (0.88 g, 1 mmol), 50% $P(t-Bu)_3$ (1.3 ml, 2.6 mmol), NaOt-Bu (9.25 g, 96.2 mmol) and toluene (370 ml) were used in the same manner as described above for the synthesis of compound Sub 2-22.

7. Synthesis Example of Sub 2-106

<Reaction Scheme 27>

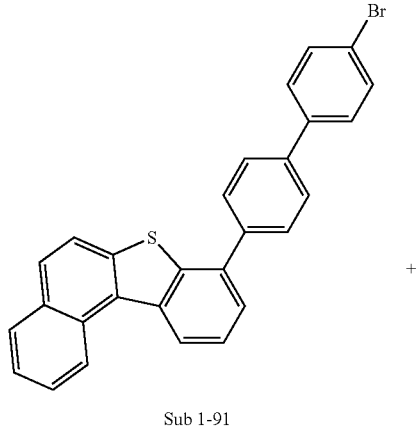

Sub 1-91

<Reaction Scheme 28>

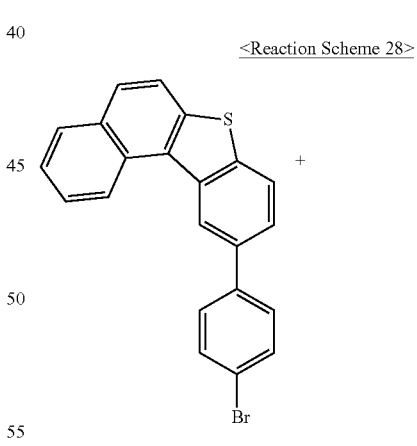

Sub 1-96

159
-continued

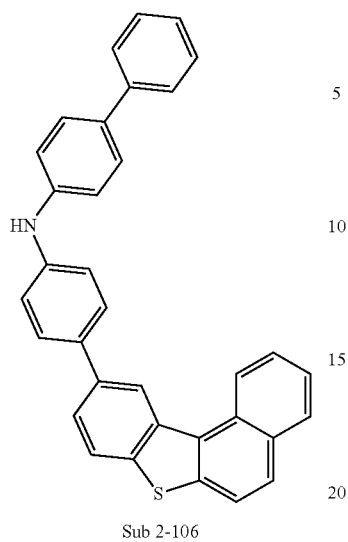
Sub 2-106

Product was obtained in the amount of 13.52 g (yield: 83%) where Sub 1-96 (13.28 g, 34.1 mmol), [1,1'-biphenyl]-4-amine (7.5 g, 44.3 mmol), Pd₂(dba)₃ (0.94 g, 1 mmol), 50% P(t-Bu)₃ (1.3 ml, 2.7 mmol), NaOt-Bu (9.84 g, 102.3 mmol) and toluene (390 ml) were used in the same manner as described above for the synthesis of compound Sub 2-22.

8. Synthesis Example of Sub 2-120

<Reaction Scheme 29>

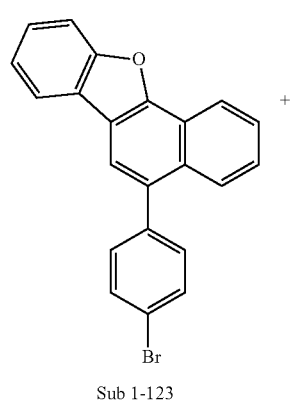
Sub 1-123

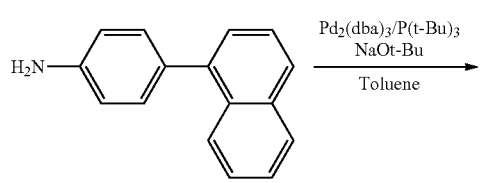

160
-continued

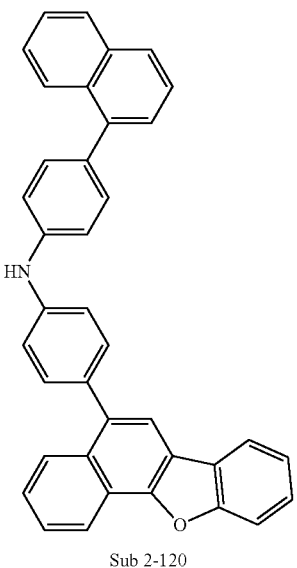
Sub 2-120

Product was obtained in the amount of 11.38 g (yield: 78%) where Sub 1-123 (10.64 g, 28.5 mmol), 4-(naphthalen-1-yl)aniline (8.13 g, 37.1 mmol), Pd₂(dba)₃ (0.78 g, 0.9 mmol), 50% P(t-Bu)₃ (1.1 ml, 2.3 mmol), NaOt-Bu (8.22 g, 85.5 mmol) and toluene (330 ml) were used in the same manner as described above for the synthesis of compound Sub 2-22.

9. Synthesis Example of Sub 2-132

<Reaction Scheme 30>

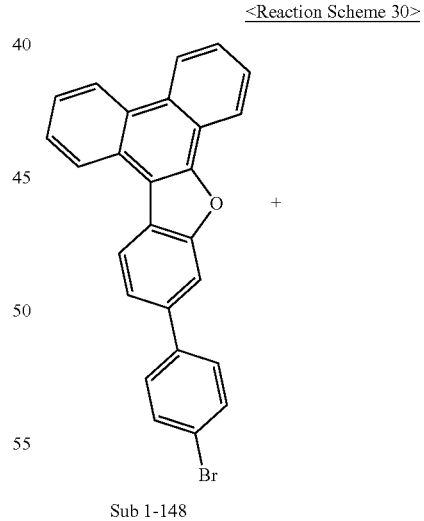
Sub 1-148

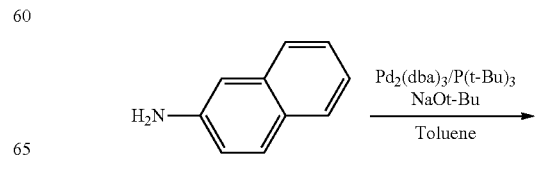

-continued

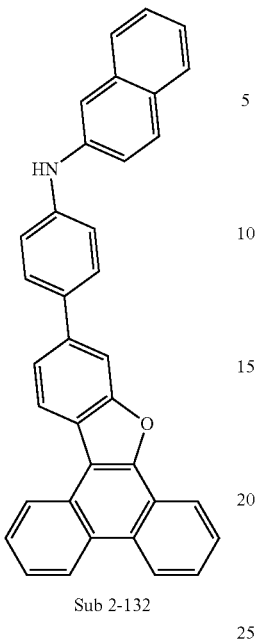
Sub 2-132

Product was obtained in the amount of 12.83 g (yield: 74%) where Sub 1-148 (15.12 g, 35.7 mmol), naphthalen-2-amine (6.65 g, 46.4 mmol), Pd$_2$(dba)$_3$ (0.98 g, 1.1 mmol), 50% P(t-Bu)$_3$ (1.4 ml, 2.9 mmol), NaOt-Bu (10.3 g, 107.2 mmol) and toluene (410 ml) were used in the same manner as described above for the synthesis of compound Sub 2-22.

Meanwhile, the compounds comprised in Sub 2 may be, but not limited to, the following compounds, and Table 2 below shows FD-MS (Field Desorption-Mass Spectrometry) data of the compounds.

Sub 2-1

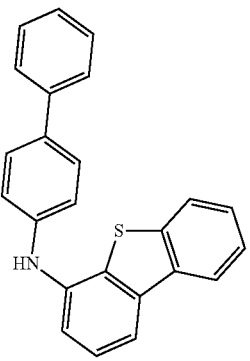

Sub 2-2

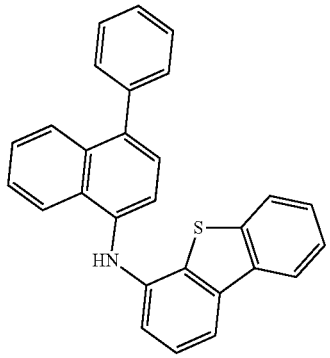

-continued

Sub 2-3

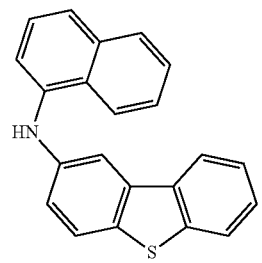

Sub 2-4

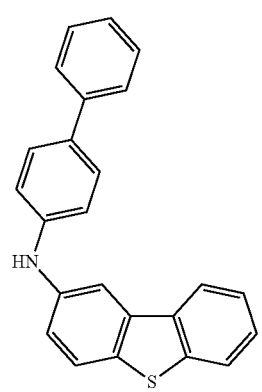

Sub 2-5

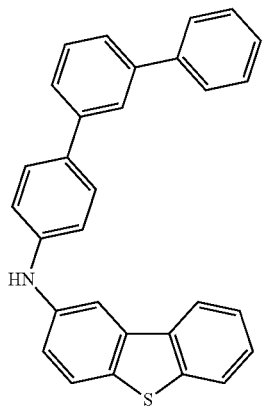

Sub 2-6

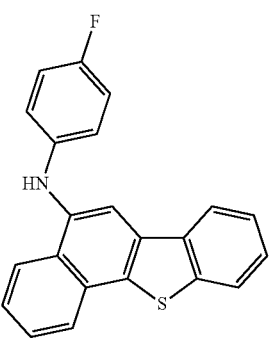

Sub 2-7
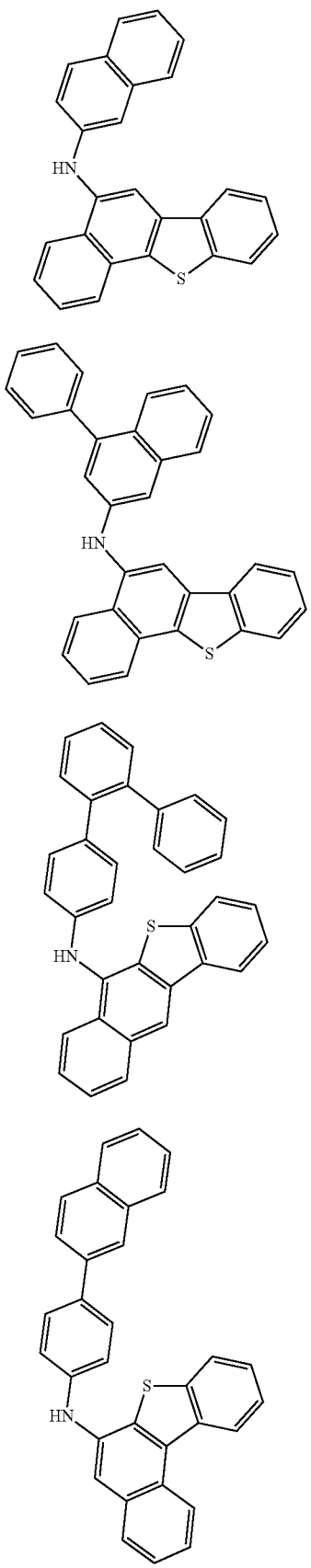
Sub 2-8
Sub 2-9
Sub 2-10
Sub 2-11
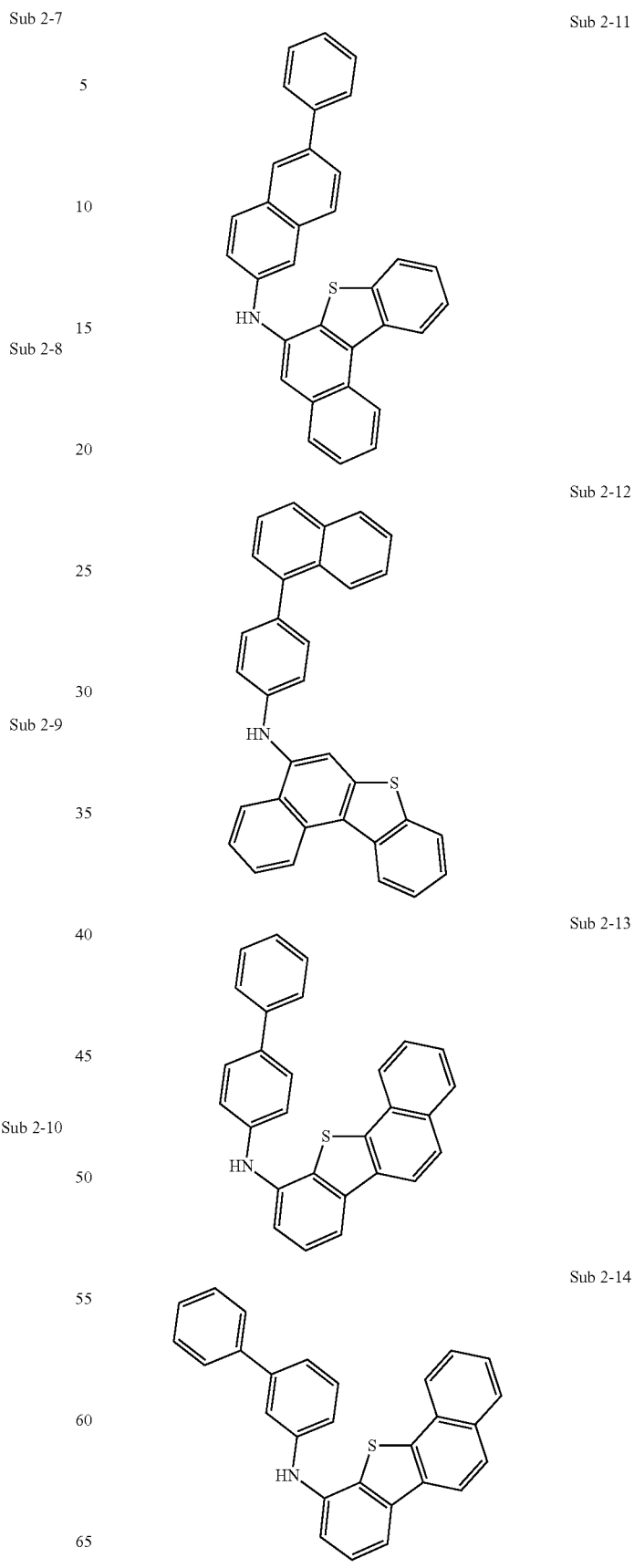
Sub 2-12
Sub 2-13
Sub 2-14

Sub 2-15
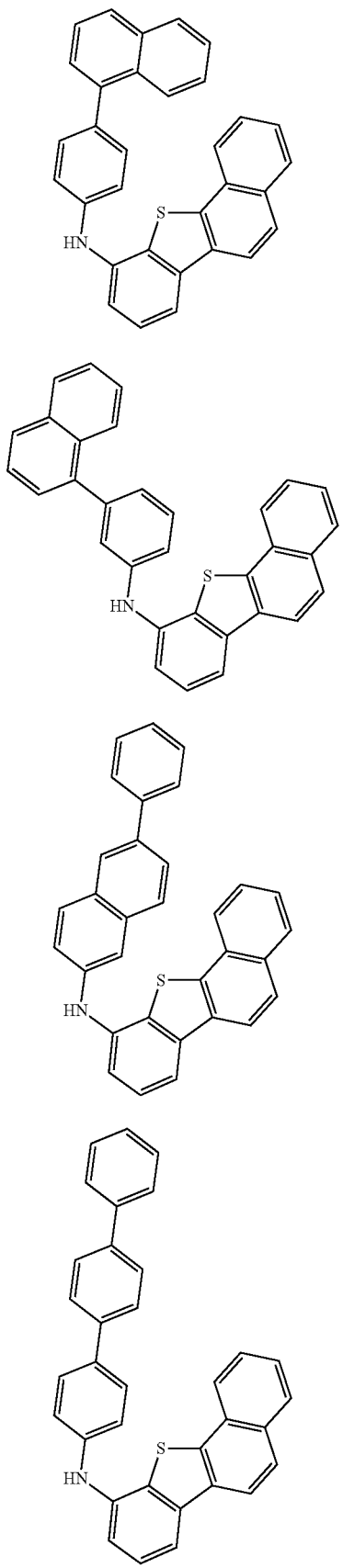
Sub 2-16
Sub 2-17
Sub 2-18
Sub 2-19
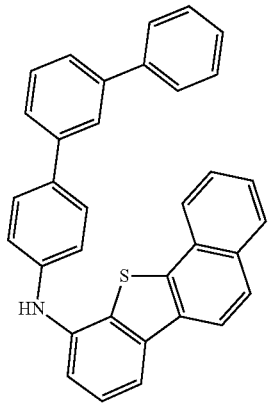
Sub 2-20
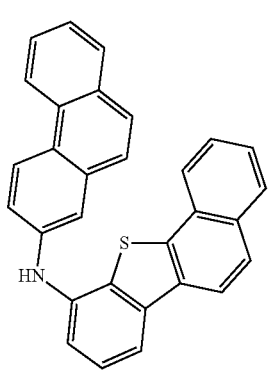
Sub 2-21
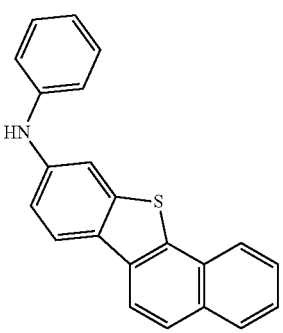
Sub 2-22
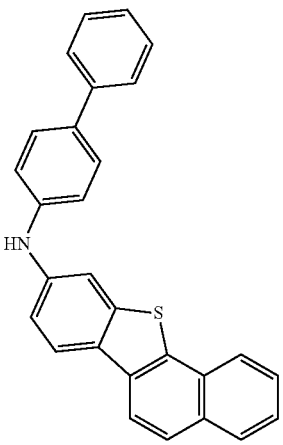

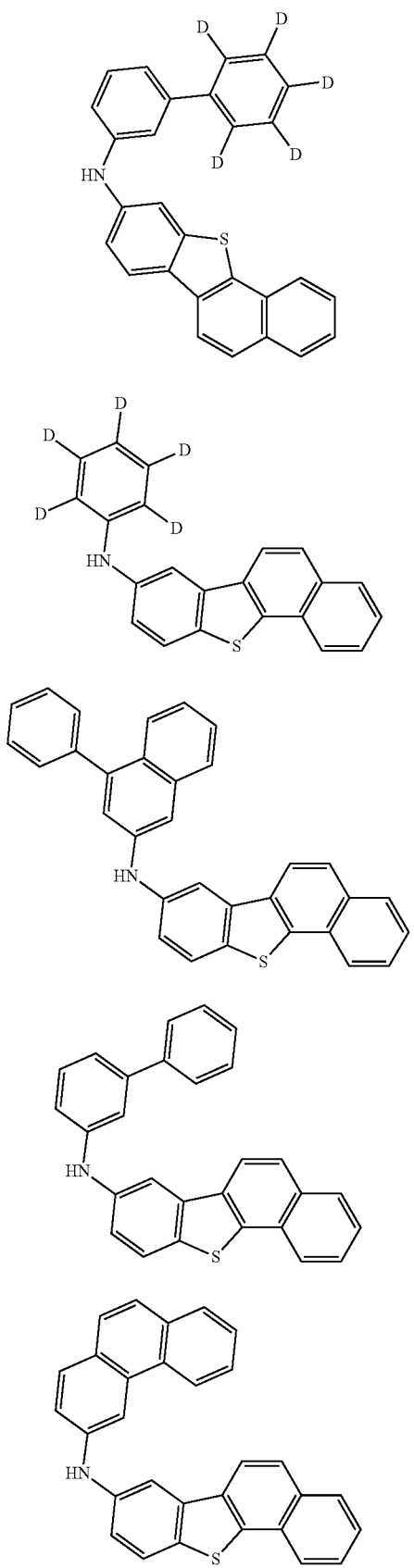

Sub 2-32
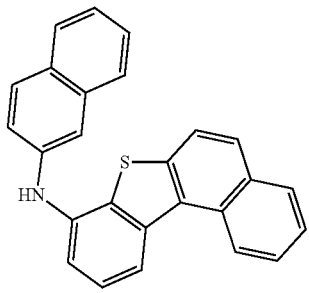
Sub 2-33
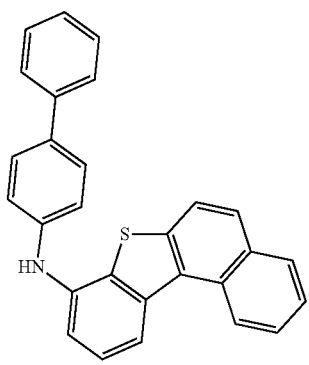
Sub 2-34
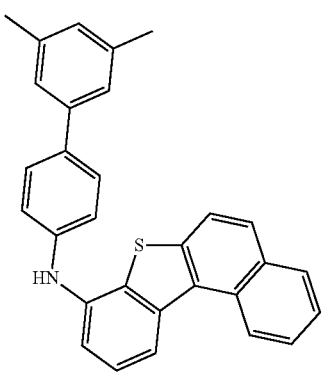
Sub 2-35
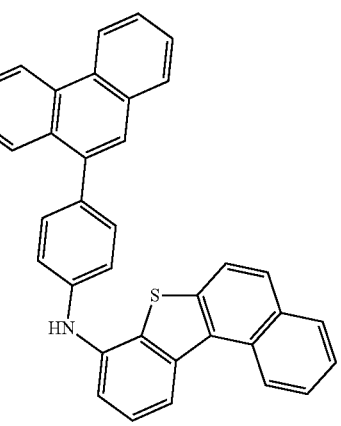
Sub 2-36
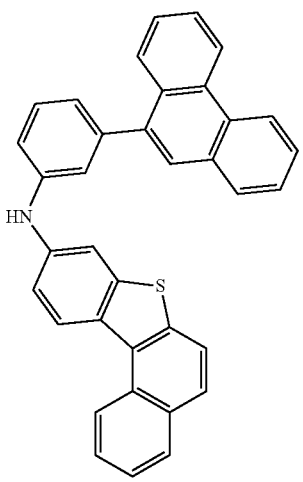
Sub 2-37
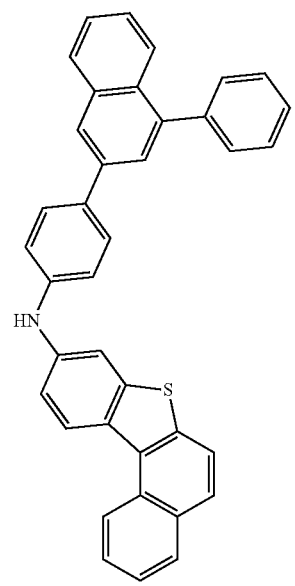
Sub 2-38
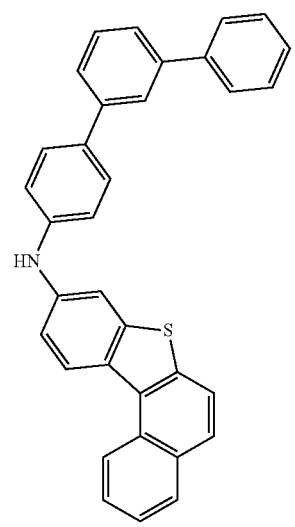

-continued
Sub 2-39
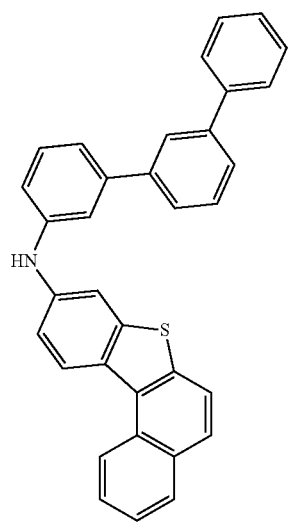
Sub 2-40
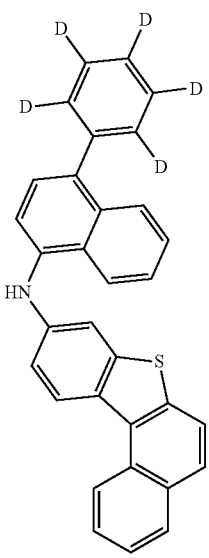
Sub 2-41
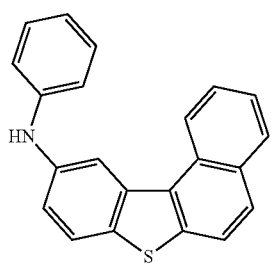
Sub 2-42
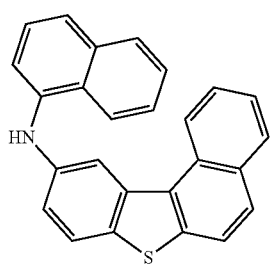
-continued
Sub 2-43
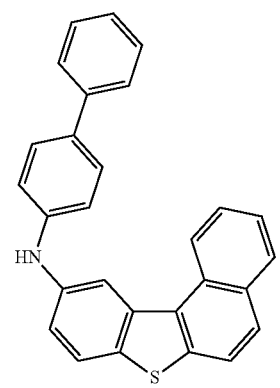
Sub 2-44
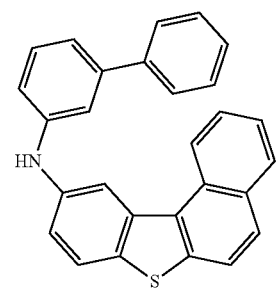
Sub 2-45
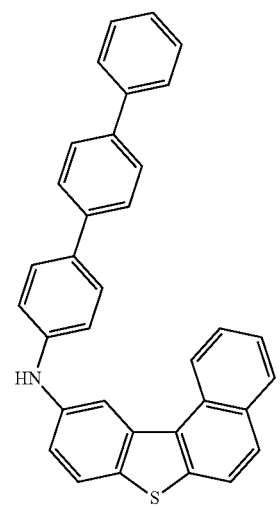
Sub 2-46
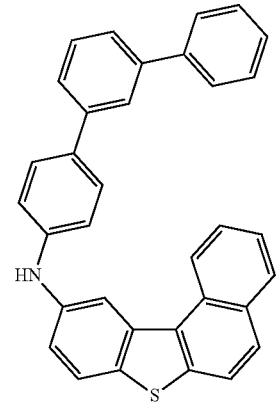

Sub 2-47
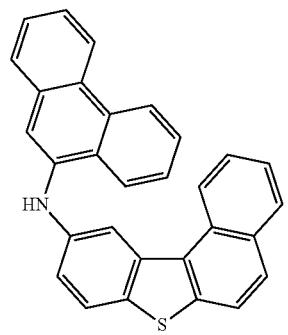
Sub 2-51
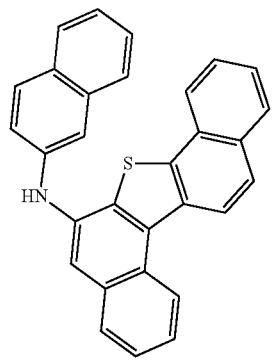
Sub 2-48
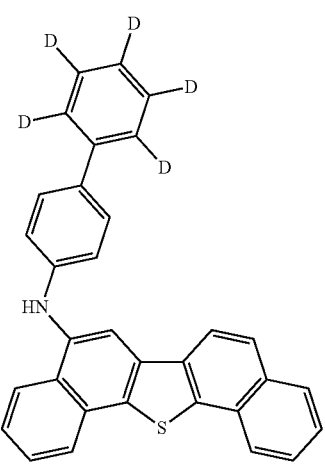
Sub 2-52
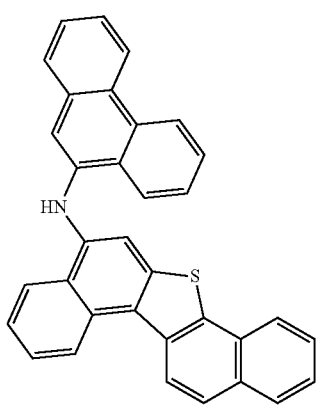
Sub 2-49
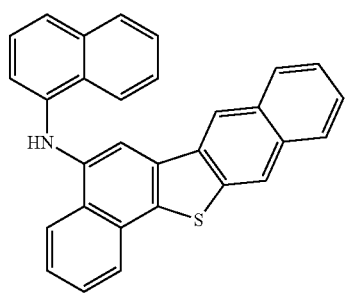
Sub 2-53
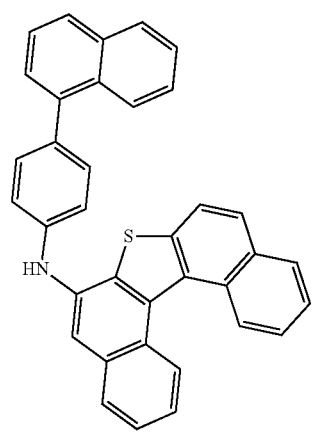
Sub 2-50
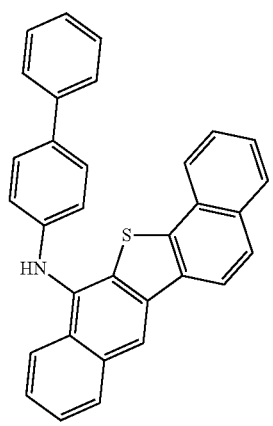
Sub 2-54
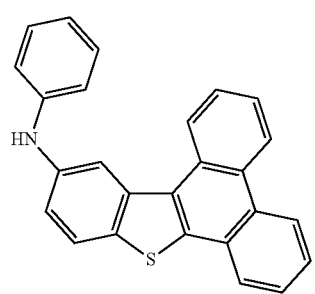

Sub 2-55
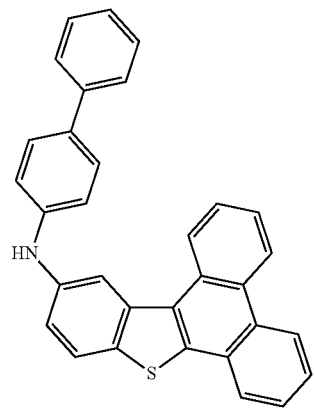
Sub 2-56
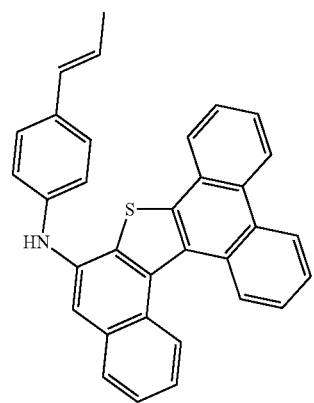
Sub 2-57
Sub 2-58
Sub 2-59
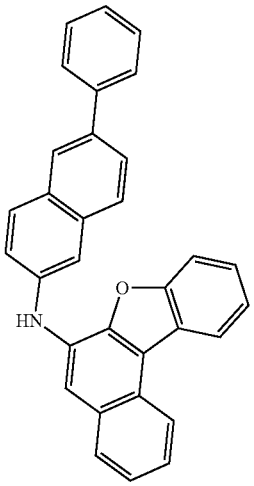
Sub 2-60
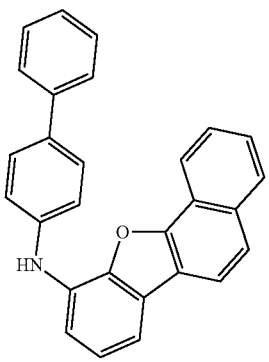
Sub 2-61
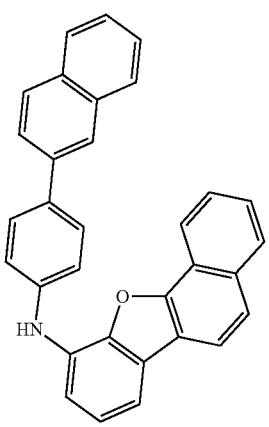

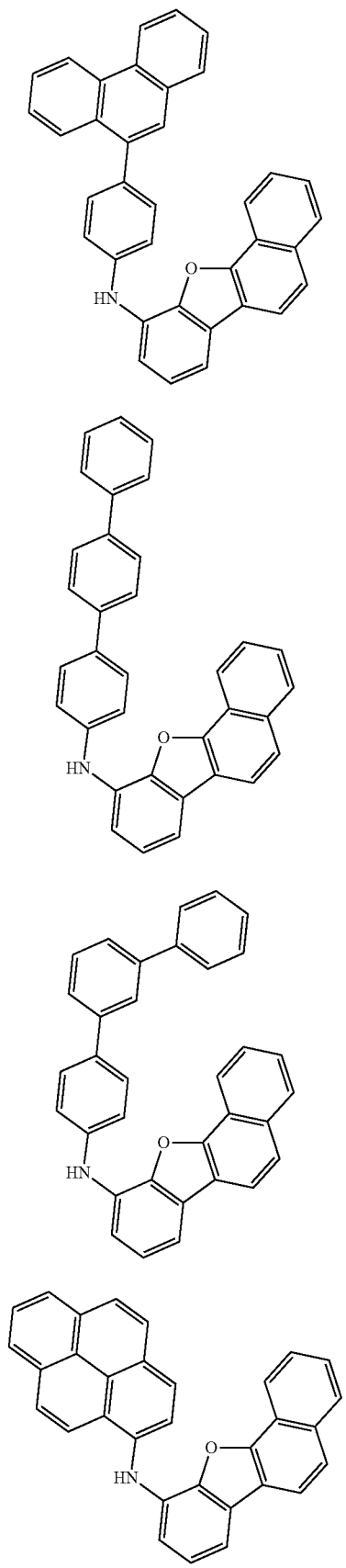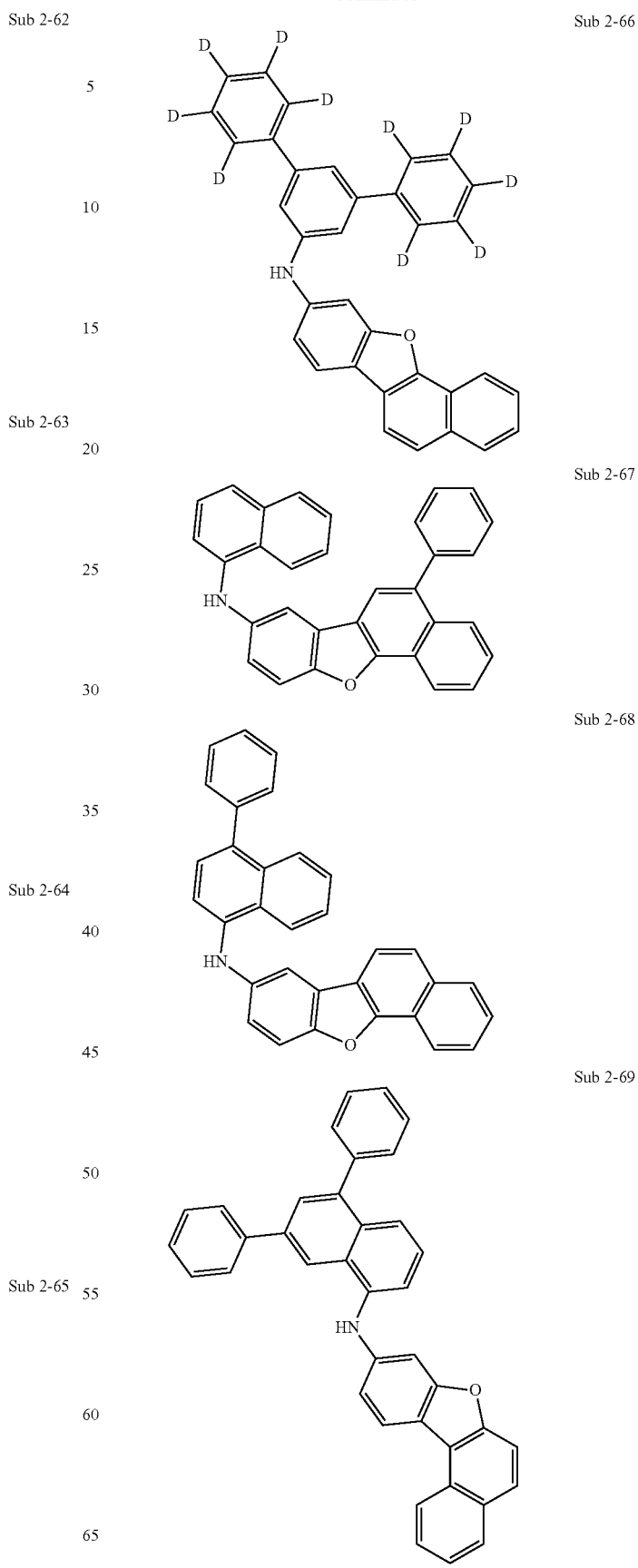

Sub 2-70
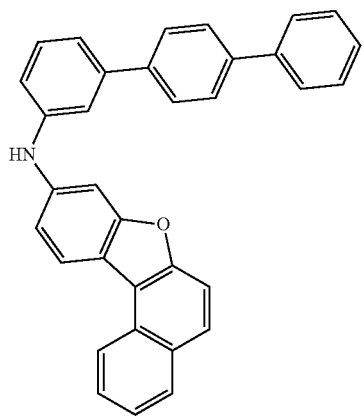
Sub 2-71
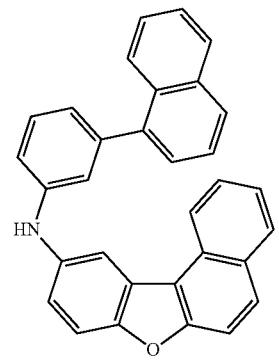
Sub 2-72
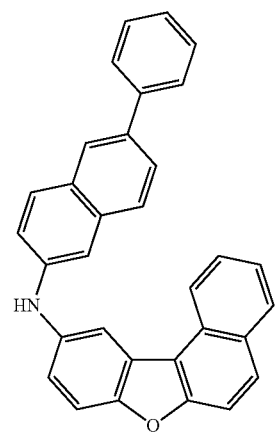
Sub 2-73
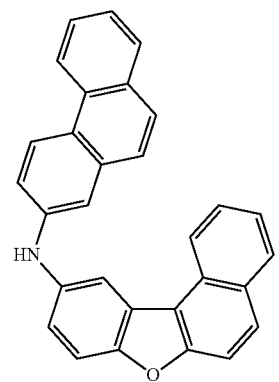
Sub 2-74
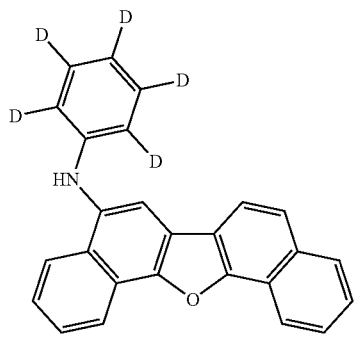
Sub 2-75
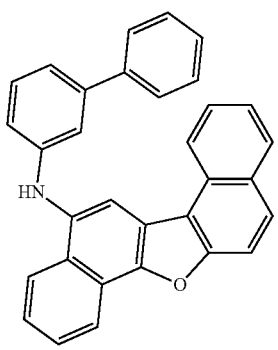
Sub 2-76
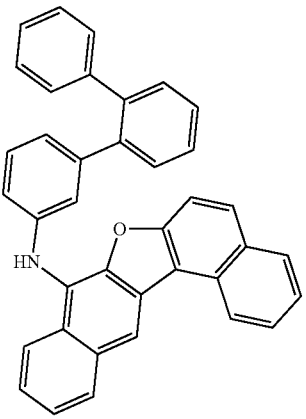
Sub 2-77
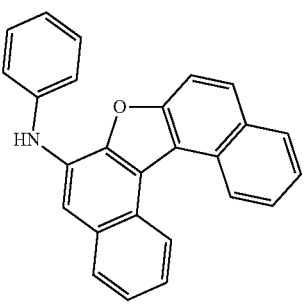

-continued
Sub 2-78
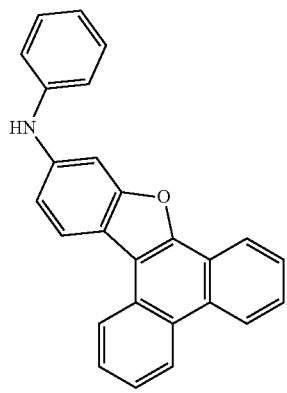
Sub 2-79
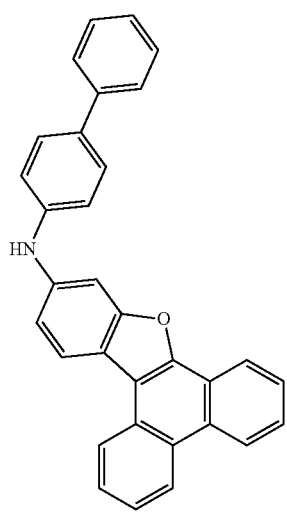
Sub 2-80
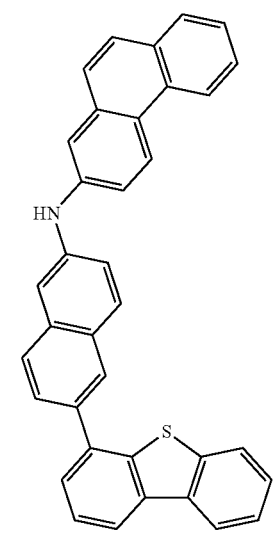
-continued
Sub 2-81
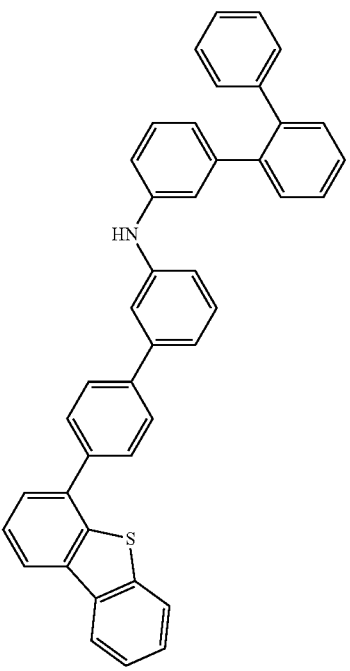
Sub 2-82
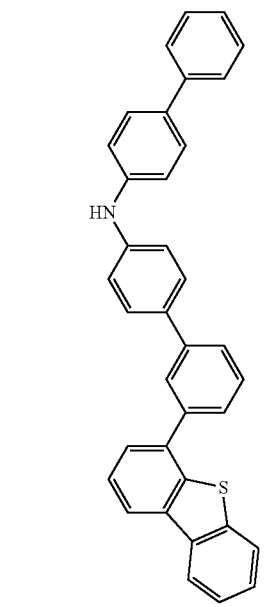

Sub 2-83
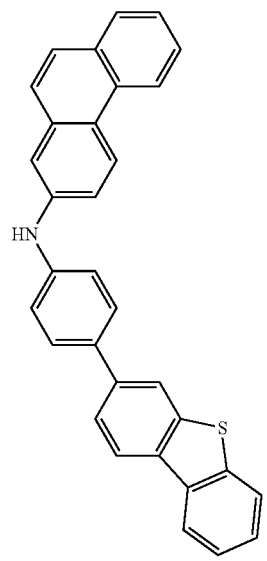
Sub 2-85
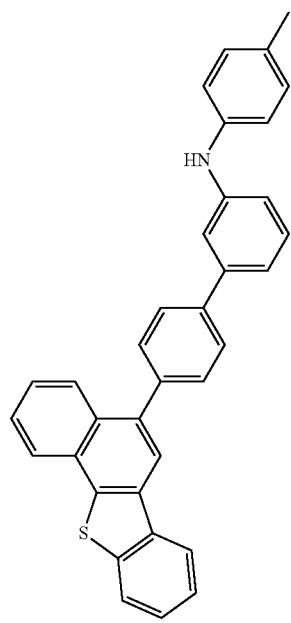
Sub 2-84
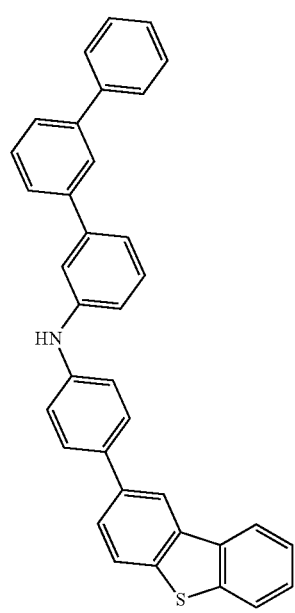
Sub 2-86
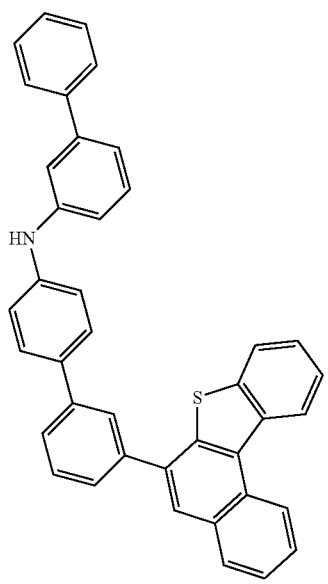

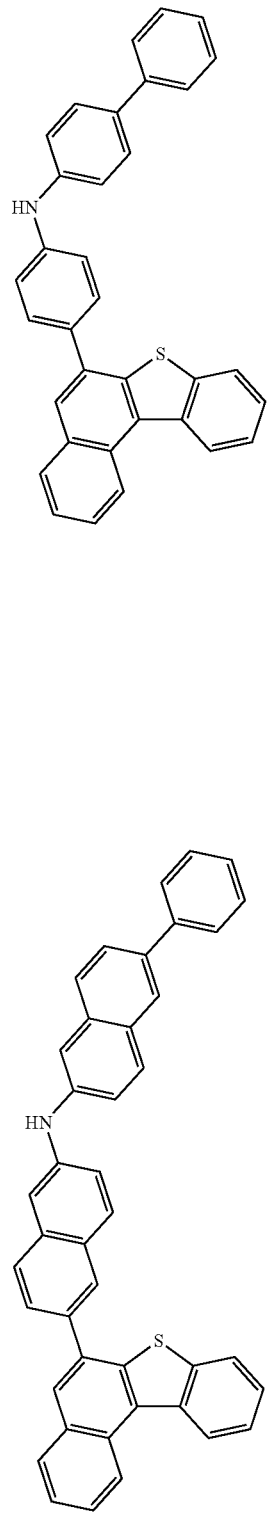
Sub 2-87
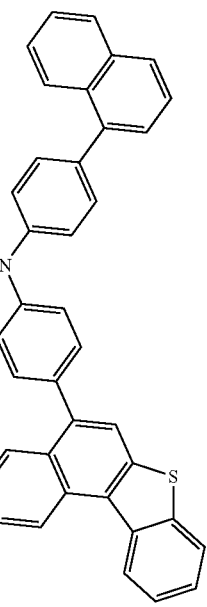
Sub 2-88
Sub 2-89
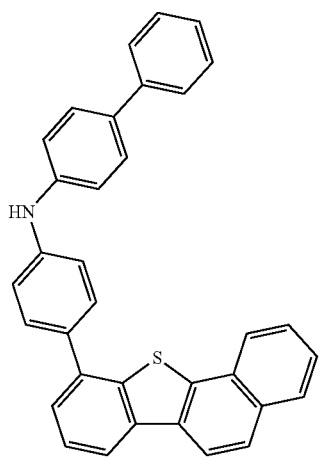
Sub 2-90
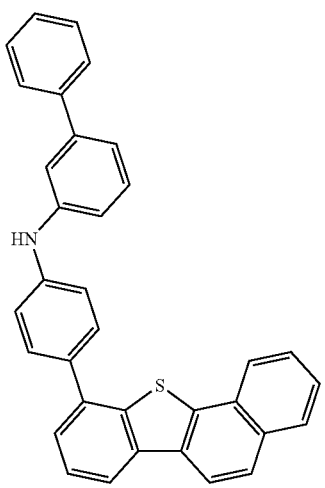
Sub 2-91

Sub 2-92
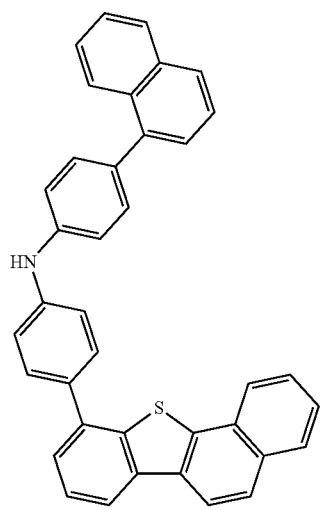
Sub 2-93
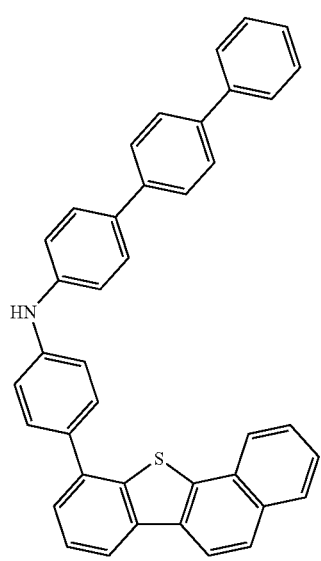
Sub 2-94
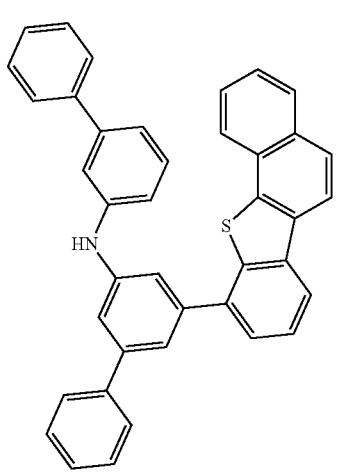
Sub 2-95
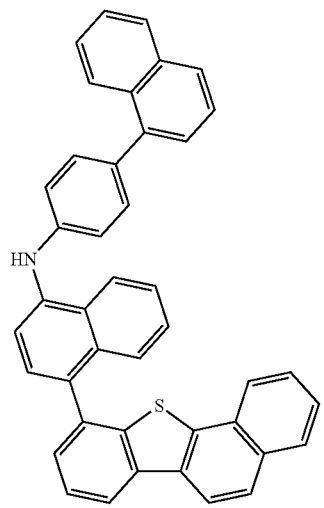
Sub 2-96
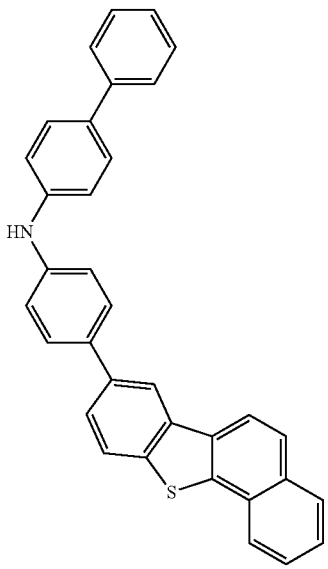

-continued
Sub 2-97
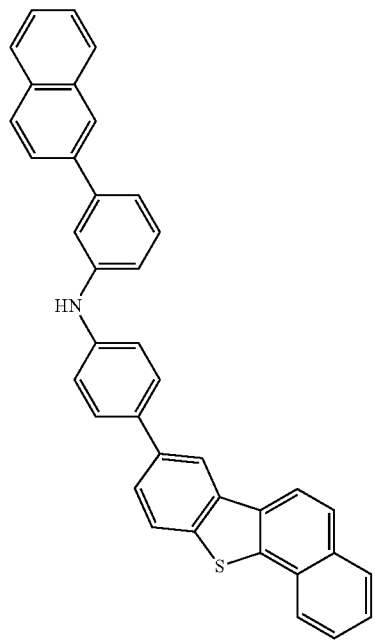
Sub 2-99
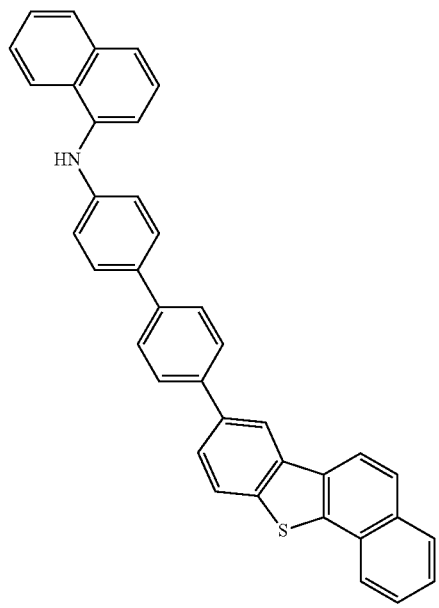
Sub 2-98
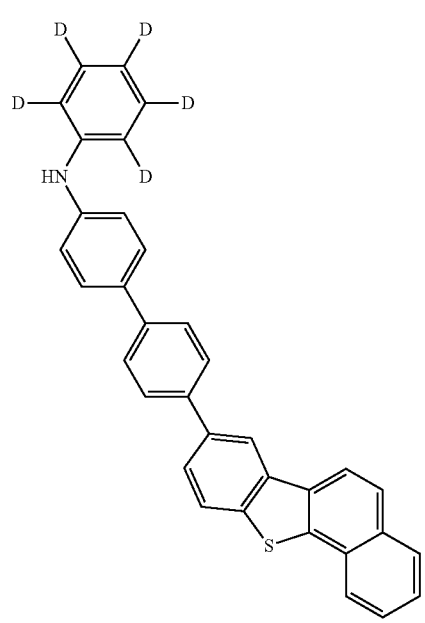
Sub 2-100
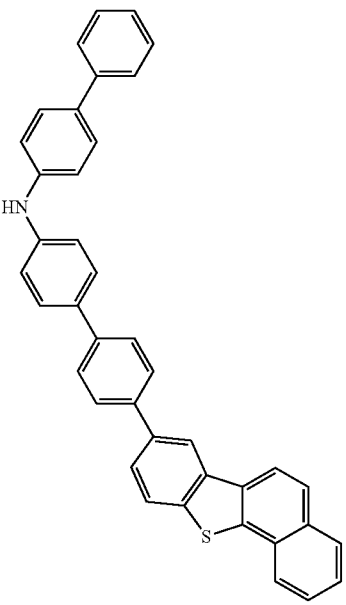

-continued
Sub 2-101
Sub 2-102
Sub 2-103
Sub 2-104
Sub 2-105
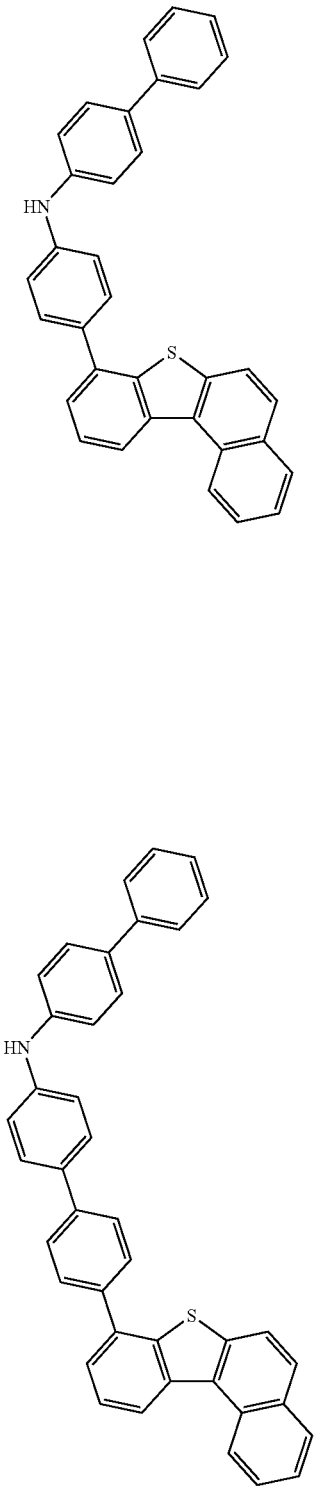
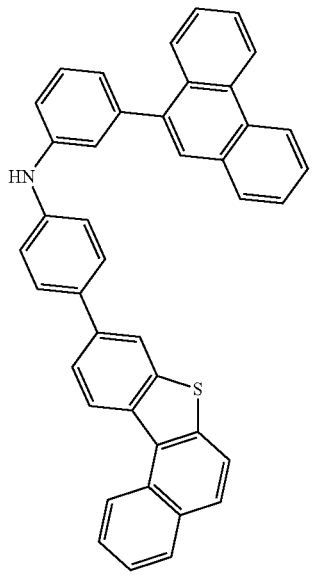
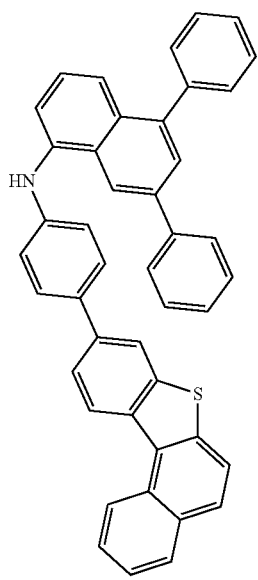
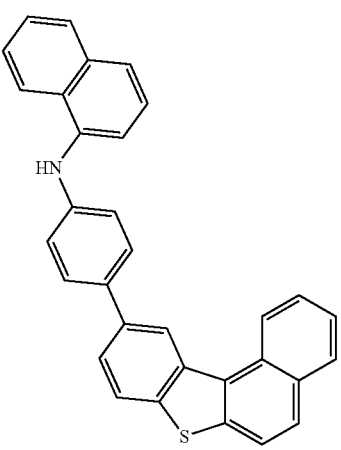

Sub 2-106
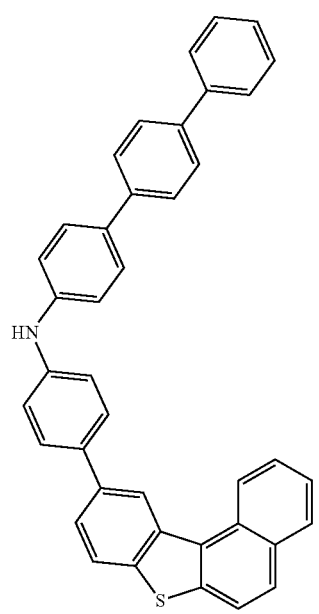
Sub 2-107
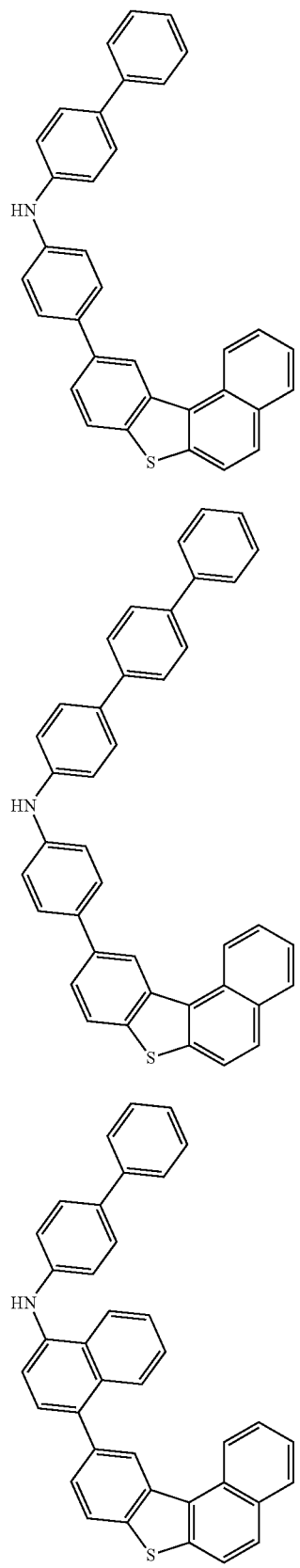
Sub 2-108
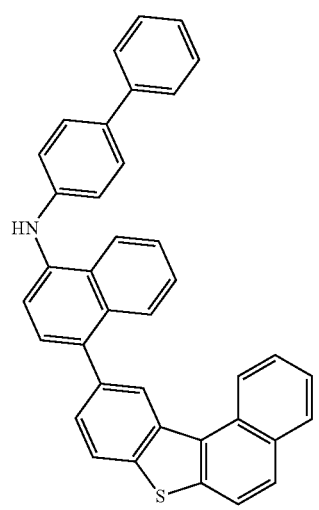
Sub 2-109
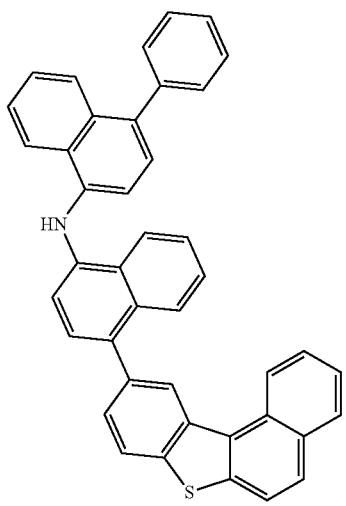
Sub 2-110
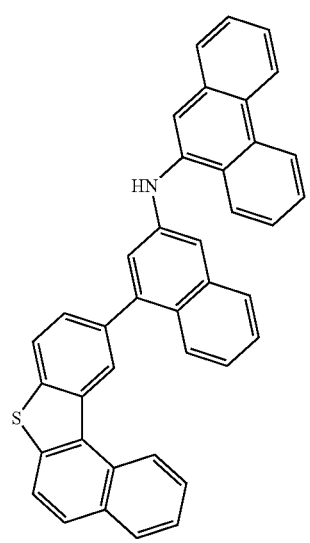
Sub 2-111
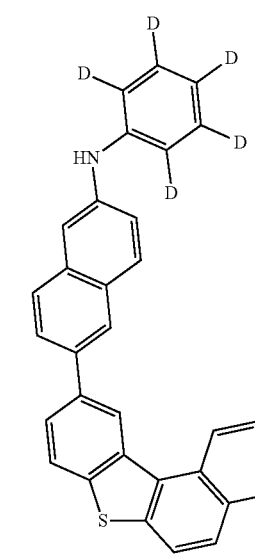

Sub 2-112
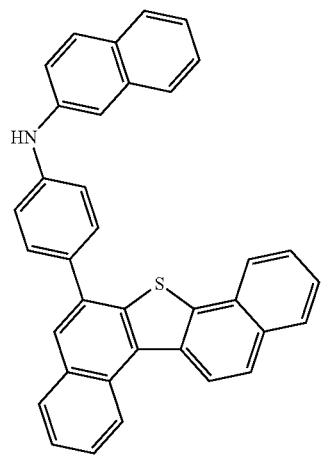
Sub 2-115
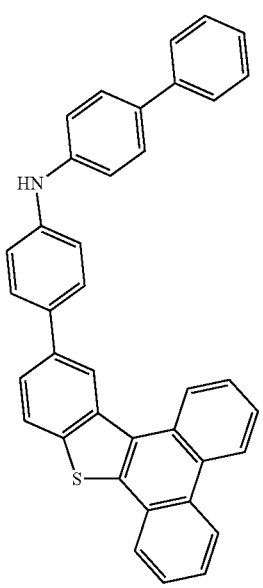
Sub 2-113
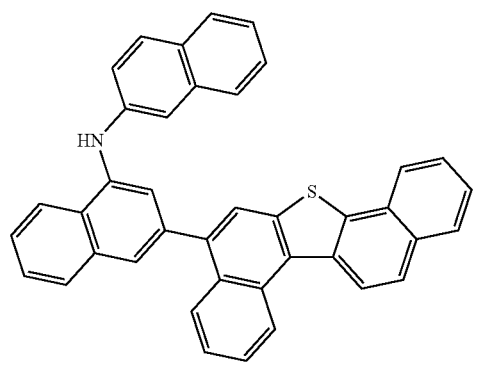
Sub 2-116
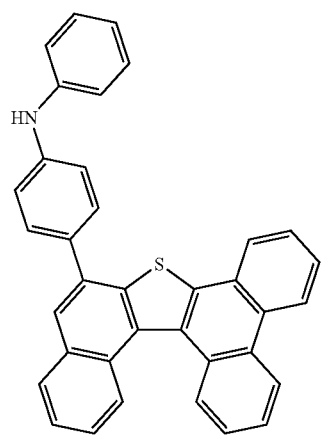
Sub 2-114
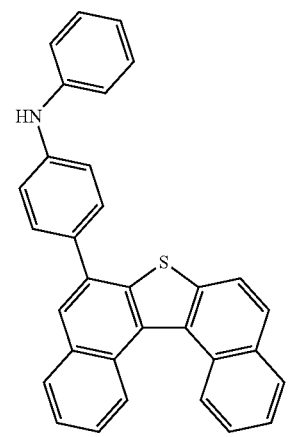
Sub 2-117
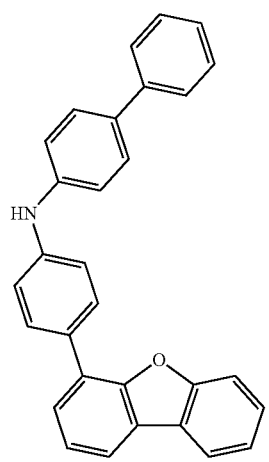

Sub 2-118
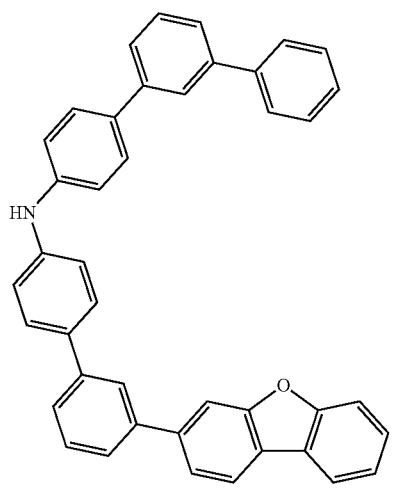
Sub 2-119
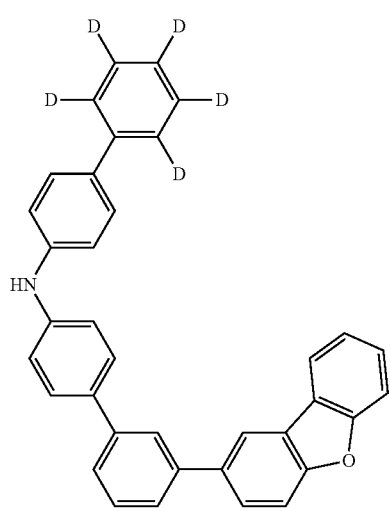
Sub 2-120
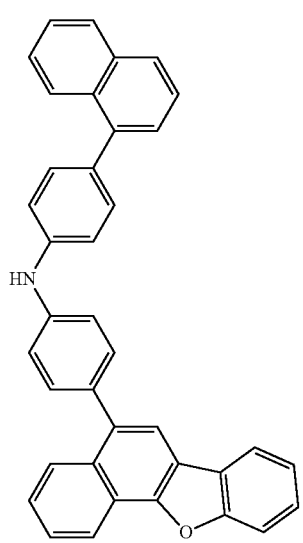
Sub 2-121
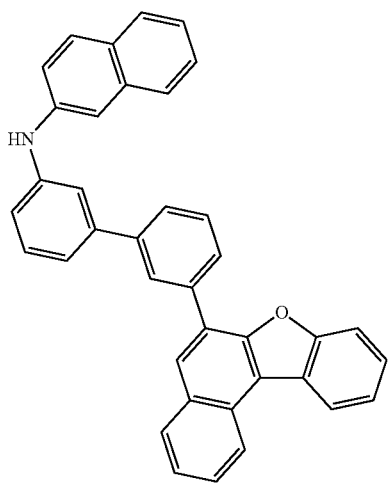
Sub 2-122
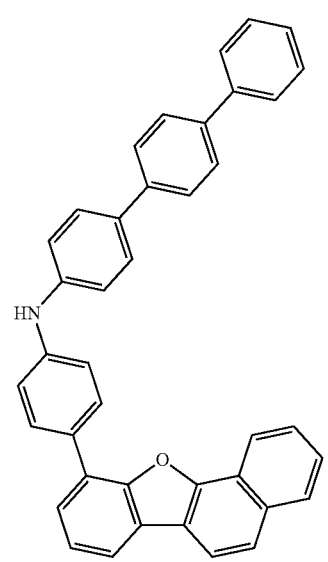
Sub 2-123
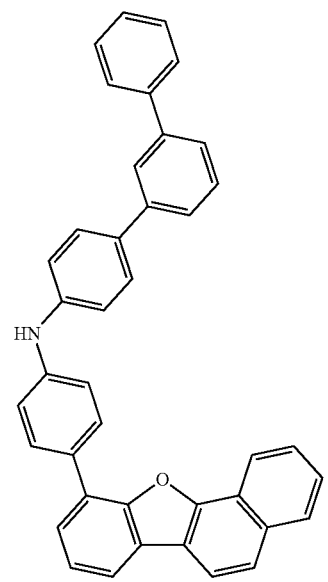

Sub 2-124
Sub 2-125
Sub 2-126
Sub 2-127
Sub 2-128
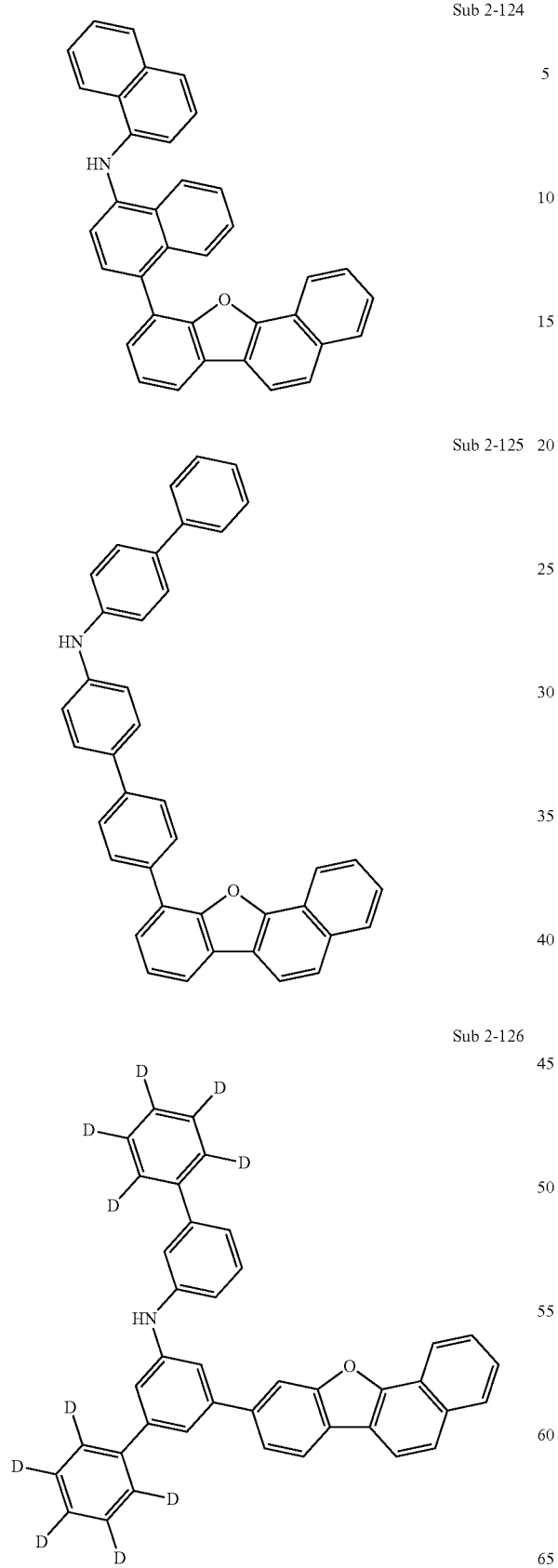
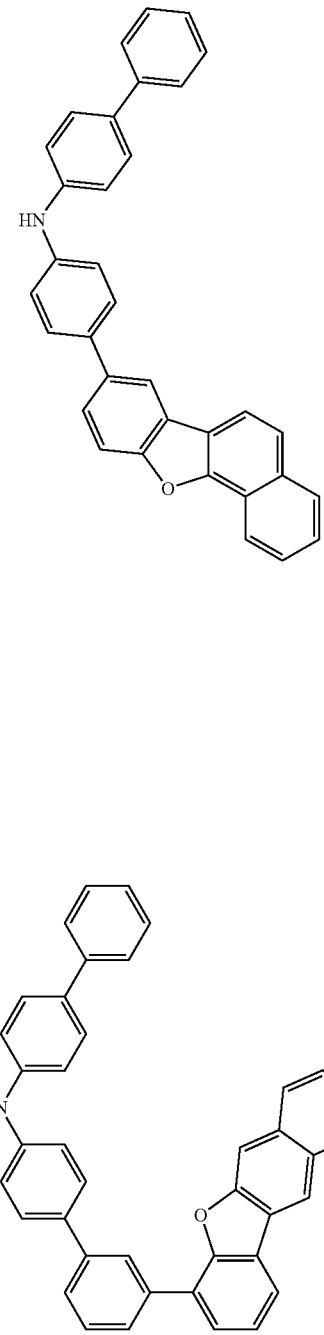

Sub 2-129
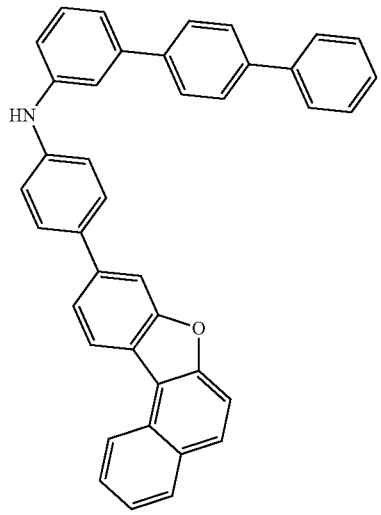

Sub 2-130
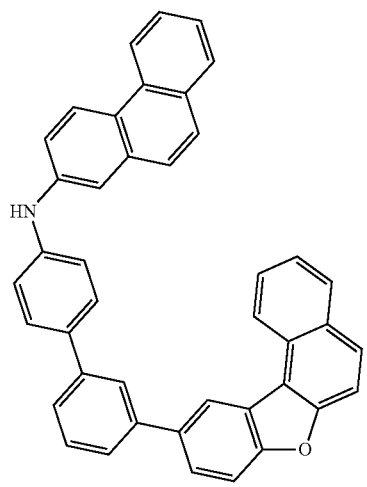

Sub 2-131
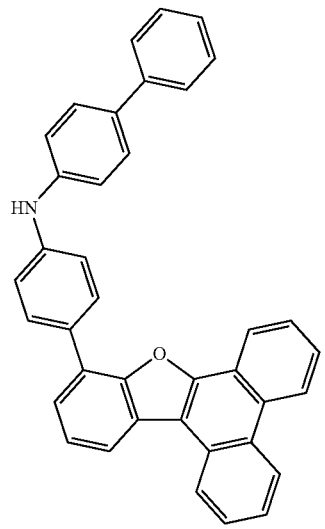

Sub 2-132
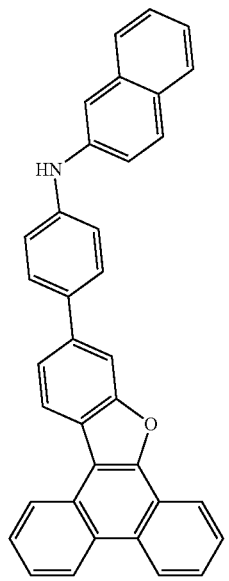

TABLE 2

| Compound | FD-MS | Compound | FD-MS |
| --- | --- | --- | --- |
| Sub 2-1 | m/z = 351.11($C_{24}H_{17}NS$ = 351.46) | Sub 2-2 | m/z = 401.12($C_{22}H_{19}NS$ = 401.52) |
| Sub 2-3 | m/z = 325.09($C_{22}H_{13}NS$ = 325.43) | Sub 2-4 | m/z = 351.11($C_{24}H_{17}NS$ = 351.46) |
| Sub 2-5 | m/z = 427.14($C_{30}H_{22}NS$ = 427.56) | Sub 2-6 | m/z = 343.08($C_{22}H_{14}FNS$ = 343.42) |
| Sub 2-7 | m/z = 375.11($C_{26}H_{17}NS$ = 375.48) | Sub 2-8 | m/z = 451.14($C_{32}H_{21}NS$ = 451.58) |
| Sub 2-9 | m/z = 477.16($C_{34}H_{23}NS$ = 477.62) | Sub 2-10 | m/z = 451.14($C_{32}H_{21}NS$ = 451.58) |
| Sub 2-11 | m/z = 451.14($C_{32}H_{21}NS$ = 451.58) | Sub 2-12 | m/z = 451.14($C_{32}H_{21}NS$ = 451.58) |
| Sub 2-13 | m/z = 401.12($C_{28}H_{19}NS$ = 401.52) | Sub 2-14 | m/z = 401.12($C_{28}H_{19}NS$ = 401.52) |
| Sub 2-15 | m/z = 451.14($C_{32}H_{21}NS$ = 451.58) | Sub 2-16 | m/z = 451.14($C_{32}H_{21}NS$ = 451.58) |
| Sub 2-17 | m/z = 451.14($C_{32}H_{21}NS$ = 451.58) | Sub 2-18 | m/z = 477.16($C_{34}H_{23}NS$ = 477.62) |
| Sub 2-19 | m/z = 477.16($C_{34}H_{23}NS$ = 477.62) | Sub 2-20 | m/z = 425.12($C_{30}H_{19}NS$ = 425.54) |
| Sub 2-21 | m/z = 325.09($C_{22}H_{13}NS$ = 325.43) | Sub 2-22 | m/z = 401.12($C_{28}H_{19}NS$ = 401.52) |
| Sub 2-23 | m/z = 406.16($C_{29}H_{14}D_5NS$ = 406.55) | Sub 2-24 | m/z = 330.12($C_{12}H_{10}D_5NS$ = 330.46) |
| Sub 2-25 | m/z = 451.14($C_{32}H_{21}NS$ = 451.58) | Sub 2-26 | m/z = 401.12($C_{28}H_{19}NS$ = 401.52) |
| Sub 2-27 | m/z = 425.12($C_{30}H_{19}NS$ = 425.54) | Sub 2-28 | m/z = 451.14($C_{32}H_{21}NS$ = 451.58) |
| Sub 2-29 | m/z = 451.14($C_{32}H_{25}NS$ = 451.58) | Sub 2-30 | m/z = 451.14($C_{32}H_{21}NS$ = 451.58) |
| Sub 2-31 | m/z = 401.12($C_{28}H_{19}NS$ = 401.52) | Sub 2-32 | m/z = 375.11($C_{26}H_{17}NS$ = 375.48) |
| Sub 2-33 | m/z = 401.12($C_{28}H_{19}NS$ = 401.52) | Sub 2-34 | m/z = 429.16($C_{30}H_{23}NS$ = 429.58) |
| Sub 2-35 | m/z = 501.16($C_{36}H_{23}NS$ = 501.64) | Sub 2-36 | m/z = 501.16($C_{36}H_{23}NS$ = 501.64) |
| Sub 2-37 | m/z = 527.17($C_{38}H_{23}NS$ = 527.68) | Sub 2-38 | m/z = 477.16($C_{34}H_{23}NS$ = 477.62) |
| Sub 2-39 | m/z = 477.16($C_{34}H_{23}NS$ = 477.62) | Sub 2-40 | m/z = 456.17($C_{32}H_{16}D_5NS$ = 456.61) |

TABLE 2-continued

| Compound | FD-MS | Compound | FD-MS |
| --- | --- | --- | --- |
| Sub 2-41 | m/z = 325.09($C_{22}H_{13}NS$ = 325.43) | Sub 2-42 | m/z = 375.11($C_{26}H_{17}NS$ = 375.48) |
| Sub 2-43 | m/z = 401.12($C_{28}H_{19}NS$ = 401.52) | Sub 2-44 | m/z = 401.12($C_{28}H_{19}NS$ = 401.52) |
| Sub 2-45 | m/z = 477.16($C_{34}H_{23}NS$ = 477.62) | Sub 2-46 | m/z = 477.16($C_{34}H_{23}NS$ = 477.62) |
| Sub 2-47 | m/z = 425.12($C_{30}H_{19}NS$ = 425.54) | Sub 2-48 | m/z = 456.17($C_{32}H_{16}D_5NS$ = 456.61) |
| Sub 2-49 | m/z = 425.12($C_{30}H_{19}NS$ = 425.54) | Sub 2-50 | m/z = 451.14($C_{32}H_{21}NS$ = 451.58) |
| Sub 2-51 | m/z = 425.12($C_{30}H_{19}NS$ = 425.54) | Sub 2-52 | m/z = 475.14($C_{34}H_{21}NS$ = 475.60) |
| Sub 2-53 | m/z = 501.16($C_{36}H_{23}NS$ = 501.64) | Sub 2-54 | m/z = 375.11($C_{26}H_{17}NS$ = 375.48) |
| Sub 2-55 | m/z = 451.14($C_{32}H_{21}NS$ = 451.58) | Sub 2-56 | m/z = 465.16($C_{33}H_{23}NS$ = 465.61) |
| Sub 2-57 | m/z = 335.13($C_{24}H_{17}NO$ = 335.40) | Sub 2-58 | m/z = 359.13($C_{26}H_{17}NO$ = 359.42) |
| Sub 2-59 | m/z = 435.16($C_{32}H_{21}NO$ = 435.52) | Sub 2-60 | m/z = 385.15($C_{28}H_{19}NO$ = 385.46) |
| Sub 2-61 | m/z = 435.16($C_{32}H_{21}NO$ = 435.52) | Sub 2-62 | m/z = 485.18($C_{36}H_{23}NO$ = 485.57) |
| Sub 2-63 | m/z = 461.18($C_{34}H_{23}NO$ = 461.55) | Sub 2-64 | m/z = 461.18($C_{34}H_{23}NO$ = 461.55) |
| Sub 2-65 | m/z = 433.15($C_{32}H_{19}NO$ = 433.50) | Sub 2-66 | m/z = 471.24($C_{34}H_{13}D_{10}NO$ = 471.61) |
| Sub 2-67 | m/z = 435.16($C_{32}H_{21}NO$ = 435.52) | Sub 2-68 | m/z = 435.16($C_{32}H_{21}NO$ = 435.52) |
| Sub 2-69 | m/z = 511.19($C_{38}H_{25}NO$ = 511.61) | Sub 2-70 | m/z = 461.18($C_{34}H_{23}NO$ = 461.55) |
| Sub 2-71 | m/z = 435.16($C_{32}H_{21}NO$ = 435.52) | Sub 2-72 | m/z = 435.16($C_{32}H_{21}NO$ = 435.52) |
| Sub 2-73 | m/z = 409.15($C_{30}H_{19}NO$ = 409.48) | Sub 2-74 | m/z = 364.16($C_{26}H_{12}D_5NO$ = 364.45) |
| Sub 2-75 | m/z = 435.16($C_{32}H_{21}NO$ = 435.52) | Sub 2-76 | m/z = 511.19($C_{38}H_{25}NO$ = 511.61) |
| Sub 2-77 | m/z = 359.13($C_{26}H_{17}NO$ = 359.42) | Sub 2-78 | m/z = 359.13($C_{26}H_{17}NO$ = 359.42) |
| Sub 2-79 | m/z = 435.16($C_{32}H_{21}NO$ = 435.52) | Sub 2-80 | m/z = 501.16($C_{36}H_{23}NS$ = 501.64) |
| Sub 2-81 | m/z = 579.20($C_{42}H_{29}NS$ = 579.75) | Sub 2-82 | m/z = 503.17($C_{36}H_{25}NS$ = 503.66) |
| Sub 2-83 | m/z = 451.14($C_{32}H_{21}NS$ = 451.58) | Sub 2-84 | m/z = 503.17($C_{36}H_{25}NS$ = 503.66) |
| Sub 2-85 | m/z = 491.17($C_{35}H_{25}NS$ = 491.64) | Sub 2-86 | m/z = 553.19($C_{40}H_{27}NS$ = 553.71) |
| Sub 2-87 | m/z = 477.16($C_{34}H_{23}NS$ = 477.62) | Sub 2-88 | m/z = 577.19($C_{42}H_{27}NS$ = 577.74) |
| Sub 2-89 | m/z = 527.17($C_{38}H_{25}NS$ = 527.68) | Sub 2-90 | m/z = 477.16($C_{34}H_{23}NS$ = 477.62) |
| Sub 2-91 | m/z = 477.16($C_{34}H_{23}NS$ = 477.62) | Sub 2-92 | m/z = 527.17($C_{38}H_{25}NS$ = 527.68) |
| Sub 2-93 | m/z = 553.19($C_{40}H_{27}NS$ = 553.71) | Sub 2-94 | m/z = 553.19($C_{40}H_{27}NS$ = 553.71) |
| Sub 2-95 | m/z = 577.19($C_{42}H_{27}NS$ = 577.74) | Sub 2-96 | m/z = 477.16($C_{34}H_{23}NS$ = 477.62) |
| Sub 2-97 | m/z = 527.17($C_{38}H_{25}NS$ = 527.68) | Sub 2-98 | m/z = 482.19($C_{34}H_{18}D_5NS$ = 482.65) |
| Sub 2-99 | m/z = 527.17($C_{38}H_{25}NS$ = 527.68) | Sub 2-100 | m/z = 553.19($C_{40}H_{27}NS$ = 553.71) |
| Sub 2-101 | m/z = 477.16($C_{34}H_{23}NS$ = 477.62) | Sub 2-102 | m/z = 553.19($C_{40}H_{27}NS$ = 553.71) |
| Sub 2-103 | m/z = 577.19($C_{42}H_{27}NS$ = 577.74) | Sub 2-104 | m/z = 603.20($C_{44}H_{29}NS$ = 603.77) |
| Sub 2-105 | m/z = 451.14($C_{32}H_{21}NS$ = 451.58) | Sub 2-106 | m/z = 477.16($C_{34}H_{23}NS$ = 477.62) |
| Sub 2-107 | m/z = 553.19($C_{40}H_{27}NS$ = 553.71) | Sub 2-108 | m/z = 527.17($C_{38}H_{25}NS$ = 527.68) |
| Sub 2-109 | m/z = 577.19($C_{42}H_{27}NS$ = 577.74) | Sub 2-110 | m/z = 551.17($C_{40}H_{25}NS$ = 551.70) |
| Sub 2-111 | m/z = 456.17($C_{32}H_{16}D_5NS$ = 456.61) | Sub 2-112 | m/z = 501.16($C_{36}H_{23}NS$ = 501.64) |
| Sub 2-113 | m/z = 551.17($C_{40}H_{25}NS$ = 551.70) | Sub 2-114 | m/z = 451.14($C_{32}H_{21}NS$ = 451.58) |
| Sub 2-115 | m/z = 527.17($C_{38}H_{25}NS$ = 527.68) | Sub 2-116 | m/z = 501.16($C_{36}H_{23}NS$ = 501.64) |
| Sub 2-117 | m/z = 411.16($C_{30}H_{21}NO$ = 411.49) | Sub 2-118 | m/z = 563.22($C_{42}H_{29}NO$ = 563.69) |
| Sub 2-119 | m/z = 492.22($C_{36}H_{20}D_5NO$ = 492.62) | Sub 2-120 | m/z = 511.19($C_{38}H_{25}NO$ = 511.61) |
| Sub 2-121 | m/z = 511.19($C_{38}H_{25}NO$ = 511.61) | Sub 2-122 | m/z = 537.21($C_{40}H_{27}NO$ = 537.65) |
| Sub 2-123 | m/z = 537.21($C_{40}H_{27}NO$ = 537.65) | Sub 2-124 | m/z = 485.18($C_{36}H_{23}NO$ = 485.57) |
| Sub 2-125 | m/z = 537.21($C_{40}H_{27}NO$ = 537.65) | Sub 2-126 | m/z = 547.27($C_{40}H_{17}D_{10}NO$ = 547.71) |
| Sub 2-127 | m/z = 461.18($C_{34}H_{23}NO$ = 461.55) | Sub 2-128 | m/z = 537.21($C_{40}H_{27}NO$ = 537.65) |
| Sub 2-129 | m/z = 537.21($C_{40}H_{27}NO$ = 537.65) | Sub 2-130 | m/z = 561.21($C_{42}H_{27}NO$ = 561.67) |
| Sub 2-131 | m/z = 511.19($C_{38}H_{25}NO$ = 511.61) | Sub 2-132 | m/z = 485.18($C_{36}H_{23}NO$ = 485.57) |

III. Synthesis of Final Product

Sub 1 (1 eq.) in a round bottom flask was dissolved in toluene, followed by adding Sub 2 (1 eq.), $Pd_2(dba)_3$ (0.03 eq.), $P(t\text{-}Bu)_3$ (0.08 eq.), NaOt-Bu (3 eq.) and then stirring at 100° C. Upon the completion of the reaction, the reaction product was extracted with $CH_2Cl_2$ and water. After that, the extracted organic layer was dried with $MgSO_4$ and then concentrated. The concentrated resultant was separated by silica gel column chromatography, and was then recrystallized, whereby a final product was obtained.

1. Synthesis Example of P-16

<Reaction Scheme 31>

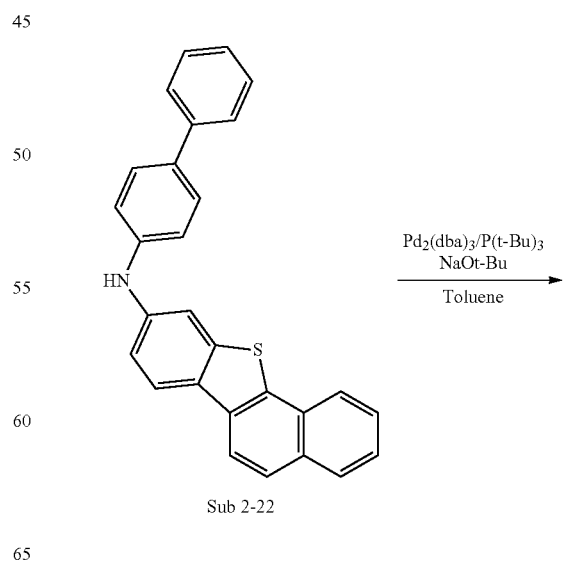

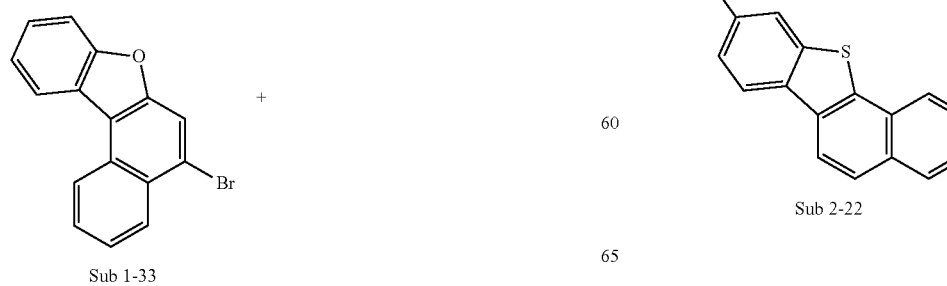

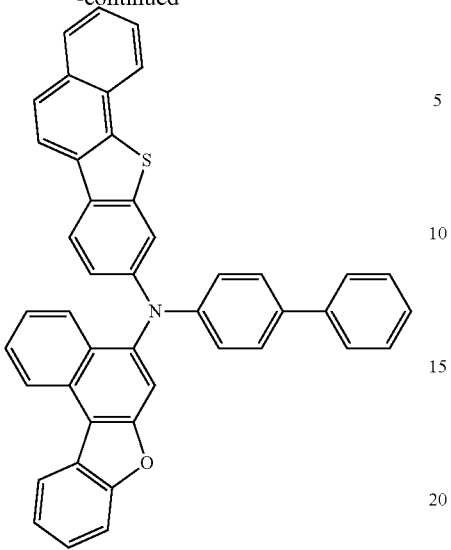

P-16

P-36

Sub 1-33 (4.22 g, 14.2 mmol) in a round bottom flask was dissolved in toluene (140 ml), followed by adding Sub 2-22 (5.7 g, 14.2 mmol), $Pd_2(dba)_3$ (0.39 g, 0.4 mmol), 50% $P(t-Bu)_3$ (0.6 ml, 1.1 mmol), NaOt-Bu (4.09 g, 42.6 mmol) and then stirring at 100° C. Upon the completion of the reaction, the reaction product was extracted with $CH_2Cl_2$ and water. After that, the extracted organic layer was dried with $MgSO_4$ and then concentrated. The concentrated resultant was separated by silica gel column chromatography, and was then recrystallized, whereby final product was obtained in the amount of 7.37 g (yield: 84%).

2. Synthesis Example of P-36

<Reaction Scheme 32>

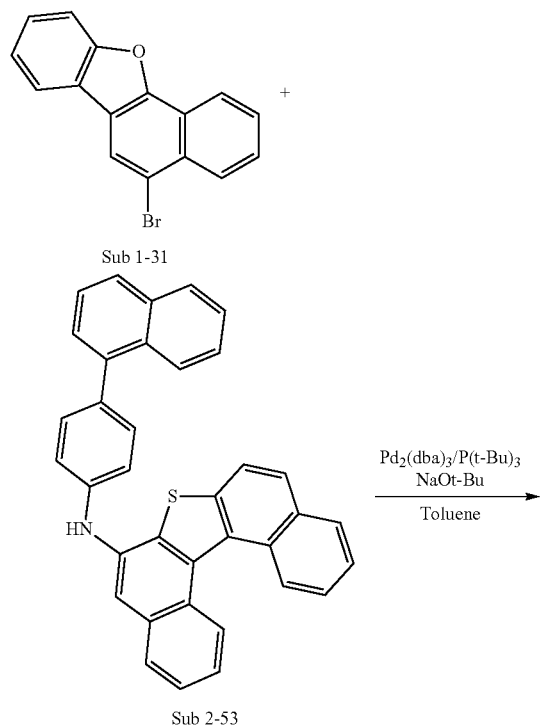

Product was obtained in the amount of 7.49 g (yield: 74%) where Sub 1-31 (4.19 g, 14.1 mmol), Sub 2-53 (7.07 g, 14.1 mmol), $Pd_2(dba)_3$ (0.39 g, 0.4 mmol), 50% $P(t-Bu)_3$ (0.5 ml, 1.1 mmol), NaOt-Bu (4.07 g, 42.3 mmol) and toluene (140 ml) were used in the same manner as described above for the synthesis of compound P-16.

3. Synthesis Example of P-47

<Reaction Scheme 33>

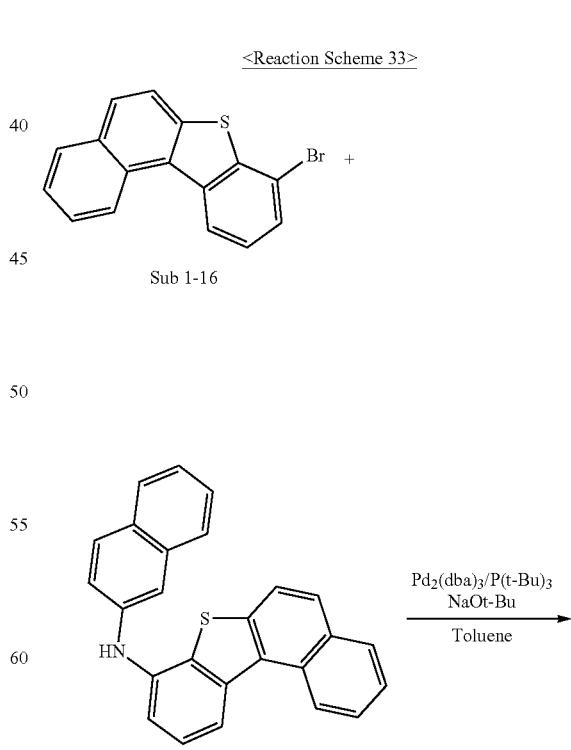

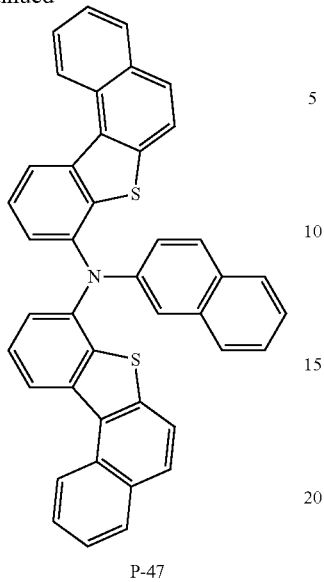

P-47

Product was obtained in the amount of 6.76 g (yield: 82%) where Sub 1-16 (4.25 g, 13.6 mmol), Sub 2-32 (5.09 g, 13.6 mmol), Pd$_2$(dba)$_3$ (0.37 g, 0.4 mmol), 50% P(t-Bu)$_3$ (0.5 ml, 1.1 mmol), NaOt-Bu (3.91 g, 40.7 mmol) and toluene (135 ml) were used in the same manner as described above for the synthesis of compound P-16.

4. Synthesis Example of P-86

<Reaction Scheme 34>

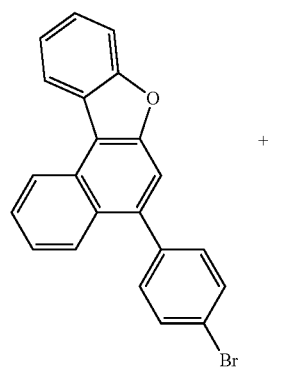

Sub 1-125

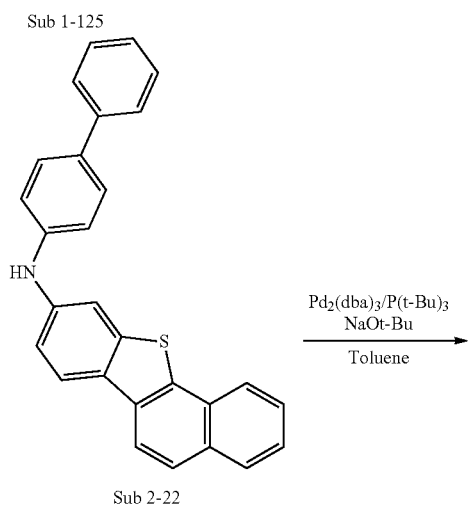

Sub 2-22

Pd$_2$(dba)$_3$/P(t-Bu)$_3$
NaOt-Bu
Toluene

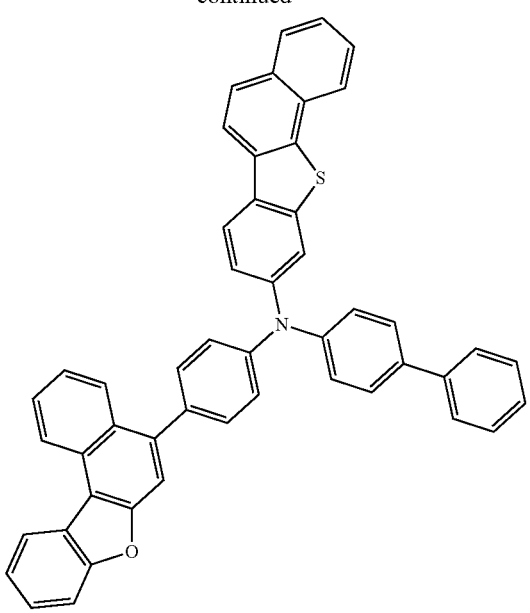

P-86

Product was obtained in the amount of 6.94 g (yield: 86%) where Sub 1-125 (4.34 g, 11.6 mmol), Sub 2-22 (4.67 g, 11.6 mmol), Pd$_2$(dba)$_3$ (0.32 g, 0.3 mmol), 50% P(t-Bu)$_3$ (0.5 ml, 0.9 mmol), NaOt-Bu (3.35 g, 34.9 mmol) and toluene (115 ml) were used in the same manner as described above for the synthesis of compound P-16.

5. Synthesis Example of P-105

<Reaction Scheme 35>

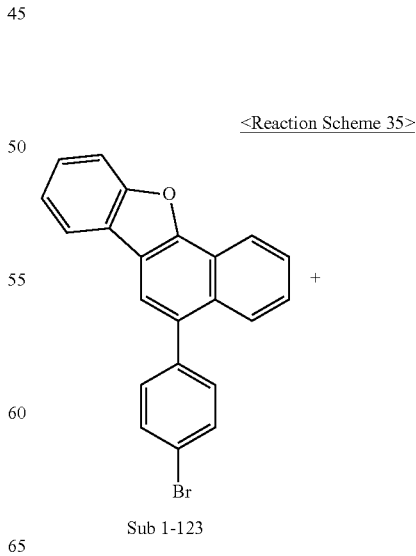

Sub 1-123

209
-continued

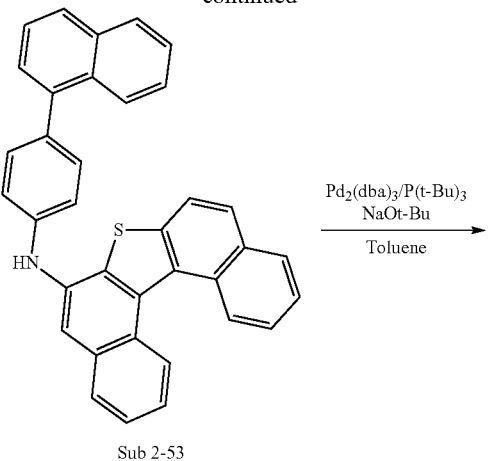

Sub 2-53

210
-continued

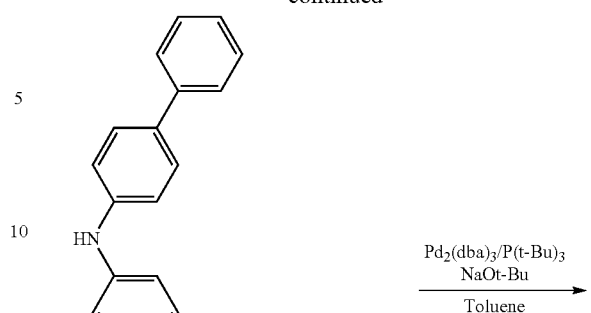

Sub 2-96

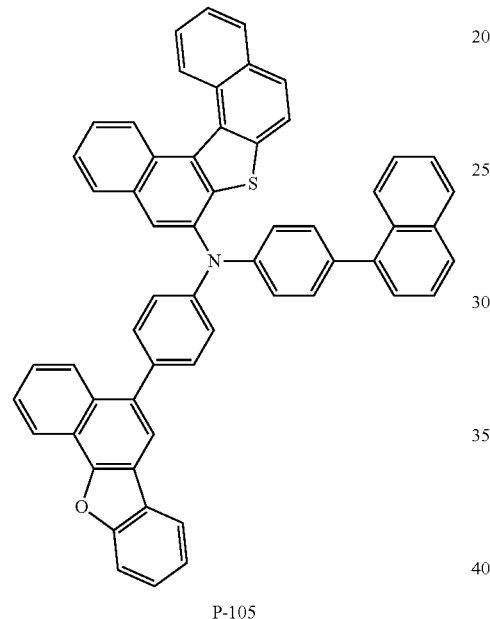

P-105

Product was obtained in the amount of 7.35 g (yield: 77%) where Sub 1-123 (4.49 g, 12 mmol), Sub 2-53 (6.03 g, 12 mmol), Pd$_2$(dba)$_3$ (0.33 g, 0.4 mmol), 50% P(t-Bu)$_3$ (0.5 ml, 1 mmol), NaOt-Bu (3.47 g, 36.1 mmol) and toluene (120 ml) were used in the same manner as described above for the synthesis of compound P-16.

6. Synthesis Example of P-150

<Reaction Scheme 36>

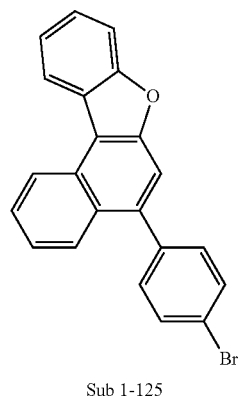

Sub 1-125

+

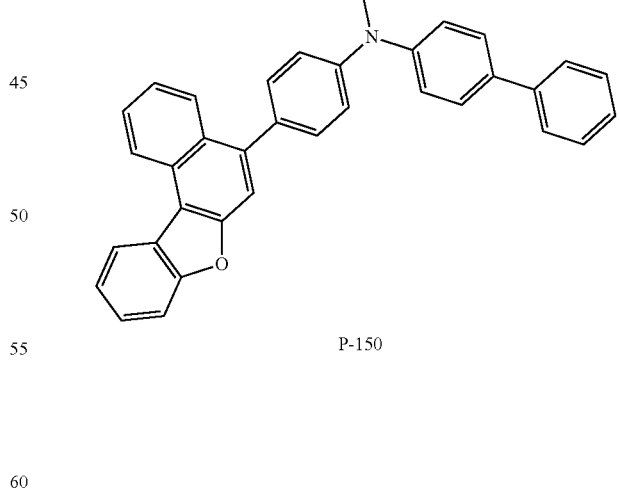

P-150

Product was obtained in the amount of 7.54 g (yield: 80%) where Sub 1-125 (4.57 g, 12.2 mmol), Sub 2-96 (5.85 g, 12.2 mmol), Pd$_2$(dba)$_3$ (0.34 g, 0.4 mmol), 50% P(t-Bu)$_3$ (0.5 ml, 1 mmol), NaOt-Bu (3.53 g, 36.7 mmol) and toluene (120 ml) were used in the same manner as described above for the synthesis of compound P-16.

7. Synthesis Example of P-165
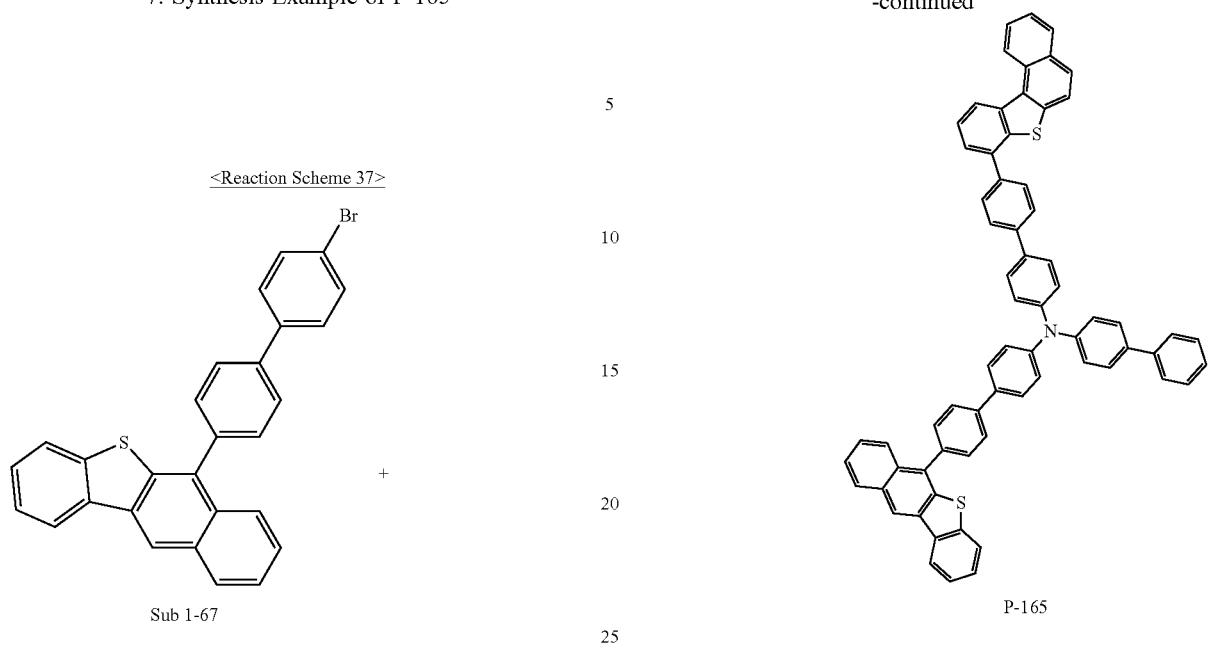
Sub 1-67
Sub 2-102
P-165
Product was obtained in the amount of 7.27 g (yield: 75%) where Sub 1-67 (4.81 g, 10.3 mmol), Sub 2-102 (5.72 g, 10.3 mmol), Pd$_2$(dba)$_3$ (0.28 g, 0.3 mmol), 50% P(t-Bu)$_3$ (0.4 ml, 0.8 mmol), NaOt-Bu (2.98 g, 31 mmol) and toluene (105 ml) were used in the same manner as described above for the synthesis of compound P-16.
8. Synthesis Example of P-166
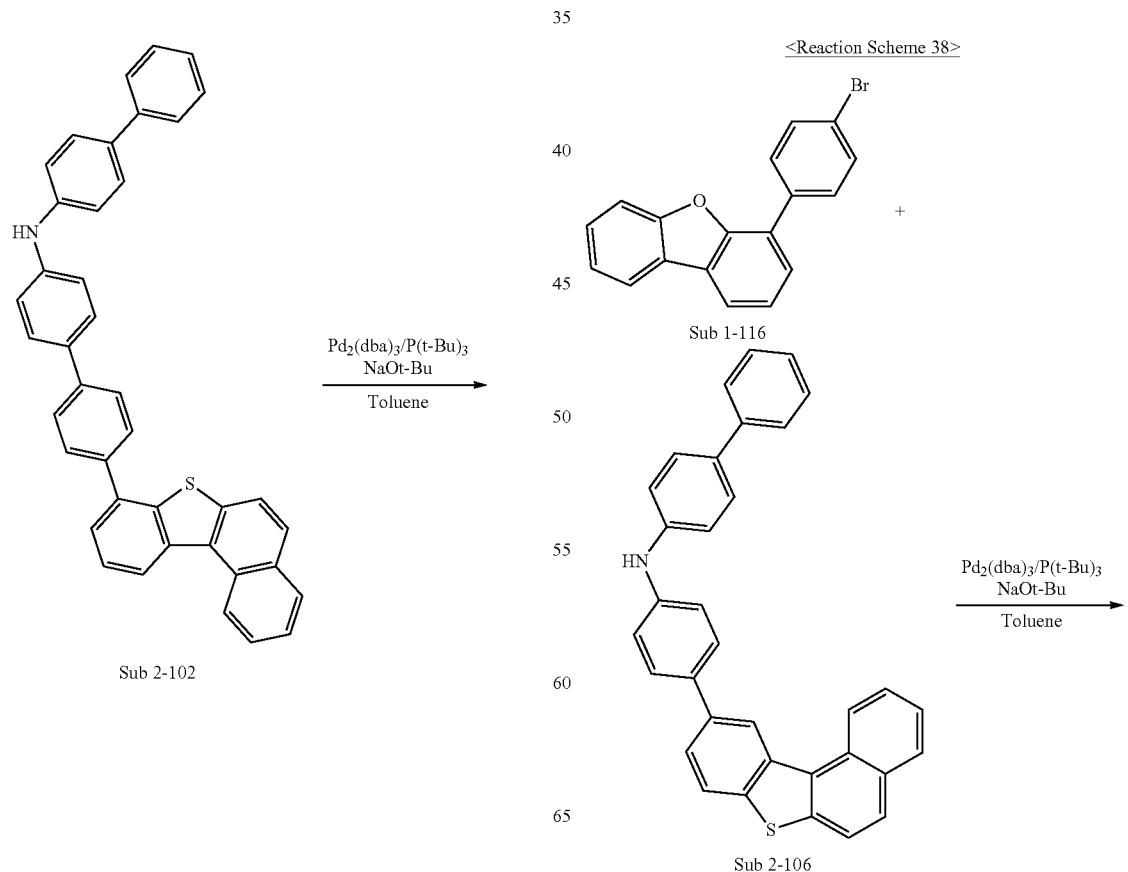
Sub 1-116
Sub 2-106

213

-continued

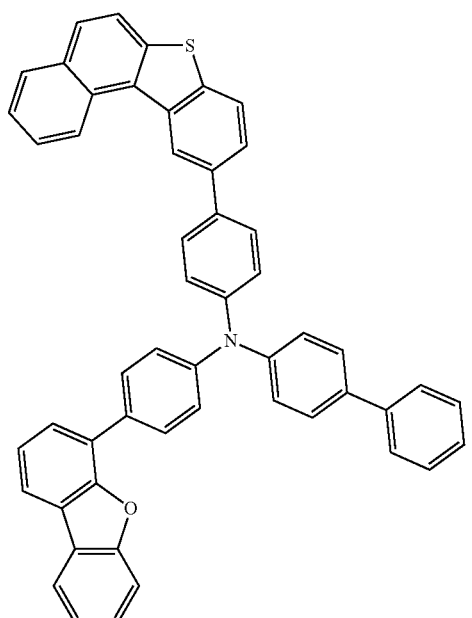

P-166

Product was obtained in the amount of 8.41 g (yield: 89%) where Sub 1-116 (4.24 g, 13.1 mmol), Sub 2-106 (6.27 g, 13.1 mmol), Pd$_2$(dba)$_3$ (0.36 g, 0.4 mmol), 50% P(t-Bu)$_3$ (0.5 ml, 1 mmol), NaOt-Bu (3.78 g, 39.4 mmol) and toluene (130 ml) were used in the same manner as described above for the synthesis of compound P-16.

9. Synthesis Example of P-169

<Reaction Scheme 39>

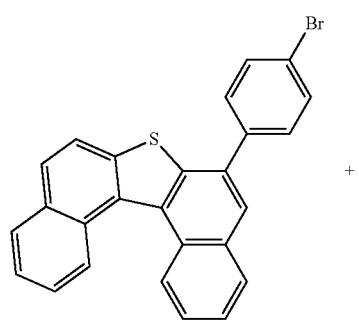

Sub 1-111

+

214

-continued

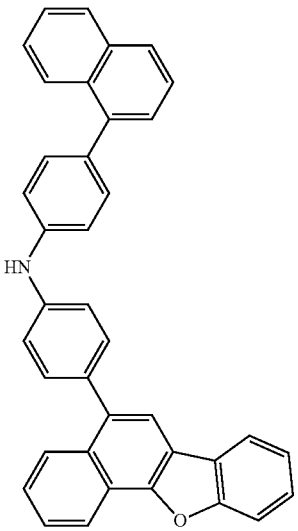

Sub 2-120

$\xrightarrow{\text{Pd}_2(\text{dba})_3/\text{P(t-Bu)}_3}{\text{NaOt-Bu}}$
Toluene

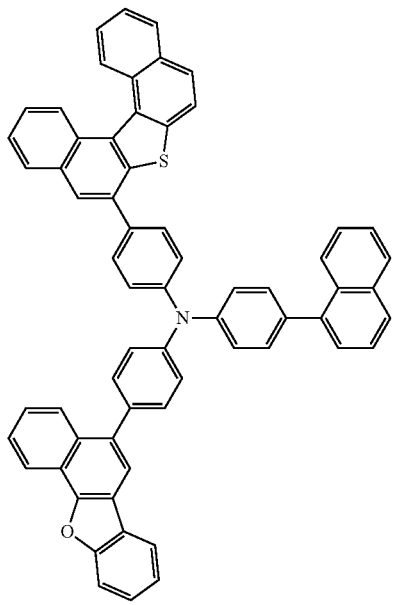

P-169

Product was obtained in the amount of 6.62 g (yield: 72%) where Sub 1-111 (4.64 g, 10.6 mmol), Sub 2-120 (5.4 g, 10.6 mmol), Pd$_2$(dba)$_3$ (0.29 g, 0.3 mmol), 50% P(t-Bu)$_3$ (0.4 ml, 0.8 mmol), NaOt-Bu (3.04 g, 31.7 mmol) and toluene (105 ml) were used in the same manner as described above for the synthesis of compound P-16.

215
10. Synthesis Example of P-179
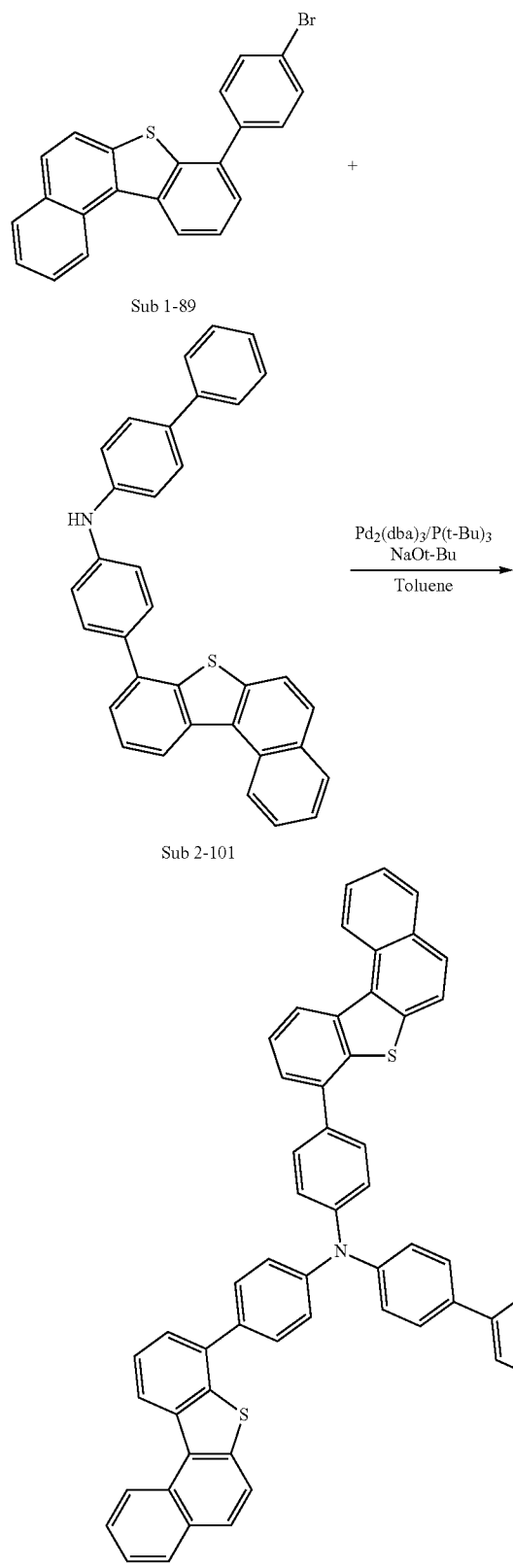
216
Product was obtained in the amount of 6.88 g (yield: 78%) where Sub 1-89 (4.37 g, 11.2 mmol), Sub 2-101 (5.36 g, 11.2 mmol), $Pd_2(dba)_3$ (0.31 g, 0.3 mmol), 50% $P(t-Bu)_3$ (0.4 ml, 0.9 mmol), NaOt-Bu (3.24 g, 33.7 mmol) and toluene (110 ml) were used in the same manner as described above for the synthesis of compound P-16.
11. Synthesis Example of P-195
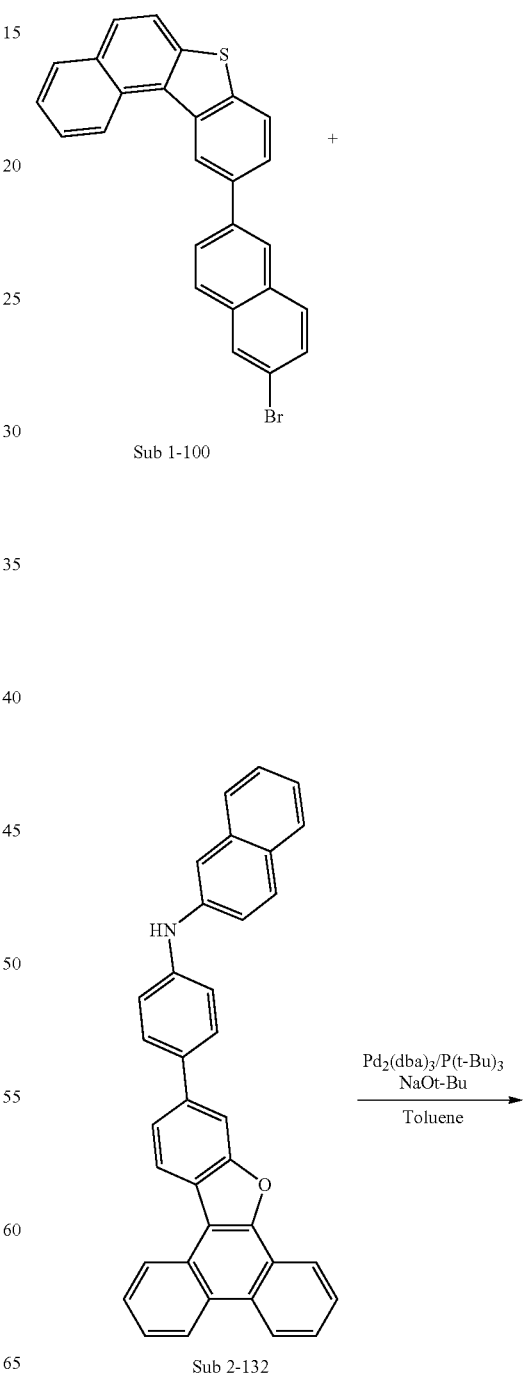

-continued

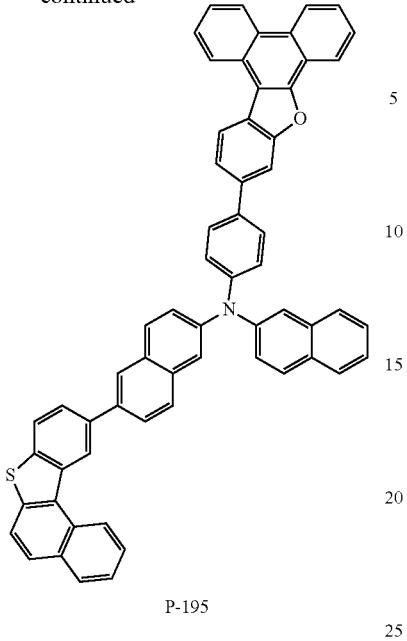

P-195

Product was obtained in the amount of 7.07 g (yield: 70%) where Sub 1-100 (5.26 g, 12 mmol), Sub 2-132 (5.81 g, 12 mmol), $Pd_2(dba)_3$ (0.33 g, 0.4 mmol), 50% $P(t-Bu)_3$ (0.5 ml, 1 mmol), NaOt-Bu (3.45 g, 35.9 mmol) and toluene (120 ml) were used in the same manner as described above for the synthesis of compound P-16.

Meanwhile, Table 3 below shows the final products P-1 to P-200 of the present invention synthesized according to the above synthesis show FD-MS data.

TABLE 3

| Compound | FD-MS | Compound | FD-MS |
| --- | --- | --- | --- |
| P-1 | m/z = 643.20($C_{46}H_{29}NOS$ = 643.79) | P-2 | m/z = 617.18($C_{44}H_{27}NOS$ = 617.76) |
| P-3 | m/z = 667.20($C_{48}H_{29}NOS$ = 667.81) | P-4 | m/z = 583.14($C_{40}H_{25}NS_2$ = 583.76) |
| P-5 | m/z = 567.17($C_{40}H_{25}NOS$ = 567.70) | P-6 | m/z = 617.18($C_{44}H_{27}NOS$ = 617.76) |
| P-7 | m/z = 617.18($C_{44}H_{27}NOS$ = 617.76) | P-8 | m/z = 633.16($C_{44}H_{27}NS_2$ = 633.82) |
| P-9 | m/z = 643.20($C_{46}H_{29}NOS$ = 643.79) | P-10 | m/z = 615.17($C_{44}H_{25}NOS$ = 615.74) |
| P-11 | m/z = 607.14($C_{42}H_{25}NS_2$ = 607.78) | P-12 | m/z = 683.17($C_{48}H_{29}NS_2$ = 683.88) |
| P-13 | m/z = 622.21($C_{44}H_{22}D_5NOS$ = 622.79) | P-14 | m/z = 667.20($C_{48}H_{29}NOS$ = 667.81) |
| P-15 | m/z = 659.17($C_{46}H_{29}NS_2$ = 659.86) | P-16 | m/z = 617.18($C_{44}H_{27}NOS$ = 617.76) |
| P-17 | m/z = 633.16($C_{44}H_{27}NS_2$ = 633.82) | P-18 | m/z = 717.21($C_{52}H_{31}NOS$ = 717.87) |
| P-19 | m/z = 693.21($C_{50}H_{31}NOS$ = 693.85) | P-20 | m/z = 717.21($C_{52}H_{31}NOS$ = 717.87) |
| P-21 | m/z = 633.16($C_{44}H_{27}NS_2$ = 633.82) | P-22 | m/z = 617.18($C_{44}H_{27}NOS$ = 617.76) |
| P-23 | m/z = 641.18($C_{46}H_{27}NOS$ = 641.78) | P-24 | m/z = 707.17($C_{50}H_{29}NS_2$ = 707.90) |
| P-25 | m/z = 743.23($C_{54}H_{33}NOS$ = 743.91) | P-26 | m/z = 703.28($C_{50}H_{21}D_{10}NOS$ = 703.91) |
| P-27 | m/z = 743.23($C_{54}H_{33}NOS$ = 743.91) | P-28 | m/z = 683.17($C_{48}H_{29}NS_2$ = 683.88) |
| P-29 | m/z = 567.17($C_{40}H_{25}NOS$ = 567.70) | P-30 | m/z = 667.20($C_{48}H_{29}NOS$ = 667.81) |
| P-31 | m/z = 693.21($C_{50}H_{31}NOS$ = 693.85) | P-32 | m/z = 733.19($C_{52}H_{31}NS_2$ = 733.94) |
| P-33 | m/z = 567.17($C_{40}H_{25}NOS$ = 567.70) | P-34 | m/z = 617.18($C_{44}H_{27}NOS$ = 617.76) |
| P-35 | m/z = 633.16($C_{44}H_{27}NS_2$ = 633.82) | P-36 | m/z = 717.21($C_{52}H_{31}NOS$ = 717.87) |
| P-37 | m/z = 567.17($C_{40}H_{25}NOS$ = 567.70) | P-38 | m/z = 583.14($C_{40}H_{25}NS_2$ = 583.76) |
| P-39 | m/z = 591.17($C_{42}H_{25}NOS$ = 591.72) | P-40 | m/z = 617.18($C_{44}H_{27}NOS$ = 617.76) |
| P-41 | m/z = 607.14($C_{42}H_{25}NS_2$ = 607.78) | P-42 | m/z = 693.21($C_{50}H_{31}NOS$ = 693.85) |
| P-43 | m/z = 638.19($C_{44}H_{22}D_5NS_2$ = 638.85) | P-44 | m/z = 643.20($C_{46}H_{29}NOS$ = 643.79) |
| P-45 | m/z = 617.18($C_{44}H_{27}NOS$ = 617.76) | P-46 | m/z = 641.18($C_{46}H_{27}NOS$ = 641.78) |
| P-47 | m/z = 607.14($C_{42}H_{25}NS_2$ = 607.78) | P-48 | m/z = 693.21($C_{50}H_{31}NOS$ = 693.85) |
| P-49 | m/z = 641.18($C_{49}H_{27}NOS$ = 641.78) | P-50 | m/z = 657.16($C_{46}H_{27}NS_2$ = 657.84) |
| P-51 | m/z = 617.18($C_{44}H_{27}NOS$ = 617.76) | P-52 | m/z = 709.19($C_{50}H_{31}NS_2$ = 709.92) |
| P-53 | m/z = 693.21($C_{50}H_{31}NOS$ = 693.85) | P-54 | m/z = 617.18($C_{44}H_{27}NOS$ = 617.76) |
| P-55 | m/z = 667.20($C_{48}H_{29}NOS$ = 667.81) | P-56 | m/z = 711.21($C_{50}H_{33}NS_2$ = 711.93) |
| P-57 | m/z = 617.18($C_{44}H_{27}NOS$ = 617.76) | P-58 | m/z = 693.21($C_{50}H_{31}NOS$ = 693.85) |
| P-59 | m/z = 596.20($C_{42}H_{20}D_5NOS$ = 596.75) | P-60 | m/z = 641.18($C_{46}H_{27}NOS$ = 641.78) |
| P-61 | m/z = 683.17($C_{48}H_{29}NS_2$ = 683.88) | P-62 | m/z = 667.20($C_{48}H_{29}NOS$ = 667.81) |
| P-63 | m/z = 667.20($C_{48}H_{29}NOS$ = 667.81) | P-64 | m/z = 717.21($C_{52}H_{31}NOS$ = 717.87) |
| P-65 | m/z = 657.16($C_{46}H_{27}NS_2$ = 657.84) | P-66 | m/z = 667.20($C_{48}H_{29}NOS$ = 667.81) |
| P-67 | m/z = 641.18($C_{46}H_{27}NOS$ = 641.78) | P-68 | m/z = 697.19($C_{49}H_{31}NS_2$ = 697.91) |

TABLE 3-continued

| Compound | FD-MS | Compound | FD-MS |
|---|---|---|---|
| P-69 | m/z = 567.17($C_{40}H_{25}NOS$ = 567.70) | P-70 | m/z = 559.14($C_{38}H_{22}FNOS$ = 559.65) |
| P-71 | m/z = 659.17($C_{46}H_{29}NS_2$ = 659.86) | P-72 | m/z = 683.17($C_{48}H_{29}NS_2$ = 683.88) |
| P-73 | m/z = 643.20($C_{46}H_{29}NOS$ = 643.79) | P-74 | m/z = 793.24($C_{58}H_{35}NOS$ = 793.97) |
| P-75 | m/z = 719.23($C_{52}H_{33}NOS$ = 719.89) | P-76 | m/z = 735.21($C_{52}H_{33}NS_2$ = 735.96) |
| P-77 | m/z = 643.20($C_{46}H_{29}NOS$ = 643.79) | P-78 | m/z = 743.23($C_{54}H_{33}NOS$ = 743.91) |
| P-79 | m/z = 785.22($C_{56}H_{35}NS_2$ = 786.01) | P-80 | m/z = 719.23($C_{52}H_{33}NOS$ = 719.89) |
| P-81 | m/z = 743.23($C_{54}H_{33}NOS$ = 743.91) | P-82 | m/z = 759.21($C_{54}H_{33}NS_2$ = 759.98) |
| P-83 | m/z = 774.28($C_{56}H_{30}D_5NOS$ = 774.98) | P-84 | m/z = 793.24($C_{58}H_{35}NOS$ = 793.97) |
| P-85 | m/z = 887.27($C_{64}H_{41}NS_2$ = 888.15) | P-86 | m/z = 693.21($C_{50}H_{31}NOS$ = 693.85) |
| P-87 | m/z = 783.21($C_{56}H_{33}NS_2$ = 784.00) | P-88 | m/z = 793.24($C_{58}H_{35}NOS$ = 793.97) |
| P-89 | m/z = 769.24($C_{56}H_{35}NOS$ = 769.95) | P-90 | m/z = 819.26($C_{60}H_{37}NOS$ = 820.01) |
| P-91 | m/z = 785.22($C_{56}H_{35}NS_2$ = 786.01) | P-92 | m/z = 693.21($C_{50}H_{31}NOS$ = 693.85) |
| P-93 | m/z = 793.24($C_{58}H_{35}NOS$ = 793.97) | P-94 | m/z = 688.21($C_{48}H_{24}D_5NS_2$ = 688.91) |
| P-95 | m/z = 743.23($C_{54}H_{33}NOS$ = 743.91) | P-96 | m/z = 779.31($C_{56}H_{25}D_{10}NOS$ = 780.01) |
| P-97 | m/z = 819.26($C_{60}H_{37}NOS$ = 820.01) | P-98 | m/z = 733.19($C_{52}H_{31}NS_2$ = 733.94) |
| P-99 | m/z = 793.24($C_{58}H_{35}NOS$ = 793.97) | P-100 | m/z = 769.24($C_{56}H_{35}NOS$ = 769.95) |
| P-101 | m/z = 885.25($C_{64}H_{39}NS_2$ = 886.13) | P-102 | m/z = 643.20($C_{46}H_{29}NOS$ = 643.79) |
| P-103 | m/z = 769.24($C_{56}H_{35}NOS$ = 769.95) | P-104 | m/z = 759.21($C_{54}H_{33}NS_2$ = 759.98) |
| P-105 | m/z = 793.24($C_{58}H_{35}NOS$ = 793.97) | P-106 | m/z = 659.17($C_{46}H_{29}NS_2$ = 659.86) |
| P-107 | m/z = 717.21($C_{52}H_{31}NOS$ = 717.87) | P-108 | m/z = 819.26($C_{60}H_{37}NOS$ = 820.01) |
| P-109 | m/z = 783.21($C_{56}H_{33}NS_2$ = 784.00) | P-110 | m/z = 795.26($C_{58}H_{37}NOS$ = 795.99) |
| P-111 | m/z = 764.24($C_{54}H_{28}D_5NS_2$ = 765.01) | P-112 | m/z = 871.29($C_{64}H_{41}NOS$ = 872.08) |
| P-113 | m/z = 769.24($C_{56}H_{35}NOS$ = 769.95) | P-114 | m/z = 717.21($C_{52}H_{31}NOS$ = 717.87) |
| P-115 | m/z = 733.19($C_{52}H_{31}NS_2$ = 733.94) | P-116 | m/z = 793.24($C_{58}H_{35}NOS$ = 793.97) |
| P-117 | m/z = 885.25($C_{64}H_{39}NS_2$ = 886.13) | P-118 | m/z = 693.21($C_{50}H_{31}NOS$ = 693.85) |
| P-119 | m/z = 709.19($C_{50}H_{31}NS_2$ = 709.92) | P-120 | m/z = 819.26($C_{60}H_{37}NOS$ = 820.01) |
| P-121 | m/z = 693.21($C_{50}H_{31}NOS$ = 693.85) | P-122 | m/z = 819.26($C_{60}H_{37}NOS$ = 820.01) |
| P-123 | m/z = 769.24($C_{56}H_{35}NOS$ = 769.95) | P-124 | m/z = 769.24($C_{56}H_{35}NOS$ = 769.95) |
| P-125 | m/z = 722.24($C_{52}H_{26}D_5NOS$ = 722.90) | P-126 | m/z = 759.21($C_{54}H_{33}NS_2$ = 759.98) |
| P-127 | m/z = 819.26($C_{60}H_{37}NOS$ = 820.01) | P-128 | m/z = 743.23($C_{54}H_{33}NOS$ = 743.91) |
| P-129 | m/z = 793.24($C_{58}H_{35}NOS$ = 793.97) | P-130 | m/z = 809.22($C_{58}H_{35}NS_2$ = 810.04) |
| P-131 | m/z = 843.26($C_{62}H_{37}NOS$ = 844.03) | P-132 | m/z = 793.24($C_{58}H_{35}NOS$ = 793.97) |
| P-133 | m/z = 823.24($C_{59}H_{37}NS_2$ = 824.06) | P-134 | m/z = 635.17($C_{44}H_{26}FNOS$ = 635.75) |
| P-135 | m/z = 785.22($C_{56}H_{35}NS_2$ = 786.01) | P-136 | m/z = 759.21($C_{54}H_{33}NS_2$ = 759.98) |
| P-137 | m/z = 719.23($C_{52}H_{33}NOS$ = 719.89) | P-138 | m/z = 869.28($C_{64}H_{39}NOS$ = 870.07) |
| P-139 | m/z = 871.29($C_{64}H_{41}NOS$ = 872.08) | P-140 | m/z = 811.24($C_{58}H_{37}NS_2$ = 812.05) |
| P-141 | m/z = 719.23($C_{52}H_{33}NOS$ = 719.89) | P-142 | m/z = 719.23($C_{52}H_{33}NOS$ = 719.89) |
| P-143 | m/z = 937.28($C_{68}H_{43}NS_2$ = 938.21) | P-144 | m/z = 795.26($C_{58}H_{37}NOS$ = 795.99) |
| P-145 | m/z = 793.24($C_{58}H_{35}NOS$ = 793.97) | P-146 | m/z = 885.25($C_{64}H_{39}NS_2$ = 886.13) |
| P-147 | m/z = 926.34($C_{68}H_{38}D_5NOS$ = 927.17) | P-148 | m/z = 769.24($C_{56}H_{35}NOS$ = 769.95) |
| P-149 | m/z = 887.27($C_{64}H_{41}NS_2$ = 888.15) | P-150 | m/z = 769.24($C_{56}H_{35}NOS$ = 769.95) |
| P-151 | m/z = 859.24($C_{62}H_{37}NS_2$ = 860.09) | P-152 | m/z = 945.31($C_{70}H_{43}NOS$ = 946.16) |
| P-153 | m/z = 845.28($C_{62}H_{39}NOS$ = 846.04) | P-154 | m/z = 971.32($C_{72}H_{45}NOS$ = 972.20) |
| P-155 | m/z = 785.22($C_{56}H_{35}NS_2$ = 786.01) | P-156 | m/z = 769.24($C_{56}H_{35}NOS$ = 769.95) |
| P-157 | m/z = 869.28($C_{64}H_{39}NOS$ = 870.07) | P-158 | m/z = 840.27($C_{60}H_{32}D_5NS_2$ = 841.10) |
| P-159 | m/z = 819.26($C_{60}H_{37}NOS$ = 820.01) | P-160 | m/z = 855.34($C_{62}H_{29}D_{10}NOS$ = 856.11) |
| P-161 | m/z = 895.29($C_{66}H_{41}NOS$ = 896.10) | P-162 | m/z = 769.24($C_{56}H_{35}NOS$ = 769.95) |
| P-163 | m/z = 919.29($C_{68}H_{41}NOS$ = 920.12) | P-164 | m/z = 921.31($C_{68}H_{43}NOS$ = 922.14) |
| P-165 | m/z = 937.28($C_{68}H_{43}NS_2$ = 938.21) | P-166 | m/z = 719.23($C_{52}H_{33}NOS$ = 719.89) |
| P-167 | m/z = 921.31($C_{68}H_{43}NOS$ = 922.14) | P-168 | m/z = 885.25($C_{64}H_{39}NS_2$ = 886.13) |
| P-169 | m/z = 869.28($C_{64}H_{39}NOS$ = 870.07) | P-170 | m/z = 735.21($C_{52}H_{33}NS_2$ = 735.96) |
| P-171 | m/z = 843.26($C_{62}H_{37}NOS$ = 844.03) | P-172 | m/z = 795.26($C_{58}H_{37}NOS$ = 795.99) |
| P-173 | m/z = 785.22($C_{56}H_{35}NS_2$ = 786.01) | P-174 | m/z = 947.32($C_{70}H_{45}NOS$ = 948.18) |
| P-175 | m/z = 859.24($C_{62}H_{37}NS_2$ = 860.09) | P-176 | m/z = 947.32($C_{70}H_{45}NOS$ = 948.18) |
| P-177 | m/z = 921.31($C_{68}H_{43}NOS$ = 922.14) | P-178 | m/z = 793.24($C_{58}H_{35}NOS$ = 793.97) |
| P-179 | m/z = 785.22($C_{56}H_{35}NS_2$ = 786.01) | P-180 | m/z = 945.31($C_{70}H_{43}NOS$ = 946.16) |
| P-181 | m/z = 885.25($C_{64}H_{39}NS_2$ = 886.13) | P-182 | m/z = 769.24($C_{56}H_{35}NOS$ = 769.95) |
| P-183 | m/z = 861.25($C_{62}H_{39}NS_2$ = 862.11) | P-184 | m/z = 895.29($C_{66}H_{41}NOS$ = 896.10) |
| P-185 | m/z = 769.24($C_{56}H_{35}NOS$ = 769.95) | P-186 | m/z = 895.29($C_{66}H_{41}NOS$ = 896.10) |
| P-187 | m/z = 769.24($C_{56}H_{35}NOS$ = 769.95) | P-188 | m/z = 921.31($C_{68}H_{43}NOS$ = 922.14) |
| P-189 | m/z = 848.29($C_{62}H_{32}D_5NOS$ = 849.06) | P-190 | m/z = 885.25($C_{64}H_{39}NS_2$ = 886.13) |
| P-191 | m/z = 921.31($C_{68}H_{43}NOS$ = 922.14) | P-192 | m/z = 819.26($C_{60}H_{37}NOS$ = 820.01) |
| P-193 | m/z = 869.28($C_{64}H_{39}NOS$ = 870.07) | P-194 | m/z = 961.28($C_{70}H_{43}NS_2$ = 962.23) |
| P-195 | m/z = 843.26($C_{62}H_{37}NOS$ = 844.03) | P-196 | m/z = 869.28($C_{64}H_{39}NOS$ = 870.07) |
| P-197 | m/z = 859.24($C_{62}H_{37}NS_2$ = 860.09) | P-198 | m/z = 783.26($C_{57}H_{37}NOS$ = 783.97) |
| P-199 | m/z = 859.24($C_{62}H_{37}NS_2$ = 860.09) | P-200 | m/z = 835.24($C_{60}H_{37}NS_2$ = 836.07) |

Meanwhile, even though the compounds of the present invention, represented by Formula 1 above, have been synthesized in the Synthesis Examples above, they are based on a Intramolecular acid-induced cyclization reaction (*J. mater. Chem.* 1999, 9, 2095.), Pd(II)-catalyzed oxidative cyclization reaction (*Org. Lett.* 2011, 13, 5504), Miyaura boration reaction, Suzuki cross-coupling reaction and Buchwald-Hartwig cross coupling reaction, and the like. Therefore, it should be apparent to those having ordinary skill in the art that the reactions could proceed even though substituents (such as $X^1$, $X^2$, A ring, B ring, $Ar^1$, $L^1$, $L^2$, $R^1$, $R^2$, m, n and so on.) defined in Formula 1 above, other than those specified in the Synthesis Examples, are used.

For example, the reaction of the starting material→Sub 1-I in Reaction Scheme 2 is based on Intramolecular acid-induced cyclization reaction, the reaction of starting material→Sub 1-I in Reaction Scheme 3 is based on Pd(II)-catalyzed oxidative cyclization reaction, the reaction of Sub 1-I→Sub 1-II in Reaction Scheme 4 is based on Suzuki cross-coupling reaction, and the reaction of the starting material→Sub 2 in Reaction Scheme 21 and Reaction Scheme 31 to Reaction Scheme 41 are based on Buchwald-Hartwig cross coupling reaction. These reactions can be conducted even with substituents that are not specifically stated.

Fabrication and Evaluation of Organic Electronic Element [Example I-1] Green OLED (a Hole Transport Layer)

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, P1-1 of the present invention was vacuum-deposited with a thickness of 60 nm on the hole injection layer to form a hole transport layer.

Subsequently, a light emitting layer with a thickness of 30 nm was formed on the hole transport layer by using 4,4'-N,N'-dicarbazole-biphenyl (hereinafter, "CBP") as a host material and tris(2-phenylpyridine)-iridium (hereinafter, "Ir(ppy)$_3$") as a dopant material in a weight ratio of 90:10.

Next, ((1,1'-bisphenyl)-4-olato)bis(2-methyl-8-quinolinolato) aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example I-2] to [Example I-65] Green Oled (a Hole Transport Layer)

The OLEDs were manufactured in the same manner as described in Example I-1, except that any one of the compounds P-4 to P-200 of the present invention in the Table 4 below was used as the hole transport layer material of the light emitting layer, instead of the inventive compound P-1.

Comparative Example I-1

An OLED was manufactured in the same manner as described in Example I-1, except that the following Comparative Compound 1 was used as the hole transport layer material, instead of the inventive compound P-1.

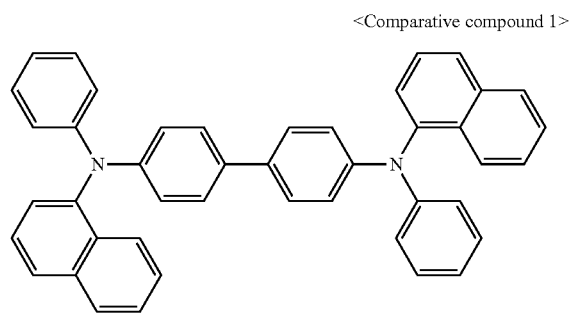 [SMILES: c1ccc(N(c2ccc(-c3ccc(N(c4ccccc4)c4cccc5ccccc45)cc3)cc2)c2cccc3ccccc23)cc1]

<Comparative compound 1>

Comparative Example I-2

An OLED was manufactured in the same manner as described in Example I-1, except that the following Comparative Compound 2 was used as the hole transport layer material, instead of the inventive compound P-1.

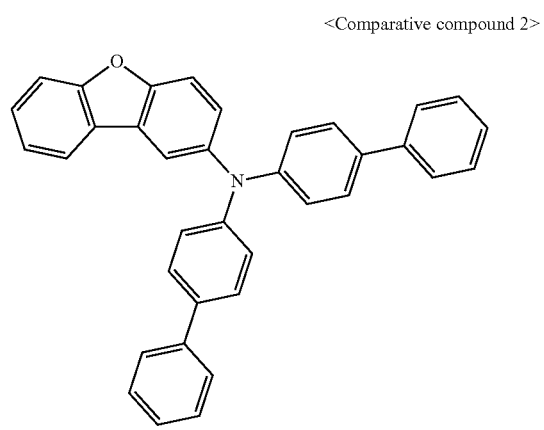 [SMILES: c1ccc(-c2ccc(N(c3ccc(-c4ccccc4)cc3)c3ccc4sc5ccccc5c4c3)cc2)cc1]

<Comparative compound 2>

Comparative Example I-3

An OLED was manufactured in the same manner as described in Example I-1, except that the following Comparative Compound 3 was used as the hole transport layer material, instead of the inventive compound P-1.

<Comparative compound 3>

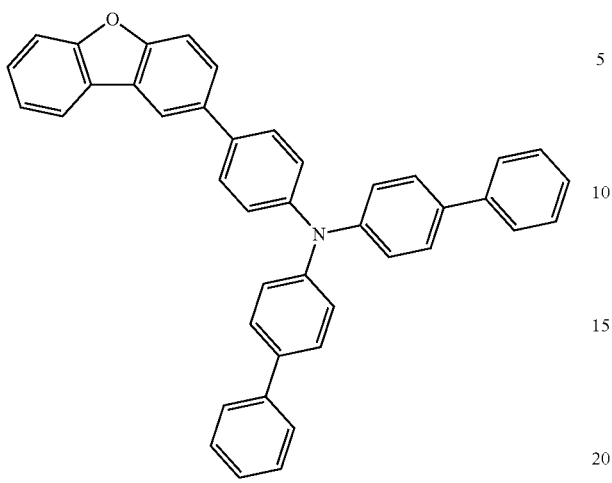

Comparative Example I-4

An OLED was manufactured in the same manner as described in Example I-1, except that the following Comparative Compound 4 was used as the hole transport layer material, instead of the inventive compound P-1.

<Comparative compound 4>

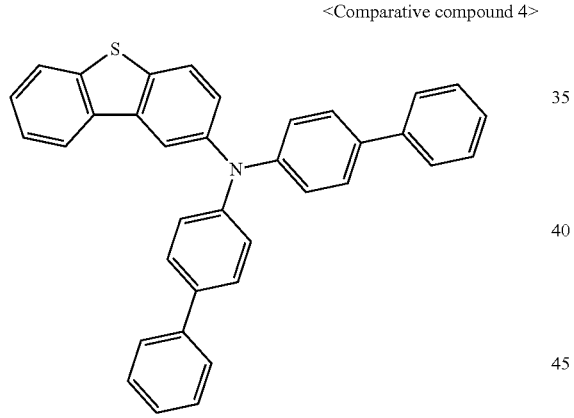

Comparative Example I-5

An OLED was manufactured in the same manner as described in Example I-1, except that the following Comparative Compound 5 was used as the hole transport layer material, instead of the inventive compound P-1.

<Comparative compound 5>

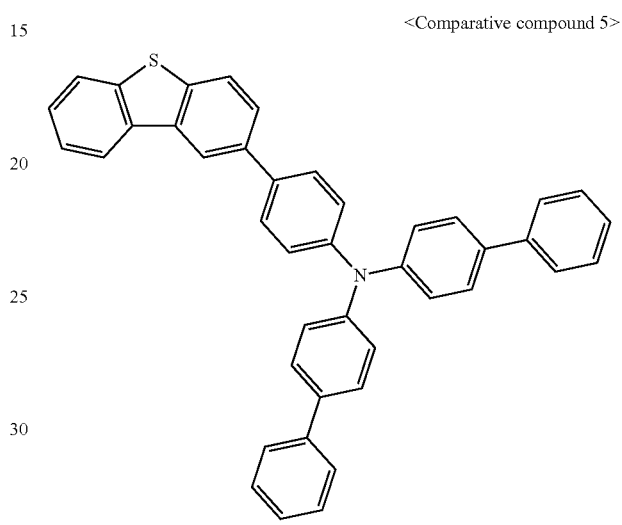

A forward bias DC voltage was applied to each of the OLEDs manufactured through the Examples I-1 to I-65 and the Comparative Examples I-1 to I-5, and electro-luminescence (EL) characteristics of the OLED were measured by PR-650 (Photoresearch). Also, T95 life span was measured by life span measuring equipment (Mcscience) at reference brightness of 5000 cd/m$^2$. Evaluation results are given in the Table 4 below.

TABLE 4

|  | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comp. Ex(I-1) | comp. Com1 | 6.0 | 21.5 | 5000 | 23.3 | 57.0 | 0.32 | 0.61 |
| comp. Ex(I-2) | comp. Com2 | 5.9 | 18.4 | 5000 | 27.2 | 73.2 | 0.32 | 0.62 |
| comp. Ex(I-3) | comp. Com3 | 5.8 | 17.3 | 5000 | 29.0 | 78.6 | 0.33 | 0.61 |
| comp. Ex(I-4) | comp. Com4 | 5.8 | 18.0 | 5000 | 27.8 | 76.4 | 0.33 | 0.62 |
| comp. Ex(I-5) | comp. Com5 | 5.8 | 16.8 | 5000 | 29.8 | 80.8 | 0.33 | 0.61 |
| Ex. (I-1) | Com. (P-1) | 5.7 | 15.3 | 5000 | 32.7 | 105.3 | 0.33 | 0.61 |
| Ex. (I-2) | Com. (P-4) | 5.6 | 14.1 | 5000 | 35.6 | 116.9 | 0.33 | 0.61 |
| Ex. (I-3) | Com. (P-8) | 5.6 | 14.1 | 5000 | 35.5 | 112.1 | 0.33 | 0.61 |
| Ex. (I-4) | Com. (P-9) | 5.6 | 14.9 | 5000 | 33.7 | 105.6 | 0.33 | 0.61 |
| Ex. (I-5) | Com. (P-13) | 5.6 | 15.0 | 5000 | 33.3 | 108.6 | 0.33 | 0.62 |
| Ex. (I-6) | Com. (P-19) | 5.7 | 15.0 | 5000 | 33.4 | 104.2 | 0.33 | 0.62 |
| Ex. (I-7) | Com. (P-22) | 5.7 | 14.1 | 5000 | 35.4 | 116.1 | 0.33 | 0.62 |
| Ex. (I-8) | Com. (P-28) | 5.6 | 14.8 | 5000 | 33.8 | 102.6 | 0.33 | 0.61 |
| Ex. (I-9) | Com. (P-30) | 5.6 | 14.6 | 5000 | 34.3 | 106.7 | 0.33 | 0.61 |

TABLE 4-continued

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Ex. (I-10) | Com. (P-33) | 5.7 | 14.7 | 5000 | 34.0 | 109.2 | 0.33 | 0.62 |
| Ex. (I-11) | Com. (P-39) | 5.6 | 15.3 | 5000 | 32.6 | 106.3 | 0.33 | 0.61 |
| Ex. (I-12) | Com. (P-43) | 5.6 | 14.8 | 5000 | 33.7 | 103.0 | 0.33 | 0.61 |
| Ex. (I-13) | Com. (P-45) | 5.6 | 14.2 | 5000 | 35.2 | 111.9 | 0.33 | 0.61 |
| Ex. (I-14) | Com. (P-47) | 5.7 | 14.3 | 5000 | 35.1 | 112.5 | 0.33 | 0.61 |
| Ex. (I-15) | Com. (P-51) | 5.6 | 14.6 | 5000 | 34.4 | 101.6 | 0.33 | 0.61 |
| Ex. (I-16) | Com. (P-52) | 5.6 | 14.3 | 5000 | 35.0 | 111.9 | 0.33 | 0.62 |
| Ex. (I-17) | Com. (P-54) | 5.7 | 14.1 | 5000 | 35.4 | 110.5 | 0.33 | 0.61 |
| Ex. (I-18) | Com. (P-57) | 5.7 | 14.4 | 5000 | 34.7 | 104.1 | 0.33 | 0.61 |
| Ex. (I-19) | Com. (P-62) | 5.7 | 15.2 | 5000 | 32.9 | 110.0 | 0.33 | 0.61 |
| Ex. (I-20) | Com. (P-66) | 5.7 | 15.0 | 5000 | 33.4 | 104.9 | 0.33 | 0.62 |
| Ex. (I-21) | Com. (P-69) | 5.6 | 14.8 | 5000 | 33.7 | 103.7 | 0.33 | 0.62 |
| Ex. (I-22) | Com. (P-73) | 5.6 | 14.0 | 5000 | 35.8 | 112.1 | 0.33 | 0.61 |
| Ex. (I-23) | Com. (P-75) | 5.7 | 14.6 | 5000 | 34.3 | 120.6 | 0.33 | 0.62 |
| Ex. (I-24) | Com. (P-77) | 5.7 | 14.1 | 5000 | 35.5 | 112.2 | 0.33 | 0.61 |
| Ex. (I-25) | Com. (P-80) | 5.6 | 14.3 | 5000 | 35.1 | 112.6 | 0.33 | 0.62 |
| Ex. (I-26) | Com. (P-82) | 5.6 | 13.6 | 5000 | 36.7 | 125.4 | 0.33 | 0.61 |
| Ex. (I-27) | Com. (P-86) | 5.6 | 13.9 | 5000 | 36.0 | 111.4 | 0.33 | 0.61 |
| Ex. (I-28) | Com. (P-89) | 5.6 | 14.0 | 5000 | 35.7 | 113.0 | 0.33 | 0.61 |
| Ex. (I-29) | Com. (P-92) | 5.5 | 13.6 | 5000 | 36.8 | 125.7 | 0.33 | 0.61 |
| Ex. (I-30) | Com. (P-95) | 5.7 | 14.5 | 5000 | 34.5 | 111.1 | 0.33 | 0.61 |
| Ex. (I-31) | Com. (P-96) | 5.6 | 14.8 | 5000 | 33.9 | 115.2 | 0.33 | 0.61 |
| Ex. (I-32) | Com. (P-97) | 5.6 | 14.9 | 5000 | 33.5 | 120.3 | 0.33 | 0.62 |
| Ex. (I-33) | Com. (P-102) | 5.7 | 14.2 | 5000 | 35.3 | 117.8 | 0.33 | 0.61 |
| Ex. (I-34) | Com. (P-106) | 5.5 | 13.6 | 5000 | 36.8 | 123.8 | 0.33 | 0.62 |
| Ex. (I-35) | Com. (P-110) | 5.6 | 14.8 | 5000 | 33.8 | 117.3 | 0.33 | 0.62 |
| Ex. (I-36) | Com. (P-114) | 5.6 | 14.4 | 5000 | 34.6 | 117.1 | 0.33 | 0.62 |
| Ex. (I-37) | Com. (P-118) | 5.6 | 13.7 | 5000 | 36.5 | 121.3 | 0.33 | 0.61 |
| Ex. (I-38) | Com. (P-121) | 5.6 | 13.1 | 5000 | 38.1 | 131.4 | 0.33 | 0.61 |
| Ex. (I-39) | Com. (P-128) | 5.7 | 14.3 | 5000 | 34.9 | 119.1 | 0.33 | 0.62 |
| Ex. (I-40) | Com. (P-135) | 5.7 | 14.7 | 5000 | 34.0 | 115.6 | 0.33 | 0.61 |
| Ex. (I-41) | Com. (P-136) | 5.7 | 13.9 | 5000 | 35.9 | 115.0 | 0.33 | 0.61 |
| Ex. (I-42) | Com. (P-137) | 5.6 | 13.7 | 5000 | 36.5 | 124.9 | 0.33 | 0.62 |
| Ex. (I-43) | Com. (P-140) | 5.5 | 13.3 | 5000 | 37.5 | 136.0 | 0.33 | 0.61 |
| Ex. (I-44) | Com. (P-141) | 5.5 | 13.7 | 5000 | 36.5 | 122.6 | 0.33 | 0.62 |
| Ex. (I-45) | Com. (P-142) | 5.6 | 13.6 | 5000 | 36.7 | 124.7 | 0.33 | 0.61 |
| Ex. (I-46) | Com. (P-144) | 5.6 | 13.8 | 5000 | 36.2 | 127.5 | 0.33 | 0.62 |
| Ex. (I-47) | Com. (P-145) | 5.6 | 14.0 | 5000 | 35.6 | 112.2 | 0.33 | 0.61 |
| Ex. (I-48) | Com. (P-148) | 5.5 | 13.9 | 5000 | 36.0 | 131.7 | 0.33 | 0.62 |
| Ex. (I-49) | Com. (P-150) | 5.6 | 13.6 | 5000 | 36.9 | 127.0 | 0.33 | 0.62 |
| Ex. (I-50) | Com. (P-155) | 5.5 | 12.9 | 5000 | 38.6 | 139.6 | 0.33 | 0.61 |
| Ex. (I-51) | Com. (P-156) | 5.6 | 12.8 | 5000 | 39.0 | 143.8 | 0.33 | 0.62 |
| Ex. (I-52) | Com. (P-159) | 5.7 | 14.1 | 5000 | 35.5 | 116.5 | 0.33 | 0.61 |
| Ex. (I-53) | Com. (P-162) | 5.6 | 13.3 | 5000 | 37.6 | 138.1 | 0.33 | 0.61 |
| Ex. (I-54) | Com. (P-166) | 5.5 | 13.5 | 5000 | 37.0 | 128.8 | 0.33 | 0.61 |
| Ex. (I-55) | Com. (P-170) | 5.5 | 13.4 | 5000 | 37.4 | 137.8 | 0.33 | 0.61 |
| Ex. (I-56) | Com. (P-172) | 5.7 | 14.1 | 5000 | 35.5 | 118.4 | 0.33 | 0.62 |
| Ex. (I-57) | Com. (P-173) | 5.5 | 13.4 | 5000 | 37.2 | 137.0 | 0.33 | 0.61 |
| Ex. (I-58) | Com. (P-178) | 5.7 | 14.0 | 5000 | 35.6 | 116.2 | 0.33 | 0.61 |
| Ex. (I-59) | Com. (P-179) | 5.6 | 12.8 | 5000 | 39.0 | 142.1 | 0.33 | 0.61 |
| Ex. (I-60) | Com. (P-182) | 5.6 | 13.6 | 5000 | 36.8 | 128.1 | 0.33 | 0.61 |
| Ex. (I-61) | Com. (P-185) | 5.5 | 13.2 | 5000 | 37.8 | 133.1 | 0.33 | 0.62 |
| Ex. (I-62) | Com. (P-187) | 5.6 | 13.2 | 5000 | 37.8 | 137.0 | 0.33 | 0.61 |
| Ex. (I-63) | Com. (P-192) | 5.5 | 13.6 | 5000 | 36.7 | 122.3 | 0.33 | 0.61 |
| Ex. (I-64) | Com. (P-198) | 5.6 | 14.2 | 5000 | 35.2 | 117.5 | 0.33 | 0.62 |
| Ex. (I-65) | Com. (P-200) | 5.7 | 14.2 | 5000 | 35.1 | 112.7 | 0.33 | 0.62 |

It can be seen from the results in Table 4 above, that the OLEDs employing the inventive compounds as hole transport layer materials showed predominantly improved luminescent efficiency and lifespan, compared to the OLEDs employing comparative compounds as a hole transport layer material.

Specially, the OLEDs using comparative compounds 2 to 5 having one of dibenzofuran or dibenzothiophene as a core showed higher luminescent efficiency than the OLEDs using NPB (comparative compound 1) used generally as a hole transport layer material. Further, the OLEDs using the inventive compounds, the compounds having both dibenzofuran and dibenzothiophene as a core and having a structure including the core fused with a aromatic ring, as a hole transport layer material showed improved luminescent efficiency and life span, compared to the OLEDs using comparative compounds 1 to 5.

This may be caused by the fact that the packing density of the inventive compounds which have a additional aromatic ring fused with two heterocyclic rings (dibenzofuran or dibenzothiophene) is higher than that of comparative compounds 2 to 5 not forming a ring when compounds are deposited during manufacturing an OLED, thereby Joule's heat generated by overvoltage is decreased, and thus the OLED has a thermal stability, and relatively high T1 prevents surplus electrons from transferring to a hole transport layer from an emission layer resulting in improving color purity and decreasing thermal damage by emitting in interface of a hole transport layer. Therefore, it is believed that the lifespan of the elements employing the inventive compounds is predominantly improved, compared to comparative compounds.

Furthermore, properties of a hole transport layer should be considered in relation with a light emitting layer(host), and one skilled in the art, even using a similar core compound, would have difficulty in inferring the characteristics shown by the hole transport layer using the compound of the present invention.

[Example II-1] Green OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and then 2-TNATA was vacuum-deposited on the ITO layer to form a hole injection layer with a thickness of 60 nm.

Subsequently, N,N'-Bis(1-naphthalenyl)-N,N'-bis-phenyl-(1,1'-biphenyl)-4,4'-diamine (hereinafter, "NPB") was vacuum-deposited with a thickness of 60 nm on the hole injection layer to form a hole transport layer.

Subsequently, the compound P-1 of the present invention was vacuum-deposited on the hole transport layer to form an emission-auxiliary layer with a thickness of 20 nm. A light emitting layer with a thickness of 30 nm was formed on the emission-auxiliary layer by using the CBP as a host material and Ir(ppy)$_3$ as a dopant material in a weight ratio of 90:10.

Next, BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example II-2] to [Example II-69] Green OLED (an Emission-Auxiliary Layer)

The OLEDs were manufactured in the same manner as described in Example II-1, except that any one of the compounds P-4 to P-200 of the present invention in the Table 5 below was used as the emission-auxiliary layer material of the light emitting layer, instead of the inventive compound P-1.

Comparative Example II-1

An OLED was manufactured in the same manner as described in Example II-1, except that Comparative Compound 6 above was used as the emission-auxiliary layer material, instead of the inventive compound P-1.

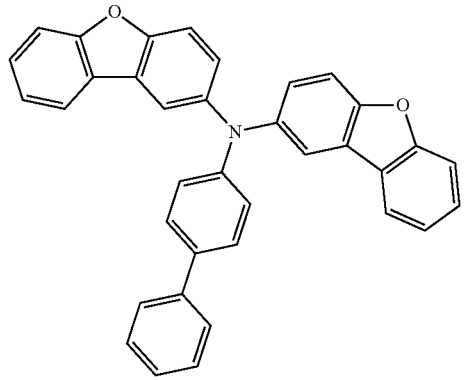

<Comparative compound 6>

Comparative Example II-2

An OLED was manufactured in the same manner as described in Example II-1, except that Comparative Compound 7 above was used as the emission-auxiliary layer material, instead of the inventive compound P-1.

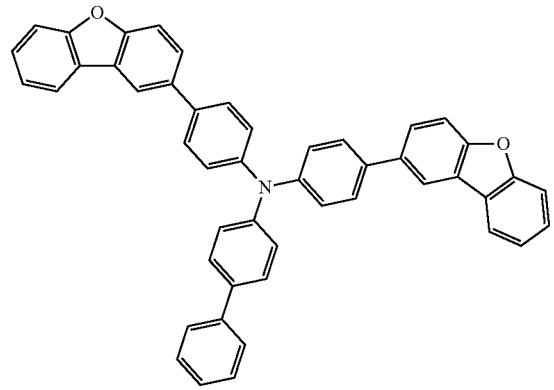

<Comparative compound 7>

Comparative Example II-3

An OLED was manufactured in the same manner as described in Example II-1, except for not forming the emission-auxiliary layer.

A forward bias DC voltage was applied to each of the OLEDs manufactured through Examples II-1 to II-69 and Comparative Example II-1 to II-3, and electro-luminescence (EL) characteristics of the OLED were measured by PR-650 (Photoresearch). Also, T95 life span was measured by life span measuring equipment (Mcscience) at reference brightness of 5000 cd/m$^2$. Table 5 below shows evaluation results of OLEDs manufactured by Examples of the present invention and Comparative Examples.

TABLE 5

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comp. Ex(II-1) | comp. Com6 | 6.5 | 14.8 | 5000 | 33.7 | 89.4 | 0.33 | 0.61 |
| comp. Ex(II-2) | comp. Com7 | 6.4 | 13.4 | 5000 | 37.2 | 108.7 | 0.33 | 0.61 |
| comp. Ex(II-3) | — | 6.0 | 21.5 | 5000 | 23.3 | 57.0 | 0.32 | 0.61 |
| Ex. (II-1) | Com. (P-1) | 6.4 | 11.0 | 5000 | 45.3 | 135.9 | 0.32 | 0.61 |
| Ex. (II-2) | Com. (P-4) | 6.3 | 10.8 | 5000 | 46.3 | 138.6 | 0.33 | 0.61 |
| Ex. (II-3) | Com. (P-8) | 6.3 | 10.8 | 5000 | 46.1 | 137.1 | 0.33 | 0.61 |
| Ex. (II-4) | Com. (P-9) | 6.3 | 11.0 | 5000 | 45.3 | 130.3 | 0.32 | 0.61 |
| Ex. (II-5) | Com. (P-16) | 6.4 | 11.1 | 5000 | 45.1 | 132.2 | 0.32 | 0.61 |
| Ex. (II-6) | Com. (P-19) | 6.4 | 11.0 | 5000 | 45.6 | 130.1 | 0.32 | 0.61 |
| Ex. (II-7) | Com. (P-22) | 6.3 | 10.8 | 5000 | 46.2 | 140.1 | 0.33 | 0.61 |
| Ex. (II-8) | Com. (P-26) | 6.3 | 10.9 | 5000 | 45.8 | 135.6 | 0.32 | 0.61 |
| Ex. (II-9) | Com. (P-30) | 6.4 | 10.9 | 5000 | 45.8 | 134.4 | 0.32 | 0.61 |
| Ex. (II-10) | Com. (P-33) | 6.4 | 11.1 | 5000 | 45.0 | 132.1 | 0.32 | 0.62 |
| Ex. (II-11) | Com. (P-43) | 6.4 | 11.0 | 5000 | 45.3 | 133.4 | 0.32 | 0.61 |
| Ex. (II-12) | Com. (P-45) | 6.4 | 10.9 | 5000 | 45.9 | 138.2 | 0.33 | 0.62 |
| Ex. (II-13) | Com. (P-47) | 6.3 | 10.9 | 5000 | 46.1 | 137.4 | 0.33 | 0.62 |
| Ex. (II-14) | Com. (P-51) | 6.3 | 10.9 | 5000 | 45.9 | 134.7 | 0.32 | 0.62 |
| Ex. (II-15) | Com. (P-52) | 6.3 | 10.7 | 5000 | 46.8 | 140.6 | 0.33 | 0.62 |
| Ex. (II-16) | Com. (P-54) | 6.3 | 10.8 | 5000 | 46.4 | 137.2 | 0.33 | 0.62 |
| Ex. (II-17) | Com. (P-57) | 6.4 | 10.9 | 5000 | 45.7 | 133.3 | 0.32 | 0.62 |
| Ex. (II-18) | Com. (P-61) | 6.4 | 11.0 | 5000 | 45.3 | 131.1 | 0.32 | 0.61 |
| Ex. (II-19) | Com. (P-67) | 6.4 | 11.1 | 5000 | 45.2 | 133.4 | 0.32 | 0.61 |
| Ex. (II-20) | Com. (P-69) | 6.4 | 11.0 | 5000 | 45.5 | 133.0 | 0.33 | 0.61 |
| Ex. (II-21) | Com. (P-73) | 6.2 | 10.7 | 5000 | 46.9 | 139.2 | 0.33 | 0.61 |
| Ex. (II-22) | Com. (P-77) | 6.3 | 10.6 | 5000 | 47.2 | 141.7 | 0.33 | 0.62 |
| Ex. (II-23) | Com. (P-80) | 6.3 | 10.6 | 5000 | 47.3 | 140.9 | 0.33 | 0.62 |
| Ex. (II-24) | Com. (P-82) | 6.2 | 10.5 | 5000 | 47.6 | 148.7 | 0.33 | 0.61 |
| Ex. (II-25) | Com. (P-86) | 6.3 | 10.7 | 5000 | 46.9 | 144.2 | 0.33 | 0.62 |
| Ex. (II-26) | Com. (P-89) | 6.2 | 10.6 | 5000 | 47.2 | 142.0 | 0.33 | 0.62 |
| Ex. (II-27) | Com. (P-91) | 6.3 | 10.5 | 5000 | 47.5 | 153.8 | 0.33 | 0.62 |
| Ex. (II-28) | Com. (P-92) | 6.3 | 10.4 | 5000 | 48.1 | 148.9 | 0.33 | 0.62 |
| Ex. (II-29) | Com. (P-96) | 6.3 | 10.8 | 5000 | 46.2 | 142.7 | 0.33 | 0.62 |
| Ex. (II-30) | Com. (P-99) | 6.4 | 10.9 | 5000 | 45.9 | 138.1 | 0.32 | 0.62 |
| Ex. (II-31) | Com. (P-102) | 6.2 | 10.6 | 5000 | 47.4 | 141.2 | 0.33 | 0.61 |
| Ex. (II-32) | Com. (P-106) | 6.3 | 10.4 | 5000 | 48.1 | 154.0 | 0.33 | 0.61 |
| Ex. (II-33) | Com. (P-112) | 6.4 | 10.8 | 5000 | 46.3 | 145.8 | 0.32 | 0.61 |
| Ex. (II-34) | Com. (P-113) | 6.3 | 10.5 | 5000 | 47.5 | 154.5 | 0.33 | 0.61 |
| Ex. (II-35) | Com. (P-118) | 6.3 | 10.4 | 5000 | 48.0 | 151.8 | 0.33 | 0.62 |
| Ex. (II-36) | Com. (P-119) | 6.2 | 10.7 | 5000 | 46.9 | 145.4 | 0.33 | 0.61 |
| Ex. (II-37) | Com. (P-121) | 6.2 | 10.4 | 5000 | 48.2 | 156.6 | 0.32 | 0.62 |
| Ex. (II-38) | Com. (P-123) | 6.3 | 10.6 | 5000 | 47.1 | 145.0 | 0.33 | 0.62 |
| Ex. (II-39) | Com. (P-128) | 6.3 | 10.6 | 5000 | 47.4 | 144.3 | 0.33 | 0.62 |
| Ex. (II-40) | Com. (P-136) | 6.2 | 10.7 | 5000 | 46.9 | 142.4 | 0.33 | 0.61 |
| Ex. (II-41) | Com. (P-137) | 6.3 | 10.4 | 5000 | 48.2 | 149.1 | 0.33 | 0.61 |
| Ex. (II-42) | Com. (P-139) | 6.2 | 10.5 | 5000 | 47.6 | 145.4 | 0.33 | 0.61 |
| Ex. (II-43) | Com. (P-140) | 6.2 | 10.2 | 5000 | 48.9 | 156.7 | 0.33 | 0.61 |
| Ex. (II-44) | Com. (P-141) | 6.3 | 10.2 | 5000 | 49.0 | 161.0 | 0.33 | 0.62 |
| Ex. (II-45) | Com. (P-142) | 6.3 | 10.3 | 5000 | 48.4 | 147.8 | 0.33 | 0.61 |
| Ex. (II-46) | Com. (P-148) | 6.2 | 10.3 | 5000 | 48.6 | 146.7 | 0.33 | 0.61 |
| Ex. (II-47) | Com. (P-153) | 6.3 | 10.3 | 5000 | 48.5 | 147.9 | 0.33 | 0.62 |
| Ex. (II-48) | Com. (P-154) | 6.3 | 10.4 | 5000 | 48.2 | 145.4 | 0.33 | 0.62 |
| Ex. (II-49) | Com. (P-155) | 6.2 | 9.9 | 5000 | 50.3 | 164.0 | 0.33 | 0.62 |
| Ex. (II-50) | Com. (P-156) | 6.2 | 10.0 | 5000 | 50.0 | 165.3 | 0.33 | 0.62 |
| Ex. (II-51) | Com. (P-162) | 6.3 | 10.2 | 5000 | 49.1 | 157.8 | 0.33 | 0.62 |
| Ex. (II-52) | Com. (P-163) | 6.3 | 10.7 | 5000 | 46.8 | 146.4 | 0.32 | 0.62 |
| Ex. (II-53) | Com. (P-164) | 6.2 | 10.4 | 5000 | 48.3 | 149.4 | 0.33 | 0.61 |
| Ex. (II-54) | Com. (P-165) | 6.2 | 10.3 | 5000 | 48.7 | 160.3 | 0.33 | 0.62 |
| Ex. (II-55) | Com. (P-166) | 6.3 | 10.2 | 5000 | 49.1 | 156.5 | 0.33 | 0.61 |
| Ex. (II-56) | Com. (P-172) | 6.3 | 10.5 | 5000 | 47.6 | 149.8 | 0.32 | 0.61 |
| Ex. (II-57) | Com. (P-173) | 6.3 | 10.2 | 5000 | 49.2 | 156.1 | 0.33 | 0.62 |
| Ex. (II-58) | Com. (P-177) | 6.2 | 10.4 | 5000 | 48.1 | 150.8 | 0.33 | 0.61 |
| Ex. (II-59) | Com. (P-178) | 6.2 | 10.6 | 5000 | 47.1 | 146.9 | 0.32 | 0.62 |
| Ex. (II-60) | Com. (P-179) | 6.2 | 10.0 | 5000 | 50.0 | 163.4 | 0.33 | 0.61 |
| Ex. (II-61) | Com. (P-182) | 6.2 | 10.3 | 5000 | 48.5 | 152.5 | 0.33 | 0.61 |
| Ex. (II-62) | Com. (P-183) | 6.3 | 10.4 | 5000 | 48.2 | 151.3 | 0.33 | 0.61 |
| Ex. (II-63) | Com. (P-185) | 6.2 | 10.2 | 5000 | 48.8 | 156.1 | 0.33 | 0.62 |
| Ex. (II-64) | Com. (P-186) | 6.3 | 10.4 | 5000 | 47.9 | 147.8 | 0.33 | 0.62 |
| Ex. (II-65) | Com. (P-187) | 6.2 | 10.1 | 5000 | 49.5 | 156.5 | 0.33 | 0.62 |
| Ex. (II-66) | Com. (P-191) | 6.2 | 10.4 | 5000 | 48.1 | 150.9 | 0.33 | 0.62 |
| Ex. (II-67) | Com. (P-192) | 6.3 | 10.3 | 5000 | 48.4 | 149.4 | 0.33 | 0.62 |
| Ex. (II-68) | Com. (P-196) | 6.2 | 10.6 | 5000 | 47.2 | 145.5 | 0.32 | 0.62 |
| Ex. (II-69) | Com. (P-200) | 6.2 | 10.3 | 5000 | 48.4 | 147.5 | 0.33 | 0.61 |

[Example III-1] Red OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm.

Subsequently, NPB was vacuum-deposited with a thickness of 60 nm on the hole injection layer to form a hole transport layer.

Subsequently, compound P-139 of the present invention was vacuum-deposited on the hole transport layer to form an emission-auxiliary layer with a thickness of 20 nm.

A light emitting layer with a thickness of 30 nm was formed on the emission-auxiliary layer by using the CBP as a host material and bis-(1-phenylisoquinolyl)iridium(III) acetylacetonate (hereinafter, "(piq)$_2$Ir(acac)") as a dopant material in a weight ratio of 95:5.

Next, BAlq was vacuum-deposited with a thickness of 10 nm on the light emitting layer to form a hole blocking layer, and Alq$_3$ was vacuum-deposited with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example III-2] to [Example III-23] Red OLED (an Emission-Auxiliary Layer)

The OLED was manufactured in the same manner as described in Example III-1, except that any one of the compounds P-143 to P-199 of the present invention in the Table 6 below was used as the emission-auxiliary layer material, instead of the inventive compound P-139.

Comparative Example III-1

An OLED was manufactured in the same manner as described in Example III-1, except that Comparative Compound 7 above was used as the emission-auxiliary layer material, instead of the inventive compound P-139.

Comparative Example III-2

An OLED was manufactured in the same manner as described in Example III-1, except for not forming the emission-auxiliary layer.

A forward bias DC voltage was applied to each of the OLEDs manufactured through Examples III-1 to III-23 of the present invention, and Comparative Examples III-1 and III-2, and electro-luminescence (EL) characteristics of the OLED were measured by PR-650 (Photoresearch). Also, T95 life span was measured by life span measuring equipment (Mcscience) at reference brightness of 2500 cd/m$^2$. Table 6 below shows evaluation results of OLEDs manufactured by Examples of the present invention and Comparative Examples.

TABLE 6

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comp. Ex(III-1) | comp. Com7 | 6.9 | 26.9 | 2500 | 9.3 | 90.2 | 0.66 | 0.32 |
| comp. Ex(III-2) | — | 6.5 | 33.8 | 2500 | 7.4 | 63.9 | 0.66 | 0.32 |
| Ex. (III-1) | Com. (P-139) | 6.7 | 18.6 | 2500 | 13.4 | 138.3 | 0.66 | 0.33 |
| Ex. (III-2) | Com. (P-143) | 6.7 | 17.2 | 2500 | 14.6 | 148.6 | 0.66 | 0.33 |
| Ex. (III-3) | Com. (P-147) | 6.7 | 17.7 | 2500 | 14.1 | 134.1 | 0.66 | 0.33 |
| Ex. (III-4) | Com. (P-149) | 6.7 | 16.8 | 2500 | 14.8 | 145.3 | 0.66 | 0.32 |
| Ex. (III-5) | Com. (P-152) | 6.8 | 19.0 | 2500 | 13.2 | 132.5 | 0.65 | 0.32 |
| Ex. (III-6) | Com. (P-154) | 6.7 | 17.2 | 2500 | 14.5 | 147.8 | 0.66 | 0.33 |
| Ex. (III-7) | Com. (P-157) | 6.8 | 18.8 | 2500 | 13.3 | 134.0 | 0.65 | 0.33 |
| Ex. (III-8) | Com. (P-158) | 6.7 | 19.2 | 2500 | 13.0 | 128.9 | 0.66 | 0.32 |
| Ex. (III-9) | Com. (P-163) | 6.8 | 18.9 | 2500 | 13.2 | 127.3 | 0.65 | 0.32 |
| Ex. (III-10) | Com. (P-164) | 6.7 | 18.1 | 2500 | 13.8 | 136.1 | 0.66 | 0.32 |
| Ex. (III-11) | Com. (P-165) | 6.7 | 17.2 | 2500 | 14.6 | 143.1 | 0.66 | 0.33 |
| Ex. (III-12) | Com. (P-167) | 6.8 | 18.8 | 2500 | 13.3 | 131.8 | 0.66 | 0.32 |
| Ex. (III-13) | Com. (P-174) | 6.7 | 18.9 | 2500 | 13.2 | 131.1 | 0.66 | 0.32 |
| Ex. (III-14) | Com. (P-175) | 6.7 | 19.5 | 2500 | 12.8 | 132.2 | 0.65 | 0.33 |
| Ex. (III-15) | Com. (P-177) | 6.7 | 17.1 | 2500 | 14.6 | 146.3 | 0.66 | 0.32 |
| Ex. (III-16) | Com. (P-180) | 6.8 | 18.2 | 2500 | 13.7 | 134.4 | 0.66 | 0.32 |
| Ex. (III-17) | Com. (P-186) | 6.8 | 19.1 | 2500 | 13.1 | 130.6 | 0.65 | 0.32 |
| Ex. (III-18) | Com. (P-189) | 6.8 | 19.0 | 2500 | 13.1 | 129.5 | 0.66 | 0.33 |
| Ex. (III-19) | Com. (P-191) | 6.8 | 18.7 | 2500 | 13.4 | 137.1 | 0.66 | 0.32 |
| Ex. (III-20) | Com. (P-194) | 6.7 | 17.2 | 2500 | 14.5 | 147.0 | 0.66 | 0.32 |
| Ex. (III-21) | Com. (P-195) | 6.7 | 19.1 | 2500 | 13.1 | 133.5 | 0.65 | 0.33 |
| Ex. (III-22) | Com. (P-198) | 6.7 | 19.3 | 2500 | 13.0 | 127.3 | 0.65 | 0.32 |
| Ex. (III-23) | Com. (P-199) | 6.7 | 18.8 | 2500 | 13.3 | 128.7 | 0.65 | 0.33 |

[Example IV-1] Blue OLED (an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm.

Subsequently, NPB was vacuum-deposited with a thickness of 60 nm on the hole injection layer to form a hole transport layer.

Subsequently, the compound P-73 of the present invention was vacuum-deposited on the hole transport layer to form an emission-auxiliary layer with a thickness of 20 nm.

A light emitting layer with a thickness of 20 nm was formed on the emission-auxiliary layer by using 9,10-Di(2-naphthyl)anthracene (hereinafter, "ADN") as a host material and BD-052X (made in Idemitsu kosan) as a dopant material in a weight ratio of 93:7.

Next, BAlq was vacuum-deposited with a thickness of 10 nm on the light emitting layer to form a hole blocking layer, and a film of $Alq_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example IV-2] to [Example IV-51] Blue OLED (an Emission-Auxiliary Layer)

The OLED was manufactured in the same manner as described in Example IV-1, except that any one of the compounds P-77 to P-200 of the present invention in the Table 7 below was used as the emission-auxiliary layer material, instead of the inventive compound P-73.

Comparative Example IV-1

An OLED was manufactured in the same manner as described in Example IV-1, except that Comparative Compound 6 above was used as the emission-auxiliary layer material, instead of the inventive compound P-73.

Comparative Example IV-2

An OLED was manufactured in the same manner as described in Example IV-1, except that Comparative Compound 7 above was used as the emission-auxiliary layer material, instead of the inventive compound P-73.

Comparative Example IV-3

An OLED was manufactured in the same manner as described in Example IV-1, except for not forming the emission-auxiliary layer.

A forward bias DC voltage was applied to each of the OLEDs manufactured through Examples IV-1 to IV-51 of the present invention, and Comparative Examples IV-1 to IV-3, and electro-luminescence (EL) characteristics of the OLED were measured by PR-650 (Photoresearch). Also, T95 life span was measured by life span measuring equipment (Mcscience) at reference brightness of 500 cd/m². Table 7 below shows evaluation results of OLEDs manufactured by Examples of the present invention and Comparative Examples.

TABLE 7

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comp. Ex(IV-1) | comp. Com6 | 5.9 | 11.9 | 500 | 4.2 | 71.5 | 0.14 | 0.12 |
| comp. Ex(IV-2) | comp. Com7 | 5.8 | 10.8 | 500 | 4.6 | 78.1 | 0.14 | 0.12 |
| comp. Ex(IV-3) | — | 5.6 | 14.3 | 500 | 3.5 | 60.8 | 0.14 | 0.13 |
| Ex. (IV-1) | Com. (P-73) | 5.8 | 9.1 | 500 | 5.5 | 117.7 | 0.14 | 0.12 |
| Ex. (IV-2) | Com. (P-77) | 5.9 | 9.6 | 500 | 5.2 | 118.8 | 0.14 | 0.12 |
| Ex. (IV-3) | Com. (P-80) | 5.9 | 9.1 | 500 | 5.5 | 118.4 | 0.14 | 0.12 |
| Ex. (IV-4) | Com. (P-82) | 5.7 | 8.7 | 500 | 5.8 | 130.0 | 0.14 | 0.11 |
| Ex. (IV-5) | Com. (P-86) | 5.8 | 9.1 | 500 | 5.5 | 120.6 | 0.14 | 0.12 |
| Ex. (IV-6) | Com. (P-89) | 5.8 | 9.2 | 500 | 5.4 | 116.8 | 0.14 | 0.11 |
| Ex. (IV-7) | Com. (P-91) | 5.8 | 8.9 | 500 | 5.6 | 124.4 | 0.14 | 0.12 |
| Ex. (IV-8) | Com. (P-92) | 5.7 | 8.5 | 500 | 5.9 | 122.0 | 0.14 | 0.12 |
| Ex. (IV-9) | Com. (P-94) | 5.9 | 9.2 | 500 | 5.4 | 120.8 | 0.14 | 0.11 |
| Ex. (IV-10) | Com. (P-97) | 5.9 | 9.8 | 500 | 5.1 | 118.7 | 0.14 | 0.12 |
| Ex. (IV-11) | Com. (P-102) | 5.9 | 9.0 | 500 | 5.5 | 120.8 | 0.14 | 0.12 |
| Ex. (IV-12) | Com. (P-105) | 5.8 | 9.2 | 500 | 5.4 | 115.5 | 0.14 | 0.11 |
| Ex. (IV-13) | Com. (P-106) | 5.7 | 8.5 | 500 | 5.9 | 126.8 | 0.14 | 0.11 |
| Ex. (IV-14) | Com. (P-110) | 5.8 | 9.8 | 500 | 5.1 | 114.4 | 0.14 | 0.11 |
| Ex. (IV-15) | Com. (P-113) | 5.7 | 8.6 | 500 | 5.8 | 125.6 | 0.14 | 0.11 |
| Ex. (IV-16) | Com. (P-118) | 5.7 | 8.9 | 500 | 5.6 | 126.2 | 0.14 | 0.12 |
| Ex. (IV-17) | Com. (P-119) | 5.9 | 9.6 | 500 | 5.2 | 119.9 | 0.14 | 0.12 |
| Ex. (IV-18) | Com. (P-121) | 5.7 | 7.9 | 500 | 6.3 | 136.1 | 0.14 | 0.12 |
| Ex. (IV-19) | Com. (P-123) | 5.8 | 9.5 | 500 | 5.3 | 119.8 | 0.14 | 0.11 |
| Ex. (IV-20) | Com. (P-128) | 5.8 | 9.0 | 500 | 5.6 | 120.0 | 0.14 | 0.12 |
| Ex. (IV-21) | Com. (P-132) | 5.9 | 9.5 | 500 | 5.3 | 118.0 | 0.14 | 0.12 |
| Ex. (IV-22) | Com. (P-136) | 5.8 | 9.4 | 500 | 5.3 | 117.1 | 0.14 | 0.11 |
| Ex. (IV-23) | Com. (P-137) | 5.7 | 8.5 | 500 | 5.9 | 129.1 | 0.14 | 0.11 |
| Ex. (IV-24) | Com. (P-140) | 5.8 | 8.0 | 500 | 6.2 | 137.6 | 0.14 | 0.11 |
| Ex. (IV-25) | Com. (P-141) | 5.7 | 8.0 | 500 | 6.2 | 140.8 | 0.14 | 0.12 |
| Ex. (IV-26) | Com. (P-142) | 5.8 | 8.4 | 500 | 6.0 | 126.4 | 0.14 | 0.11 |
| Ex. (IV-27) | Com. (P-148) | 5.7 | 8.4 | 500 | 5.9 | 130.2 | 0.14 | 0.11 |
| Ex. (IV-28) | Com. (P-150) | 5.7 | 8.0 | 500 | 6.3 | 132.1 | 0.14 | 0.11 |
| Ex. (IV-29) | Com. (P-153) | 5.7 | 8.5 | 500 | 5.9 | 134.0 | 0.14 | 0.12 |
| Ex. (IV-30) | Com. (P-154) | 5.8 | 8.3 | 500 | 6.0 | 130.6 | 0.14 | 0.11 |
| Ex. (IV-31) | Com. (P-155) | 5.7 | 7.3 | 500 | 6.9 | 147.6 | 0.14 | 0.11 |
| Ex. (IV-32) | Com. (P-156) | 5.7 | 7.3 | 500 | 6.9 | 146.5 | 0.14 | 0.12 |
| Ex. (IV-33) | Com. (P-162) | 5.7 | 7.6 | 500 | 6.6 | 137.7 | 0.14 | 0.11 |
| Ex. (IV-34) | Com. (P-164) | 5.8 | 8.6 | 500 | 5.8 | 127.5 | 0.14 | 0.12 |
| Ex. (IV-35) | Com. (P-165) | 5.8 | 7.9 | 500 | 6.4 | 139.1 | 0.14 | 0.12 |
| Ex. (IV-36) | Com. (P-166) | 5.7 | 7.6 | 500 | 6.6 | 136.9 | 0.14 | 0.12 |

TABLE 7-continued

| Compound | | Voltage (V) | Current Density (mA/cm2) | Brightness (cd/m2) | Efficiency (cd/A) | Lifetime T(95) | CIE x | CIE y |
|---|---|---|---|---|---|---|---|---|
| Ex. (IV-37) | Com. (P-169) | 5.8 | 8.2 | 500 | 6.1 | 127.2 | 0.14 | 0.11 |
| Ex. (IV-38) | Com. (P-170) | 5.7 | 7.8 | 500 | 6.4 | 141.7 | 0.14 | 0.12 |
| Ex. (IV-39) | Com. (P-173) | 5.8 | 7.9 | 500 | 6.4 | 135.1 | 0.14 | 0.11 |
| Ex. (IV-40) | Com. (P-177) | 5.7 | 8.1 | 500 | 6.1 | 126.4 | 0.14 | 0.11 |
| Ex. (IV-41) | Com. (P-179) | 5.7 | 7.3 | 500 | 6.9 | 148.2 | 0.14 | 0.12 |
| Ex. (IV-42) | Com. (P-182) | 5.7 | 8.6 | 500 | 5.8 | 128.1 | 0.14 | 0.11 |
| Ex. (IV-43) | Com. (P-183) | 5.8 | 8.6 | 500 | 5.8 | 129.2 | 0.14 | 0.12 |
| Ex. (IV-44) | Com. (P-185) | 5.8 | 7.6 | 500 | 6.6 | 135.9 | 0.14 | 0.11 |
| Ex. (IV-45) | Com. (P-186) | 5.7 | 8.5 | 500 | 5.9 | 130.0 | 0.14 | 0.11 |
| Ex. (IV-46) | Com. (P-187) | 5.7 | 7.9 | 500 | 6.3 | 136.6 | 0.14 | 0.11 |
| Ex. (IV-47) | Com. (P-191) | 5.7 | 8.2 | 500 | 6.1 | 129.4 | 0.14 | 0.12 |
| Ex. (IV-48) | Com. (P-192) | 5.8 | 8.3 | 500 | 6.0 | 131.9 | 0.14 | 0.11 |
| Ex. (IV-49) | Com. (P-195) | 5.7 | 9.0 | 500 | 5.5 | 130.5 | 0.14 | 0.12 |
| Ex. (IV-50) | Com. (P-196) | 5.7 | 8.8 | 500 | 5.7 | 126.9 | 0.14 | 0.12 |
| Ex. (IV-51) | Com. (P-200) | 5.8 | 8.3 | 500 | 6.0 | 132.0 | 0.14 | 0.12 |

[Example V-1] Blue OLED (a Hole Transport and an Emission-Auxiliary Layer)

Organic light emitting diodes (OLEDs) were fabricated according to a conventional method by using a compound of the present invention as an emission-auxiliary layer material.

First, an ITO layer (anode) was formed on a glass substrate, and 2-TNATA was vacuum-deposited on the ITO layer to form a hole injection layer with a thickness of 60 nm.

Subsequently, the compound P-185 of the present invention was vacuum-deposited with a thickness of 60 nm on the hole injection layer to form a hole transport layer.

Subsequently, the compound P-140 of the present invention was vacuum-deposited on the hole transport layer to form an emission-auxiliary layer with a thickness of 20 nm.

A light emitting layer with a thickness of 30 nm was formed on the emission-auxiliary layer by using ADN as a host material and BD-052X (made in Idemitsu kosan) as a dopant material in a weight ratio of 93:7.

Next, BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example V-2] to [Example V-12] Blue OLED (a Hole Transport and an Emission-Auxiliary Layer)

The OLED was manufactured in the same manner as described in Example IV-1, except that any one of the compounds P-141 to P-187 of the present invention in the Table 8 below was used as the emission-auxiliary layer material, instead of the inventive compound P-140.

A forward bias DC voltage was applied to each of the OLEDs manufactured through Examples V-1 to V-12 of the present invention, and electro-luminescence (EL) characteristics of the OLED were measured by PR-650 (Photoresearch). Also, T95 life span was measured by life span measuring equipment (Mcscience) at reference brightness of 500 cd/m$^2$. Table 8 below shows evaluation results of OLEDs manufactured by Examples of the present invention.

TABLE 8

| Compound | | Voltage (V) | Current Density (mA/cm2) | Brightness (cd/m2) | Efficiency (cd/A) | Lifetime T(95) | CIE x | CIE y |
|---|---|---|---|---|---|---|---|---|
| Ex. (V-1) | Com. (P-140) | 5.8 | 6.9 | 500 | 7.2 | 155.3 | 0.14 | 0.12 |
| Ex. (V-2) | Com. (P-141) | 5.8 | 7.0 | 500 | 7.2 | 156.7 | 0.14 | 0.11 |
| Ex. (V-3) | Com. (P-155) | 5.7 | 6.6 | 500 | 7.5 | 161.9 | 0.14 | 0.11 |
| Ex. (V-4) | Com. (P-156) | 5.7 | 6.7 | 500 | 7.5 | 159.4 | 0.14 | 0.12 |
| Ex. (V-5) | Com. (P-162) | 5.7 | 6.9 | 500 | 7.3 | 157.2 | 0.14 | 0.12 |
| Ex. (V-6) | Com. (P-165) | 5.8 | 7.0 | 500 | 7.2 | 155.3 | 0.14 | 0.11 |
| Ex. (V-7) | Com. (P-166) | 5.8 | 7.0 | 500 | 7.2 | 154.3 | 0.14 | 0.12 |
| Ex. (V-8) | Com. (P-170) | 5.7 | 7.0 | 500 | 7.1 | 156.8 | 0.14 | 0.12 |
| Ex. (V-9) | Com. (P-173) | 5.7 | 6.9 | 500 | 7.3 | 156.5 | 0.14 | 0.12 |
| Ex. (V-10) | Com. (P-179) | 5.7 | 6.6 | 500 | 7.6 | 161.1 | 0.14 | 0.12 |
| Ex. (V-11) | Com. (P-185) | 5.8 | 7.0 | 500 | 7.2 | 156.2 | 0.14 | 0.12 |
| Ex. (V-12) | Com. (P-187) | 5.8 | 7.0 | 500 | 7.2 | 157.9 | 0.14 | 0.12 |

It can be seen from the results in Tables 5 to 7 above, that the OLEDs employing the inventive compounds as emission-auxiliary layer material showed predominantly improved luminescent efficiency and lifespan, compared to the OLEDs employing comparative compounds II-1 to IV-2 as emission-auxiliary layer material.

Specifically, it can be confirmed that the OLEDs employing comparative compounds 6 and 7, and the present invention compounds as an emission-auxiliary layer material showed improved luminescent efficiency and lifespan, compared to the OLEDs not having an auxiliary emission layer, especially, the OLEDs using the present invention compounds showed predominantly improved efficiency and long life span.

This is believed because the structure having additional aromatic ring fused with two heterocyclic rings(dibenzofuran or dibenzothiophene) core acts as main factor to improve the performance of OLED resulting in a charge balance and an effective electron blocking abilities.

Further, comparing the present invention compounds having both dibenzofuran and dibenzothiophene, or two dibenzothiophenes with comparative compounds 6 and 7 having two dibenzofurans as a core, it is confirmed that HOMO energy level of compounds having dibenzothiophene instead of dibenzofuran is deeper, and thus a hole can more smoothly transfer to an light emitting layer and exiton can be generated more easily in the light emitting layer resulting in improved efficiency.

Overall, it can be confirmed that a band gap, electrical properties and interfacial properties are largly varied depending on introducing dibenzothiophene into two heterocyclic rings(dibenzofuran or dibenzothiophene) and additionally fusing an aromatic ring, and this acts as main factor to improve the performance of OLED.

Further, the inventive compounds can be employed as both a hole transport layer material and an emission-auxiliary layer material, even though the properties of OLEDs employing the iventive compounds as only any one of a hole transport layer material or an emission-auxiliary layer material are described above.

It can be confirmed from the results in Tables 7 and 8 above, that the examples V-1 to V-12 of the present invention employing the inventive compound P-185 as a hole transport layer material and the inventive compounds as an emission-auxiliary layer material showed predominantly improved luminescent efficiency and lifespan, compared to the examples IV-1 to IV-51 employing NPB as a hole transport layer material and the inventive compounds as an emission-auxiliary layer material.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formulas 3 to 11 below:

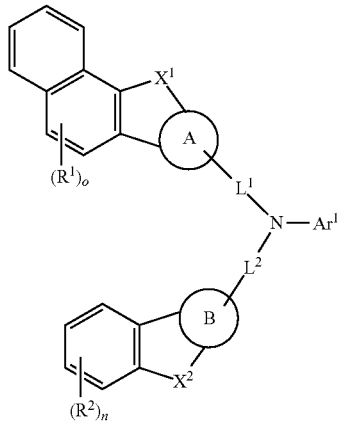

<Formula 3>

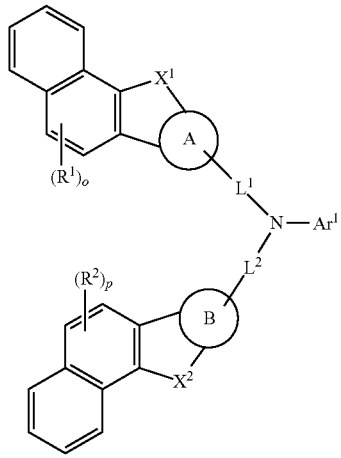

<Formula 4>

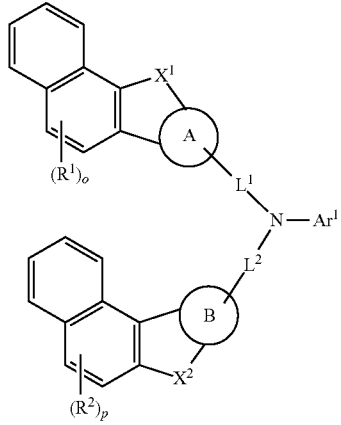

<Formula 5>

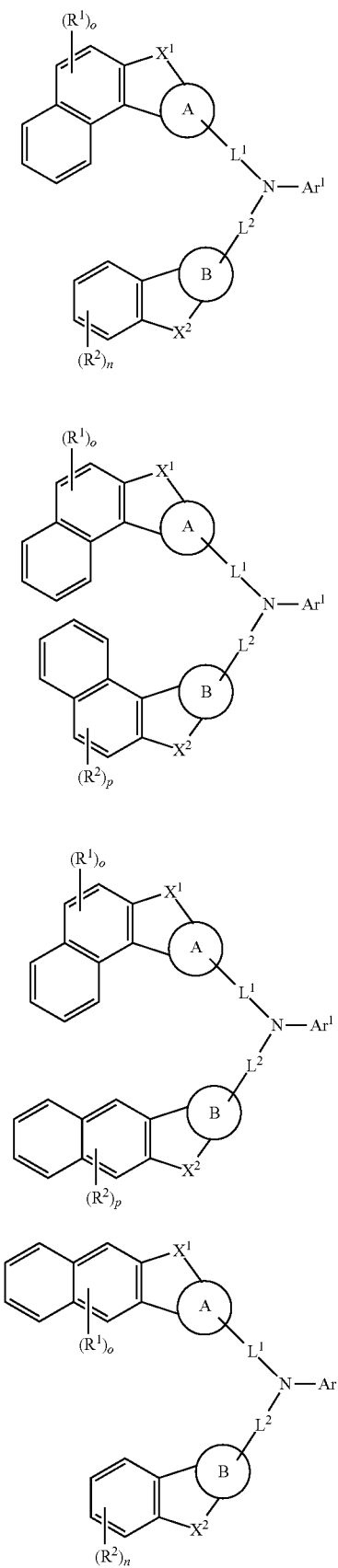

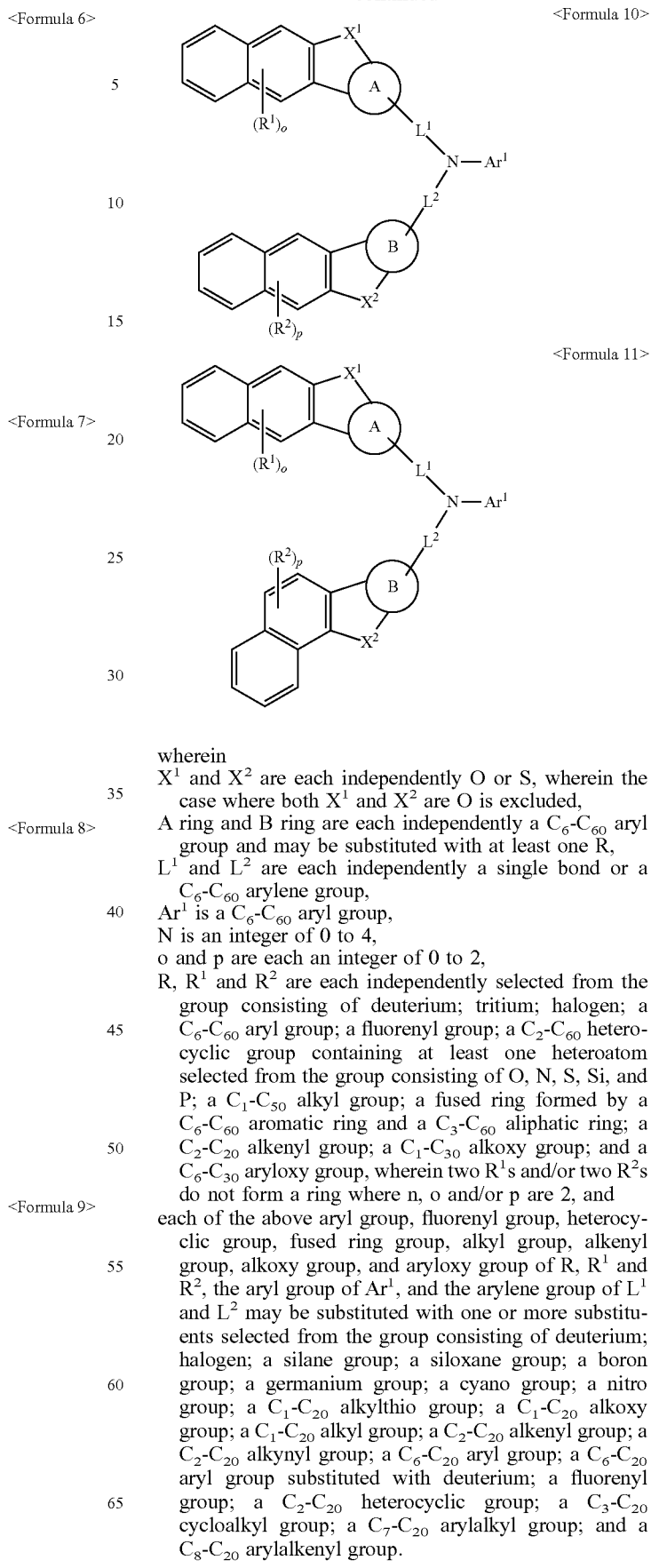

wherein
$X^1$ and $X^2$ are each independently O or S, wherein the case where both $X^1$ and $X^2$ are O is excluded,
A ring and B ring are each independently a $C_6$-$C_{60}$ aryl group and may be substituted with at least one R,
$L^1$ and $L^2$ are each independently a single bond or a $C_6$-$C_{60}$ arylene group,
$Ar^1$ is a $C_6$-$C_{60}$ aryl group,
N is an integer of 0 to 4,
o and p are each an integer of 0 to 2,
R, $R^1$ and $R^2$ are each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a $C_1$-$C_{50}$ alkyl group; a fused ring formed by a $C_6$-$C_{60}$ aromatic ring and a $C_3$-$C_{60}$ aliphatic ring; a $C_2$-$C_{20}$ alkenyl group; a $C_1$-$C_{30}$ alkoxy group; and a $C_6$-$C_{30}$ aryloxy group, wherein two $R^1$s and/or two $R^2$s do not form a ring where n, o and/or p are 2, and
each of the above aryl group, fluorenyl group, heterocyclic group, fused ring group, alkyl group, alkenyl group, alkoxy group, and aryloxy group of R, $R^1$ and $R^2$, the aryl group of $Ar^1$, and the arylene group of $L^1$ and $L^2$ may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group.

2. A compound selected from the group consisting of one of the compounds below:
P-1
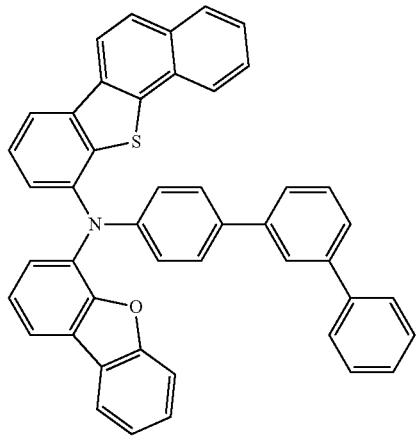
P-2
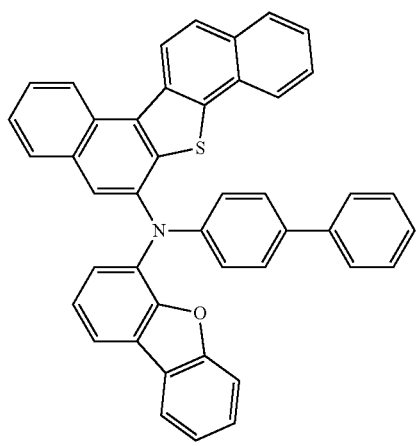
P-3
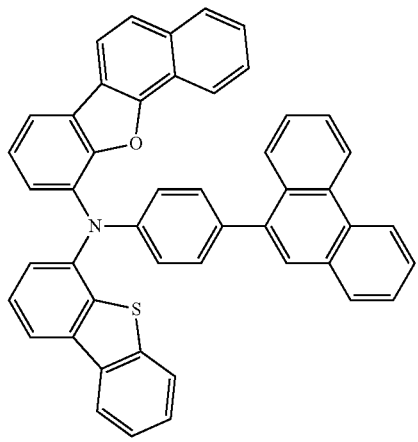
P-4
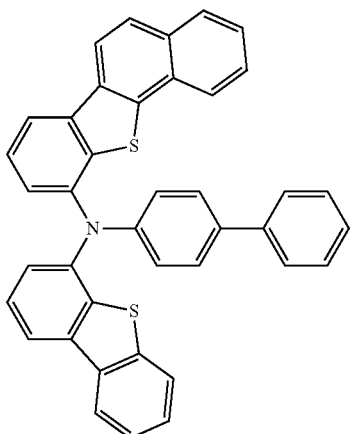
P-5
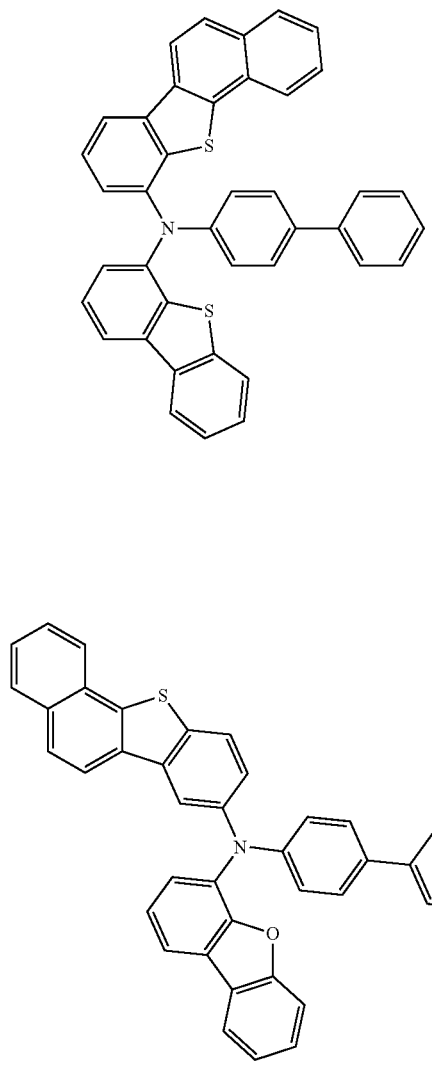
P-6
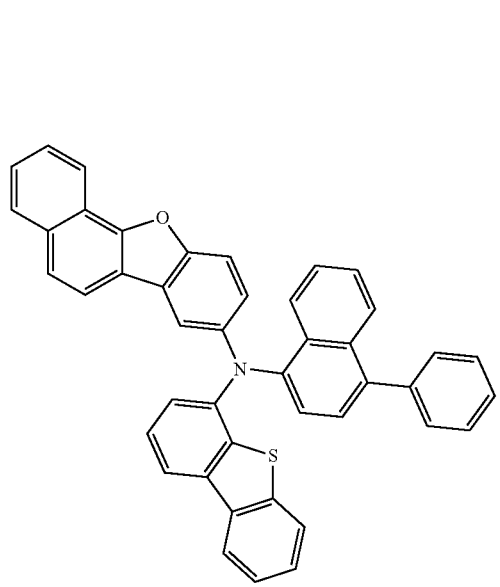

P-7
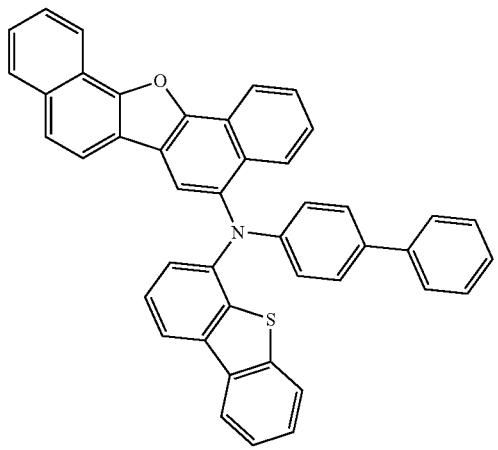
P-10
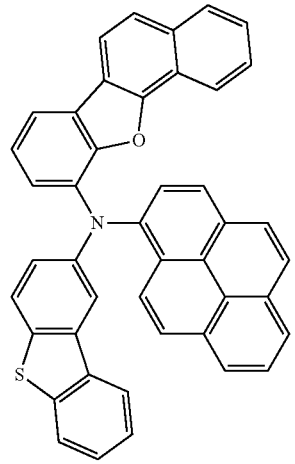
P-8
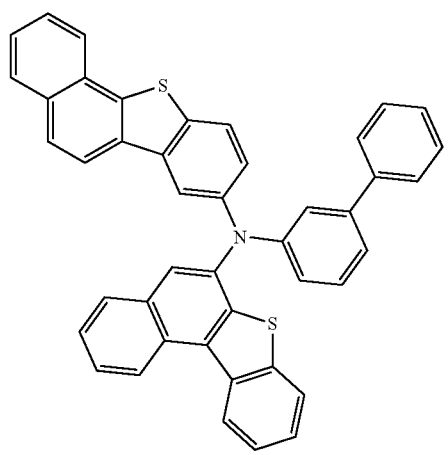
P-11
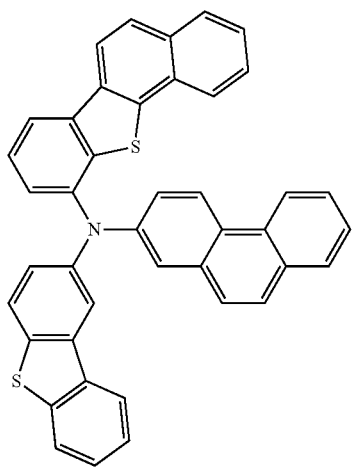
P-9
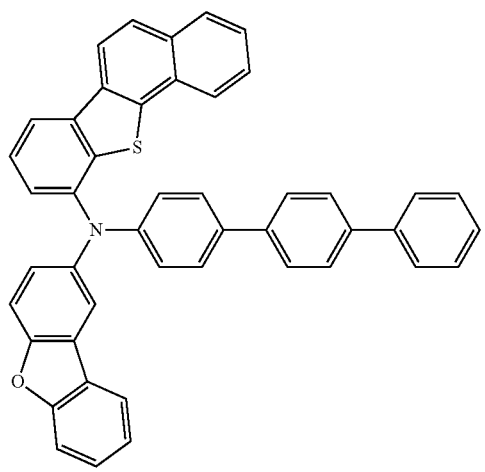
P-12
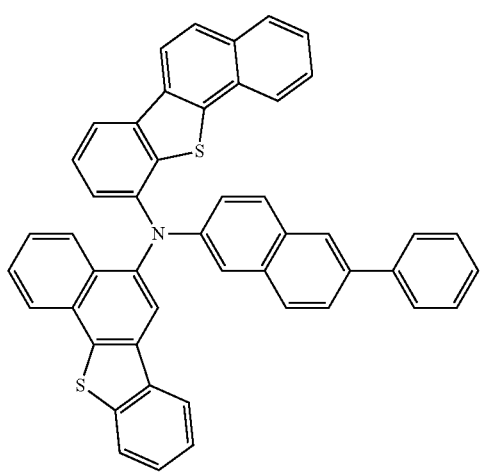

P-13
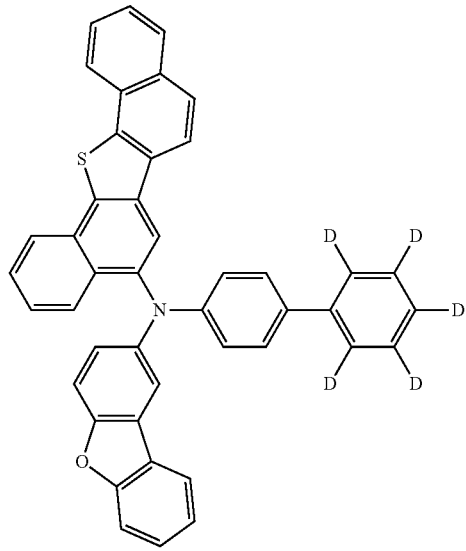
P-14
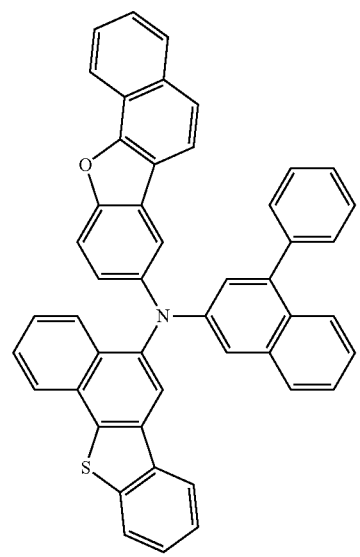
P-15
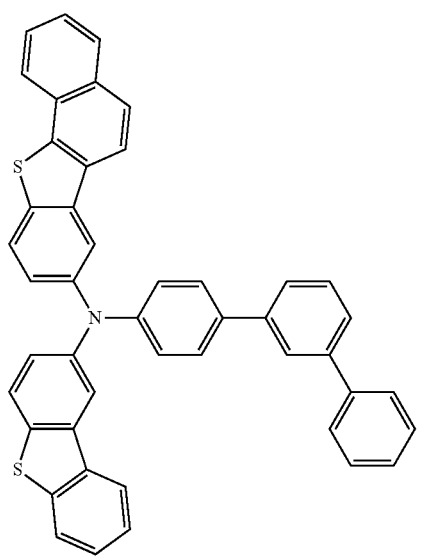
P-16
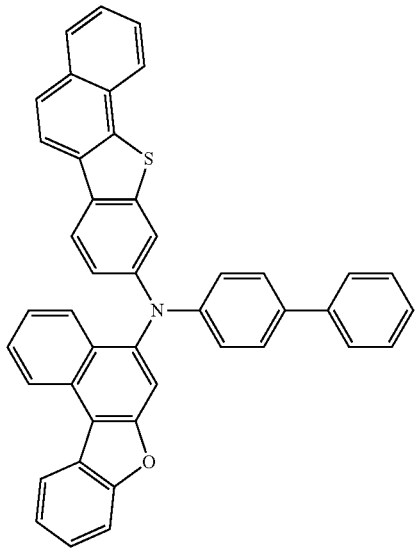
P-17
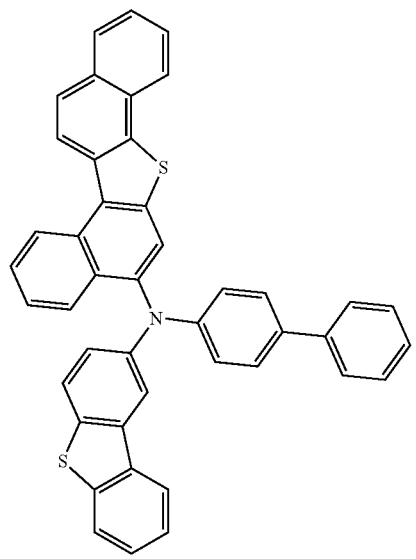
P-18
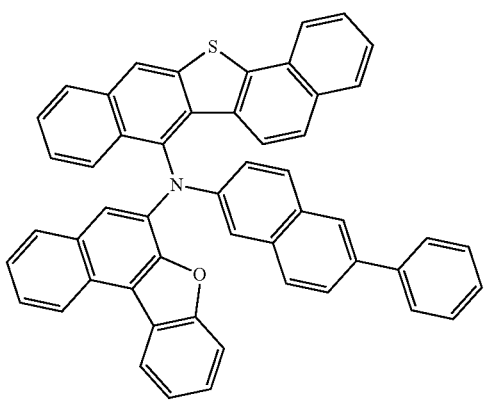

P-19
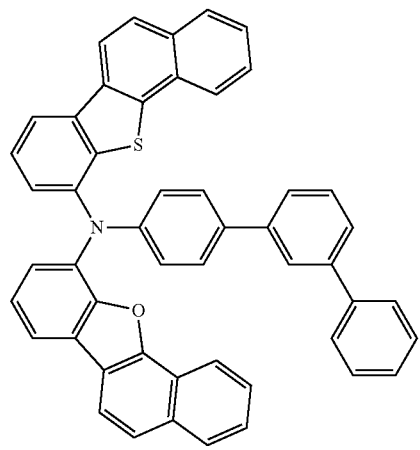
P-20
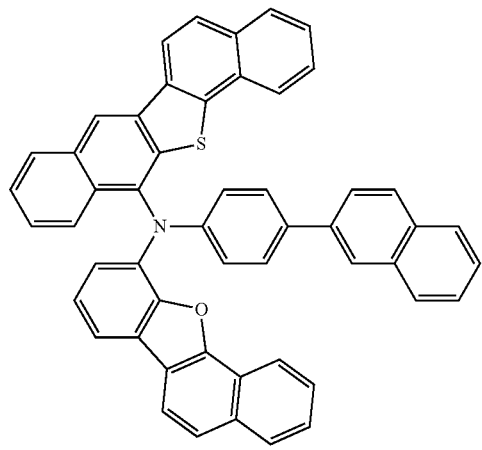
P-21
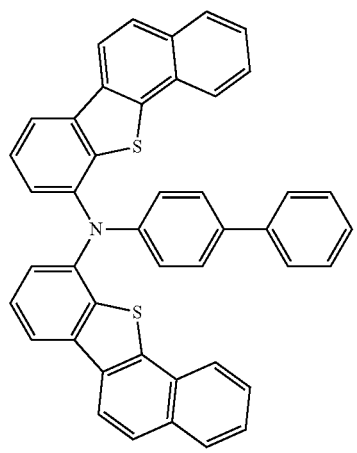
P-22
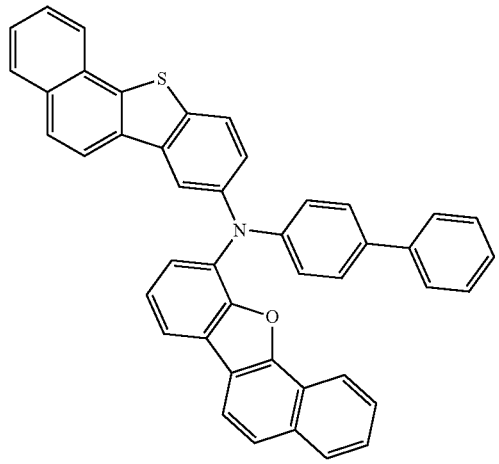
P-23
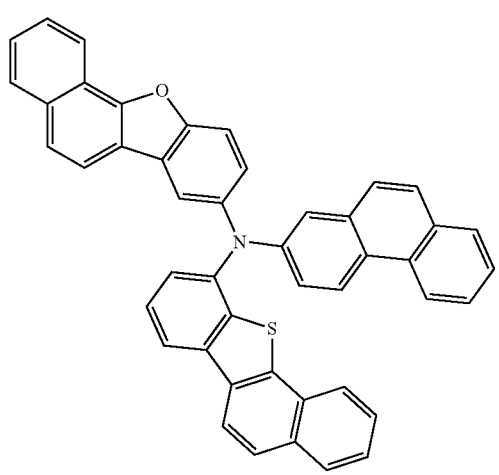
P-24
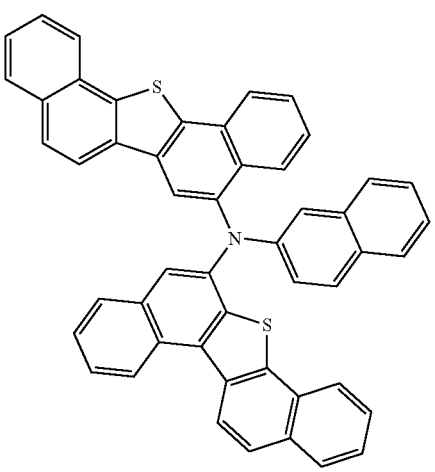

P-25
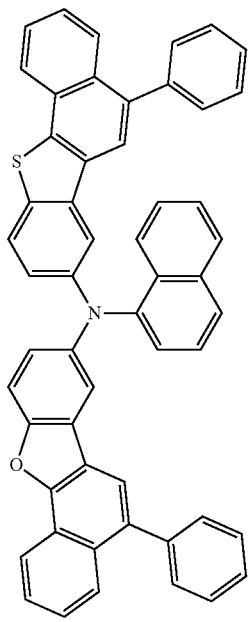
P-26
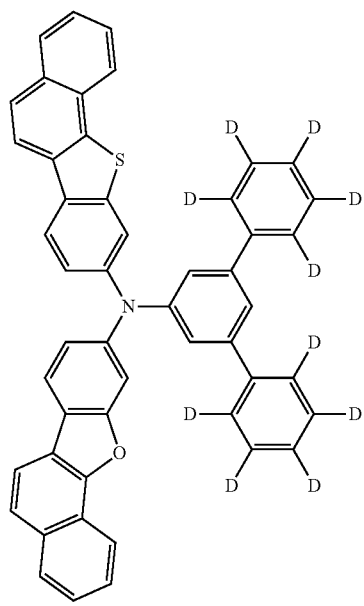
P-27
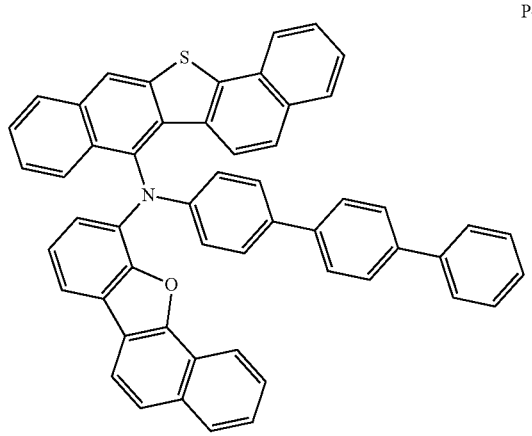
P-28
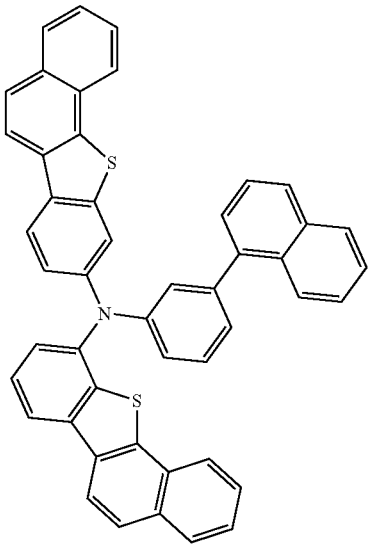
P-29
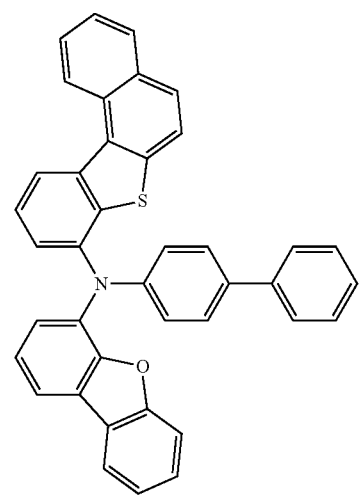
P-30
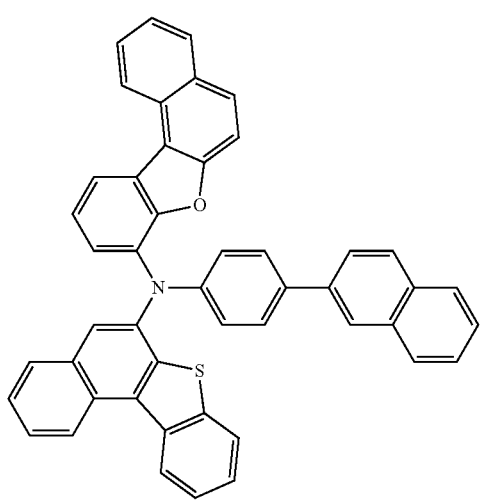

P-31
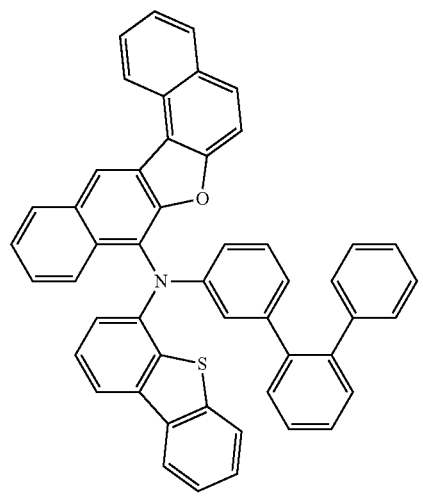
P-32
P-33
P-34
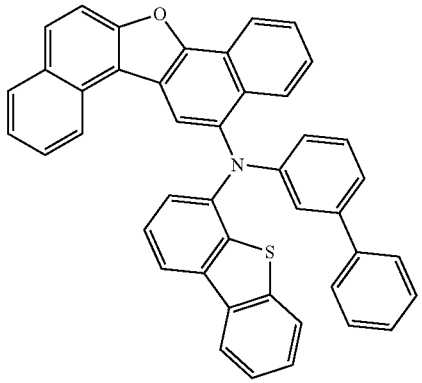
P-35
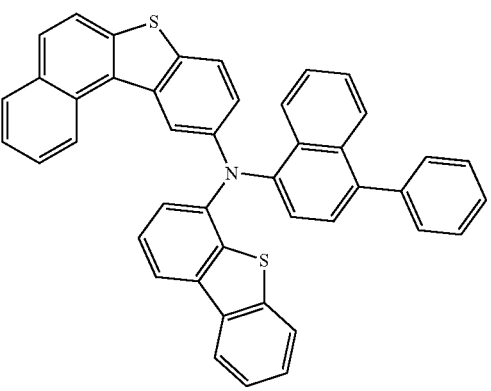
P-36
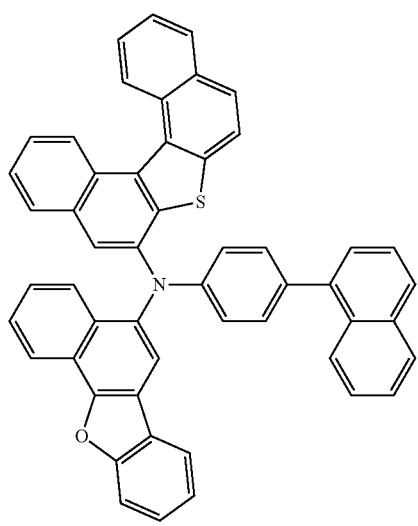

P-37
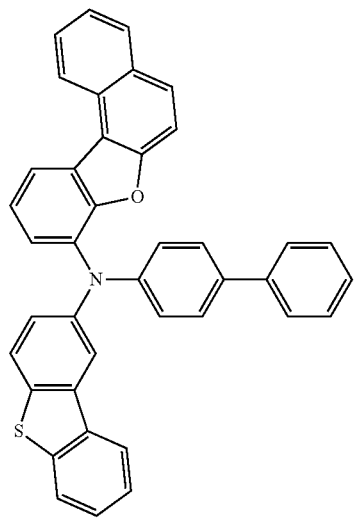
P-40
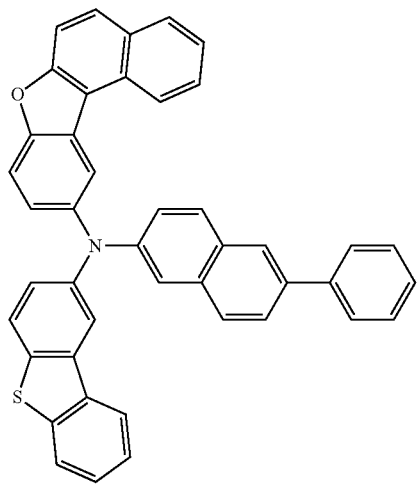
P-38
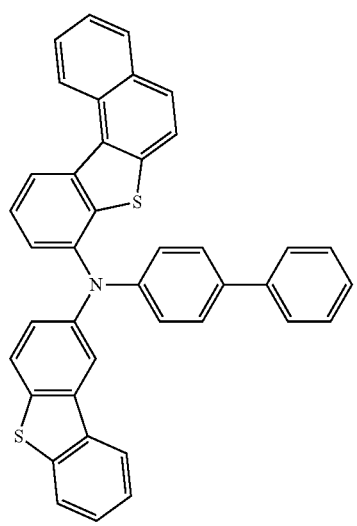
P-41
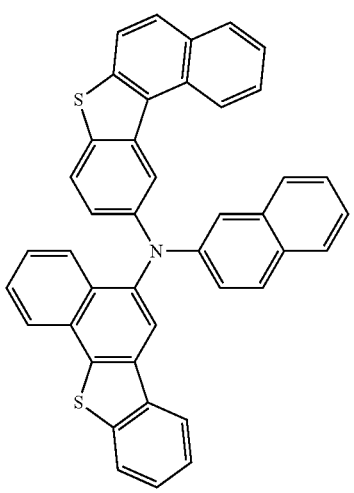
P-39
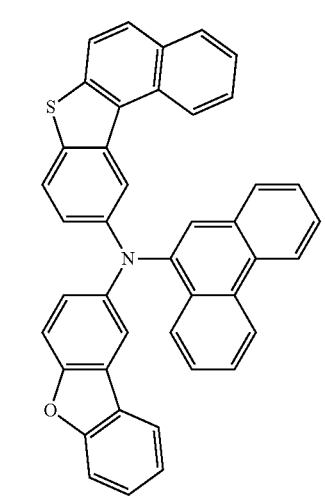
P-42
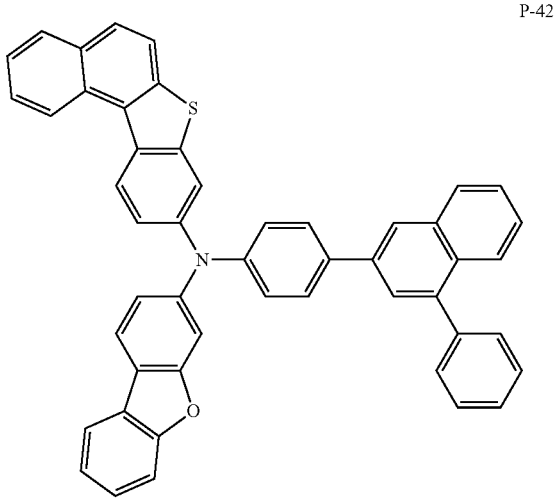

P-43
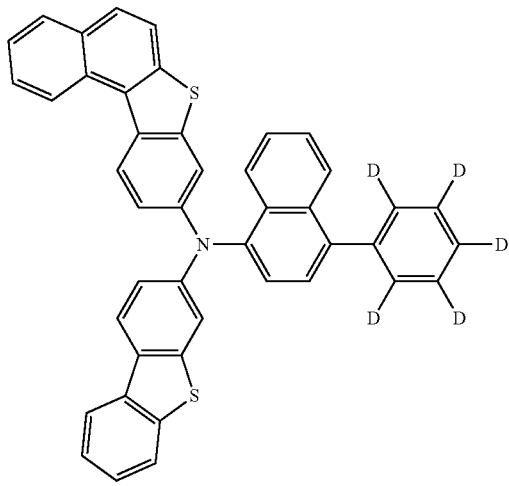
P-44
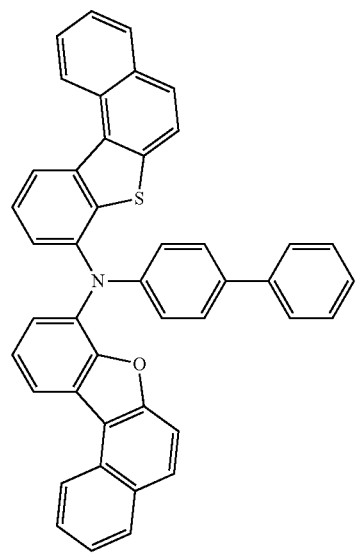
P-45
P-46
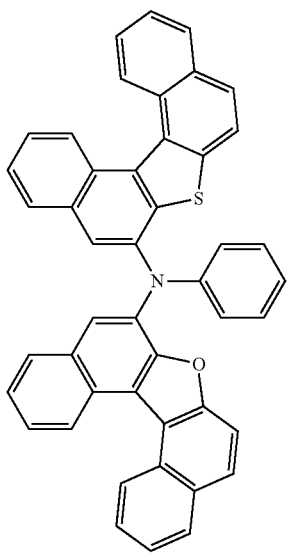
P-47
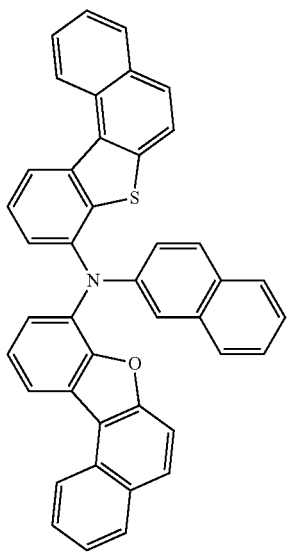
P-48
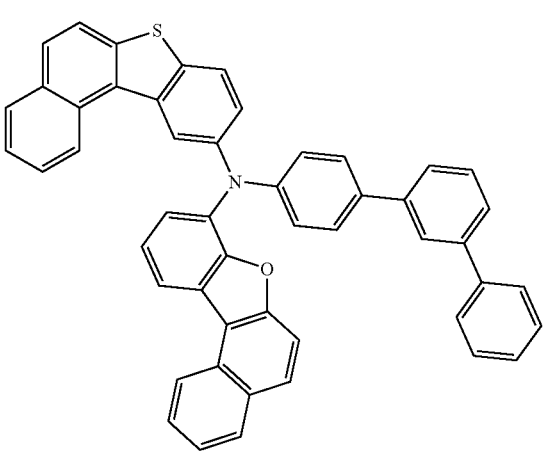

-continued
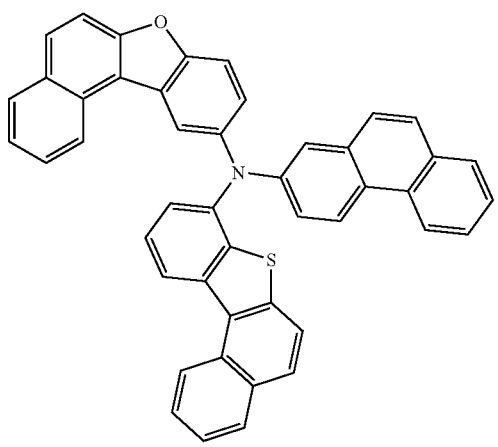
P-49
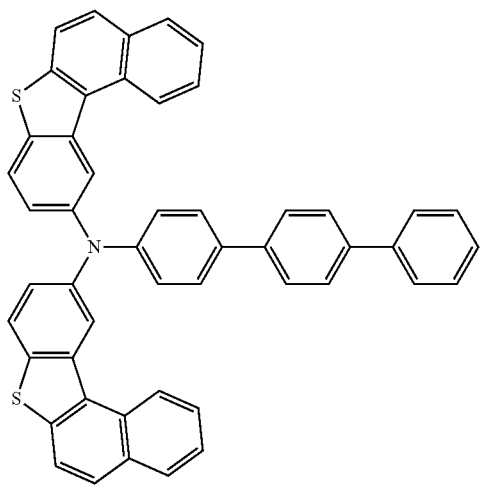
P-52
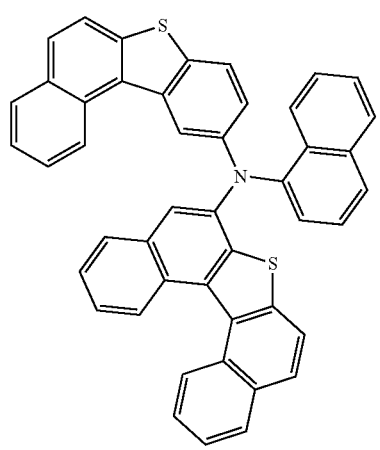
P-50
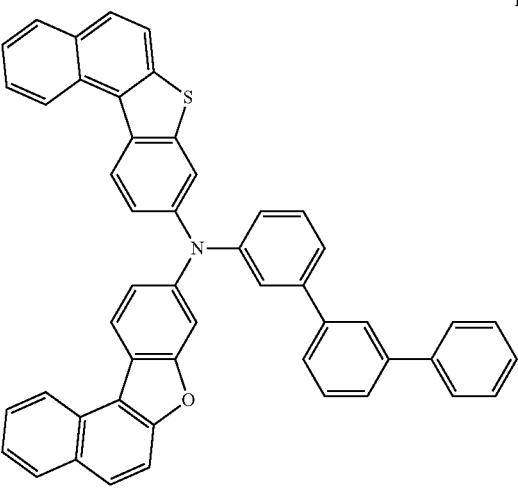
P-53
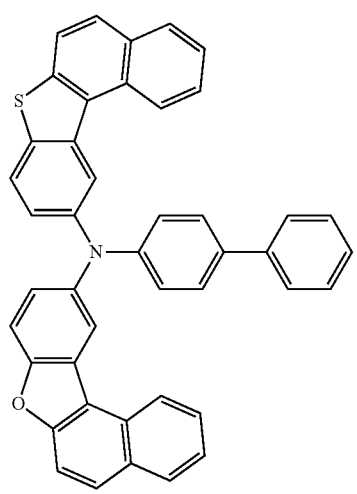
P-51
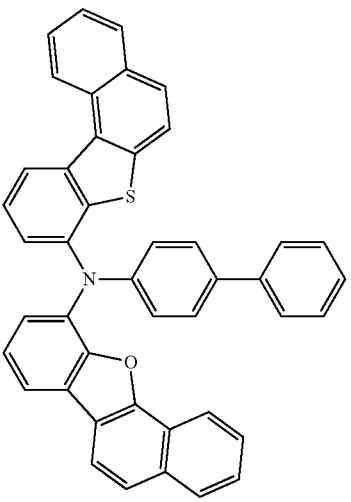
P-54

P-55
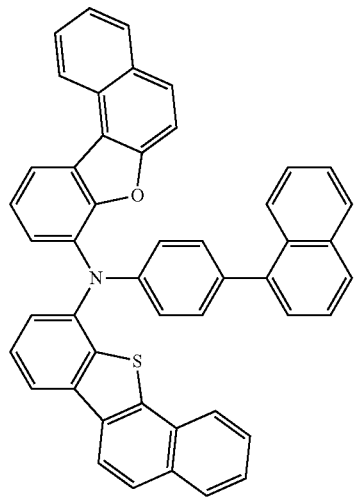
P-56
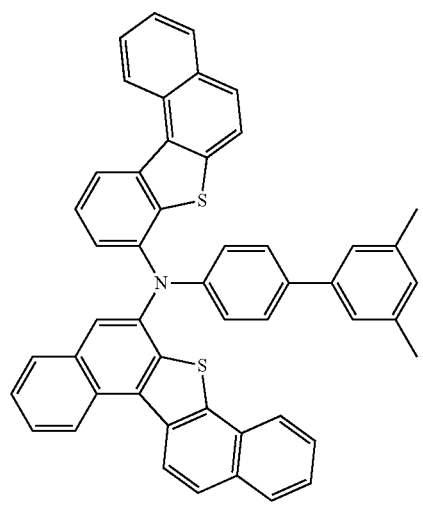
P-57
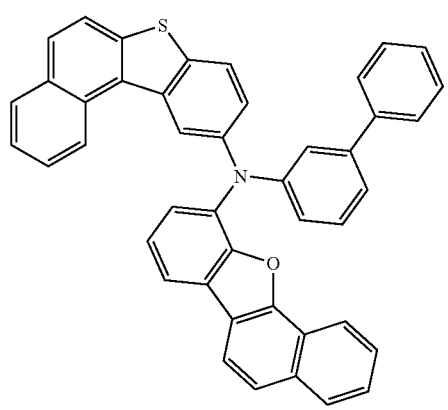
P-58
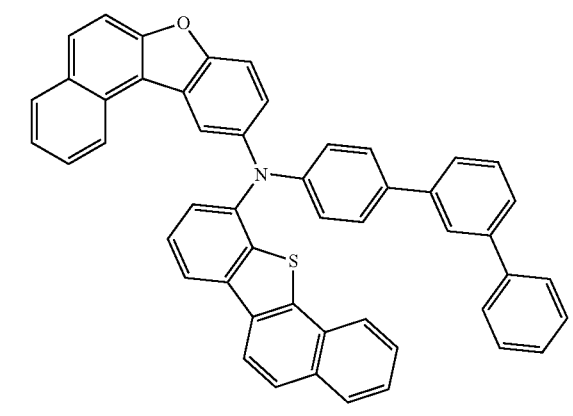
P-59
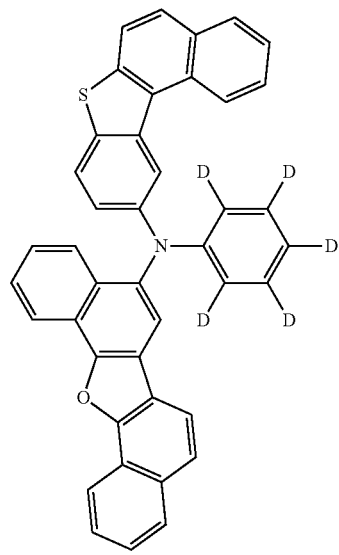
P-60
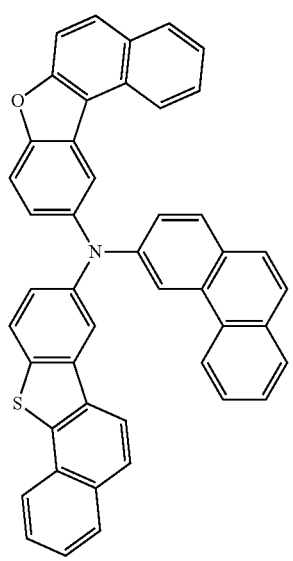

P-61
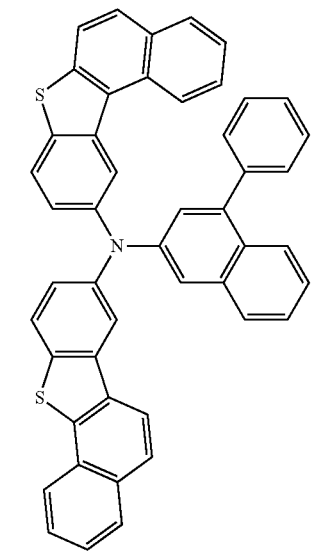
P-62
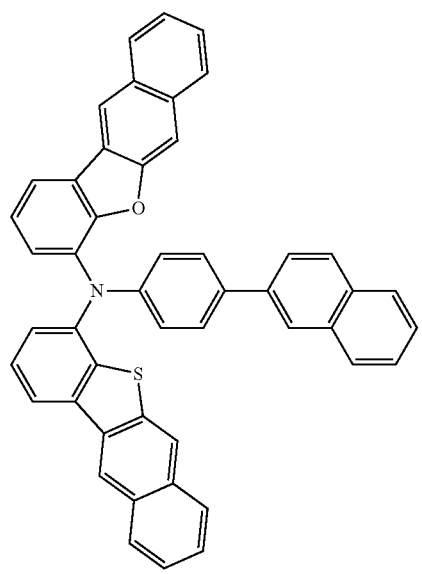
P-63
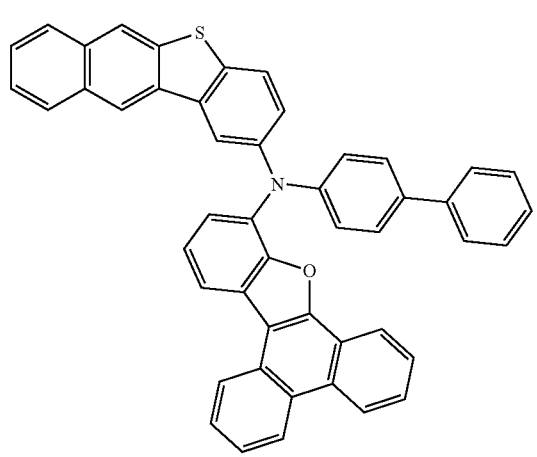
P-64
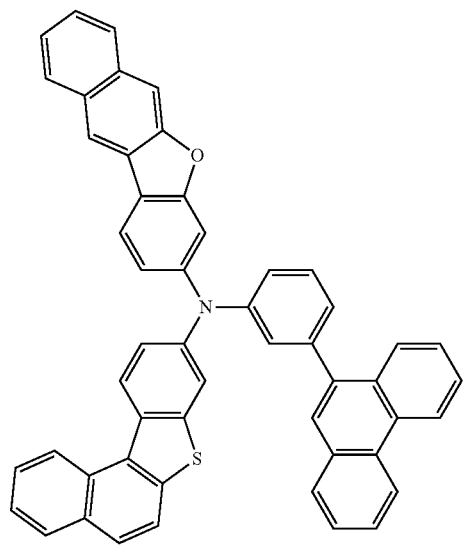
P-65
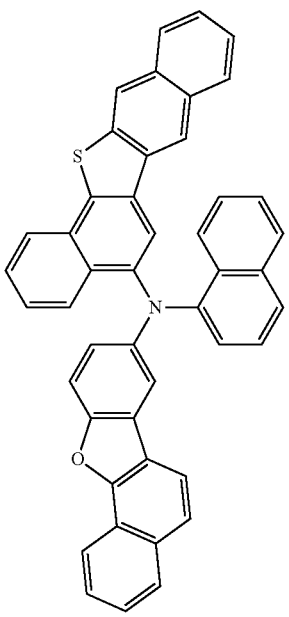

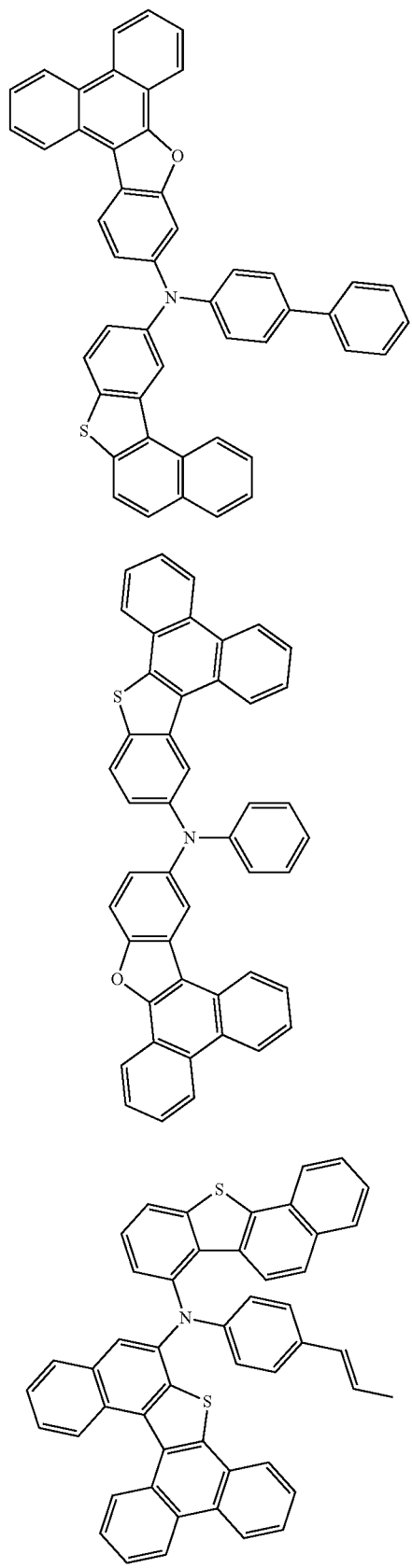
P-66
P-67
P-68
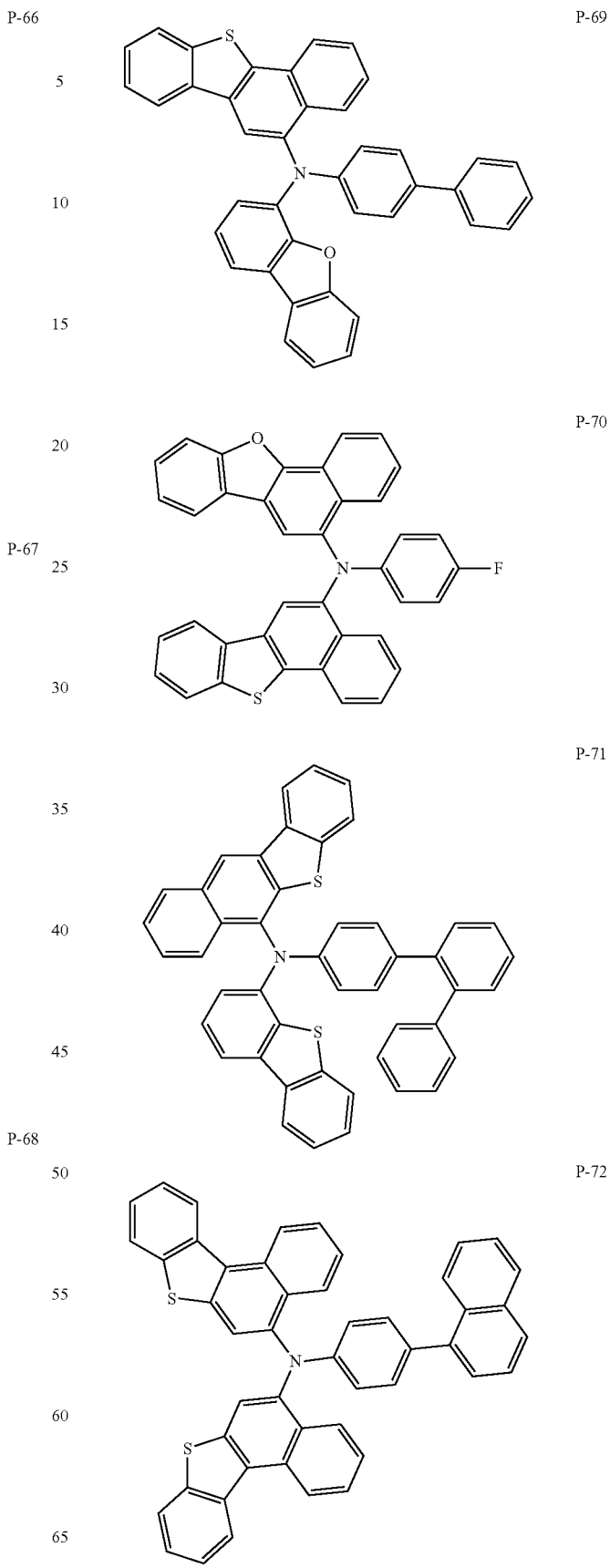
P-69
P-70
P-71
P-72

P-73
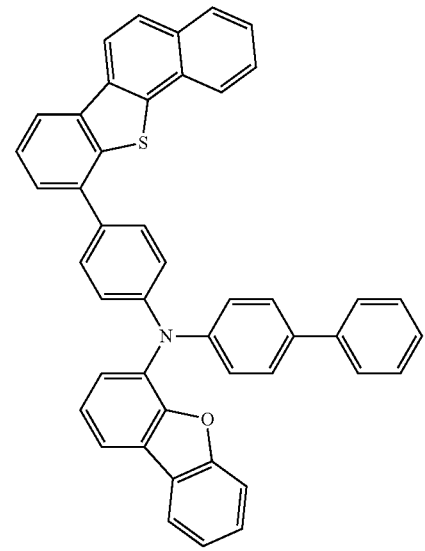
P-74
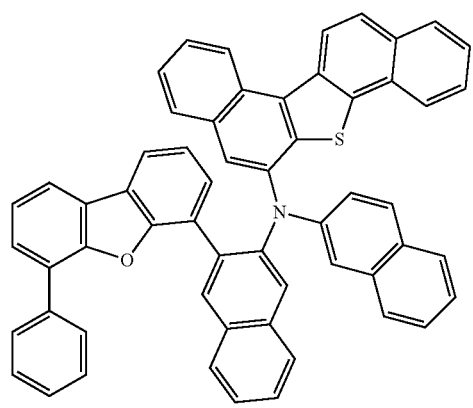
P-75
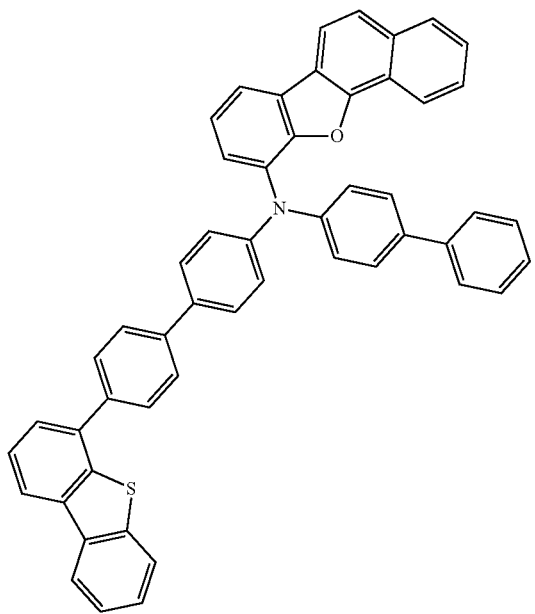
P-76
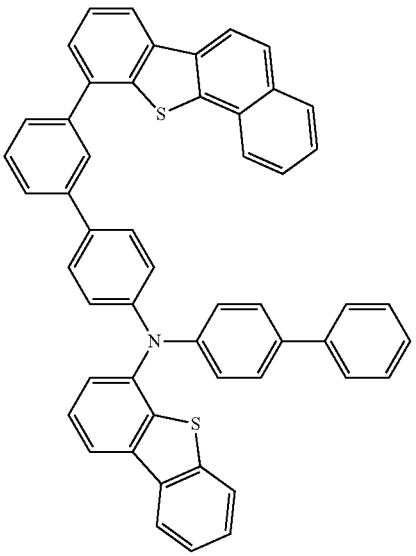
P-77
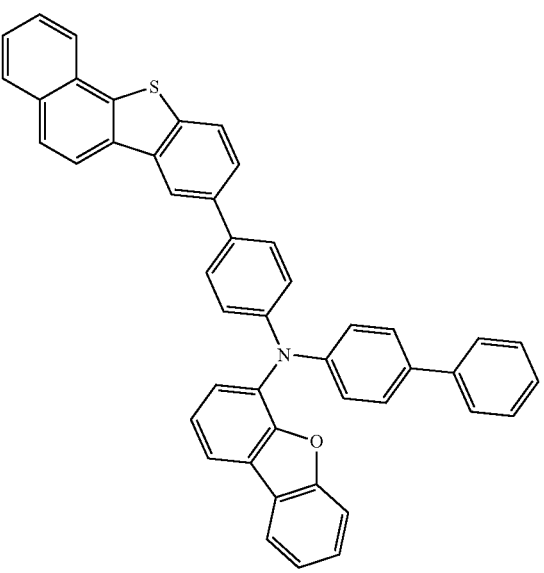

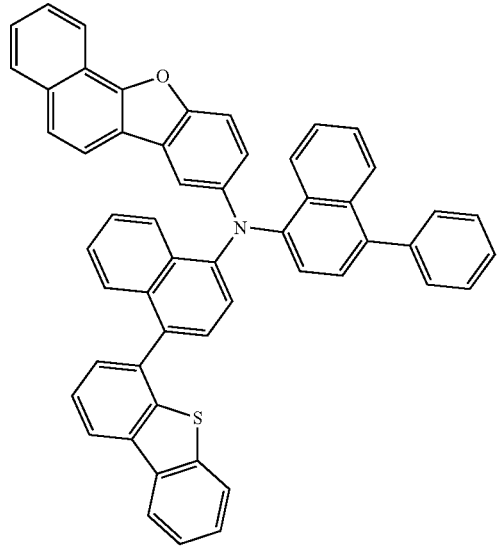
P-78
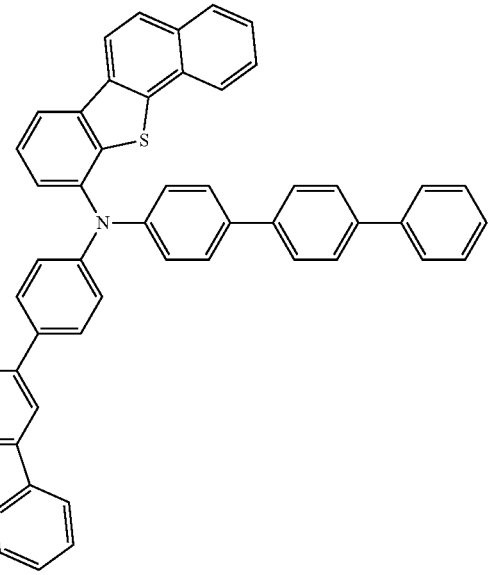
P-80
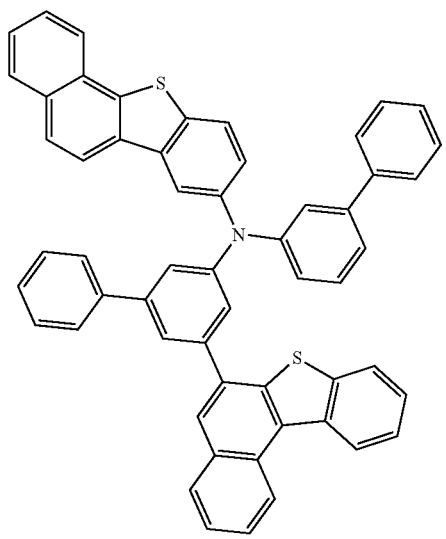
P-79
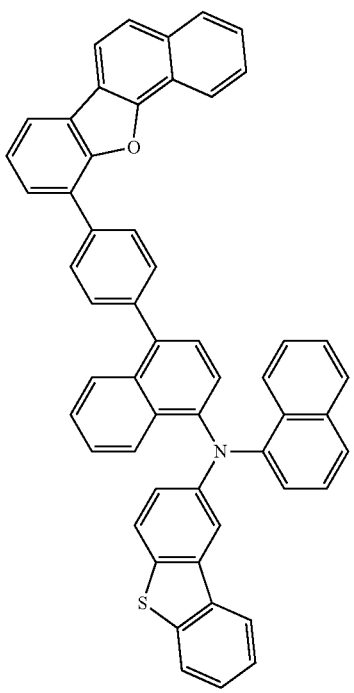
P-81

P-82
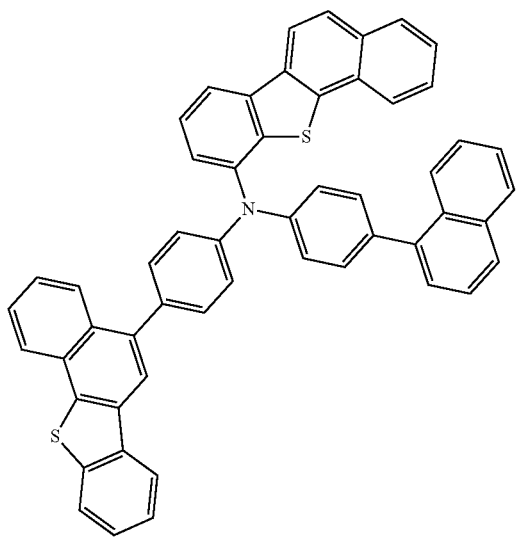
P-83
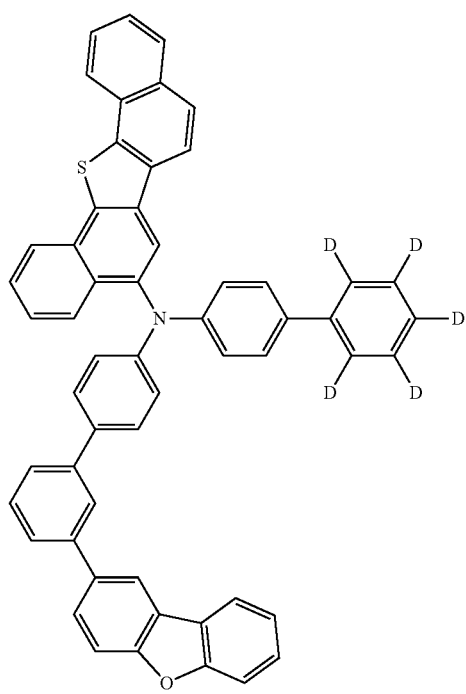
P-84
P-85
P-86
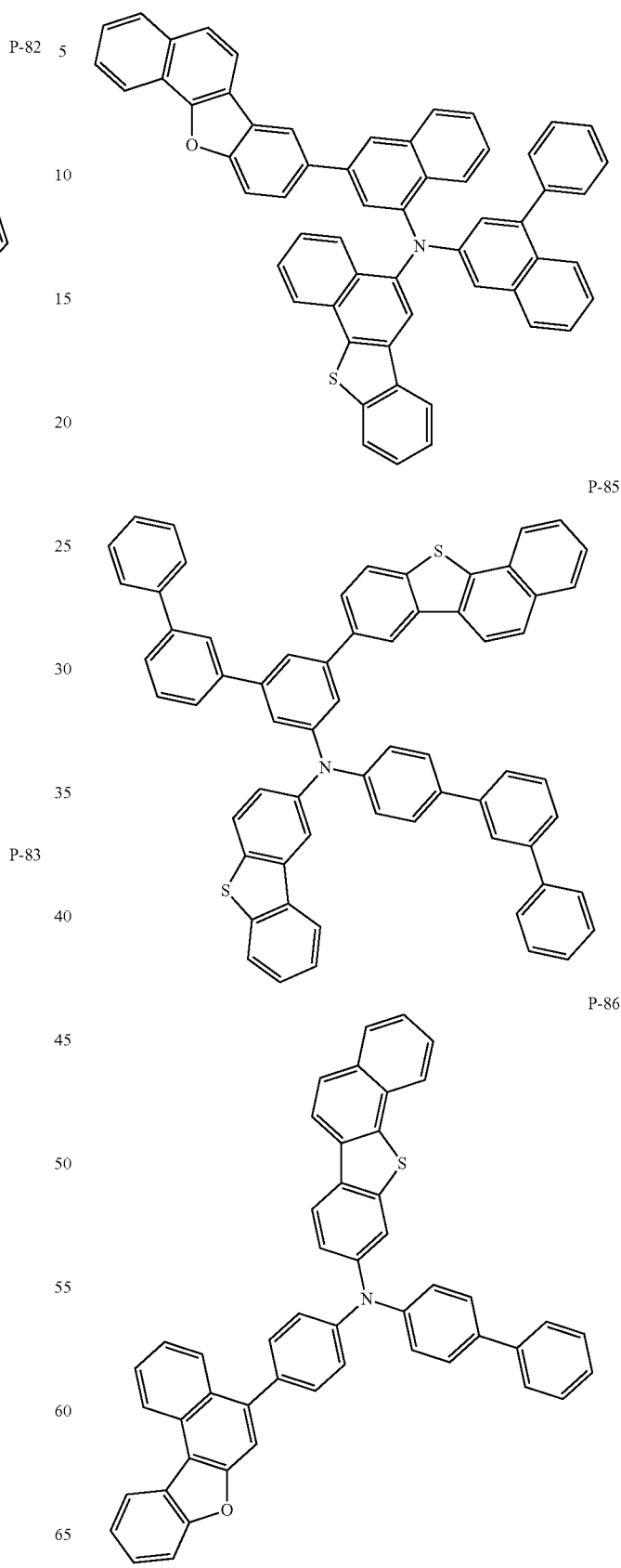

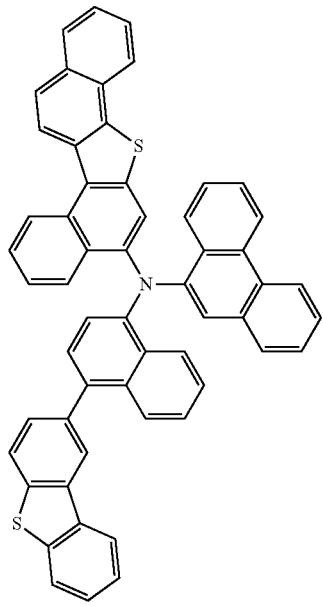
P-87
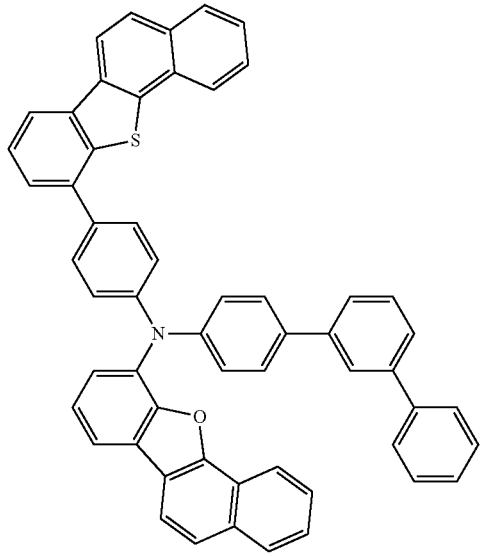
P-89
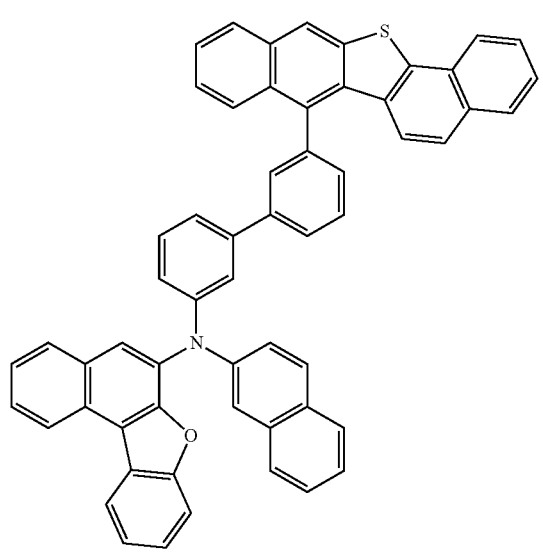
P-88
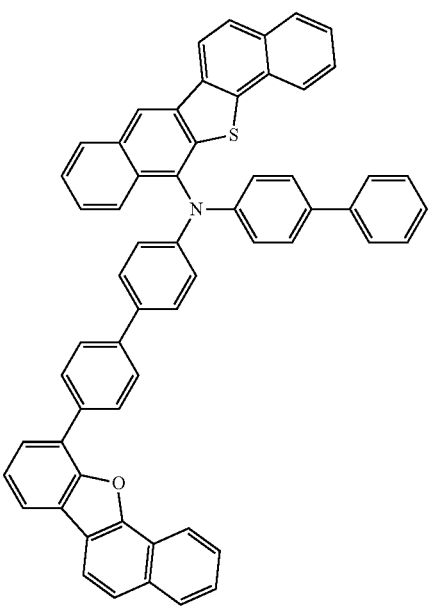
P-90

-continued
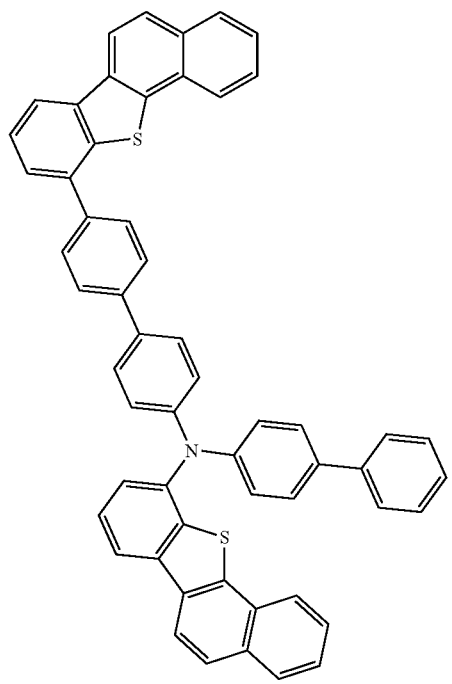
P-91
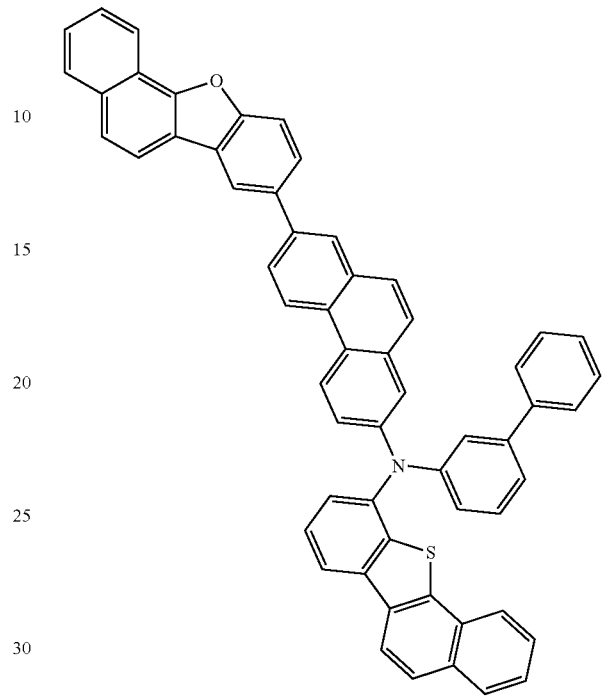
P-93
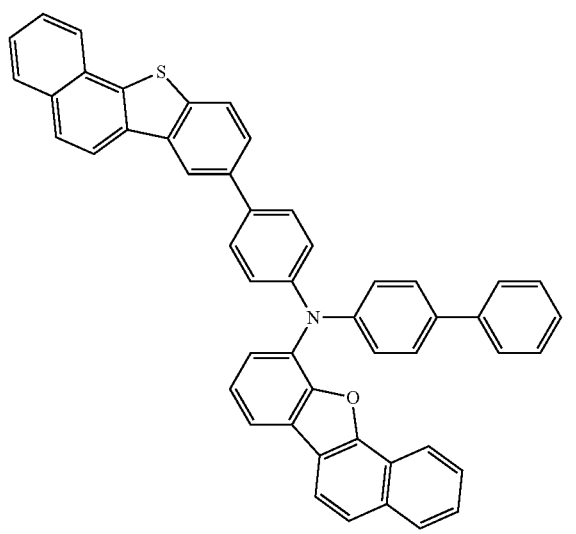
P-92
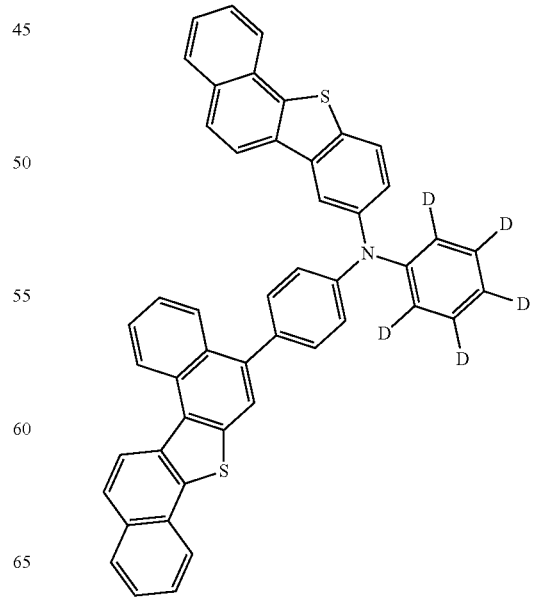
P-94

P-95
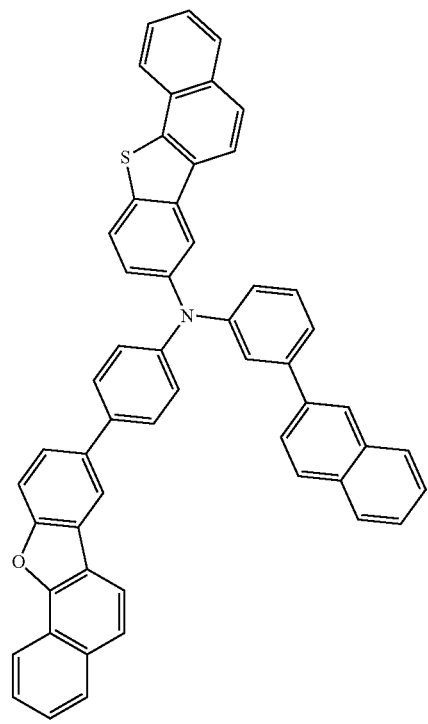
P-96
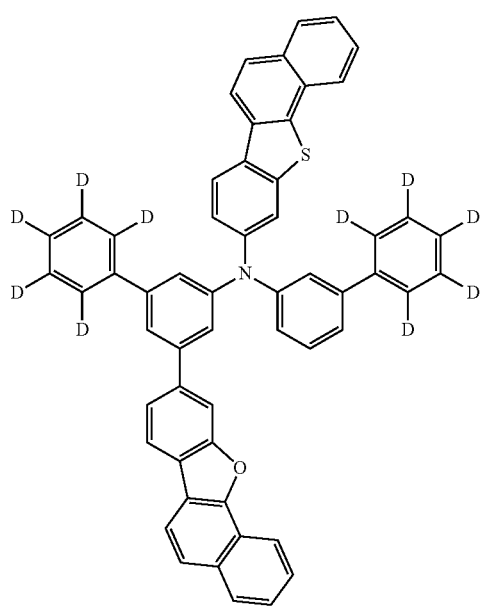
P-97
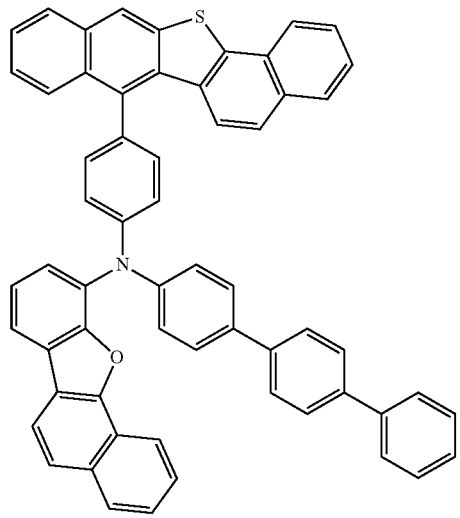
P-98
P-99
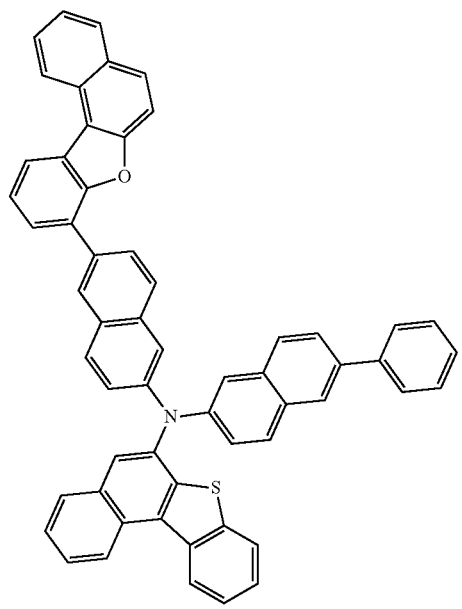

P-100
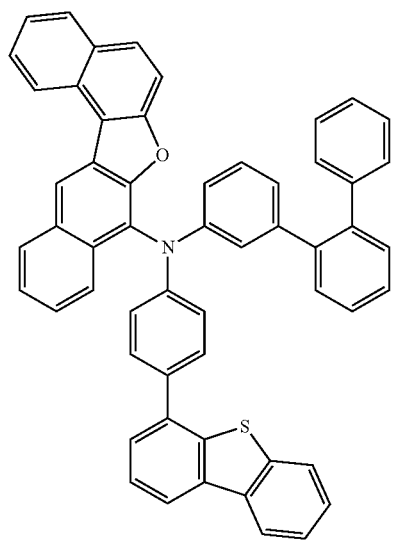
P-101
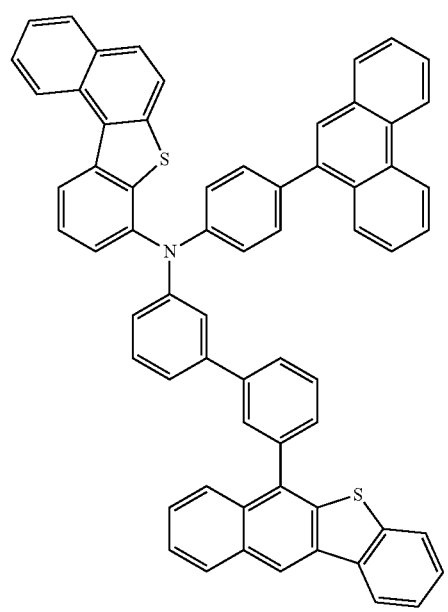
P-102
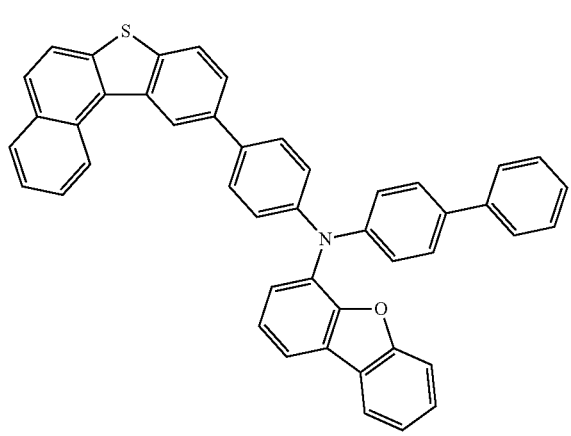
P-103
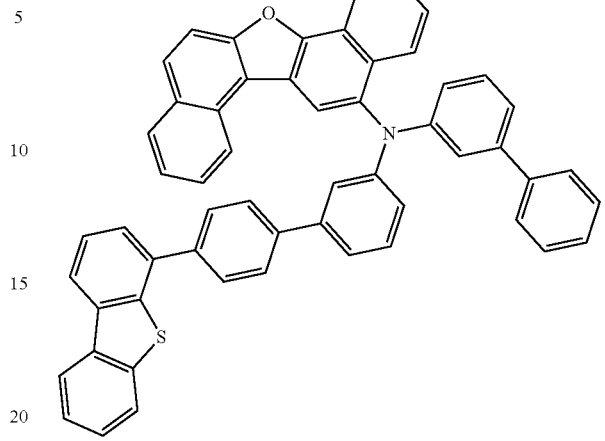
P-104
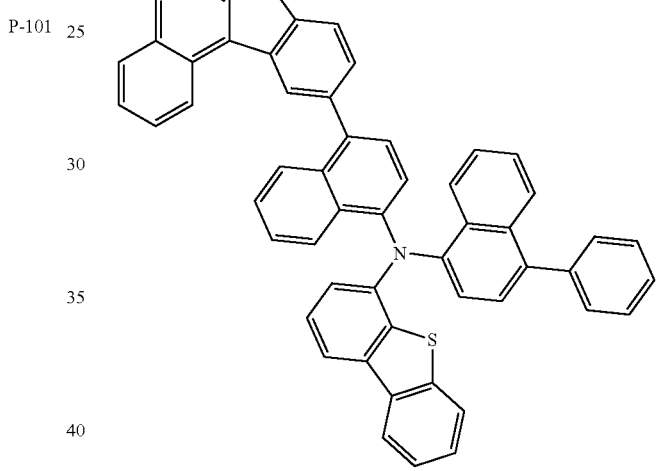
P-105
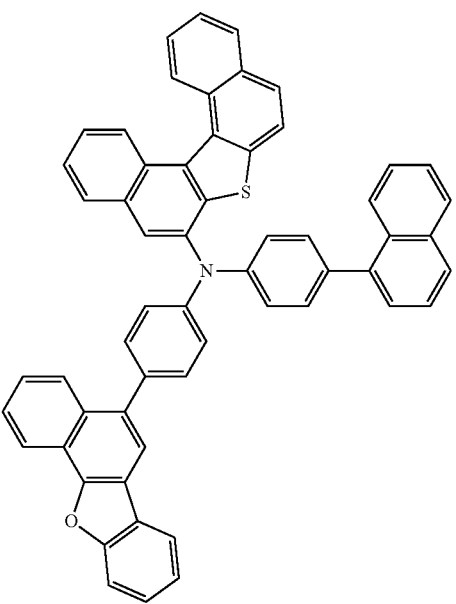

-continued
P-106
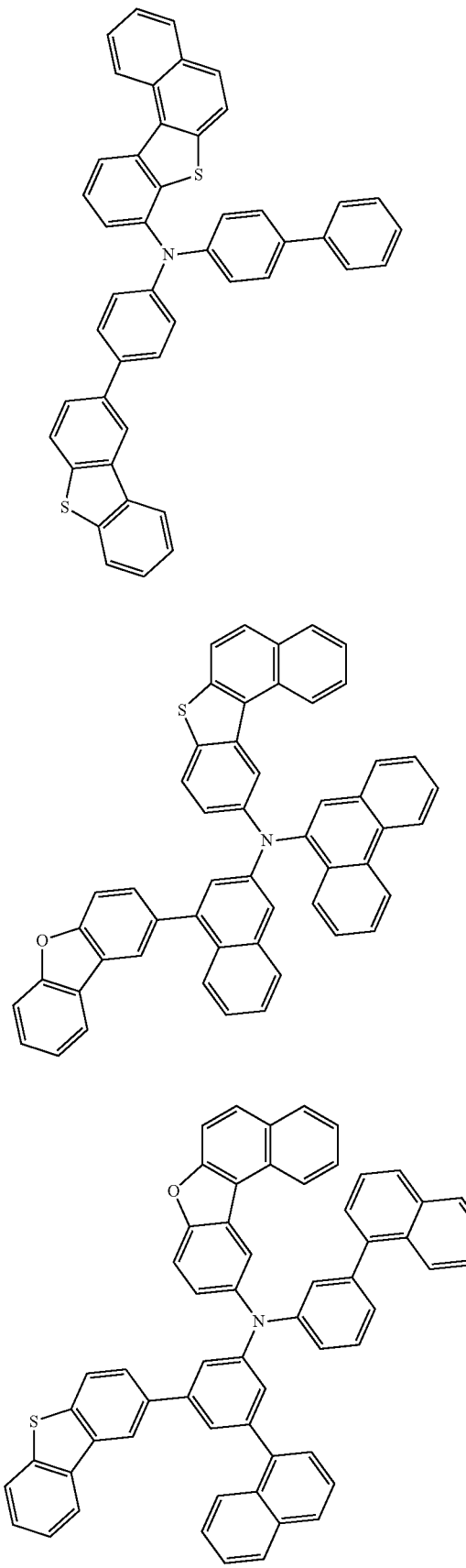
P-107
P-108
-continued
P-109
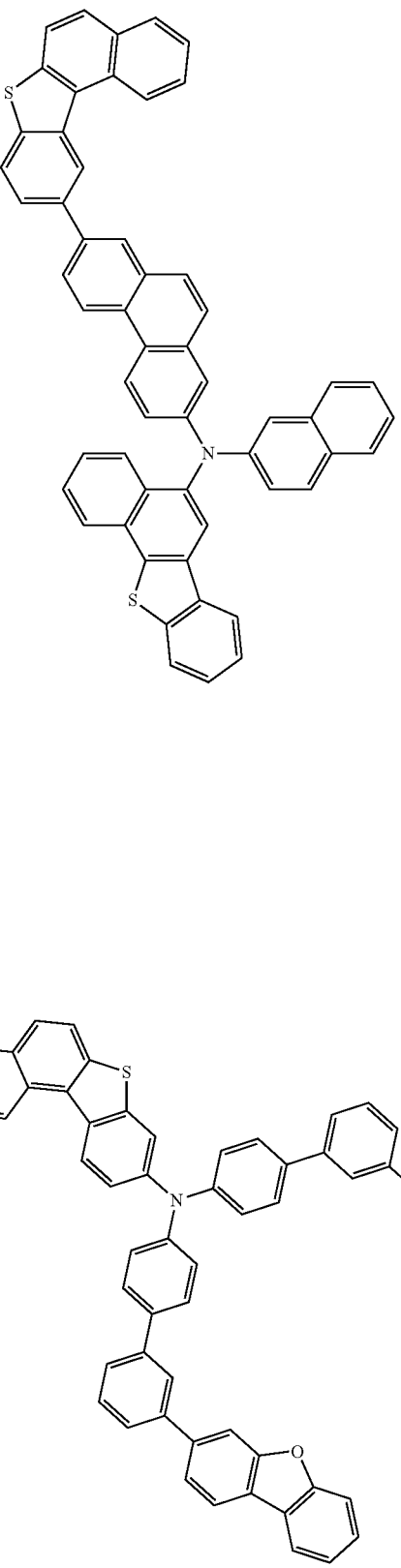
P-110

P-111
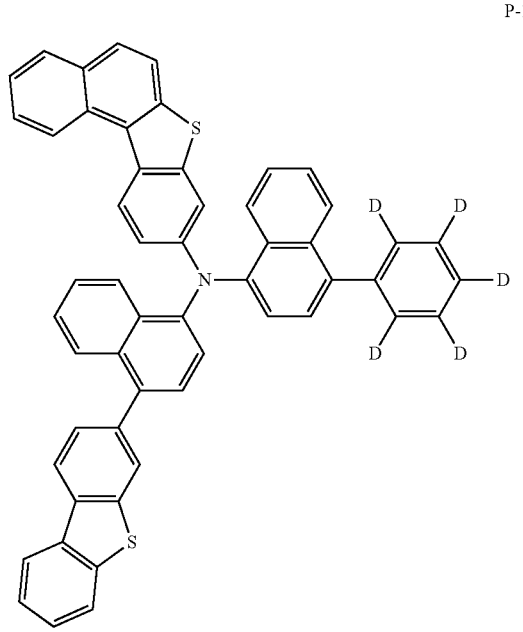
P-113
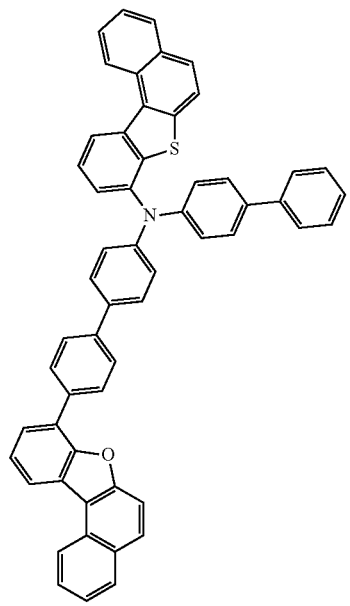
P-112
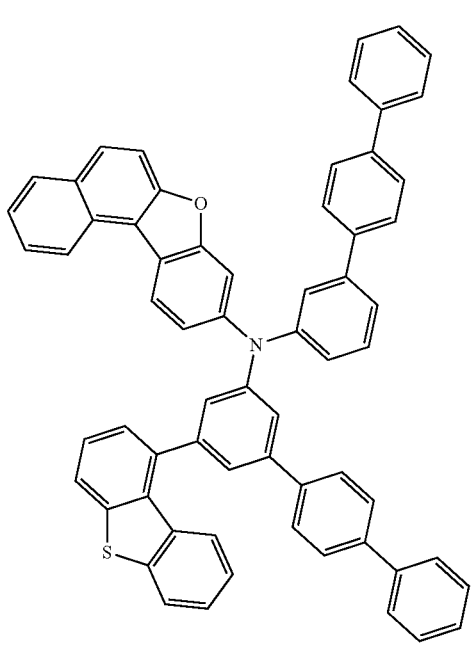
P-114
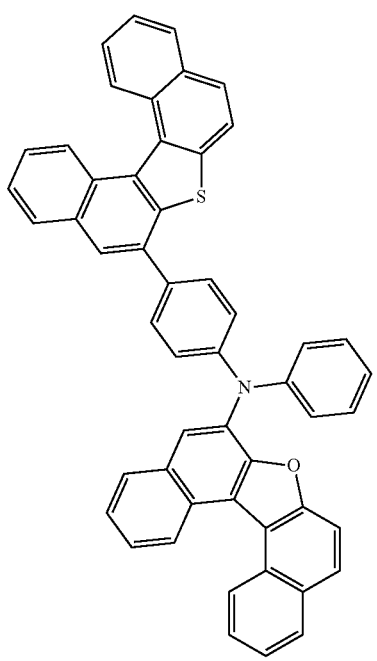

P-115
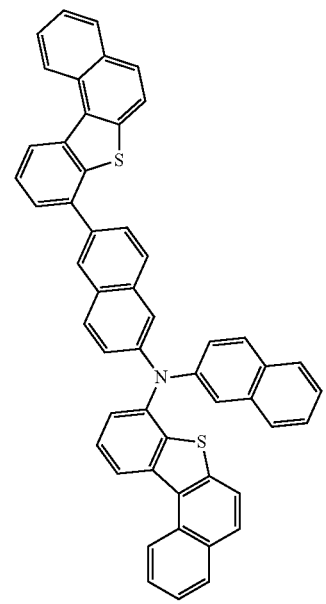
P-116
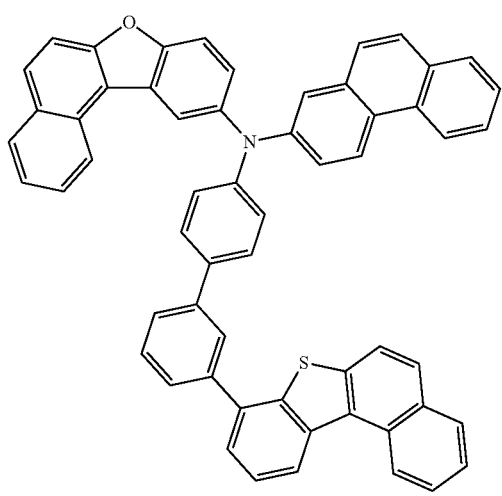
P-117
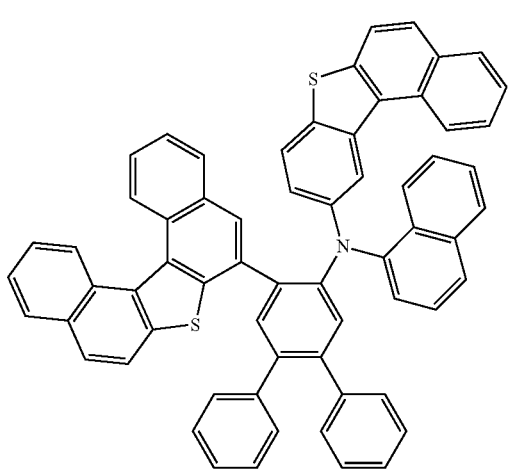
P-118
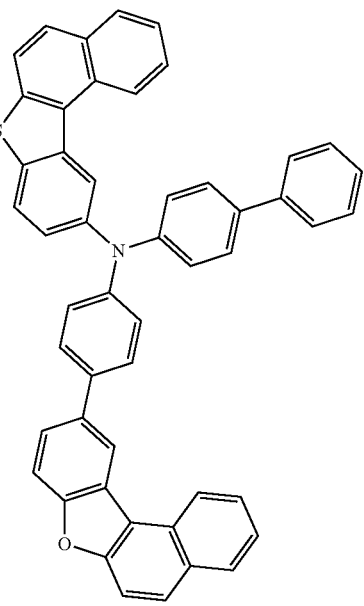
P-119
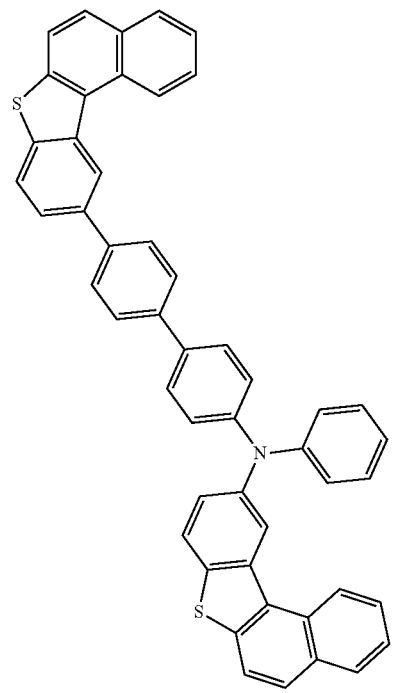

P-120
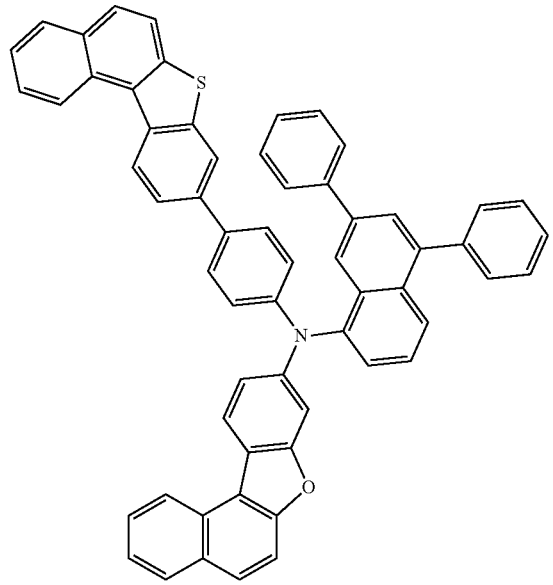
P-121
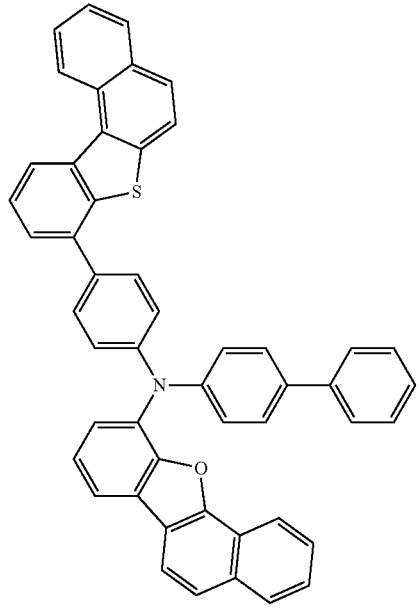
P-122
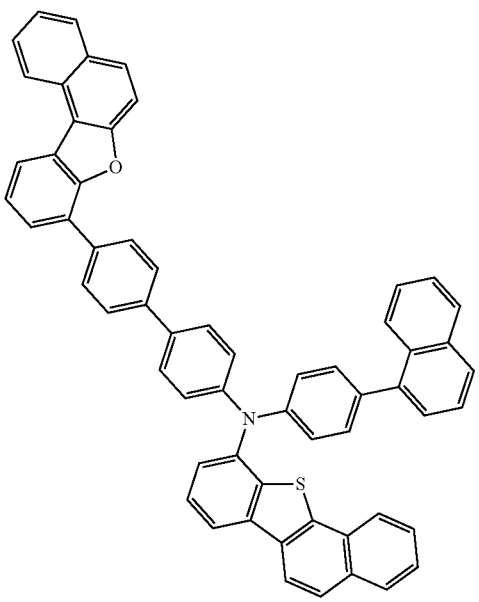
P-123
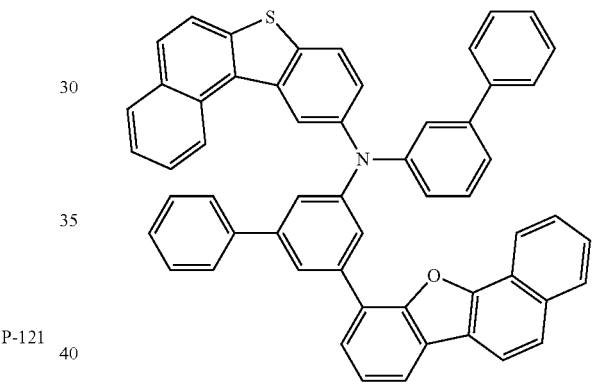
P-124
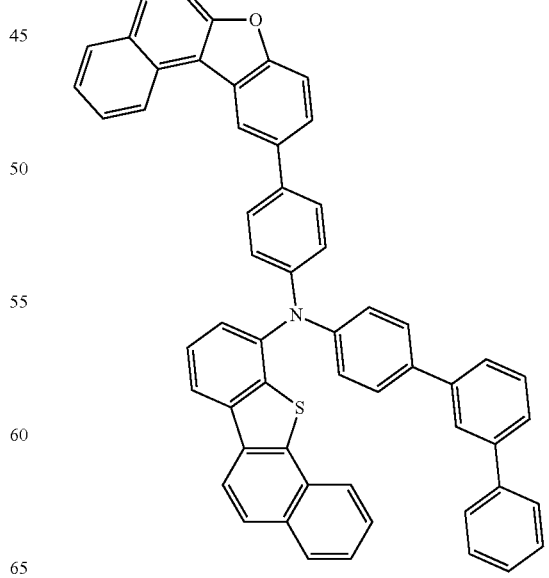

P-125
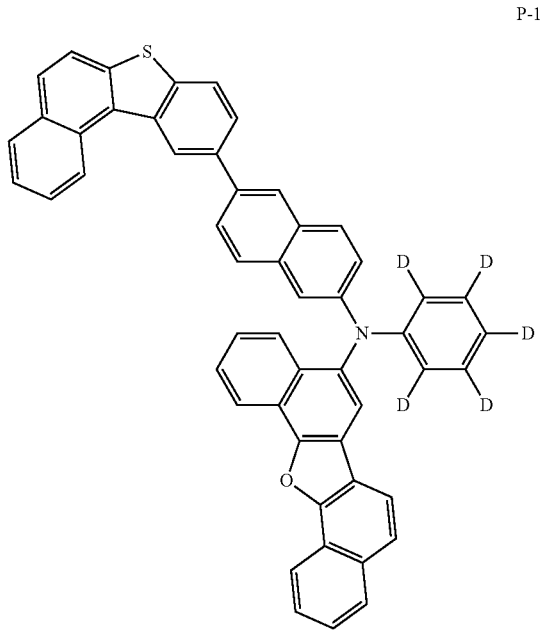
P-127
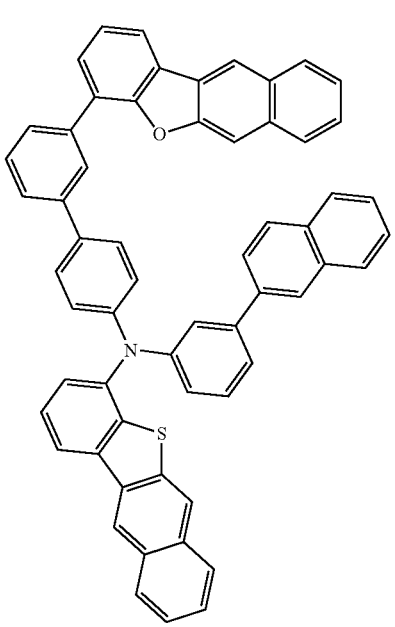
P-126
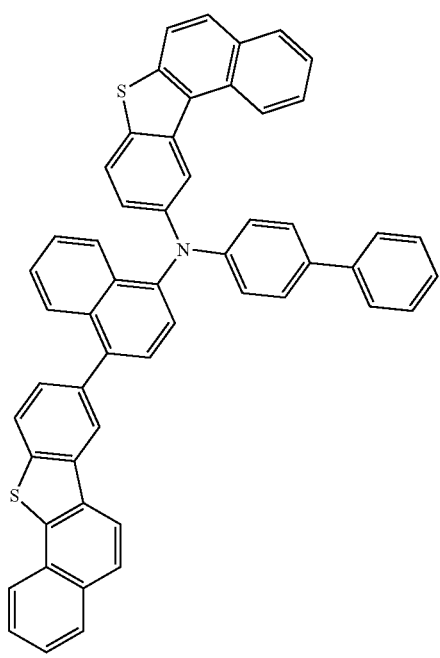
P-128
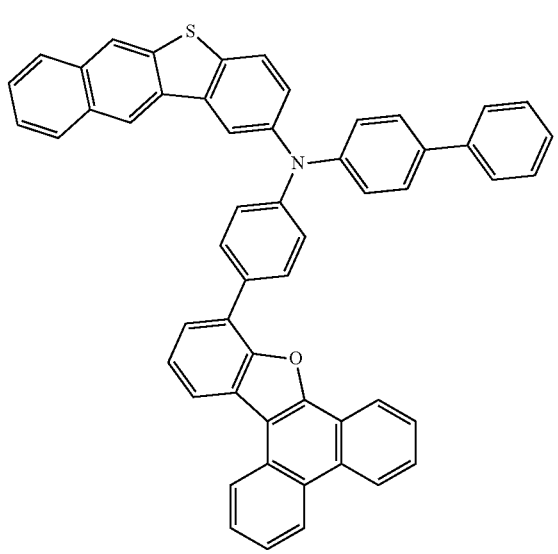

-continued
P-129
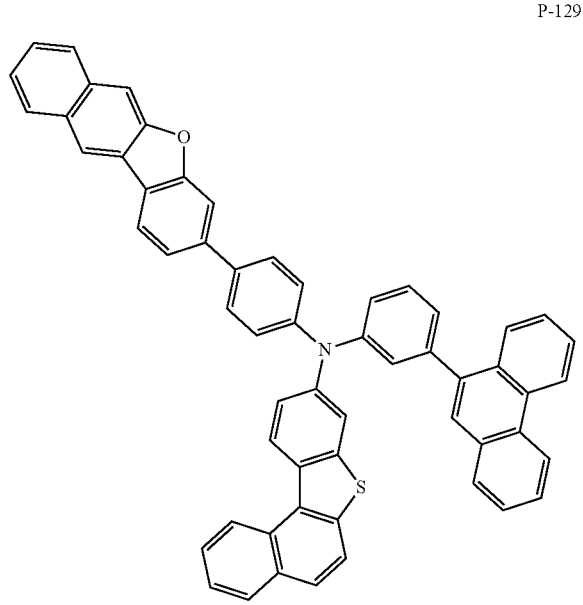
P-131
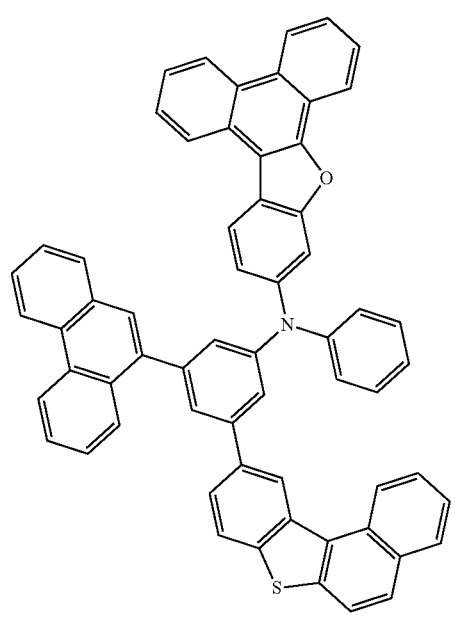
P-130
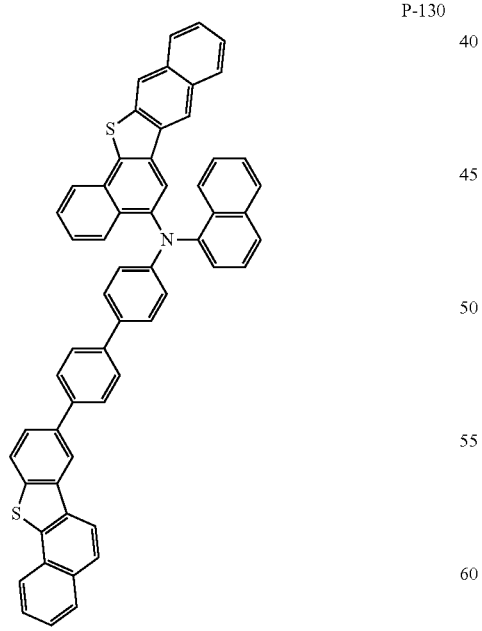
P-132
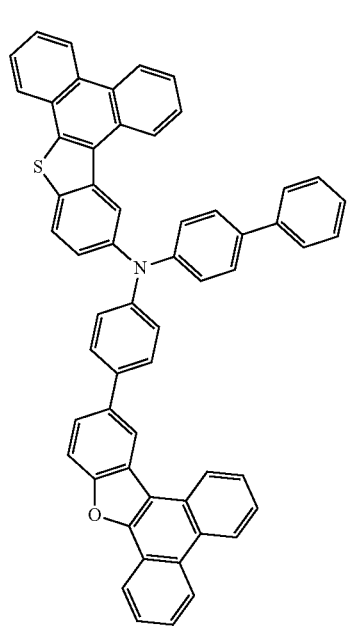

P-133
P-134
P-135
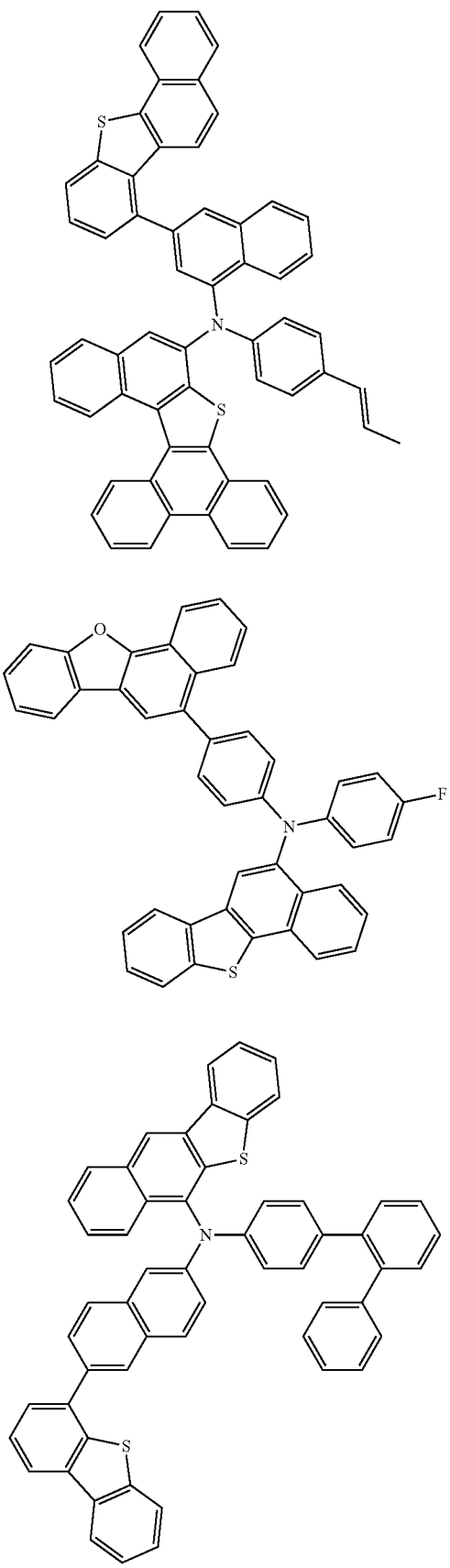
P-136
P-137
P-138
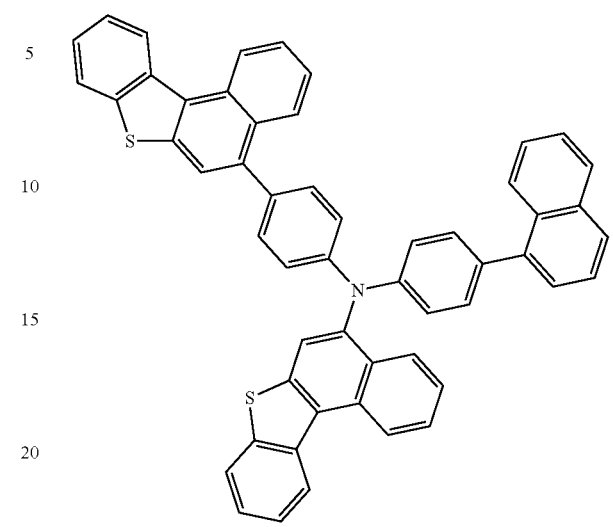
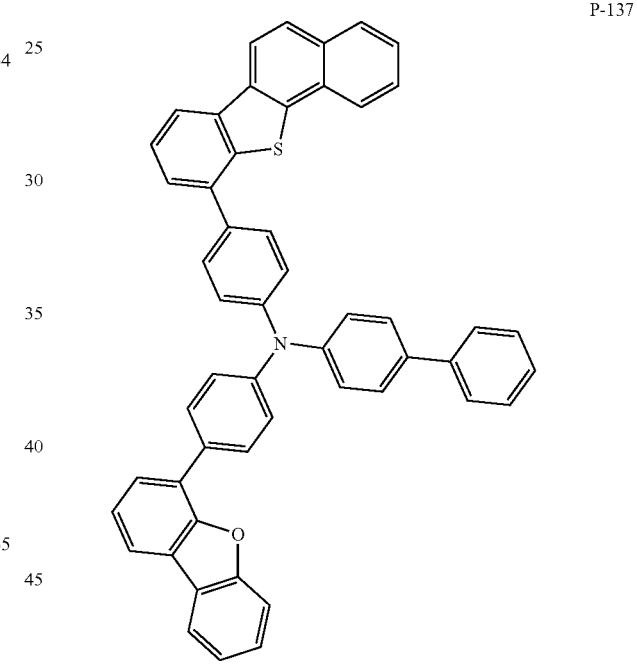
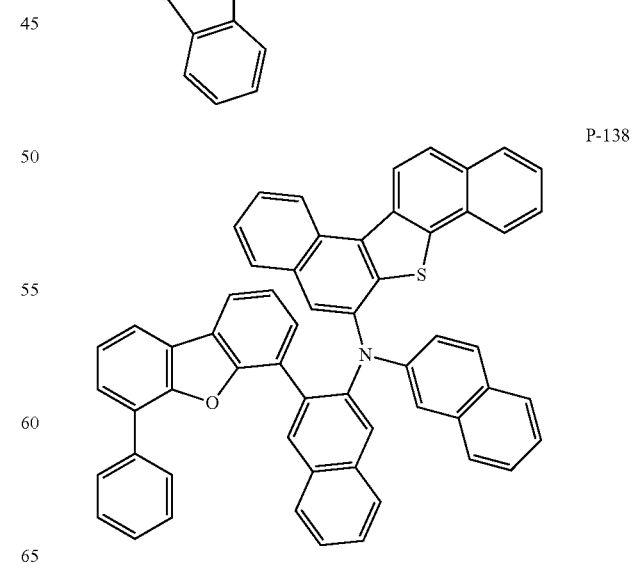

-continued
P-139
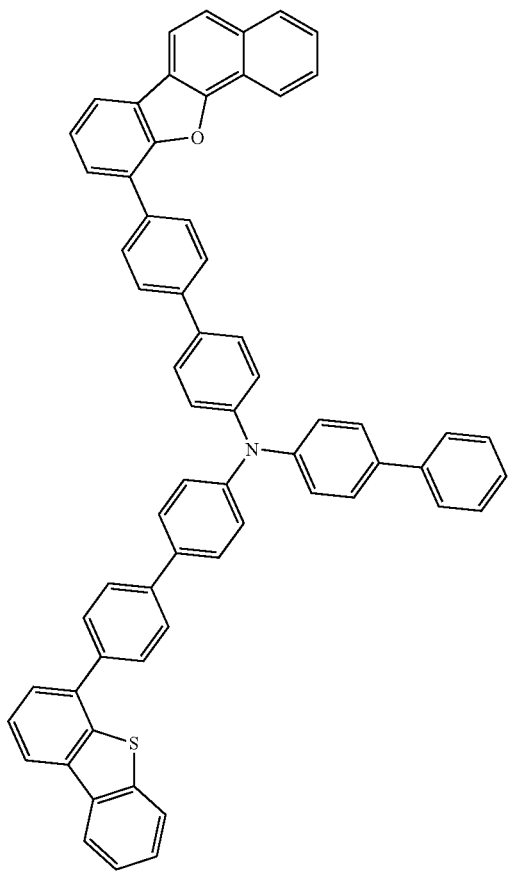
P-140
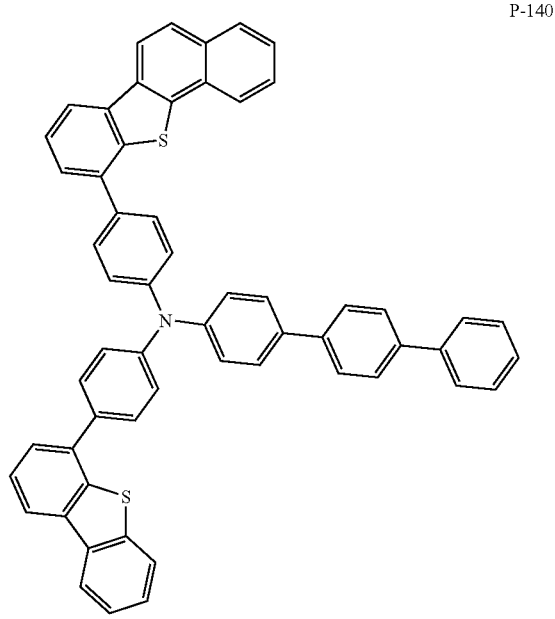
-continued
P-141
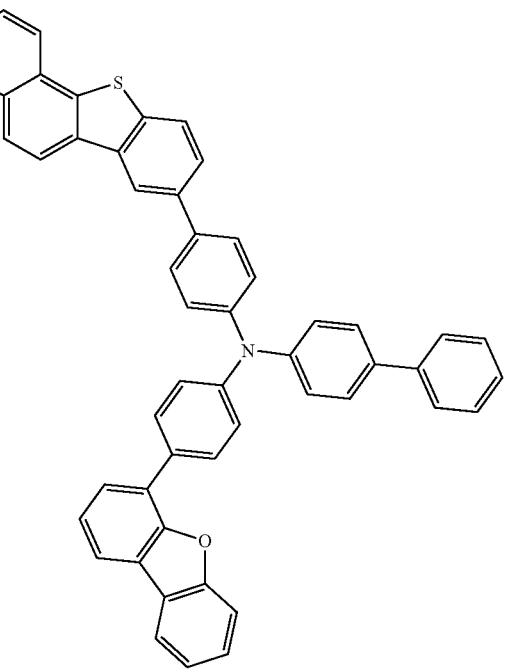
P-142
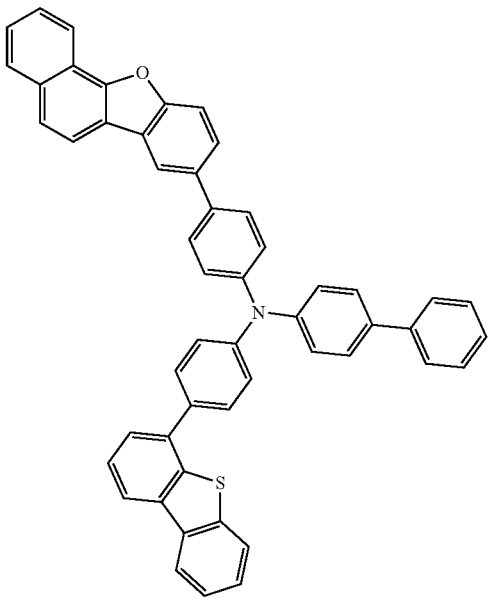

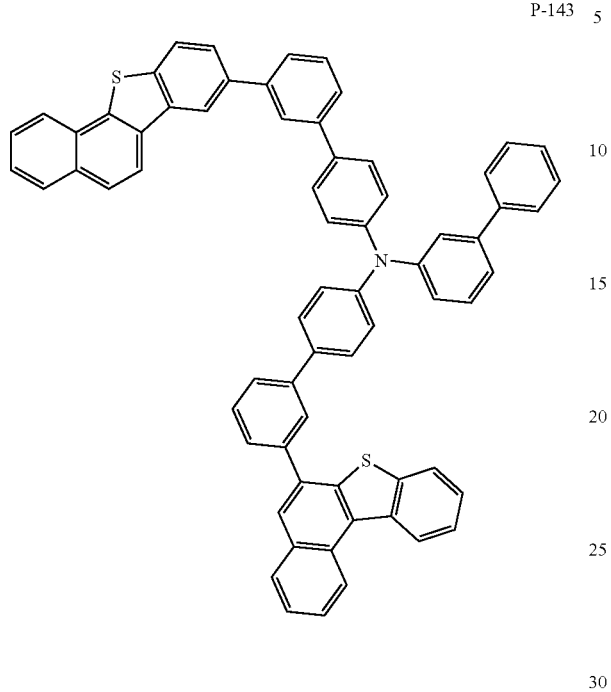
P-143
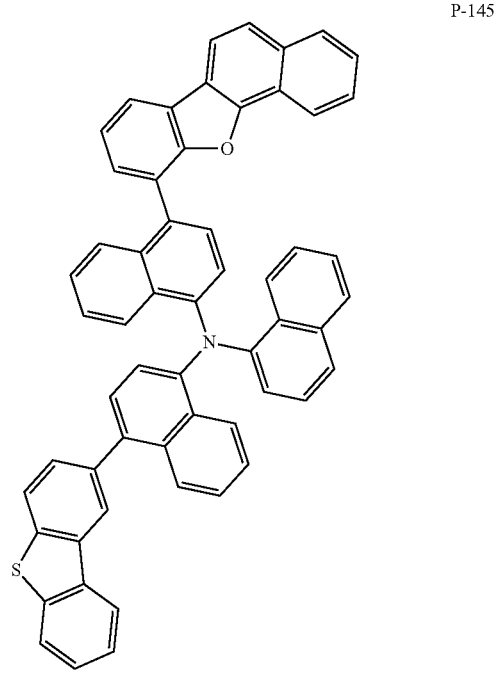
P-145
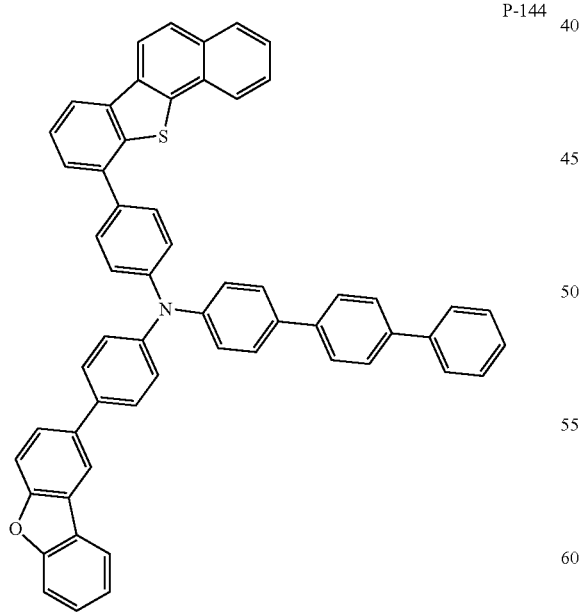
P-144
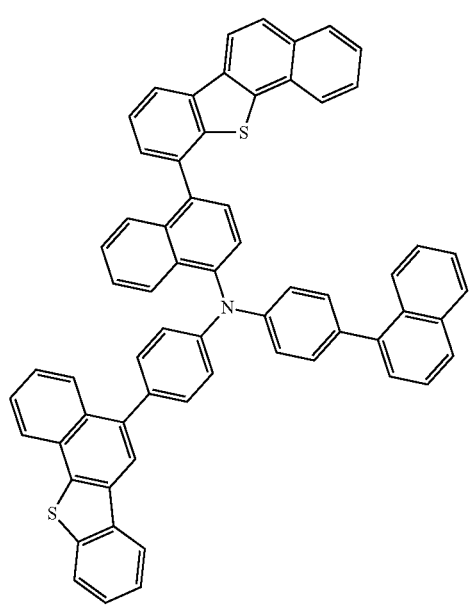
P-146

P-147
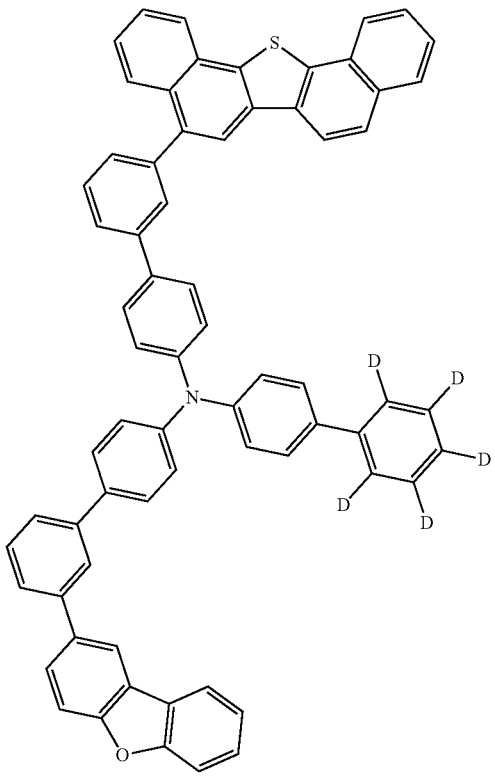
P-148
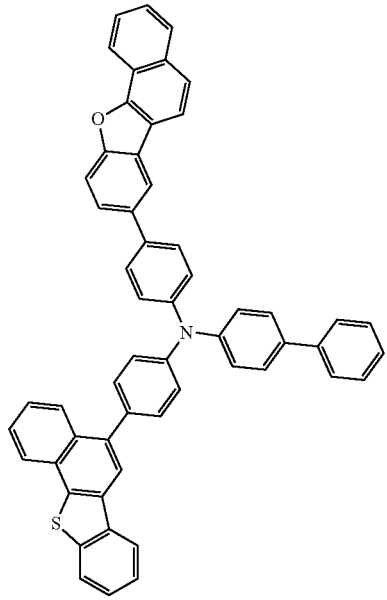
P-149
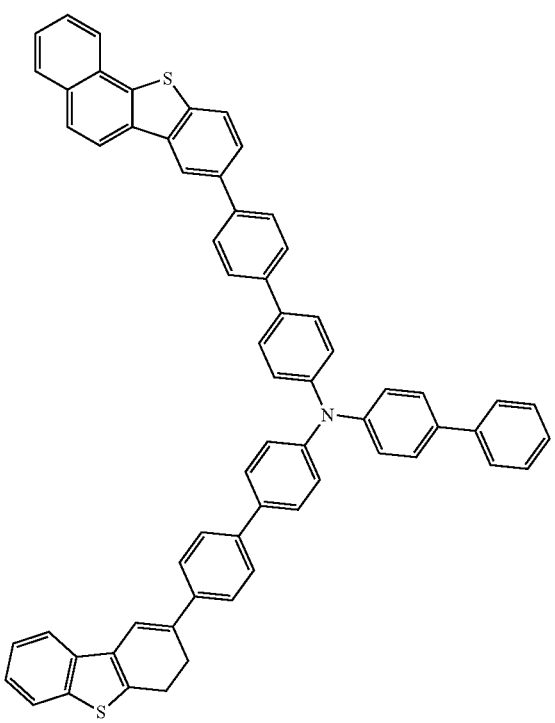
P-150
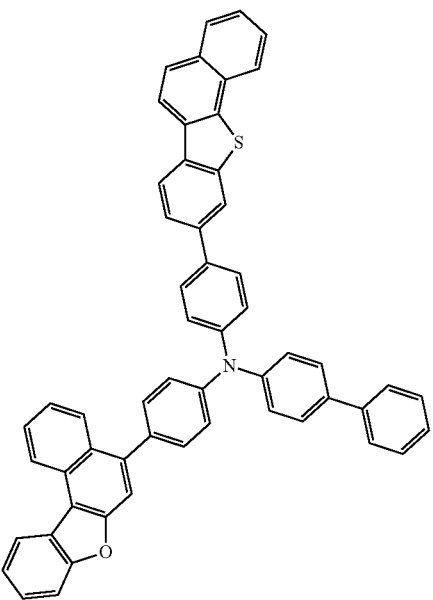

P-151
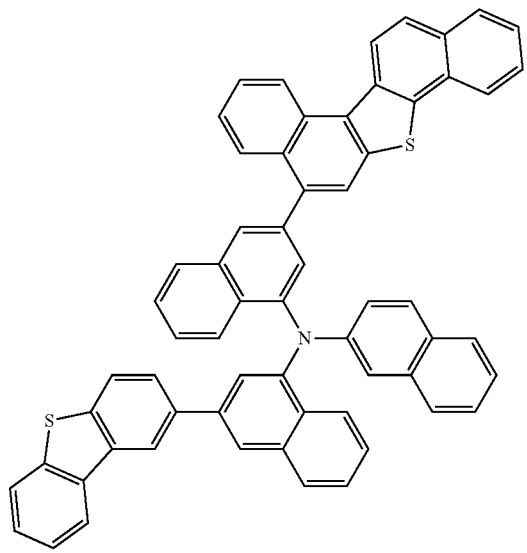
P-153
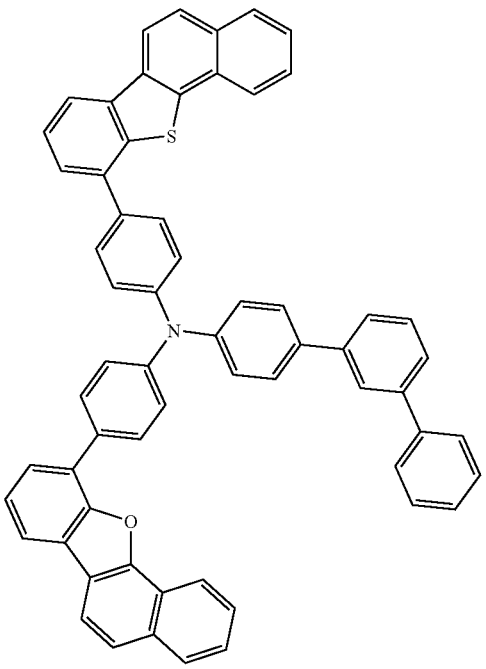
P-152
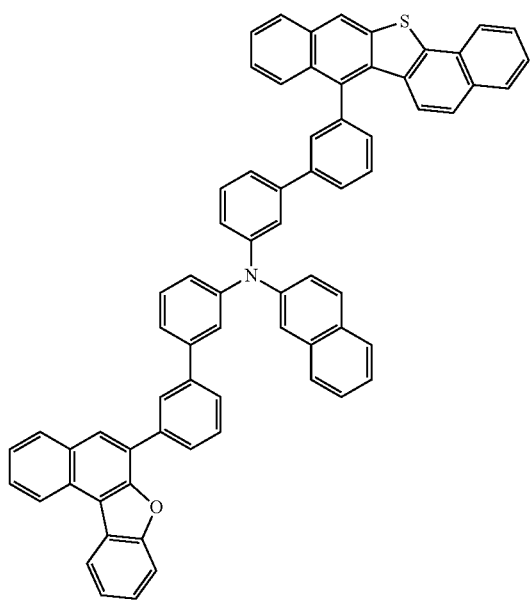
P-154
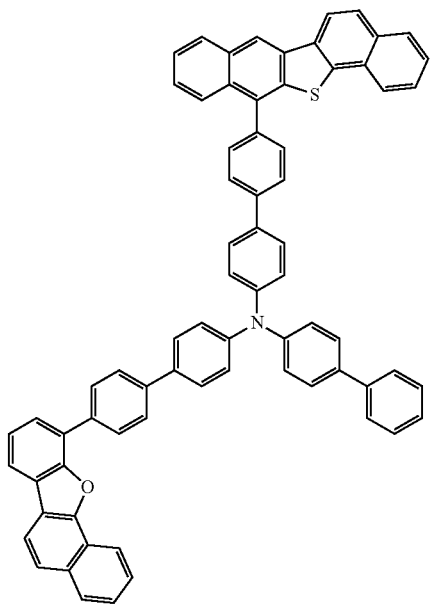

P-155
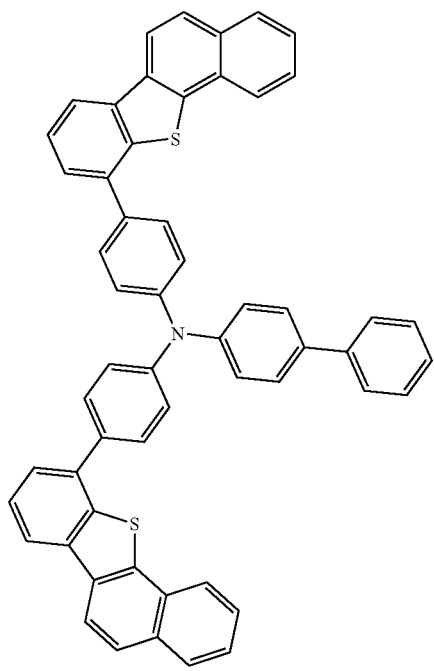
P-156
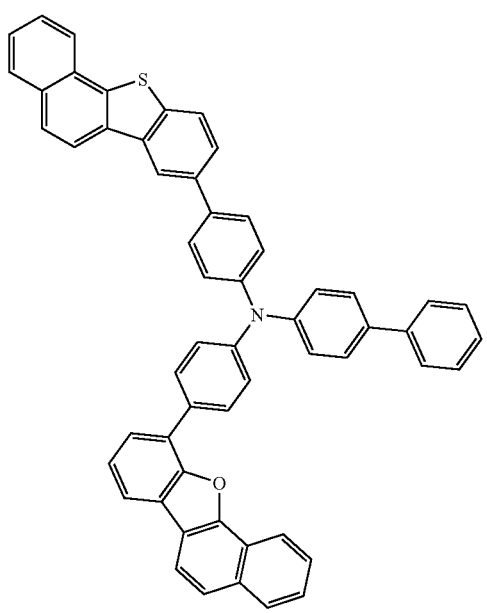
P-157
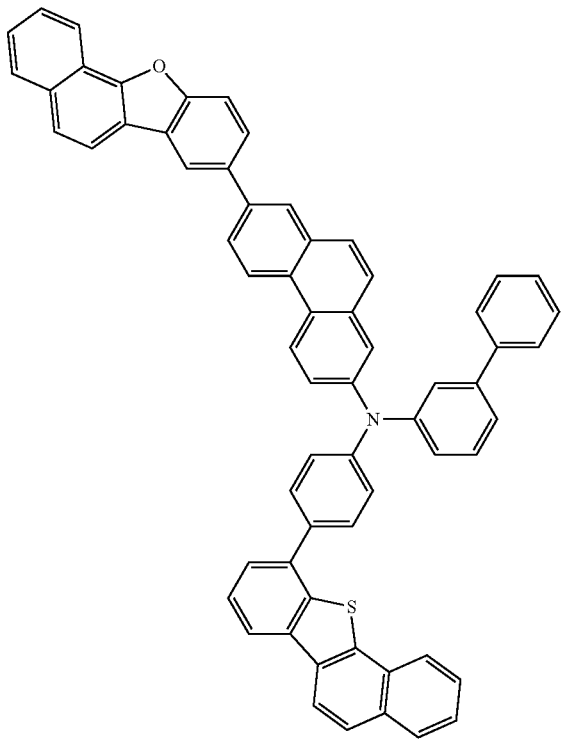
P-158
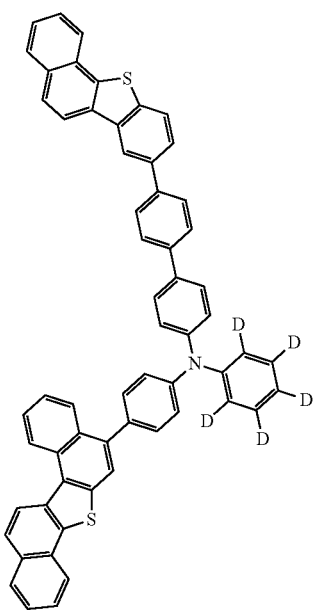

P-159
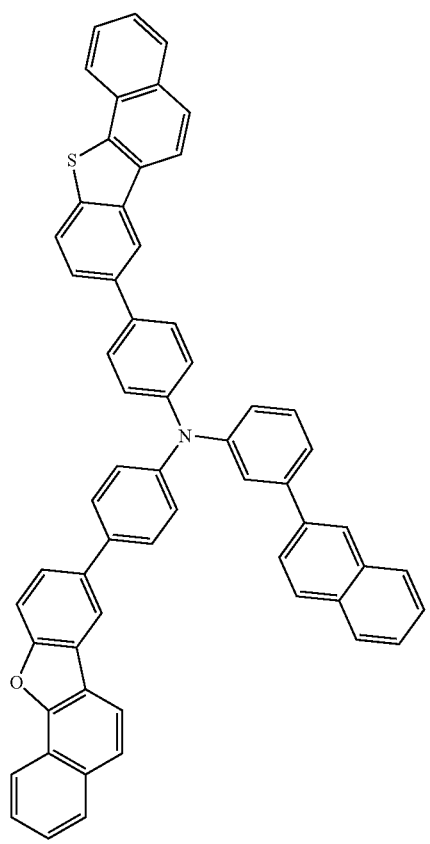
P-160
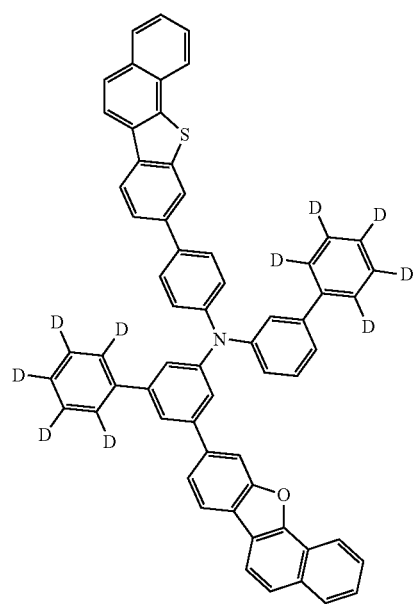
P-161
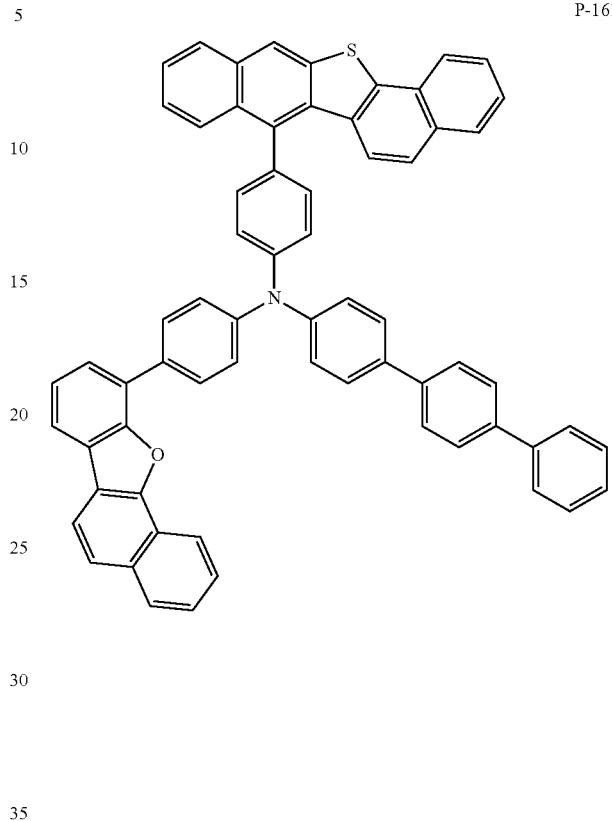
P-162
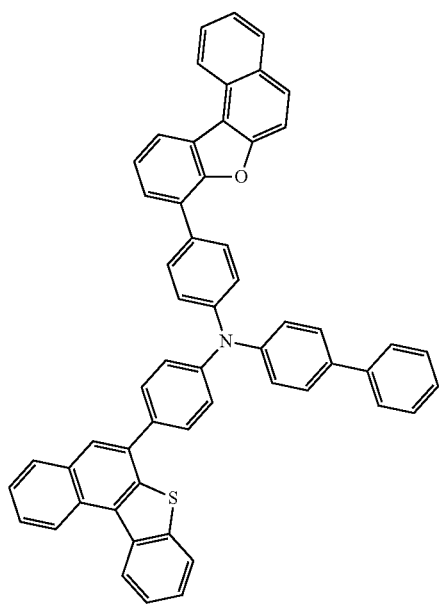

P-163
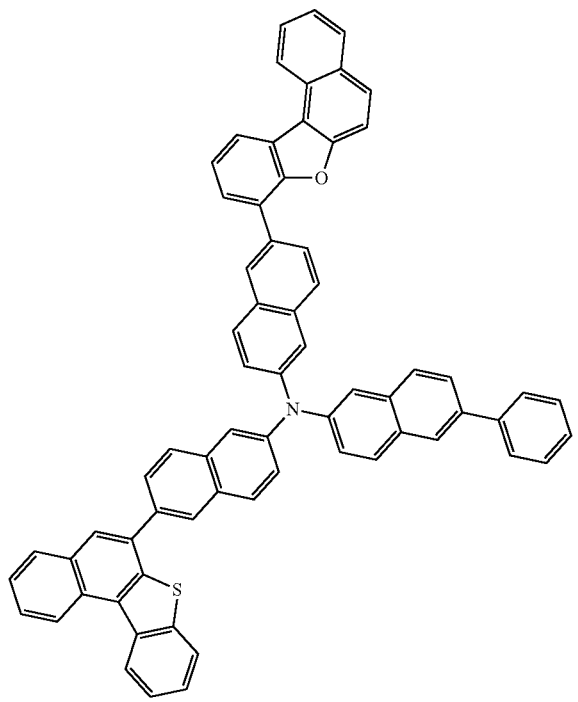
P-164
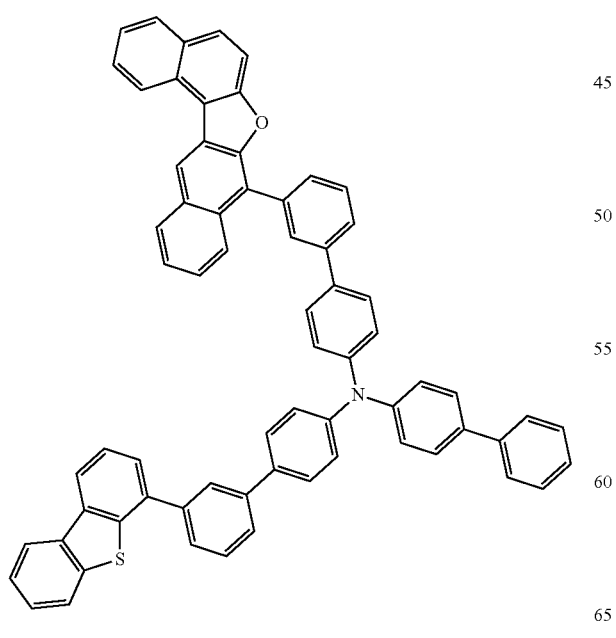
P-165
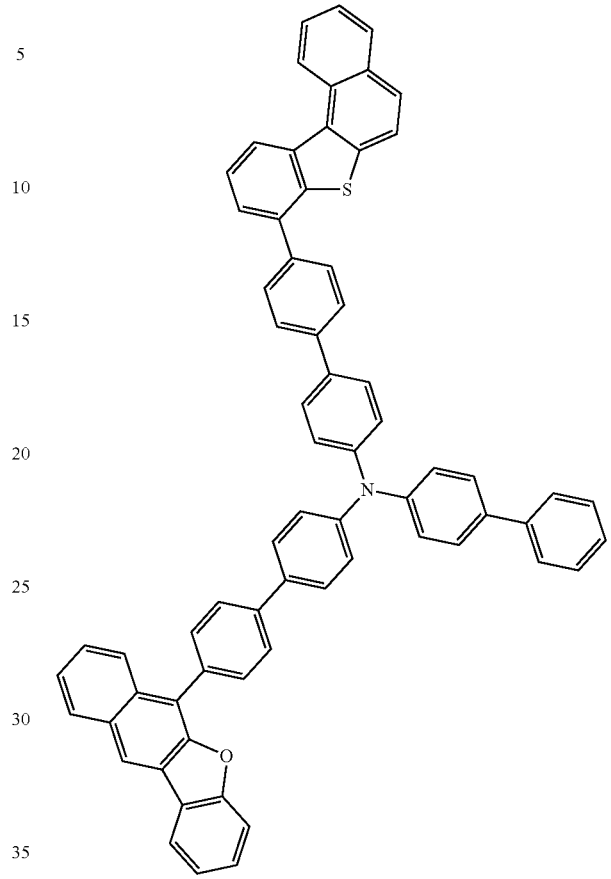
P-166
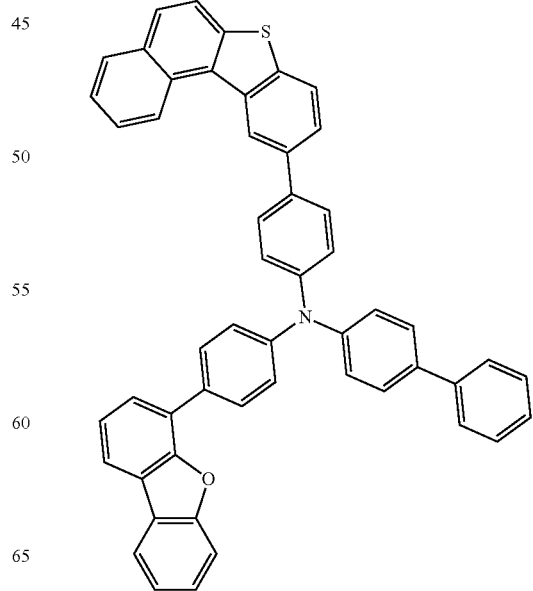

-continued
P-167
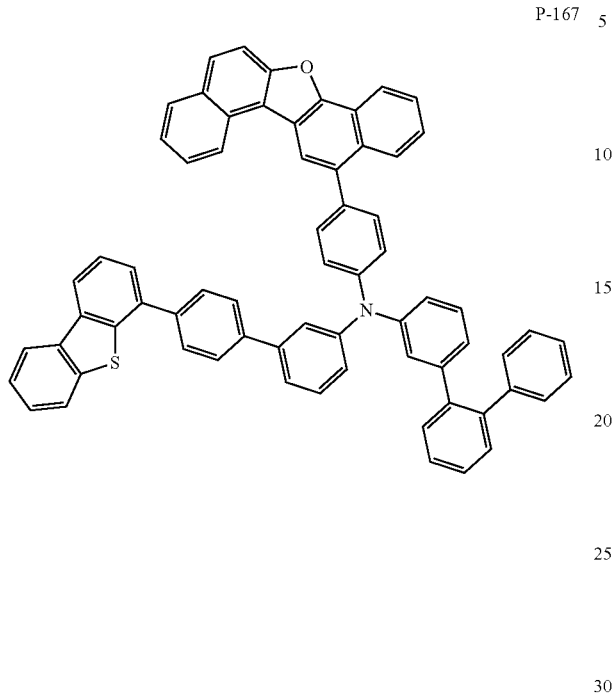
P-168
P-169
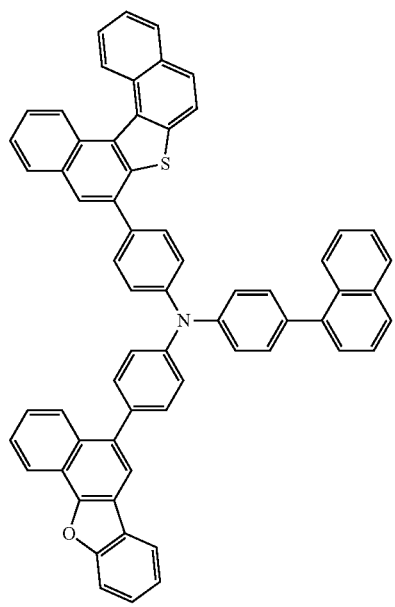
P-170
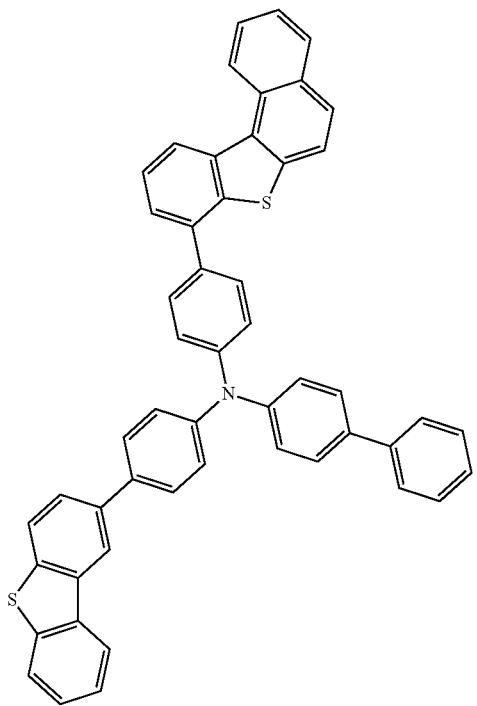

P-171
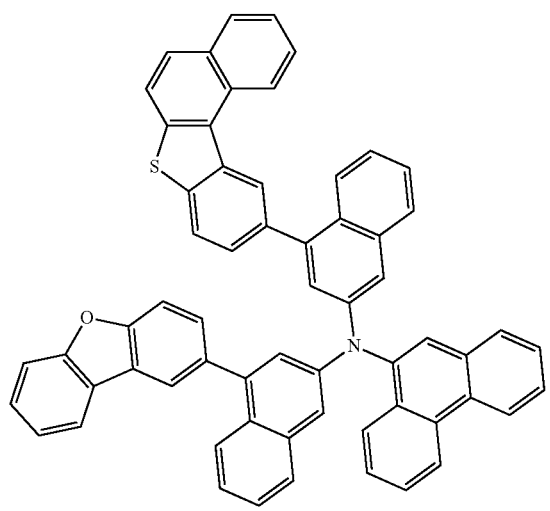
P-172
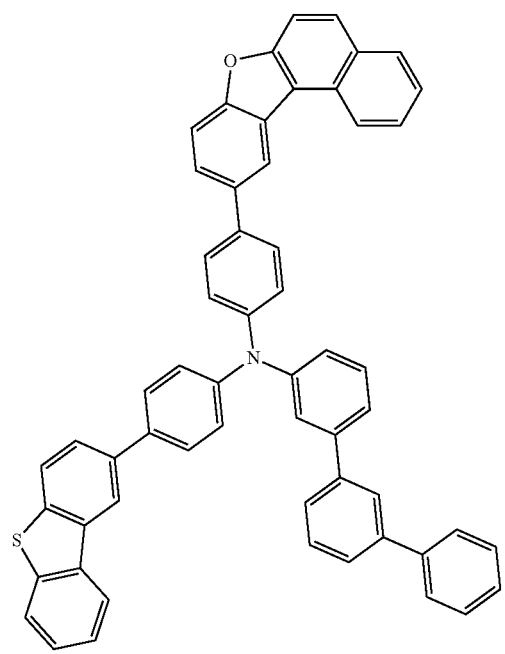
P-173
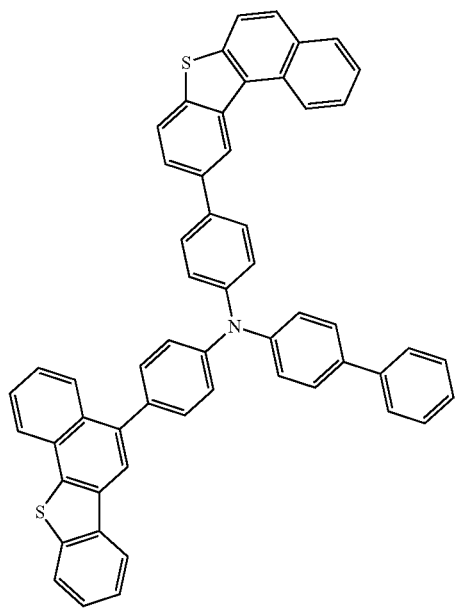
P-174
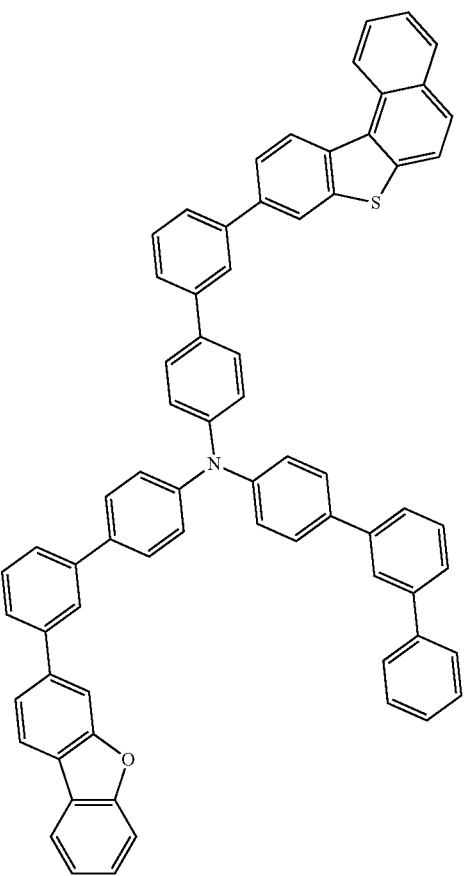

-continued
P-175
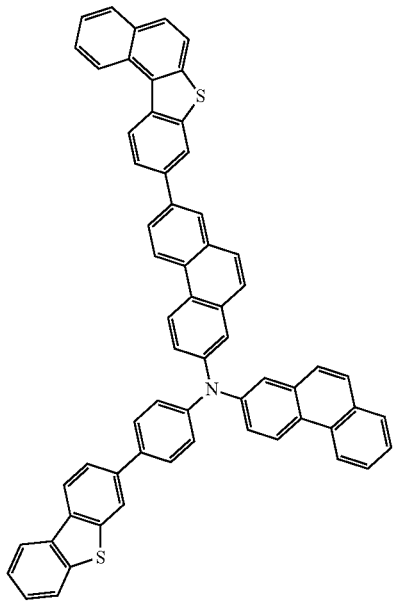
P-176
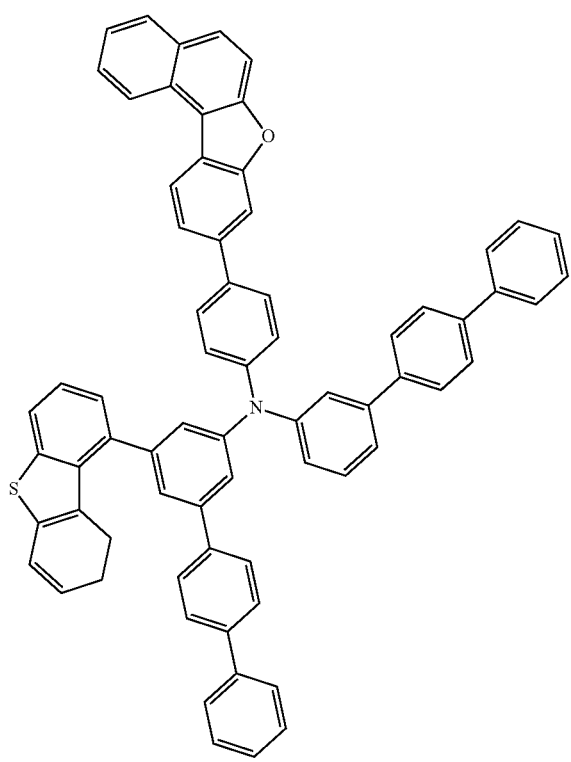
-continued
P-177
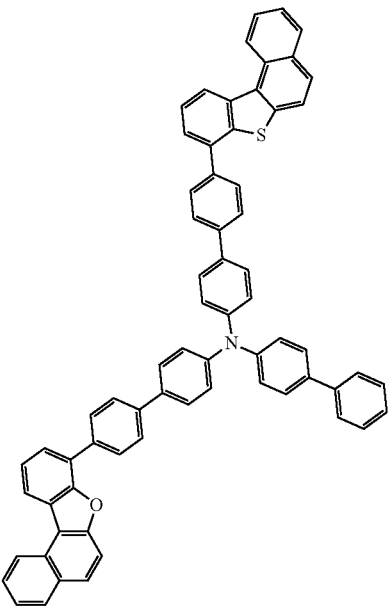
P-178
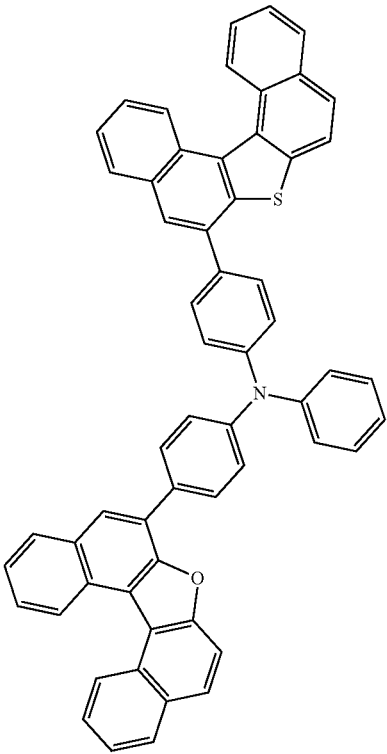

-continued
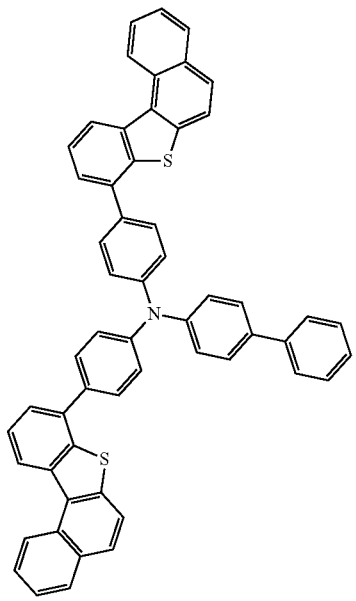
P-179
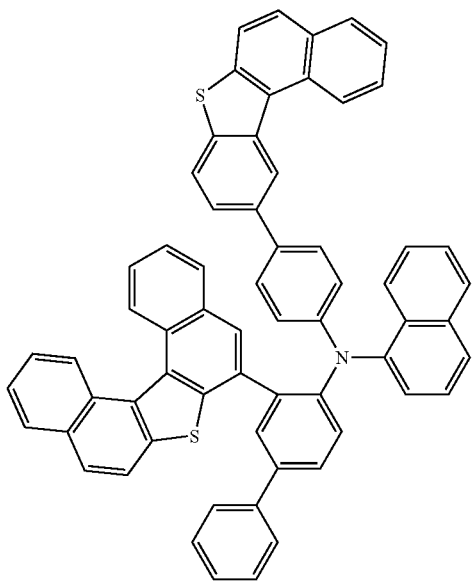
P-181
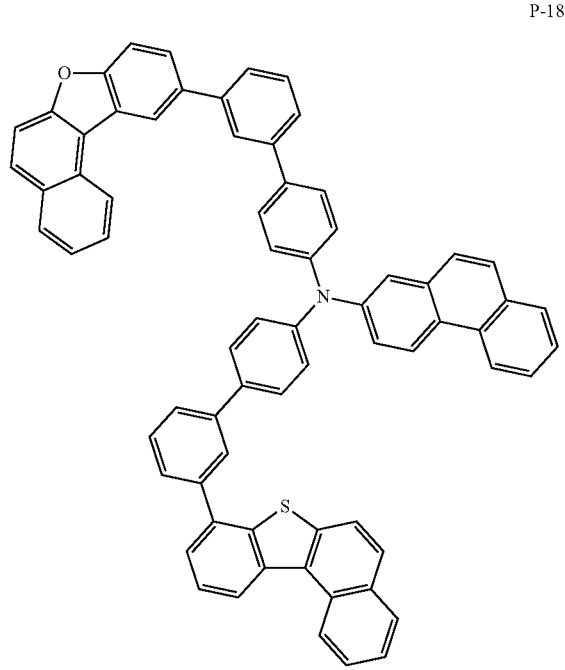
P-180
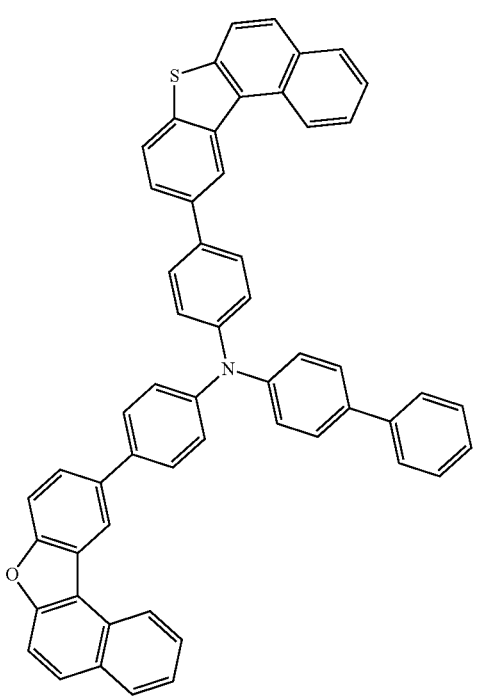
P-182

P-183
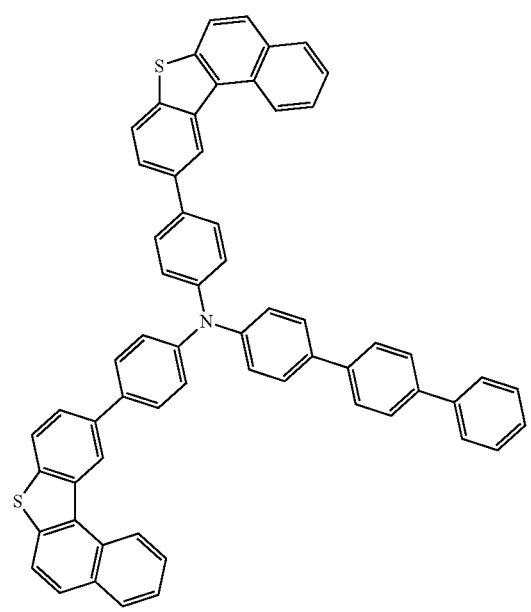
P-185
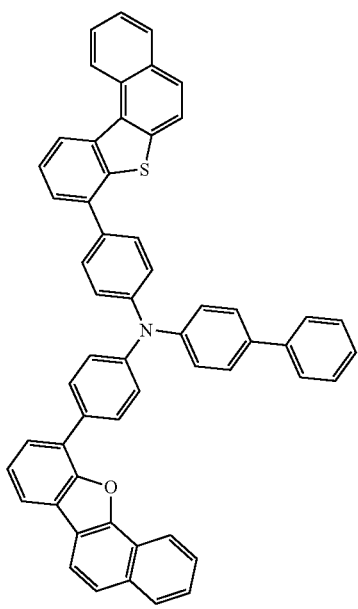
P-184
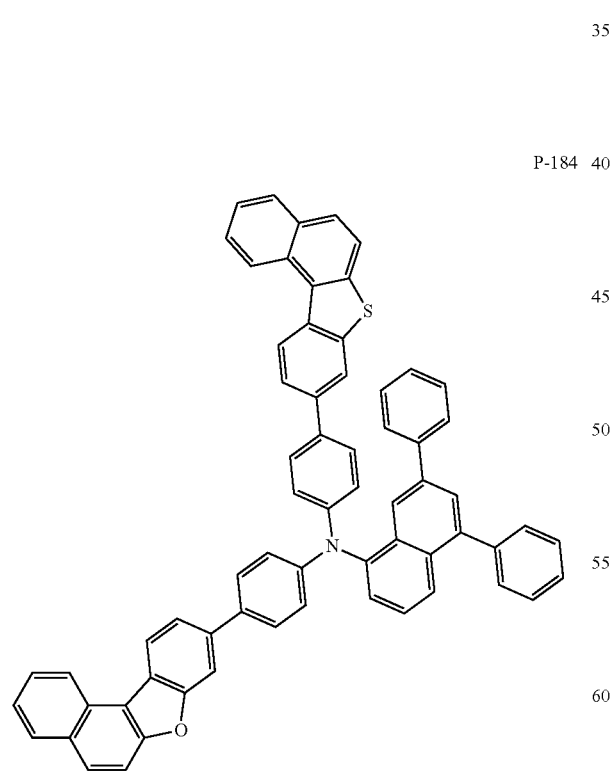
P-186
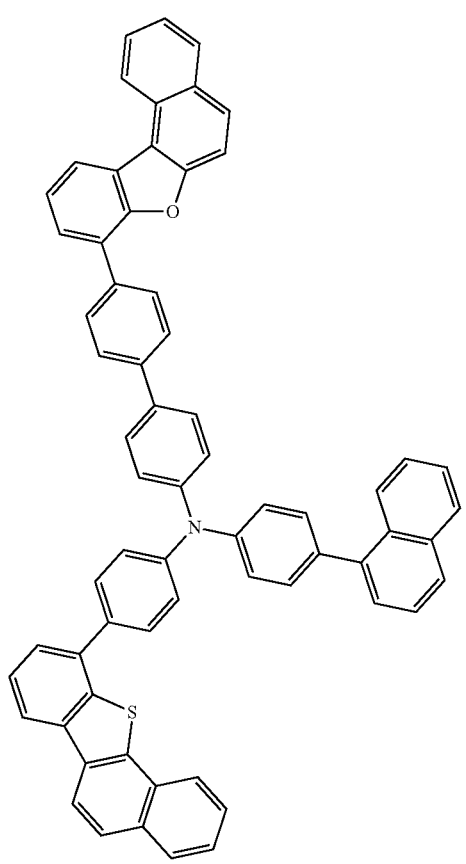

P-187
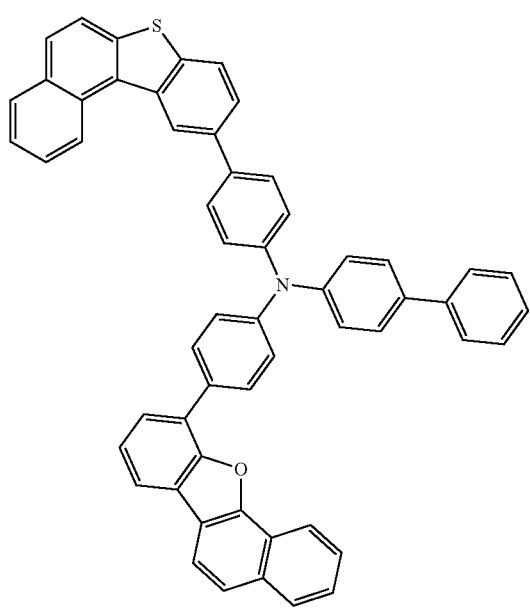
P-189
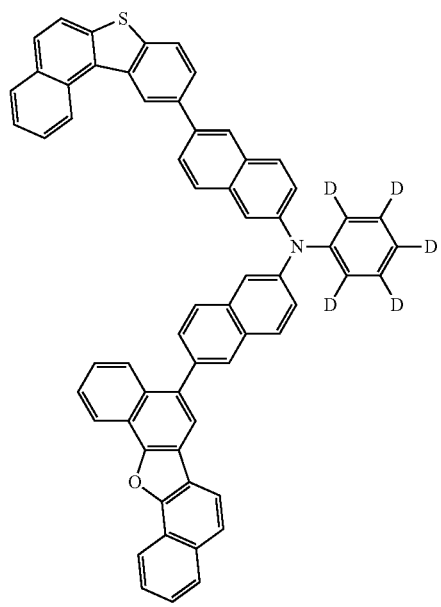
P-188
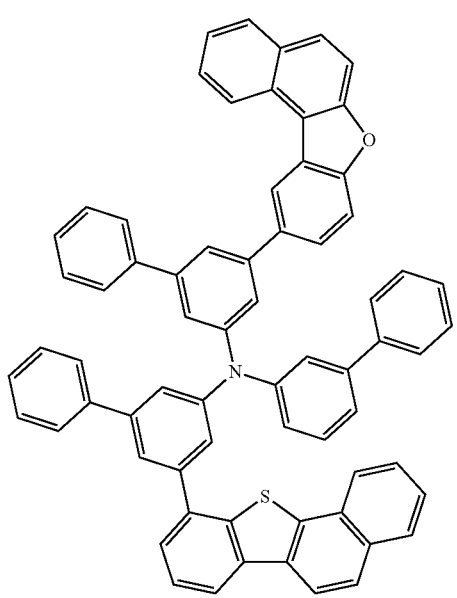
P-190
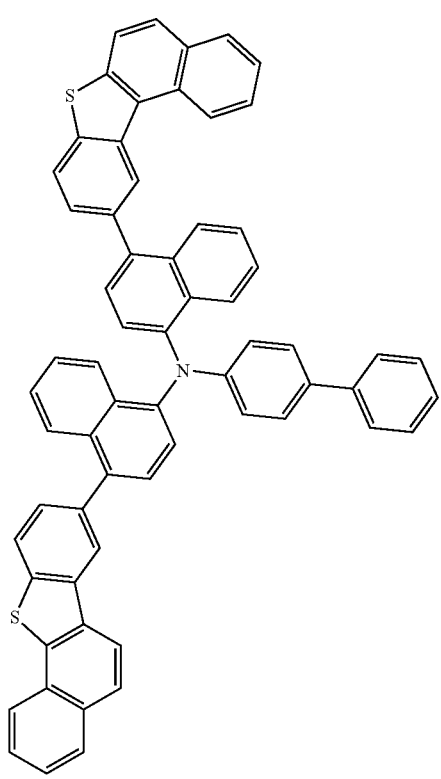

P-191
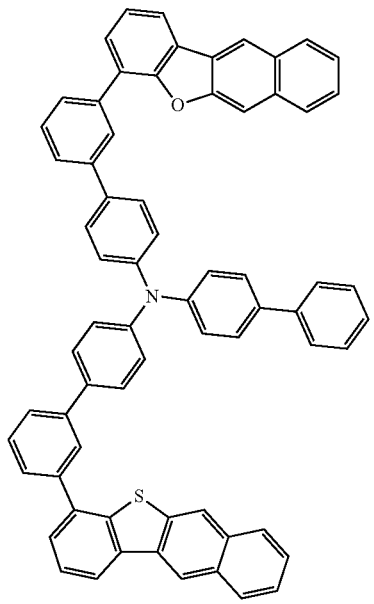
P-192
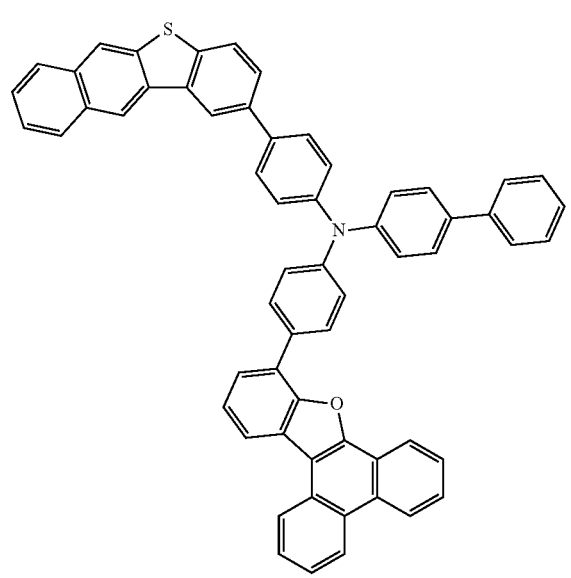
P-193
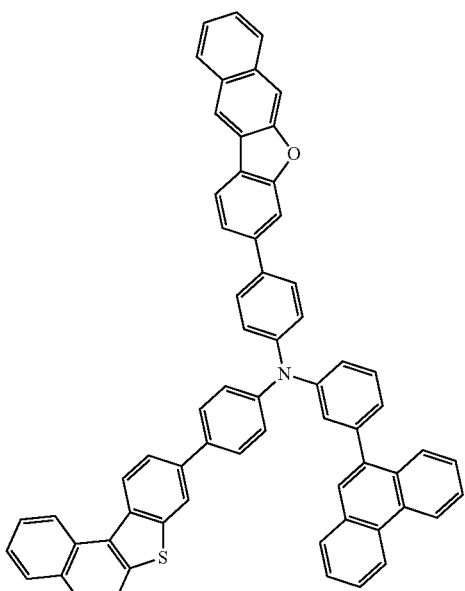
P-194
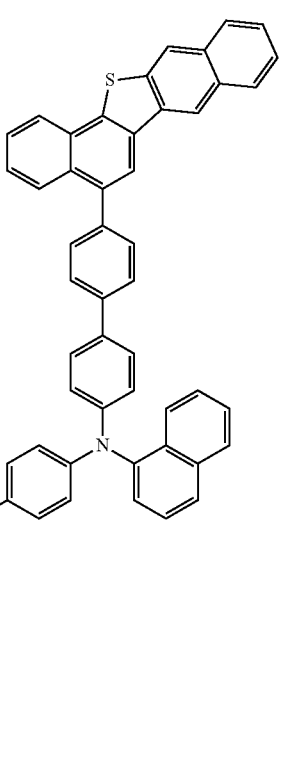

-continued
P-195
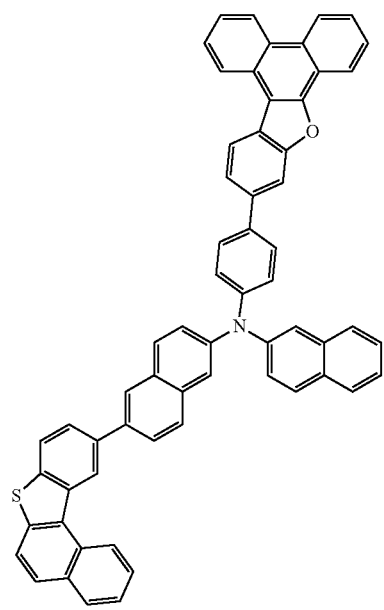
P-197
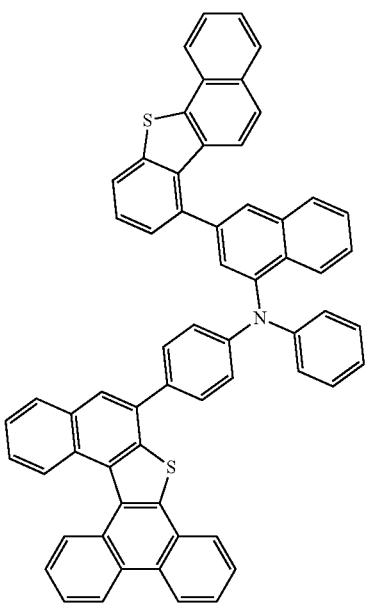
P-196
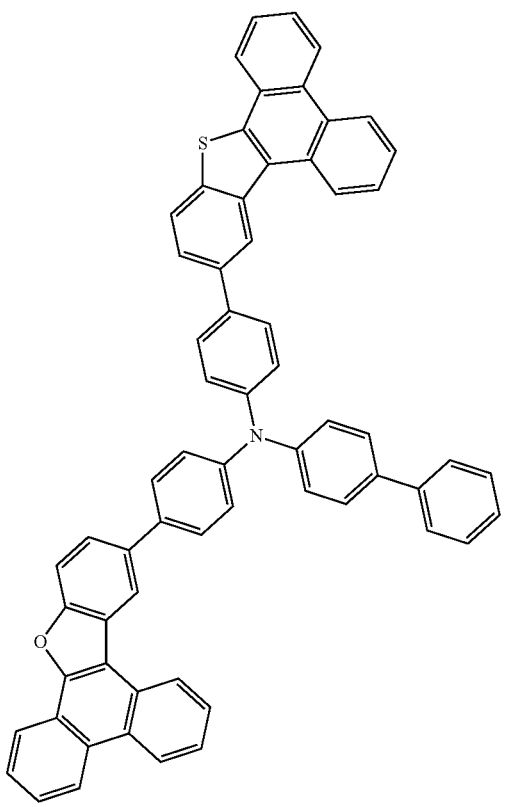
P-198
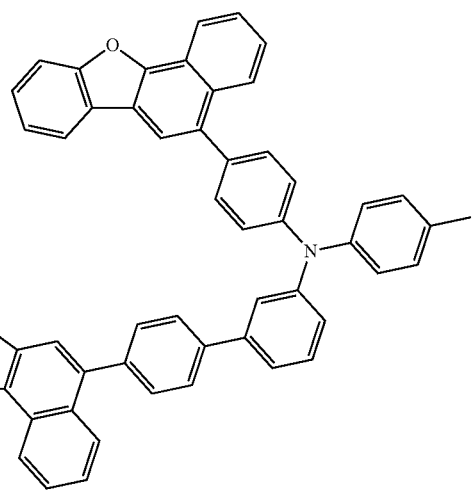

P-199

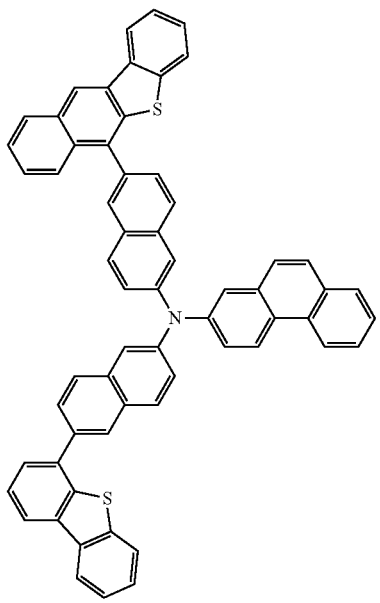

P-200

3. An organic electric element comprising a first electrode, a second electrode, and an organic material layer disposed between the first electrode and the second electrode, wherein the organic material layer comprises the compound of claim 1.

4. The organic electric element of claim 3, wherein the compound is comprised in at least one of a hole injection layer, a hole transport layer, an emission-auxiliary layer and an light emitting layer, and the compound is a single compound or a mixture of two or more different compounds.

5. The organic electric element of claim 3, wherein the organic material layer is formed by any one of the processes of spin coating, nozzle printing, inkjet printing, slot coating, dip coating and roll-to-roll.

6. An electronic device comprising a display device, which comprises the organic electric element of claim 3, and a control unit for driving the display device.

7. The electronic device of claim 6, wherein the organic electric element comprises at least one of an organic light emitting diode, an organic solar cell, an organic photo conductor, an organic transistor, and an element for monochromatic or white illumination.

8. The compound of claim 1, wherein A ring and B ring are each independently any one of 1 to 1d below:

1a

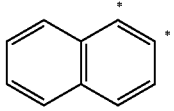
1b

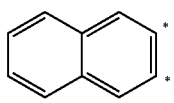
1c

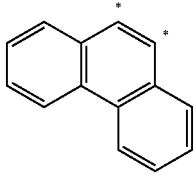
1d wherein, * indicates the position of bonding.

9. An organic electric element comprising a first electrode, a second electrode, and an organic material layer disposed between the first electrode and the second electrode, wherein the organic material layer comprises the compound of claim 2.

10. An electronic device comprising a display device, which comprises the organic electric element of claim 9, and a control unit for driving the display device.

* * * * *